US010207315B2

(12) United States Patent
Appleby et al.

(10) Patent No.: US 10,207,315 B2
(45) Date of Patent: Feb. 19, 2019

(54) SYSTEMS, DEVICES, AND/OR METHODS FOR MANUFACTURING CASTINGS

(71) Applicant: Mikro Systems, Inc., Charlottesville, VA (US)

(72) Inventors: Michael P. Appleby, Crozet, VA (US); Iain Fraser, Ruckersville, VA (US); John Paulus, Afton, VA (US)

(73) Assignee: UNITED TECHNOLOGIES CORPORATION, Farmington, CT (US)

( * ) Notice: Subject to any disclaimer, the term of this patent is extended or adjusted under 35 U.S.C. 154(b) by 189 days.

(21) Appl. No.: 14/935,484

(22) Filed: Nov. 9, 2015

(65) Prior Publication Data

US 2016/0082502 A1 Mar. 24, 2016

Related U.S. Application Data

(63) Continuation of application No. 13/121,086, filed as application No. PCT/US2009/058220 on Sep. 24, 2009, now Pat. No. 9,315,663.
(Continued)

(51) Int. Cl.
*B22C 9/04* (2006.01)
*B23P 15/24* (2006.01)
(Continued)

(52) U.S. Cl.
CPC .............. *B22C 9/04* (2013.01); *B22C 9/10* (2013.01); *B23P 15/246* (2013.01);
(Continued)

(58) Field of Classification Search
CPC ........................................................ B22C 9/04
See application file for complete search history.

(56) References Cited

U.S. PATENT DOCUMENTS

| 408,677 A | 8/1889 | Tabor |
| 460,377 A | 9/1891 | Lake |

(Continued)

FOREIGN PATENT DOCUMENTS

| CA | 2448736 | 8/2010 |
| DE | 19712442 | 10/1998 |

(Continued)

OTHER PUBLICATIONS

Desai, Upendra, "New Fabrication Methodology for Fine Feature High Aspect Ratio Structures Made from High Z Materials", Part of the SPIE Conference on Micromachining and Microfabrication Process Technology V, Sep. 22, 1999, 7 pages page(s), vol. v. 3874, SPIE, U.S.

(Continued)

*Primary Examiner* — William P Watkins, III
(74) *Attorney, Agent, or Firm* — Cantor Colburn LLP

(57) ABSTRACT

Certain exemplary embodiments can provide a composition, system, machine, device, manufacture, circuit, and/or user interface adapted for, and/or a method and/or machine-readable medium comprising machine-implementable instructions for, activities that can comprise, after removing a cast device from a stack-lamination-derived mold, said cast device formed from a molding composition, applying a desired shape to said cast device to form a shaped cast device, said molding composition comprising: a ceramic composition comprising silica; an cycloaliphatic epoxy binder composition, said cycloaliphatic epoxy binder composition present in said molding composition in an amount up to 30% by weight of said molding composition; a silicone composition comprising a siloxane resin, said silicone composition present in said molding composition in an amount up to 30% by weight of said molding composition; and a (Continued)

solvent composition adapted to dissolve said cycloaliphatic epoxy binder composition and said silicone composition.

15 Claims, 87 Drawing Sheets

Related U.S. Application Data

(60) Provisional application No. 61/100,427, filed on Sep. 26, 2008.

(51) Int. Cl.
  *B29C 33/30* (2006.01)
  *B29C 33/38* (2006.01)
  *C08L 63/00* (2006.01)
  *C08L 83/04* (2006.01)
  *B22C 9/10* (2006.01)
  *A61B 6/00* (2006.01)

(52) U.S. Cl.
  CPC ............ *B29C 33/301* (2013.01); *B29C 33/38* (2013.01); *B29C 33/3835* (2013.01); *C08L 63/00* (2013.01); *C08L 83/04* (2013.01); *A61B 6/4258* (2013.01); *Y10T 428/24479* (2015.01)

(56) References Cited

U.S. PATENT DOCUMENTS

| | | |
|---|---|---|
| 1,164,987 A | 12/1915 | Bucky |
| 2,679,172 A | 3/1951 | Clevenger |
| 2,903,390 A | 9/1959 | Kojima |
| 2,961,751 A | 11/1960 | Operhall |
| 3,312,583 A | 4/1967 | Rochlis |
| 3,379,812 A | 4/1968 | Yakovou |
| 3,676,541 A | 7/1972 | Nishi |
| 3,829,536 A | 8/1974 | Alvarez |
| 3,889,921 A | 6/1975 | Weber |
| 3,950,651 A | 4/1976 | Flocee |
| 3,957,715 A | 5/1976 | Lirones |
| 3,964,534 A | 6/1976 | Rabinowitz |
| 3,988,586 A | 10/1976 | Stuart |
| 3,988,589 A | 10/1976 | Leask |
| 4,001,069 A | 1/1977 | DiMatteo |
| 4,012,549 A | 3/1977 | Slysh |
| 4,054,800 A | 10/1977 | Leask |
| 4,075,483 A | 2/1978 | Tancrell |
| 4,091,289 A | 5/1978 | LeMay |
| 4,190,450 A | 2/1980 | Robb |
| 4,273,178 A | 6/1981 | Goloff |
| 4,284,121 A | 8/1981 | Horton |
| 4,288,697 A | 9/1981 | Albert |
| 4,317,036 A | 2/1982 | Wang |
| 4,355,400 A | 10/1982 | Doemer et al. |
| 4,356,400 A | 10/1982 | Polizzi |
| 4,460,832 A | 7/1984 | Bigham |
| 4,465,540 A | 8/1984 | Albert |
| 4,518,631 A | 5/1985 | Antonen |
| 4,534,813 A | 8/1985 | Williamson |
| 4,641,270 A | 2/1987 | Lalloz |
| 4,708,626 A | 11/1987 | Sakai |
| 4,748,328 A | 5/1988 | Chang et al. |
| 4,752,352 A | 6/1988 | Feygin |
| 4,801,379 A | 1/1989 | Ehrsam et al. |
| 4,812,236 A | 3/1989 | Ehrsam |
| 4,825,646 A | 5/1989 | Challoner et al. |
| 4,837,187 A | 6/1989 | Frank |
| 4,856,043 A | 8/1989 | Zola |
| 4,868,843 A | 9/1989 | Nunan |
| 4,915,757 A | 4/1990 | Rando |
| 4,951,305 A | 8/1990 | Moore et al. |
| 5,002,889 A | 3/1991 | Klein |
| 5,014,763 A | 5/1991 | Frank |
| 5,017,317 A | 5/1991 | Marcus |
| 5,031,483 A | 7/1991 | Weaver |
| 5,043,014 A * | 8/1991 | Flochel ............... B22C 1/2286 106/38.27 |
| 5,043,043 A | 8/1991 | Howe et al. |
| 5,088,047 A | 2/1992 | Bynum |
| 5,126,529 A | 6/1992 | Weiss |
| 5,127,037 A | 6/1992 | Bynum |
| 5,147,761 A | 9/1992 | Wessells et al. |
| 5,150,183 A | 9/1992 | Mikosch |
| 5,183,598 A | 2/1993 | Hellé |
| 5,190,637 A | 3/1993 | Guckel |
| 5,192,559 A | 3/1993 | Hull |
| 5,198,680 A | 3/1993 | Kurakake |
| 5,203,944 A | 4/1993 | Prinz |
| 5,206,983 A | 5/1993 | Guckel et al. |
| 5,207,371 A | 5/1993 | Prinz |
| 5,208,431 A | 5/1993 | Uchiyama |
| 5,216,616 A | 6/1993 | Masters |
| 5,252,881 A | 10/1993 | Muller et al. |
| 5,260,009 A | 11/1993 | Penn |
| 5,286,573 A | 2/1994 | Prinz |
| 5,301,863 A | 4/1994 | Prinz |
| 5,303,459 A | 4/1994 | Kurakake |
| 5,306,447 A | 4/1994 | Marcus |
| 5,319,014 A | 6/1994 | Moorman |
| 5,335,255 A | 8/1994 | Seppi |
| 5,340,512 A | 8/1994 | Slocum |
| 5,348,693 A | 9/1994 | Taylor |
| 5,378,583 A | 1/1995 | Guckel et al. |
| 5,384,339 A | 1/1995 | Starkey |
| 5,394,932 A | 3/1995 | Carozza |
| 5,398,193 A | 3/1995 | deAngelis |
| 5,447,068 A | 9/1995 | Tang |
| 5,450,183 A | 9/1995 | O'Leary |
| 5,450,751 A | 9/1995 | Putty et al. |
| 5,459,320 A | 10/1995 | Danet et al. |
| 5,479,981 A | 1/1996 | Kim |
| 5,483,387 A | 1/1996 | Bauhahn et al. |
| 5,512,754 A | 4/1996 | Enos |
| 5,514,232 A | 5/1996 | Burns |
| 5,531,568 A | 7/1996 | Broadhead |
| 5,551,904 A | 9/1996 | Hedges et al. |
| 5,555,481 A | 9/1996 | Rock |
| 5,559,708 A | 9/1996 | Turnbull |
| 5,576,147 A | 11/1996 | Guckel et al. |
| 5,581,592 A | 12/1996 | Zarnoch |
| 5,596,504 A | 1/1997 | Tata |
| 5,606,589 A | 2/1997 | Pellegrino et al. |
| 5,620,854 A | 4/1997 | Holzrichter et al. |
| 5,637,169 A | 6/1997 | Hull |
| 5,638,212 A | 6/1997 | Meyers et al. |
| 5,644,177 A | 7/1997 | Guckel et al. |
| 5,681,661 A | 10/1997 | Kelly |
| 5,692,507 A | 12/1997 | Seppi et al. |
| 5,702,384 A | 12/1997 | Umeyama et al. |
| 5,712,435 A | 1/1998 | Feagin |
| 5,717,213 A | 2/1998 | Stoub |
| 5,718,618 A | 2/1998 | Guckel et al. |
| 5,721,687 A | 2/1998 | Lamartine et al. |
| 5,729,585 A | 3/1998 | Pellegrino et al. |
| 5,751,000 A | 5/1998 | McCroskey |
| 5,763,318 A | 6/1998 | Bertin et al. |
| 5,773,116 A | 6/1998 | Lamartine et al. |
| 5,778,468 A | 7/1998 | Saarela et al. |
| 5,786,597 A | 7/1998 | Lingren et al. |
| 5,795,748 A | 8/1998 | Cottingham |
| 5,799,057 A | 8/1998 | Hoffman |
| 5,812,629 A | 9/1998 | Clauser |
| 5,814,235 A | 9/1998 | Pellegrino et al. |
| 5,814,807 A | 9/1998 | Musha et al. |
| 5,836,150 A | 11/1998 | Garcia |
| 5,847,958 A | 12/1998 | Shaikh |
| 5,849,229 A | 12/1998 | Holtzberg |
| 5,851,897 A | 12/1998 | Wu |
| 5,855,718 A | 1/1999 | Nguyen |
| 5,875,527 A | 3/1999 | Lacey |
| 5,879,489 A | 3/1999 | Burns |
| 5,900,350 A | 5/1999 | Provost |
| 5,902,538 A | 5/1999 | Kruger |

(56) References Cited

U.S. PATENT DOCUMENTS

| | | |
|---|---|---|
| 5,912,201 A | 6/1999 | Couture |
| 5,924,277 A | 7/1999 | Beattie et al. |
| 5,925,308 A | 7/1999 | Fewkes |
| 5,929,446 A | 7/1999 | Plummer et al. |
| 5,932,940 A | 8/1999 | Epstein et al. |
| 5,945,131 A | 8/1999 | Harvey |
| 5,947,181 A | 9/1999 | Davis |
| 5,949,850 A | 9/1999 | Tang |
| 5,955,801 A | 9/1999 | Romero et al. |
| 5,955,818 A | 9/1999 | Bertin et al. |
| 5,961,458 A | 10/1999 | Carroll |
| 5,962,949 A | 10/1999 | Dhuler et al. |
| 5,963,788 A | 10/1999 | Barron et al. |
| 5,985,204 A | 11/1999 | Otsuka et al. |
| 5,994,801 A | 11/1999 | Garcia |
| 5,994,816 A | 11/1999 | Dhuler et al. |
| 5,998,260 A | 12/1999 | Lin |
| 5,998,509 A | 12/1999 | Hayase |
| 6,004,500 A | 12/1999 | Safari et al. |
| 6,007,765 A | 12/1999 | Oversberg |
| 6,011,265 A | 1/2000 | Sauli |
| 6,014,419 A | 1/2000 | Hu |
| 6,017,410 A | 1/2000 | Baccini |
| 6,018,422 A | 1/2000 | Feldman |
| 6,018,566 A | 1/2000 | Eberhard |
| 6,018,680 A | 1/2000 | Flower |
| 6,021,358 A | 2/2000 | Sachs |
| 6,039,556 A | 3/2000 | Jens |
| 6,055,899 A | 5/2000 | Feit et al. |
| 6,068,684 A | 5/2000 | Overton |
| 6,075,840 A | 6/2000 | Pellegrino et al. |
| 6,083,452 A | 7/2000 | Kirby |
| 6,084,626 A | 7/2000 | Ramanujan et al. |
| 6,084,980 A | 7/2000 | Nguyen |
| 6,088,102 A | 7/2000 | Manhart |
| 6,099,289 A | 8/2000 | Jens |
| 6,124,663 A | 9/2000 | Haake et al. |
| 6,126,775 A | 10/2000 | Cullen |
| 6,133,670 A | 10/2000 | Rodgers et al. |
| 6,134,294 A | 10/2000 | Gibbs |
| 6,134,301 A | 10/2000 | Mruzek |
| 6,143,293 A | 11/2000 | Weiss |
| 6,149,160 A | 11/2000 | Stephens et al. |
| 6,152,181 A | 11/2000 | Wapner |
| 6,155,634 A | 12/2000 | Oehlerking et al. |
| 6,156,246 A | 12/2000 | Chatterjee |
| 6,159,407 A | 12/2000 | Krinke |
| 6,162,040 A | 12/2000 | Clune |
| 6,163,939 A | 12/2000 | Lacey |
| 6,165,406 A | 12/2000 | Jang |
| 6,172,364 B1 | 1/2001 | Ogasawara |
| 6,175,615 B1 | 1/2001 | Guru et al. |
| 6,179,601 B1 | 1/2001 | Kruger |
| 6,185,278 B1 | 2/2001 | Appleby et al. |
| 6,188,743 B1 | 2/2001 | Tybinkowski et al. |
| 6,190,594 B1 | 2/2001 | Gorman |
| 6,193,923 B1 | 2/2001 | Leyden |
| 6,197,180 B1 | 3/2001 | Kelly |
| 6,206,679 B1 | 3/2001 | Provost |
| 6,210,644 B1 | 4/2001 | Trokhan et al. |
| 6,219,015 B1 | 4/2001 | Bloom et al. |
| 6,224,807 B1 | 5/2001 | Clune |
| 6,226,120 B1 | 5/2001 | Feldman |
| 6,230,408 B1 | 5/2001 | Ehrfeld |
| 6,241,934 B1 | 6/2001 | Everett |
| 6,242,163 B1 | 6/2001 | Stampfl et al. |
| 6,245,184 B1 | 6/2001 | Riedner |
| 6,245,249 B1 | 6/2001 | Yamada |
| 6,245,487 B1 | 6/2001 | Randall |
| 6,245,849 B1 | 6/2001 | Morales et al. |
| 6,248,419 B1 | 6/2001 | Kennedy |
| 6,250,070 B1 | 6/2001 | Kreiner et al. |
| 6,252,938 B1 | 6/2001 | Tang |
| 6,258,311 B1 | 7/2001 | Jens |
| 6,261,066 B1 | 7/2001 | Linnemann et al. |
| 6,261,506 B1 | 7/2001 | Nguyen |
| 6,270,335 B2 | 8/2001 | Leyden |
| 6,276,313 B1 | 8/2001 | Yang et al. |
| 6,280,090 B1 | 8/2001 | Stephens et al. |
| 6,285,739 B1 | 9/2001 | Rudin |
| 6,286,289 B1 | 9/2001 | Powell |
| 6,299,300 B1 | 10/2001 | Silverbrook |
| 6,304,626 B1 | 10/2001 | Adachi |
| 6,307,815 B1 | 10/2001 | Polosky et al. |
| 6,310,419 B1 | 10/2001 | Wood |
| 6,314,887 B1 | 11/2001 | Robinson |
| 6,318,069 B1 | 11/2001 | Falce et al. |
| 6,318,849 B1 | 11/2001 | Silverbrook |
| 6,324,259 B1 | 11/2001 | Lehmann |
| 6,324,748 B1 | 12/2001 | Dhuler et al. |
| 6,328,903 B1 | 12/2001 | Vernon, Sr. |
| 6,333,584 B1 | 12/2001 | Jerman et al. |
| 6,336,318 B1 | 1/2002 | Falce et al. |
| 6,338,199 B1 | 1/2002 | Chigira et al. |
| 6,338,249 B1 | 1/2002 | Pai |
| 6,340,222 B1 | 1/2002 | Silverbrook |
| 6,344,392 B1 | 2/2002 | Liaw |
| 6,346,030 B1 | 2/2002 | Morales |
| 6,350,983 B1 | 2/2002 | Kaldor et al. |
| 6,352,656 B1 | 3/2002 | Kimura |
| 6,360,424 B1 | 3/2002 | Mehregany et al. |
| 6,363,712 B1 | 4/2002 | Sniegowski et al. |
| 6,363,843 B1 | 4/2002 | Daniel et al. |
| 6,365,900 B1 | 4/2002 | Mestais |
| 6,366,643 B1 | 4/2002 | Davis |
| 6,367,911 B1 | 4/2002 | Windel et al. |
| 6,373,158 B1 | 4/2002 | Hsu et al. |
| 6,373,919 B1 | 4/2002 | Horiuchi |
| 6,375,871 B1 | 4/2002 | Bentsen et al. |
| 6,375,880 B1 | 4/2002 | Cooper |
| 6,376,148 B1 | 4/2002 | Liu |
| 6,381,846 B2 | 5/2002 | Insley et al. |
| 6,382,588 B1 | 5/2002 | Hierold |
| 6,383,601 B2 | 5/2002 | Prins |
| 6,386,015 B1 | 5/2002 | Rader et al. |
| 6,387,305 B1 | 5/2002 | Jens |
| 6,387,713 B2 | 5/2002 | Hara |
| 6,392,187 B1 | 5/2002 | Johnson |
| 6,392,313 B1 | 5/2002 | Epstein et al. |
| 6,392,524 B1 | 5/2002 | Biegelsen et al. |
| 6,393,685 B1 | 5/2002 | Collins |
| 6,395,126 B1 | 5/2002 | Cullen |
| 6,396,677 B1 | 5/2002 | Chua et al. |
| 6,397,677 B1 | 6/2002 | Kinsley et al. |
| 6,397,793 B2 | 6/2002 | Yang et al. |
| 6,398,490 B1 | 6/2002 | Antonsson |
| 6,399,010 B1 | 6/2002 | Guertin |
| 6,401,004 B1 | 6/2002 | Yamazaki |
| 6,404,942 B1 | 6/2002 | Edwards et al. |
| 6,406,658 B1 | 6/2002 | Manners |
| 6,408,884 B1 | 6/2002 | Kamholz et al. |
| 6,409,072 B1 | 6/2002 | Breuer et al. |
| 6,410,213 B1 | 6/2002 | Raguin et al. |
| 6,411,672 B1 | 6/2002 | Sasaki |
| 6,415,860 B1 | 7/2002 | Kelly et al. |
| 6,416,168 B1 | 7/2002 | Silverbrook |
| 6,426,145 B1 | 7/2002 | Moroni |
| 6,433,657 B1 | 8/2002 | Chen |
| 6,438,210 B1 | 8/2002 | Castleberry |
| 6,440,284 B1 | 8/2002 | Dubrow |
| 6,445,840 B1 | 9/2002 | Fernandez et al. |
| 6,447,727 B1 | 9/2002 | Parce et al. |
| 6,450,047 B2 | 9/2002 | Swedberg et al. |
| 6,453,083 B1 | 9/2002 | Husain et al. |
| 6,454,945 B1 | 9/2002 | Weigl et al. |
| 6,457,629 B1 | 10/2002 | White |
| 6,458,263 B1 | 10/2002 | Morales et al. |
| 6,462,858 B1 | 10/2002 | MacDonald et al. |
| 6,463,115 B1 | 10/2002 | Horiuchi |
| 6,463,349 B2 | 10/2002 | White |
| 6,467,138 B1 | 10/2002 | Aime |
| 6,468,039 B1 | 10/2002 | Lehman |
| 6,471,471 B1 | 10/2002 | Bouyer |
| 6,471,800 B2 | 10/2002 | Jang |

(56) References Cited

U.S. PATENT DOCUMENTS

| | | |
|---|---|---|
| 6,472,459 B2 | 10/2002 | Morales et al. |
| 6,479,824 B1 | 11/2002 | Hoffman |
| 6,480,320 B2 | 11/2002 | Nasiri |
| 6,484,050 B1 | 11/2002 | Carroll |
| 6,490,496 B1 | 12/2002 | Dacey |
| 6,505,089 B1 | 1/2003 | Yang |
| 6,508,971 B2 | 1/2003 | Leyden |
| 6,519,313 B2 | 2/2003 | Venkataramani |
| 6,519,500 B1 | 2/2003 | White |
| 6,524,507 B1 | 2/2003 | Clune |
| 6,543,099 B1 | 4/2003 | Filion |
| 6,557,607 B2 | 5/2003 | Yamada |
| 6,572,910 B2 | 6/2003 | Lanner |
| 6,575,218 B1 | 6/2003 | Burns |
| 6,588,484 B1 | 7/2003 | Fosaaen |
| 6,611,731 B2 | 8/2003 | Duffin |
| 6,612,811 B2 | 9/2003 | Morgan |
| 6,613,438 B1 | 9/2003 | Hein et al. |
| 6,615,899 B1 | 9/2003 | Woodward |
| 6,616,884 B1 | 9/2003 | Sorensen |
| 6,616,885 B2 | 9/2003 | Lombardi |
| 6,627,030 B2 | 9/2003 | Yang |
| 6,627,835 B1 | 9/2003 | Chung |
| 6,660,209 B2 | 12/2003 | Leyden |
| 6,663,810 B1 | 12/2003 | Lee |
| 6,682,684 B1 | 1/2004 | Jamalabad |
| 6,682,688 B1 | 1/2004 | Higashi |
| 6,713,199 B2 | 3/2004 | Girardie |
| 6,731,438 B2 | 5/2004 | Stern |
| 6,745,446 B1 | 6/2004 | Barlier |
| 6,780,368 B2 | 8/2004 | Liu |
| 6,784,433 B2 | 8/2004 | Zur |
| 6,812,061 B1 | 11/2004 | Feierabend |
| 6,829,536 B2 | 12/2004 | Moore |
| 6,839,408 B2 | 1/2005 | Tang |
| 6,881,950 B2 | 4/2005 | Schlaf |
| 6,987,836 B2 | 1/2006 | Tang |
| 7,057,245 B2 | 6/2006 | Feierabend |
| 7,074,358 B2 | 7/2006 | Gybin |
| 7,077,638 B2 | 7/2006 | Leyden |
| 7,097,729 B2 | 8/2006 | Barlier |
| 7,112,797 B2 | 9/2006 | Hoge |
| 7,141,080 B2 | 11/2006 | Feierabend |
| 7,141,812 B2 * | 11/2006 | Appleby .............. B29C 33/302 250/505.1 |
| 7,165,936 B2 | 1/2007 | Elpern |
| 7,170,140 B2 | 1/2007 | Dutoit |
| 7,203,569 B2 | 4/2007 | Liang |
| 7,235,166 B2 | 6/2007 | Cohen |
| 7,252,861 B2 | 8/2007 | Smalley |
| 7,371,046 B2 | 5/2008 | Lee |
| 7,410,606 B2 | 8/2008 | Appleby |
| 7,411,204 B2 | 8/2008 | Appleby |
| 7,413,001 B2 | 8/2008 | Wang |
| 7,462,852 B2 | 12/2008 | Appleby |
| 7,514,482 B2 | 4/2009 | Treadway |
| 7,518,136 B2 | 4/2009 | Appleby |
| 7,717,677 B1 | 5/2010 | Liang |
| 7,785,098 B1 | 8/2010 | Appleby |
| 7,893,413 B1 | 2/2011 | Appleby |
| 2001/0022416 A1 | 9/2001 | Harada |
| 2001/0031531 A1 | 10/2001 | Liaw |
| 2001/0034114 A1 | 10/2001 | Liaw |
| 2001/0038803 A1 | 11/2001 | Morales |
| 2002/0087073 A1 | 7/2002 | Hoffman |
| 2002/0093115 A1 | 7/2002 | Jang |
| 2002/0123683 A1 | 9/2002 | Hoffman |
| 2002/0149137 A1 | 10/2002 | Jang |
| 2002/0181647 A1 | 12/2002 | Venkataramani et al. |
| 2003/0004407 A1 | 1/2003 | Carroll |
| 2003/0023149 A1 | 1/2003 | Montemagno |
| 2003/0026386 A1 | 2/2003 | Tang |
| 2003/0057096 A1 | 3/2003 | Morales |
| 2003/0128812 A1 | 7/2003 | Appleby et al. |
| 2003/0128813 A1 | 7/2003 | Appleby et al. |
| 2003/0157347 A1 | 8/2003 | Zhang |
| 2003/0235272 A1 | 12/2003 | Appleby |
| 2004/0006405 A1 | 1/2004 | Chen |
| 2004/0086458 A1 | 5/2004 | Kohn |
| 2004/0094287 A1 | 5/2004 | Wang |
| 2004/0120464 A1 | 6/2004 | Hoffman |
| 2004/0128016 A1 | 7/2004 | Stewart |
| 2004/0217291 A1 | 11/2004 | Hoge |
| 2004/0218713 A1 | 11/2004 | Hoffman |
| 2004/0227092 A1 | 11/2004 | Ratzmann |
| 2005/0131106 A1 | 6/2005 | Tonapi et al. |
| 2005/0199166 A1 | 9/2005 | Kennedy |
| 2005/0206048 A1 | 9/2005 | Ryu |
| 2005/0269052 A1 | 12/2005 | Lynch |
| 2005/0281701 A1 | 12/2005 | Lynch |
| 2007/0036844 A1 | 2/2007 | Ma |
| 2007/0118212 A1 | 5/2007 | Hossainy |
| 2007/0158014 A1 | 7/2007 | Schwenn |
| 2008/0053638 A1 | 3/2008 | Appleby |
| 2008/0164001 A1 | 7/2008 | Morris |
| 2008/0169081 A1 | 7/2008 | Frasier |
| 2008/0216983 A1 | 9/2008 | Whitton |
| 2008/0246180 A1 | 10/2008 | Appleby |
| 2009/0084933 A1 | 4/2009 | Appleby |
| 2009/0209745 A1 | 8/2009 | Zhao |
| 2009/0272874 A1 | 11/2009 | Appleby |
| 2010/0096778 A1 | 4/2010 | Appleby |
| 2011/0014474 A1 | 1/2011 | Appleby |
| 2011/0113627 A1 | 5/2011 | Alquier |
| 2012/0186082 A1 | 7/2012 | Tardif |

FOREIGN PATENT DOCUMENTS

| | | |
|---|---|---|
| EP | 0273181 | 7/1988 |
| EP | 0586153 | 3/1994 |
| EP | 0789057 | 8/1997 |
| EP | 0818256 | 1/1998 |
| EP | 1108518 | 6/2001 |
| EP | 1193721 | 4/2002 |
| EP | 1935532 | 6/2008 |
| JP | 60259420 | 12/1985 |
| JP | 01077890 | 3/1989 |
| JP | 02099260 A2 | 4/1990 |
| JP | 02212112 | 8/1990 |
| JP | 08230049 | 9/1996 |
| JP | 08276438 | 10/1996 |
| JP | 10109313 | 4/1998 |
| JP | 2001-162658 | 6/2001 |
| JP | 2003252960 | 9/2003 |
| WO | WO02098624 | 12/2002 |
| WO | WO08059272 | 5/2008 |

OTHER PUBLICATIONS

Hexcel Corporation, "HexWeb Honeycomb Attributes and Properties", Nov. 1, 1999, 39 page(s), Hexcel Corporation.

Himmer, "Lamination of Metal Sheets", Jun. 1, 1999, Computers in Industry, Elsevier Science, V(39) No. 1.

Kessenikh, "Dependence of the Electrical Conductivity of an Epoxy Compound on Electric Field Intensity", Jan. 1, 1967, 3 page(s), Izvestiya VUZ, Fizika, Soviet Physics Journal, vol. 10, No, 11.

Misiolek, "Rapid Prototyping of Extrusion Dies Using Layer-Based Techniques", Feb. 1, 1999, Journal of Materials Engineering and Performance, V8(1).

Newport Corporation, "Image of Isolator with Protrusing Undercut—Faraday Optical Isolator, Free-Space", Jan. 1, 1996, 2 page(s), www.newport.com.

Padalino, "CAD/CAM Systems and Their Integration in Mold Design", Oct. 1, 1996, Plastics Engineering V(52) 10.

Walczyk, "Rapid Tooling for Sheet Metal Foaming Using Profiled Edge Laminations-Design Principles and Demonstration", Nov. 1, 1998, Transactions of American Society of Mechanical Engineers, Series B: Journal of Engineering for Industry, V(120), 4.

Week, "Fabrication of Microcomponents using Ultraprecision Machine Tools", Jan. 1, 1997, 4 page(s), Nanotechnology, No. 8, 1997. IOP Publishing Ltd.

(56) References Cited

OTHER PUBLICATIONS

Minco, "Investment Casting Product Data Sheet", before Sep. 8, 2008, 1 pages, Minco Inc.; Midway, TN.
Precision MetalSmiths, Inc,, "Ten Most Asked Questions About Investment Casting", before Sep. 25, 2008, Precision MetalSmiths, Cleveland, OH.
European Office Action for Application No. EP 09 737 7489; dated Aug. 17, 2015; 5 pages.
European Office Action for Application No. EP 12 19 1595; dated Jul. 6, 2017; 5 pages.
International Preliminary Report on Patentability International Application No. PCT/US2009/058220; International filed Sep. 24, 2009; dated Jul. 4, 2011; 12 pages.
International Search Report and Written Opinion of the International Searching Authority; International Application No. PCT/US2009/058220; International filed Sep. 24, 2009; dated Aug. 4, 2010; 21 pages.
European Office Action for Application No. EP 12 19 1595; dated Dec. 5, 2017.
European Office Action for Application No. EP 12 19 1597; dated Jan. 31, 2018.
European Office Action for Application No. EP 12 191 590; dated Dec. 5, 2017.
European Search Report for Application No. EP 12 19 1590; dated Aug. 8, 2016.
European Search Report for Application No. EP 12 19 1595; dated Aug. 8, 2016.
European Search Report for Application No. EP 12 19 1597; dated Aug. 8, 2016.

* cited by examiner

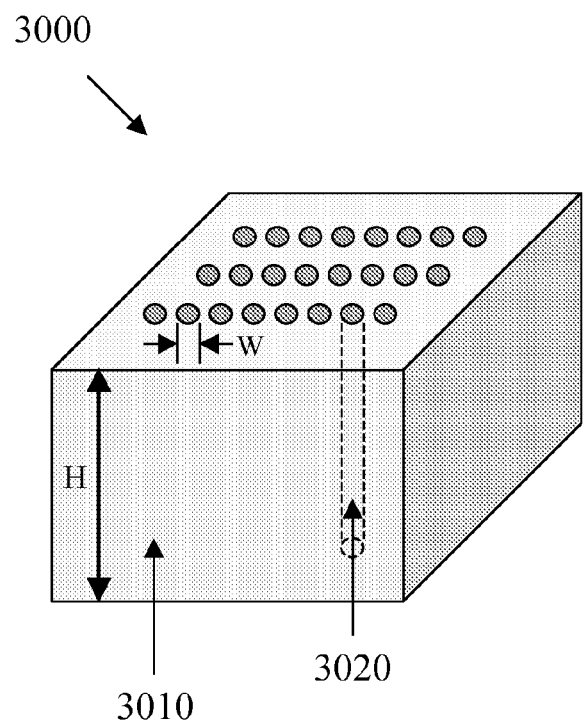
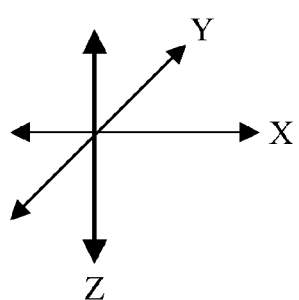
FIG. 3

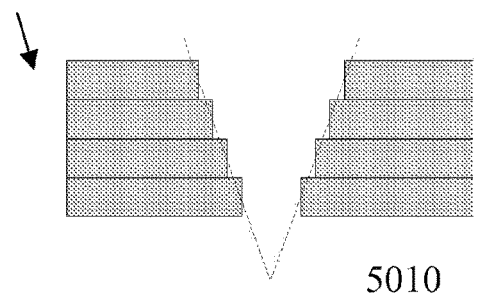
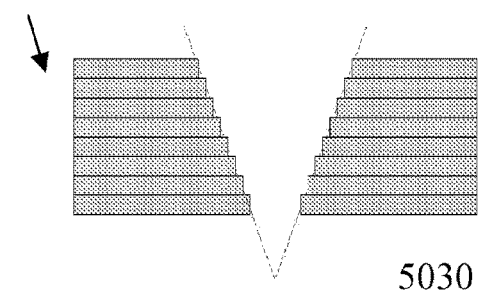
FIG. 5B          FIG. 5C
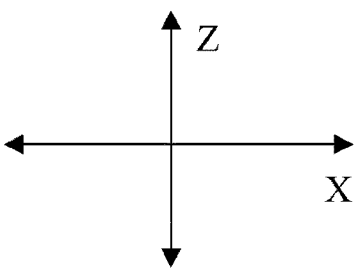
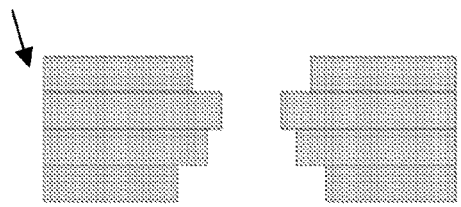
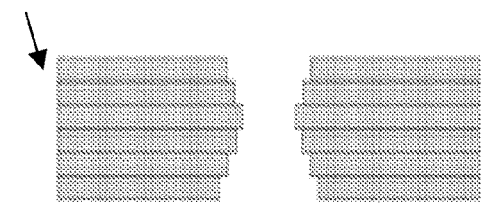
FIG. 5D          FIG. 5E

10010

10020

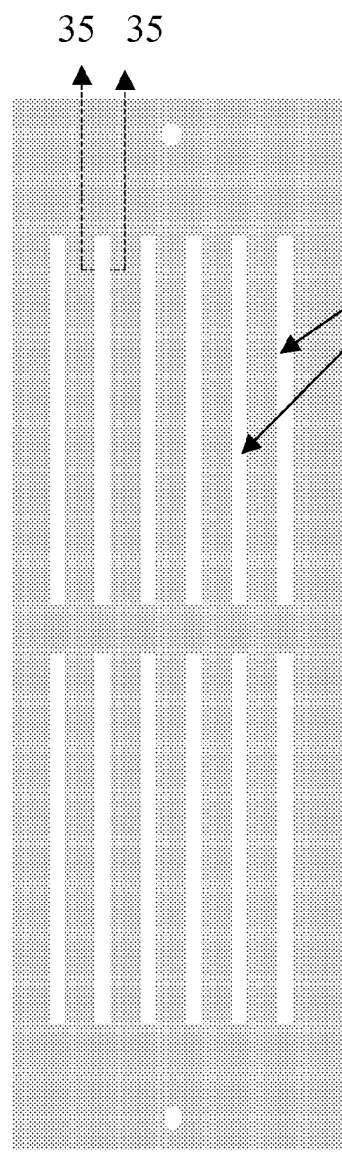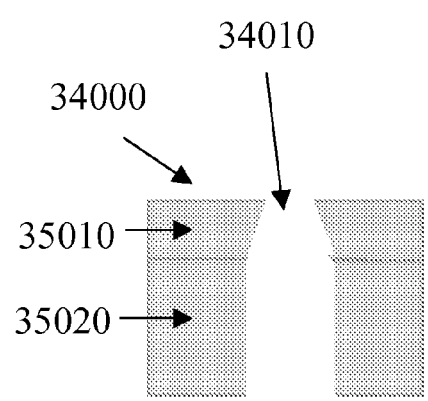
FIG. 34
FIG. 35

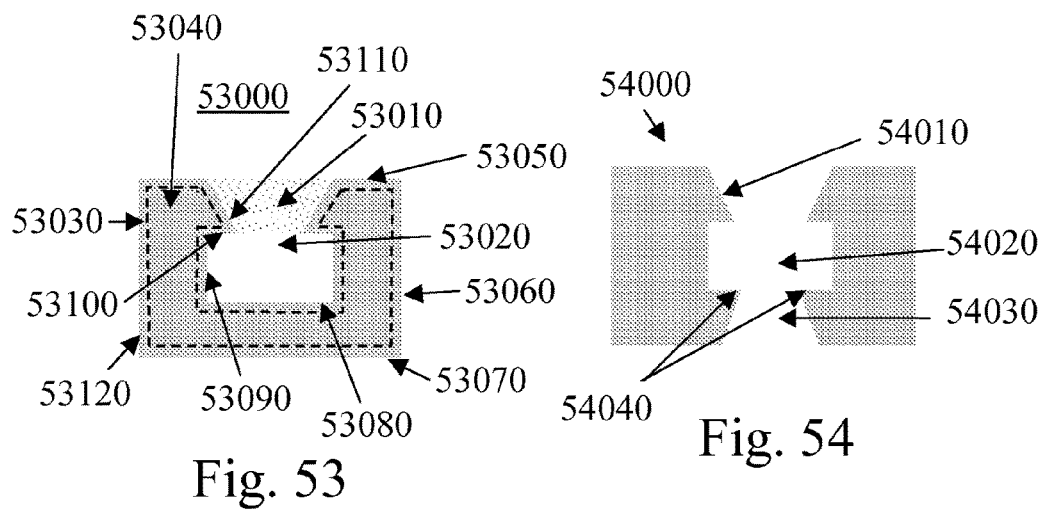
Fig. 53
Fig. 54
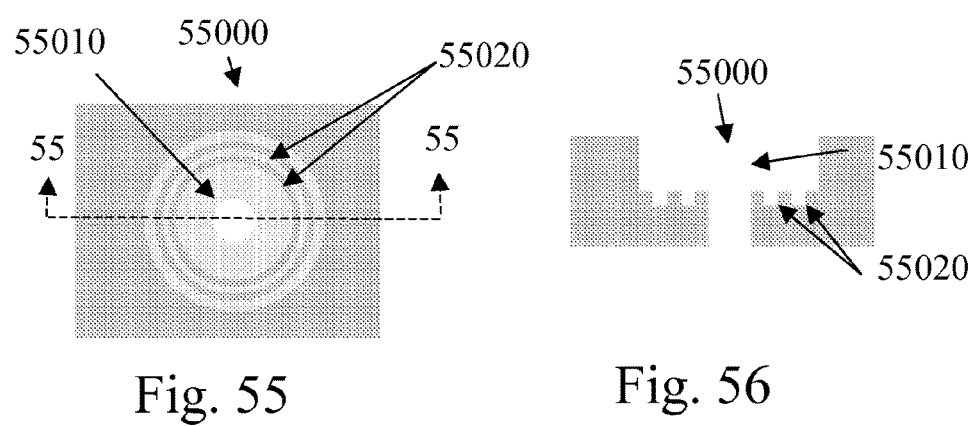
Fig. 55
Fig. 56

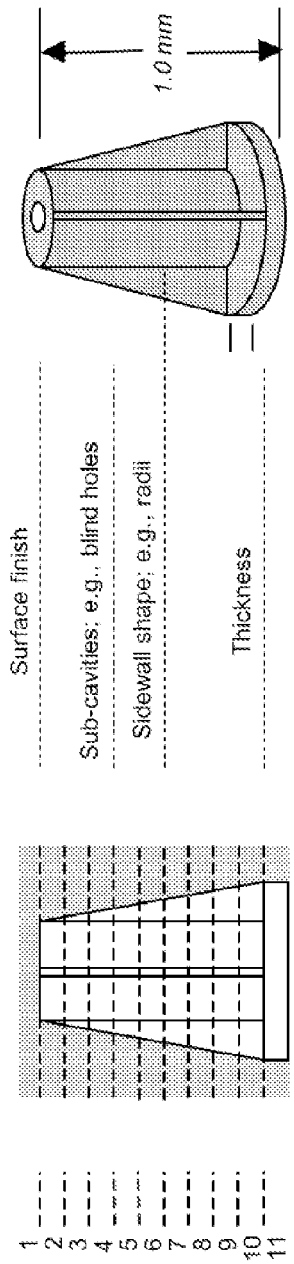
FIG. 57A
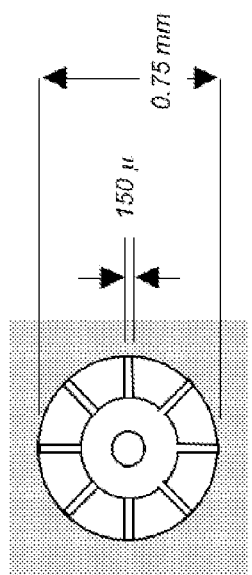
FIG. 57B
FIG. 57C

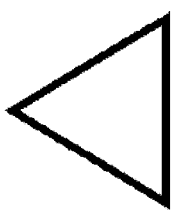
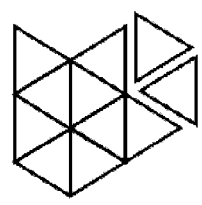
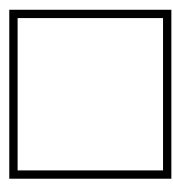
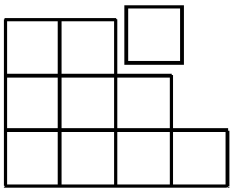
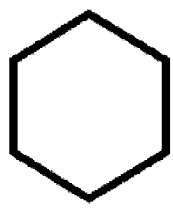
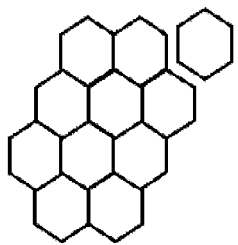
FIG. 70

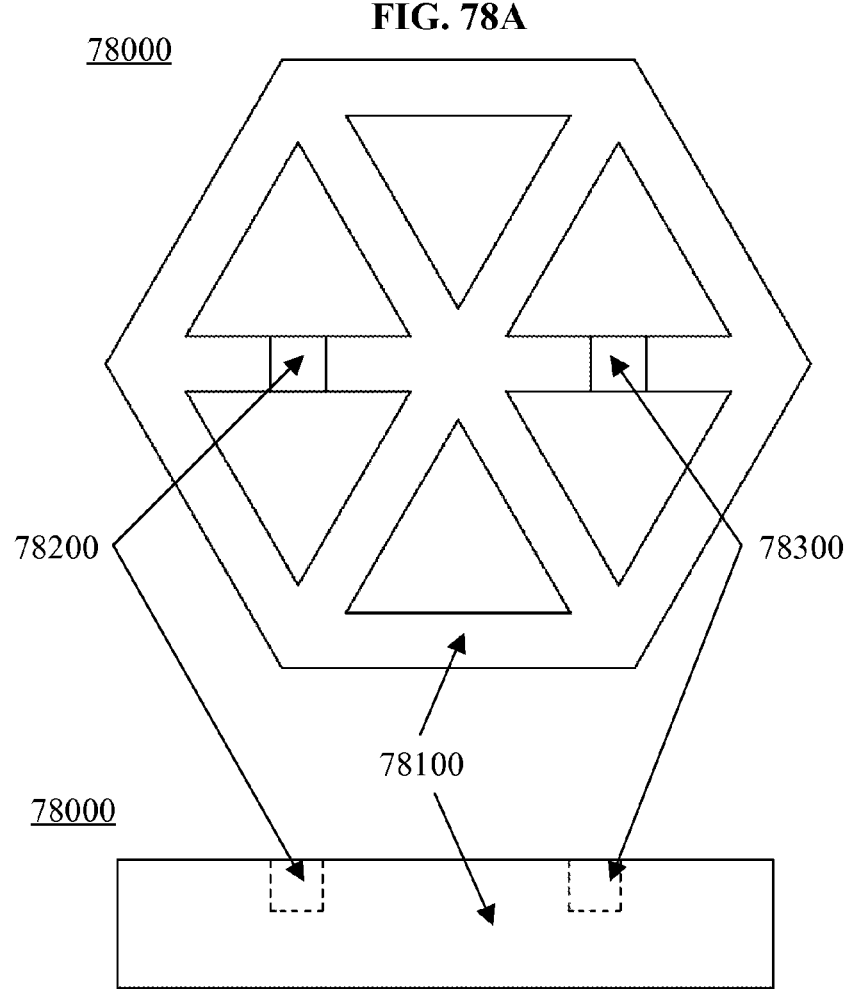

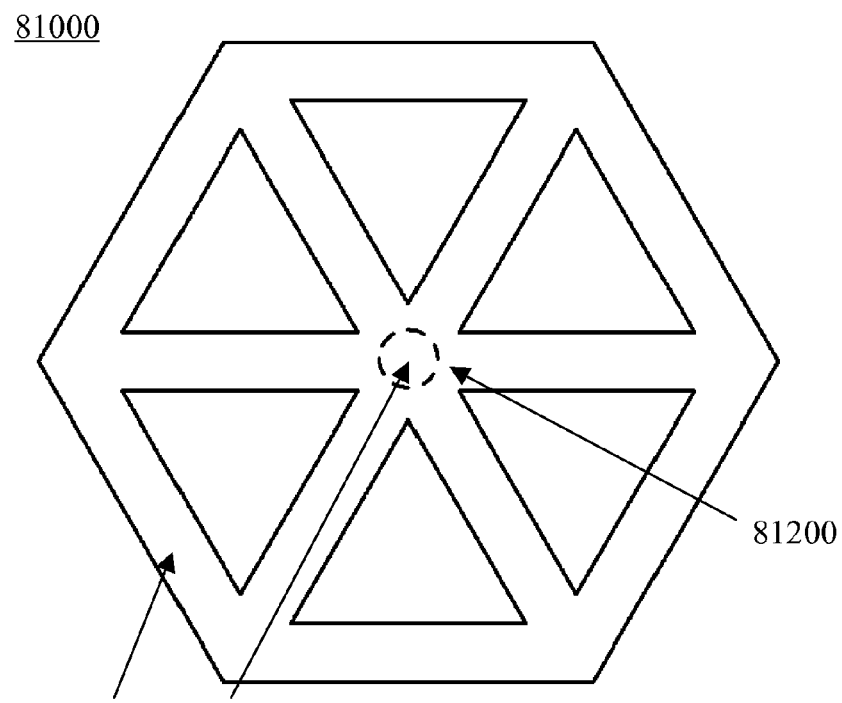
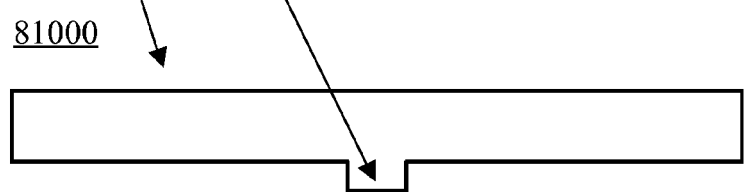
FIG. 81B

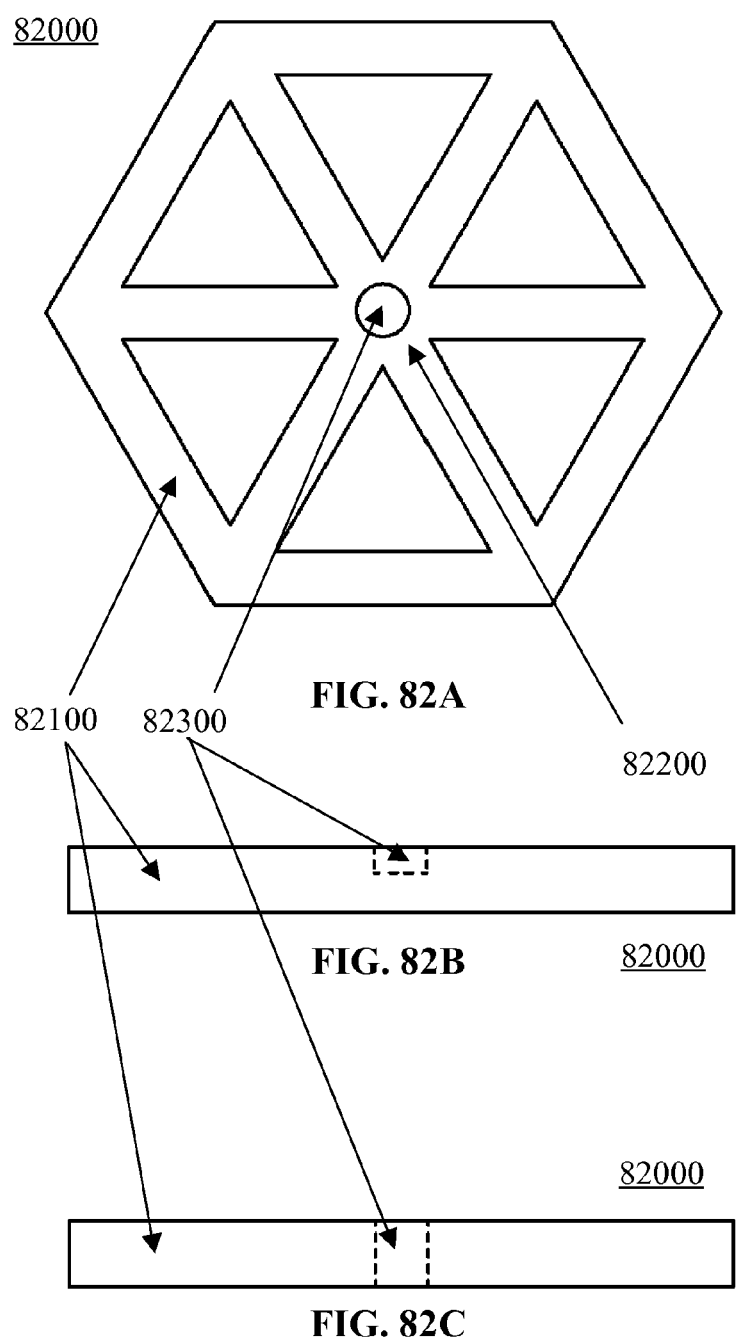

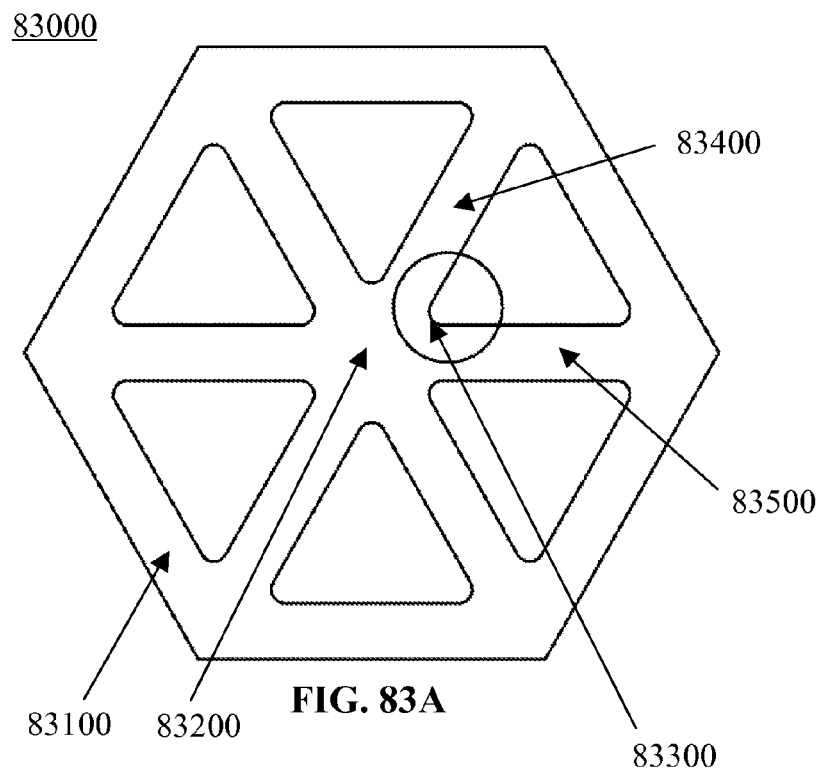
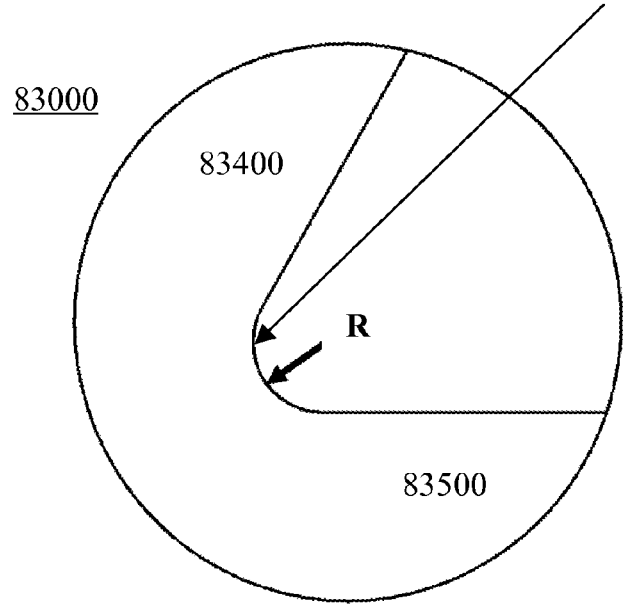

SYSTEMS, DEVICES, AND/OR METHODS FOR MANUFACTURING CASTINGS

CROSS-REFERENCES TO RELATED APPLICATIONS

This application claims priority to, and incorporates herein in its entirety, U.S. Provisional Patent Application Ser. No. 61/100,427, filed 26 Sep. 2008.

BRIEF DESCRIPTION OF THE DRAWINGS

A wide variety of potential practical and useful embodiments will be more readily understood through the following detailed description of certain exemplary embodiments, with reference to the accompanying exemplary drawings in which:

FIG. 3 is a perspective view of an exemplary casting that illustrates aspect ratio;

FIGS. 5B-5E are exemplary alternative cross-sectional views of an exemplary stack lamination mold taken at section lines 5-5 of FIG. 5A;

FIG. 34 is a top view of an exemplary micro-machined layer;

FIG. 35 is a cross-sectional view of a laminated slit taken along section lines 35-35 of FIG. 34;

FIG. 53 is a cross-sectional view taken at lines 52-52 of FIG. 52 of an exemplary microwell;

FIG. 54 is a cross-sectional view taken at lines 52-52 of FIG. 52 of an alternative exemplary microwell;

FIG. 55 is a top view of exemplary microwell;

FIG. 56 is a cross-sectional view of an exemplary microwell, taken at lines 55-55 of FIG. 55;

FIGS. 57A-C illustrate an exemplary embodiment of a microstructure derived from a finite element analysis (FEA) and formed via an exemplary method described herein;

FIG. 70 illustrates some exemplary embodiments of tessellation;

FIG. 78A is a top view of an exemplary embodiment of a system 78000 comprising an channeled isogrid;

FIG. 78B is a front view of an exemplary embodiment of the system 78000 of FIG. 78A;

FIG. 81A is a top view of an exemplary embodiment of a system 81000 comprising an isogrid stacking positioner;

FIG. 81B is a front view of an exemplary embodiment of system 81000 of FIG. 81A;

FIG. 82A is a top view of an exemplary embodiment of a system 82000 comprising an isogrid stacking positioner;

FIG. 82B is a front view of an exemplary embodiment of system 82000 of FIG. 82A;

FIG. 82C is a front view of an exemplary embodiment of system 82000 of FIG. 82A;

FIG. 83A is a top view of an exemplary embodiment of a system 83000 comprising a fillet joining two ligaments at a node;

FIG. 83B is a front view of an exemplary embodiment of system 83000 of FIG. 83A;

FIG. 104 is a perspective view of an exemplary embodiment of a shaped cast part attached to an exemplary device not formed via a stack lamination mold;

FIG. 105 is a perspective view of an exemplary embodiment of a turbo-machine;

FIG. 106 is a schematic diagram of an exemplary embodiment of a turbo-machine, and FIG. 107 is a perspective view of an exemplary embodiment of a turbo-machine part.

DETAILED DESCRIPTION

Figure 1:
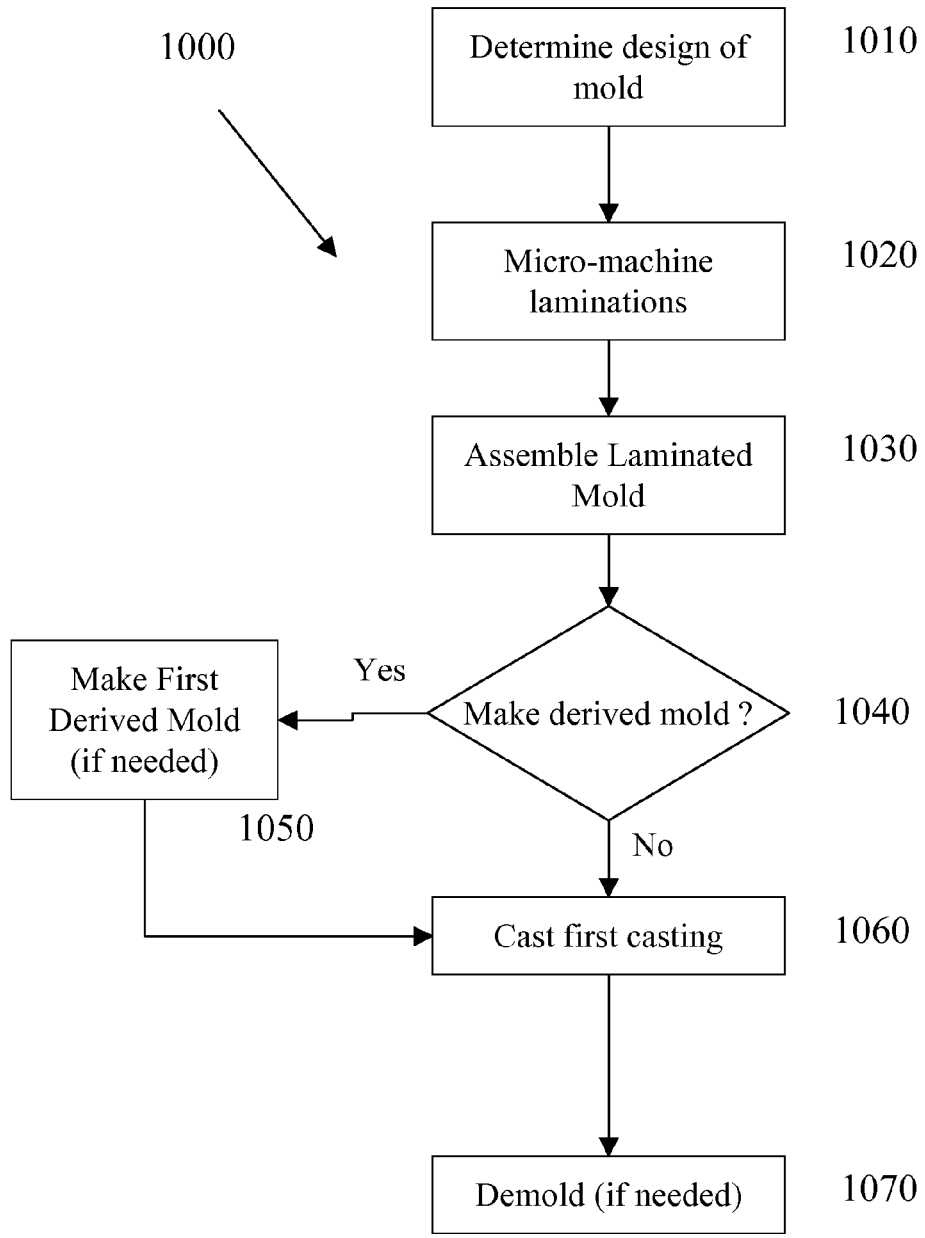
FIG. 1 is a flowchart of an exemplary method.

Certain exemplary embodiments can combine certain techniques of stack lamination with certain molding processes to manufacture a final product. As a result of the stack lamination techniques, precision micro-scale cavities of predetermined shapes can be engineered into the stack lamination. Rather than have the stack lamination embody the final product, however, the stack lamination can be used as an intermediate in a casting or molding process.

In certain exemplary embodiments, the stack lamination ("laminated mold") can be made up of layers comprising metallic, polymeric, and/or ceramic material. The mold can be a positive replication of a predetermined end product or a negative replication thereof. The mold can be filled with a first cast material and allowed to solidify. A first cast product can be demolded from the mold. The first cast material can comprise a flexible polymer such as silicone rubber.

Certain exemplary embodiments of a method can further include surrounding the first cast product with a second casting material and allowing the second cast material to solidify. Still further, a second cast product can be demolded from the first cast product.

Some exemplary embodiments can further include positioning an insert into the cavity prior to filling the mold with the first cast material, wherein the insert occupies only a portion of the space defined by the cavity. The second cast product can be nonplanar. The end product and/or the mold cavity can have an aspect ratio greater that 100:1. The end product can be attached to the substrate or it can be a free-standing structure.

In certain exemplary embodiments, the master mold can be fabricated using diverse micro-machining methods, which can allow hybrid integration of various disciplines. In certain exemplary embodiments, the master mold can be fabricated using high-precision lithographic techniques, which can allow production of accurate molds, castings, and features having virtually any shape.

In certain exemplary embodiments, layers for master mold fabrication can be produced by using low cost materials and low cost manufacturing methods such as photo-chemical machining. In certain exemplary embodiments, the layers used for master mold fabrication can have sub-cavities with controlled depths and shapes. These cavities can be used to produce integrated micro-features in cast objects.

In certain exemplary embodiments, the master molds can be produced over large areas. This allows the production of large batches of cast micro-devices or large macro devices with incorporated arrays of micro features. In certain exemplary embodiments, master molds and castings can be produced having extremely high-aspect ratios. Aspect ratio's greater than 400:1 can be achieved using photo-chemical machining combined with precision stack lamination.

In certain exemplary embodiments, hundreds to thousands of individual structures can be batch produced simultaneously, eliminating the need to produce 3D micro-structures one at a time. In certain exemplary embodiments, many diverse materials can be used to create advanced molds and/or cast devices. This can greatly enhance design and fabrication opportunities for low cost, application specific devices. Materials can include, but are not limited to, polymers, epoxy resins, polyesters, acrylics, ceramics, powder metals, castable metals, urethanes, silicon, and/or rubber etc. Materials can also be integrated for production of "smart" materials needed for fabricating advanced MEMS devices. Smart materials would include those having functional properties such as for example conductivity, electrostrictivity, piezoelectricity, magnetic, elastic, thermal, density, and/or chemical resistivity, etc.

In certain exemplary embodiments, the micro devices and/or structures can be produced as free form or attached structures. This can be achieved through molding and casting designs or through secondary machining techniques. In certain exemplary embodiments, micro devices can be produced outside of clean room facilities, thereby potentially lowering production overhead costs.

In certain exemplary embodiments, by using lithographic techniques for producing master molds and/or micro devices, arrays of devices or micro features can be accurately integrated and aligned with standard microelectronics. In certain exemplary embodiments, through the fabrication method used for producing the master molds, highly accurate, three dimensional engineering and production of micro scale devices can be possible. In certain exemplary embodiments, through the use of flexible molds, highly accurate, three dimensional engineering and production of non-planar, micro scale devices is possible. Non-planar shapes can include, but are not limited to, curves, arcs, diameters, spherical radii, inside and outside diameters of cylinders, etc.

FIG. 1 is a flowchart of an exemplary embodiment of a method 1000. At activity 1010, a mold design is determined. At activity 1020, the layers of the mold ("laminations") are fabricated. At activity 1030, the laminations are stacked and assembled into a mold (a derived mold could be produced at this point as shown in FIG. 1). At activity 1060, a first casting is cast. At activity 1070, the first casting is demolded.

Figure 2:
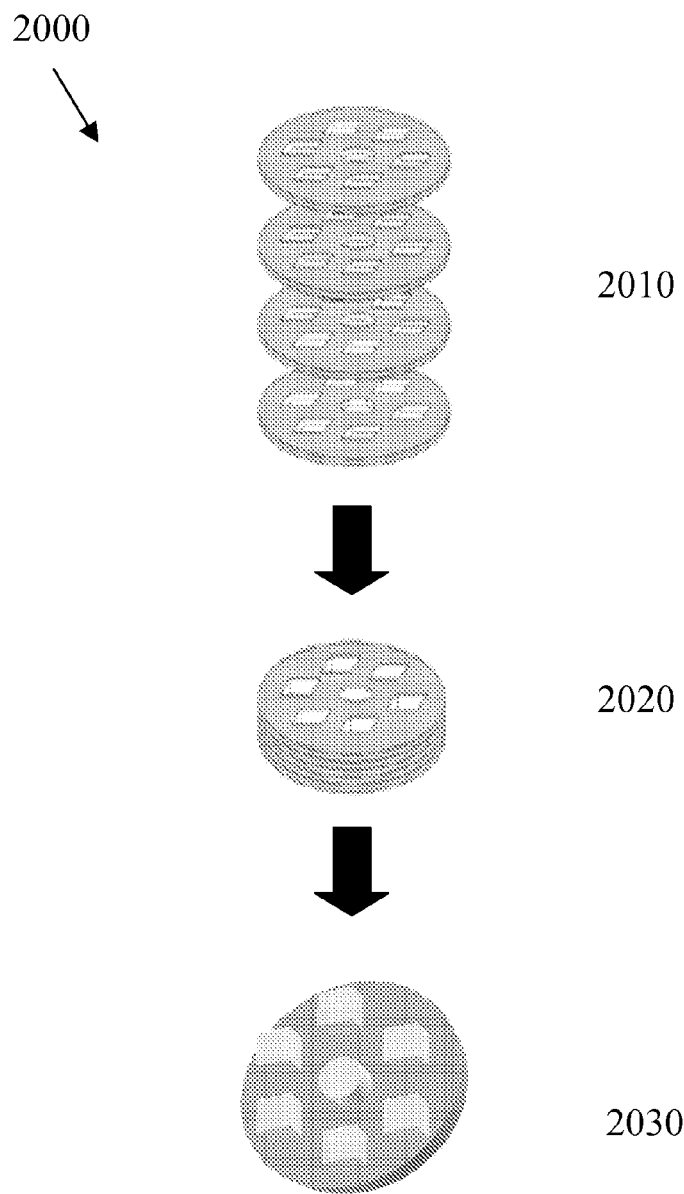
FIG. 2 is a flow diagram of exemplary items fabricated using an exemplary method.

FIG. 2 is a flow diagram of exemplary items fabricated during a method 2000. Layers 2010 can be stacked to form a mold or stacked lamination 2020. A molding or casting material can be applied to mold 2020 to create a molding or casting 2030, that can be demolded from mold 2020.

FIG. 3 is a perspective view of an exemplary molding 3000 that demonstrates a parameter referred to herein as "aspect ratio" which is described below. Molded block 3010 has numerous through-holes 3020, each having a height H and a diameter or width W. For the purposes of this application, aspect ratio is defined as the ratio of height to width or H/W of a feature, and can apply to any "negative" structural feature, such as a space, channel, through-hole, cavity, etc., and can apply to a "positive" feature, such as a wall, projection, protrusion, etc., with the height of the feature measured along the Z-axis. Note that all features can be "bordered" by at least one "wall". For a positive feature, the wall is part of the feature. For a negative feature, the wall at least partially defines the feature.

FIG. 3 also demonstrates the X-, Y-, and Z-directions or axes. For the purposes of this application, the dimensions measured in the X- and Y-directions define a top surface of a structure (such as a layer, a stack lamination mold, or negative and/or positive replications thereof) when viewed from the top of the structure. The Z-direction is the third dimension perpendicular to the X-Y plane, and corresponds to the line of sight when viewing a point on a top surface of a structure from directly above that point.

Certain embodiments of a method can control aspect ratios for some or all features in a laminated mold, derived mold, and/or cast item (casting). The ability to attain relatively high aspect ratios can be affected by a feature's geometric shape, size, material, and/or proximity to another feature. This ability can be enhanced using certain embodiments. For example, through-features of a mold, derived mold, and/or final part, having a width or diameter of approximately 5 microns, can have a dimension along the Z axis (height) of approximately 100 microns, or approximately 500 microns or any value in the range there between (implying an aspect ratio of approximately 20:1, 100:1, or any value in the range therebetween, including, for example:

20:1 to 30:1, 20:1 to 40:1, 20:1 to 50:1, 20:1 to 60:1, 20:1 to 70:1, 20:1 to 80:1, 20:1 to 90:1, 20:1 to 100:1,

30:1 to 40:1, 30:1 to 50:1, 30:1 to 60:1, 30:1 to 70:1, 30:1 to 80:1, 30:1 to 90:1, 30:1 to 100:1,

40:1 to 50:1, 40:1 to 60:1, 40:1 to 70:1, 40:1 to 80:1, 40:1 to 90:1, 40:1 to 100:1,

50:1 to 60:1, 50:1 to 70:1, 50:1 to 80:1, 50:1 to 90:1, 50:1 to 100:1,

60:1 to 70:1, 60:1 to 80:1, 60:1 to 90:1, 60:1 to 100:1,

70:1 to 80:1, 70:1 to 90:1, 70:1 to 100:1,

80:1 to 90:1, 80:1 to 100:1, etc).

As another example, a through slit having a width of approximately 20 microns can have a height of approximately 800 microns, or approximately 1600 microns, or any value in the range therebetween (implying an aspect ratio of approximately 40:1, 80:1, or any value in the range therebetween, including, for example:

40:1 to 50:1, 40:1 to 60:1, 40:1 to 70:1, 40:1 to 80:1,

50:1 to 60:1, 50:1 to 70:1, 50:1 to 80:1,

60:1 to 70:1, 60:1 to 80:1,

70:1 to 80:1, etc).

As yet another example, the same approximately 20 micron slit can be separated by an approximately 15 micron wide wall in an array, where the wall can have a dimension along the Z axis (height) of approximately 800 microns, or approximately 1600 microns, or any value in the range therebetween (implying an aspect ratio of approximately 53:1, 114:1, or any value in the range therebetween, including, for example:

53:1 to 60:1, 53:1 to 70:1, 53:1 to 80:1, 53:1 to 90:1, 53:1 to 100:1, 53:1 to 110:1, 53:1 to 114:1,

60:1 to 70:1, 60:1 to 80:1, 60:1 to 90:1, 60:1 to 100:1, 60:1 to 110:1, 60:1 to 114:1,

70:1 to 80:1, 70:1 to 90:1, 70:1 to 100:1, 70:1 to 110:1, 70:1 to 114:1,

80:1 to 90:1, 80:1 to 100:1, 90:1 to 110:1, 90:1 to 114:1,

90:1 to 100:1, 90:1 to 110:1, 90:1 to 114:1,

100:1 to 110:1, 100:1 to 114:1, etc.).

Still another example is an array of square-shaped openings having sides that are approximately 0.850 millimeters wide, each opening separated by approximately 0.150 millimeter walls, with a dimension along the Z axis of approximately 30 centimeters. In this example the approximately 0.850 square openings have an aspect ratio of approximately 353:1, and the approximately 0.150 walls have an aspect ratio of approximately 2000:1, with lesser aspect ratios possible. Thus, the aspect ratio of the openings can be approximately 10:1, or approximately 350:1, or any value in the range therebetween, including for example:

10:1 to 20:1, 10:1 to 30:1, 10:1 to 40:1, 10:1 to 50:1, 10:1 to 60:1, 10:1 to 70:1, 10:1 to 80:1, 10:1 to 90:1, 10:1 to 100:1, 10:1 to 150:1, 10:1 to 200:1, 10:1 to 250:1, 10:1 to 300:1, 10:1 to 350:1,

20:1 to 30:1, 20:1 to 40:1, 20:1 to 50:1, 20:1 to 60:1, 20:1 to 70:1, 20:1 to 80:1, 20:1 to 90:1, 20:1 to 100:1, 20:1 to 150:1, 20:1 to 200:1, 20:1 to 250:1, 20:1 to 300:1, 20:1 to 350:1,

30:1 to 40:1, 30:1 to 50:1, 30:1 to 60:1, 30:1 to 70:1, 30:1 to 80:1, 30:1 to 90:1, 30:1 to 100:1, 30:1 to 150:1, 30:1 to 200:1, 30:1 to 250:1, 30:1 to 300:1, 30:1 to 350:1,

40:1 to 50:1, 40:1 to 60:1, 40:1 to 70:1, 40:1 to 80:1, 40:1 to 90:1, 40:1 to 100:1, 40:1 to 150:1, 40:1 to 200:1, 40:1 to 250:1, 40:1 to 300:1, 40:1 to 350:1,

50:1 to 60:1, 50:1 to 70:1, 50:1 to 80:1, 50:1 to 90:1, 50:1 to 100:1, 50:1 to 150:1, 50:1 to 200:1, 50:1 to 250:1, 50:1 to 300:1, 50:1 to 350:1,

75:1 to 80:1, 75:1 to 90:1, 75:1 to 100:1, 75:1 to 150:1, 75:1 to 200:1, 75:1 to 250:1, 75:1 to 300:1, 75:1 to 350:1,

100:1 to 150:1, 100:1 to 200:1, 100:1 to 250:1, 100:1 to 300:1, 100:1 to 350:1,

150:1 to 200:1, 150:1 to 250:1, 150:1 to 300:1, 150:1 to 350:1,

200:1 to 250:1, 200:1 to 300:1, 200:1 to 350:1,

250:1 to 300:1, 250:1 to 350:1,

300:1 to 350:1, etc.

Moreover, the aspect ratio of the walls can be approximately 10:1, or approximately 2000:1, or any value in the range therebetween, including for example:

10:1 to 20:1, 10:1 to 30:1, 10:1 to 40:1, 10:1 to 50:1, 10:1 to 100:1, 10:1 to 200:1, 10:1 to 500:1, 10:1 to 1000:1, 10:1 to 2000:1,

20:1 to 30:1, 20:1 to 40:1, 20:1 to 50:1, 20:1 to 100:1, 20:1 to 200:1, 20:1 to 500:1, 20:1 to 1000:1, 20:1 to 2000:1,

30:1 to 40:1, 30:1 to 50:1, 30:1 to 100:1, 30:1 to 200:1, 30:1 to 500:1, 30:1 to 1000:1, 30:1 to 2000:1,

40:1 to 50:1, 40:1 to 100:1, 40:1 to 200:1, 40:1 to 500:1, 40:1 to 1000:1, 40:1 to 2000:1,

50:1 to 100:1, 50:1 to 200:1, 50:1 to 500:1, 50:1 to 1000:1, 50:1 to 2000:1, 100:1 to 200:1, 100:1 to 500:1, 100:1 to 1000:1, 100:1 to 2000:1,

200:1 to 500:1, 200:1 to 1000:1, 200:1 to 2000:1,

500:1 to 1000:1, 500:1 to 2000:1,

1000:1 to 2000:1, etc.

Another example of aspect ratio is the space between solid (positive) features of a mold, derived mold, and/or casting. For example, as viewed from the top, a casting can have two or more solid rectangles measuring approximately 50 microns wide by approximately 100 microns deep with an approximately 5 micron space therebetween (either width-wise or depth-wise). The rectangles can have a height of 100 microns, or 500 microns, or any value in the range therebetween (implying an aspect ratio of 20:1, or 100:1, or any value therebetween, including, for example:

20:1 to 30:1, 20:1 to 40:1, 20:1 to 50:1, 20:1 to 60:1, 20:1 to 70:1, 20:1 to 80:1, 20:1 to 90:1, 20:1 to 100:1,

30:1 to 40:1, 30:1 to 50:1, 30:1 to 60:1, 30:1 to 70:1, 30:1 to 80:1, 30:1 to 90:1, 30:1 to 100:1,

40:1 to 50:1, 40:1 to 60:1, 40:1 to 70:1, 40:1 to 80:1, 40:1 to 90:1, 40:1 to 100:1,

50:1 to 60:1, 50:1 to 70:1, 50:1 to 80:1, 50:1 to 90:1, 50:1 to 100:1,

60:1 to 70:1, 60:1 to 80:1, 60:1 to 90:1, 60:1 to 100:1,

70:1 to 80:1, 70:1 to 90:1, 70:1 to 100:1,

80:1 to 90:1, 80:1 to 100:1, etc).

In another example the same rectangles can have a space there between of approximately 20 microns, and the rectangles can have dimensions along the Z axis of approximately 800 microns, or approximately 5000 microns, or any value therebetween (implying an aspect ratio of approximately 40:1, or 250:1, or any value therebetween, including, for example:

- 40:1 to 50:1, 40:1 to 75:1, 40:1 to 100:1, 40:1 to 150:1, 40:1 to 200:1, 40:1 to 250:1,
- 75:1 to 100:1, 75:1 to 150:1, 75:1 to 200:1, 75:1 to 250:1,
- 100:1 to 150:1, 100:1 to 200:1, 100:1 to 250:1,
- 150:1 to 200:1, 150:1 to 250:1,
- 200:1 to 250:1, etc).

Figure 4:
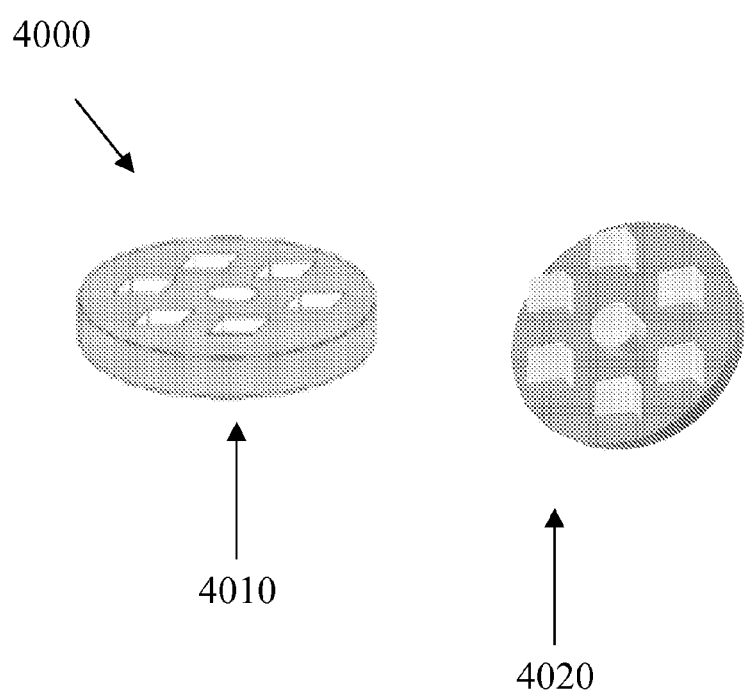
FIG. 4 is an assembly view of an exemplary assembly.

FIG. 4 is an assembly view of an exemplary assembly 4000 that includes mold 4010 and cast part 4020 formed from mold 4010. Because certain exemplary embodiments can utilize lithographically-derived micro-machining techniques (or in some cases, non-lithographically-derived micro-machining techniques, such as laser machining) combined with molding and/or casting, laminated molds can be conceived as negatives 4010 or positives 4020 of the desired end product. The terms "negative" or "positive" replications can be subjective terms assigned to different stages of reaching an end product. For certain embodiments, any intermediate or the end product can be considered a negative or positive replication depending on a subject's point of view. For the purpose of this application, a "positive" replication is an object (whether an intermediate or an end product) that geometrically resembles at least a portion of the spatial form of the end product. Conversely, a "negative" replication is a mold that geometrically defines at least a portion of the spatial form of the end product. The following parameters are described for the purpose of demonstrating some of the potential design parameters of certain embodiments of a method.

Layer Thickness

Figure 5A:
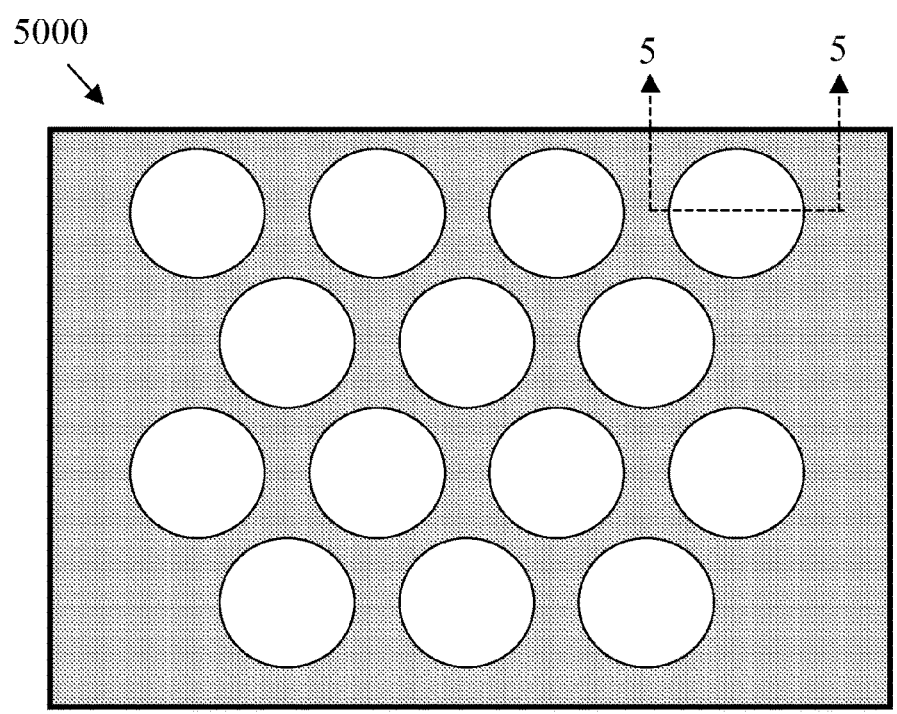
FIG. 5A is a top view of an exemplary stack lamination mold.

One design parameter can be the thickness of the micro-machined layers of the stack lamination mold. According to certain exemplary embodiments, to achieve high-aspect ratios, multiple micro-machined foils or layers can be stacked in succession and bonded together. In certain exemplary embodiments, the layer thickness can have a dimensional role in creating the desired shape in the third dimension. FIG. 5A is a top view of an exemplary stack lamination mold 5000. FIGS. 5B-5E are exemplary alternative cross-sectional views of exemplary stack lamination mold 5000 taken at section lines 5-5 of FIG. 5A. As shown in FIG. 5B and FIG. 5D, respectively, stacks 5010 and 5020 utilize relatively thick layers. As shown in FIG. 5C and FIG. 5E, respectively, stacks 5030 and 5040 utilize relatively thinner layers in succession to smooth out resolution along the z-axis. Specific layers can have multiple functions that can be achieved through their thickness or other incorporated features described herein.

Cross-Sectional Shape of Layer

Figure 6:
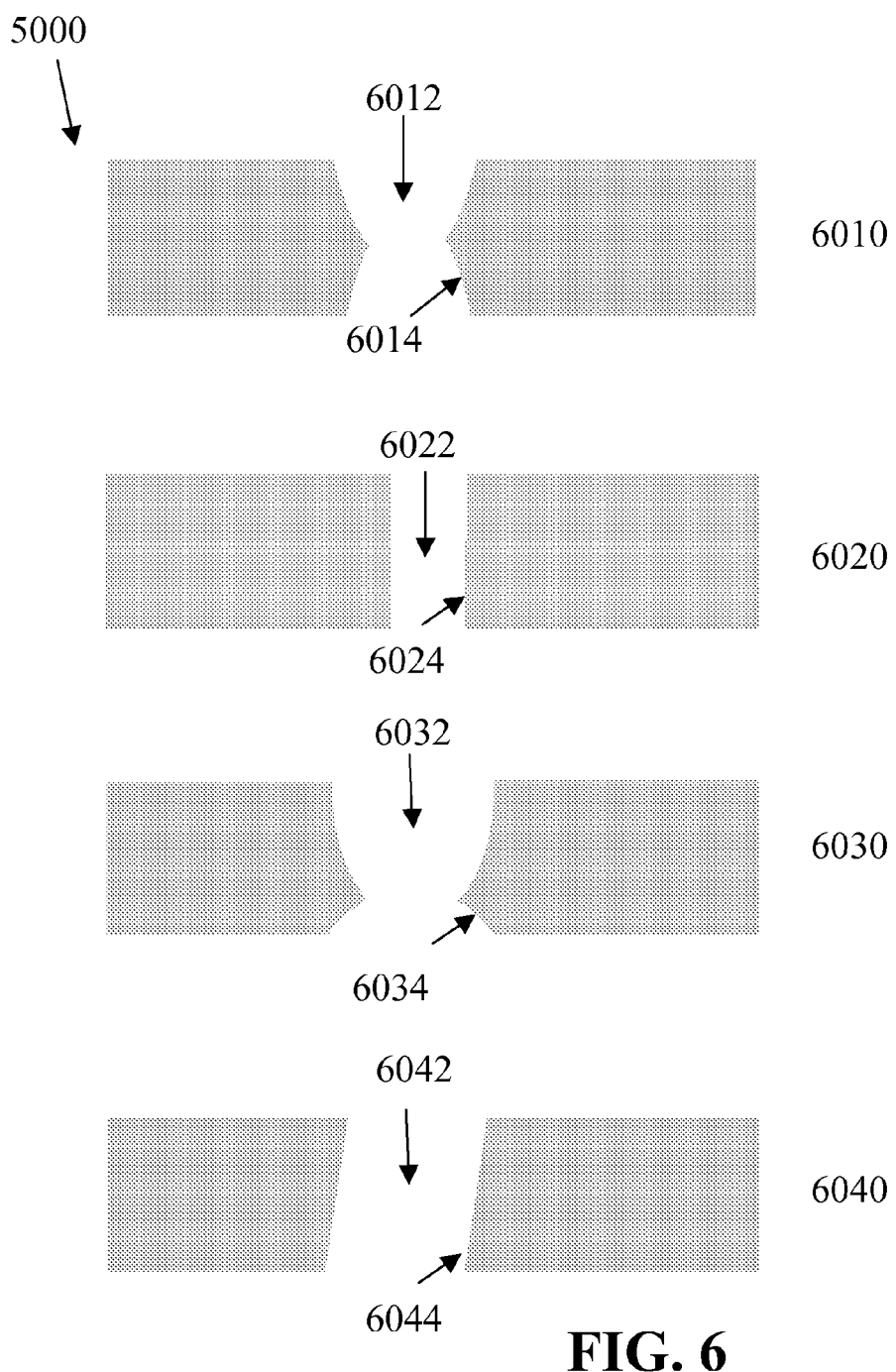
FIG. 6 is an unassembled cross-sectional view of an alternative exemplary stack lamination mold taken at section lines 5-5 of FIG. 5A.

One design parameter can be the cross sectional shape of a given layer in the mold. Through the use of etching and/or deposition techniques, many cross sectional shapes can be obtained. FIG. 6 is an unassembled cross-sectional view of an alternative exemplary stack lamination mold 5000 taken at section lines 5-5 of FIG. 5A. Each of exemplary layers 6010, 6020, 6030, and 6040 of FIG. 6 define an exemplary through-feature 6012, 6022, 6032, 6042, respectively, each having a different shape, orientation, and/or configuration. These through-features 6012, 6022, 6032, 6042 are bordered by one or more "sidewalls" 6014, 6024, 6034, and 6044, respectively, as they are commonly referred to in the field of lithographic micro-machining.

Etching disciplines that can be utilized for a layer of the mold can be broadly categorized as isotropic (non-linear) or anisotropic (linear), depending on the shape of the remaining sidewalls. Isotropic often refers to those techniques that produce one or more radial or hour glassed shaped sidewalls, such as those shown in layer 6010. Anisotropic techniques produce one or more sidewalls that are more vertically straight, such as those shown in layer 6020.

Additionally, the shape of a feature that can be etched through a foil of the mold can be controlled by the depth of etching on each surface and/or the configuration of the photo-mask. In the case of photo-chemical-machining, a term such as 90/10 etching is typically used to describe the practice of etching 90% through the foil thickness, from one side of the foil, and finishing the etching through the remaining 10% from the other side, such as shown on layer 6030. Other etch ratios can be obtained, such as 80/20, 70/30, and/or 65/35, etc., for various foils and/or various features on a given foil.

Also, the practice of displacing the positional alignment of features from the top mask to the bottom mask can be used to alter the sidewall conditions for a layer of the mold, such as shown in layer 6040.

Figure 7:
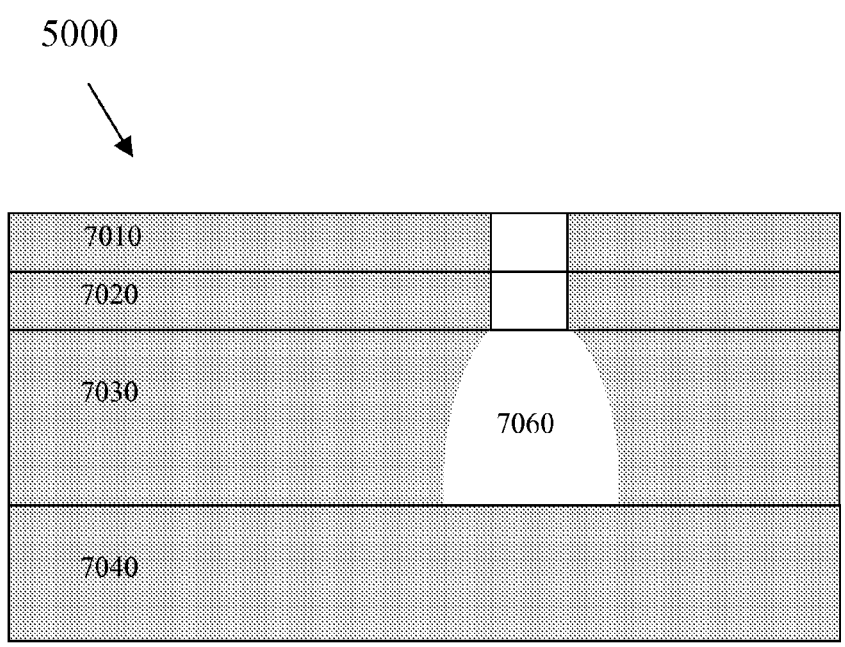
FIG. 7 is a cross-sectional view of an exemplary alternative stack lamination mold taken at section lines 5-5 of FIG. 5A.

By using these and/or other specific conditions as design parameters, layers can be placed to contribute to the net shape of the 3-dimensional structure, and/or provide specific function to that region of the device. For example, an hourglass sidewall could be used as a fluid channel and/or to provide structural features to the device. FIG. 7 is a cross-sectional view of an alternative exemplary stack lamination mold taken at section line 5-5 of FIG. 5A. FIG. 7 shows a laminated mold 5000 having layers 7010, 7020, 7030, 7040 that define cavity 7060. To achieve this, layers 7010, 7020 are etched anisotropically to have straight sidewalls, while layer 7030 is thicker than the other layers and is etched isotropically to form the complex shaped cross-section shown.

Cross-Sectional Surface Condition of Layer

Figure 8:
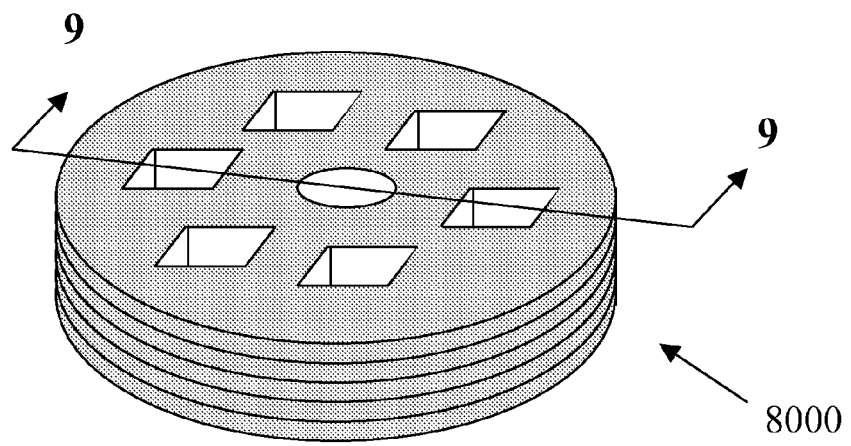
FIG. 8 is a perspective view of an exemplary laminated mold.
Figure 9:
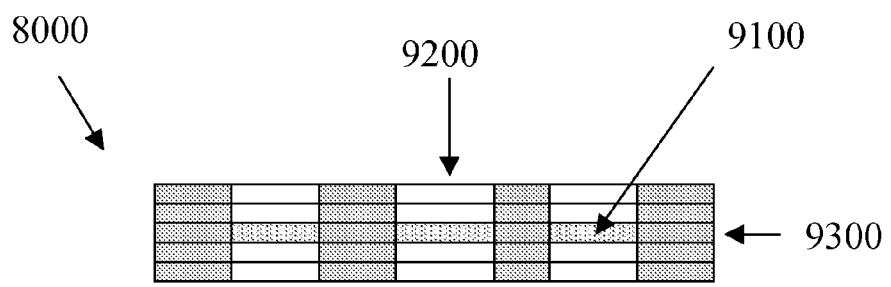
FIG. 9 is a cross-section of an exemplary mold taken along lines 9-9 of FIG. 8.

Another design parameter when creating advanced three-dimensional structures can be the cross-sectional surface condition of the layers used to create a laminated mold. As is the case with sidewall shape, surface condition can be used to provide additional function to a structure or a particular region of the structure. FIG. 8 is a perspective view of a generic laminated mold 8000. FIG. 9 is a cross-section of mold 8000 taken at lines 9-9 of FIG. 8. Any sidewall surface, top or bottom surface can be created with one or more specific finish conditions on all layers or on selected layers, such as for example, forming a relatively rough surface on at least a portion of a sidewall 9100 of certain through-features 9200 of layer 9300. As another example, chemical and/or ion etching can be used to produce very smooth, polished surfaces through the use of selected materials and/or processing techniques. Similarly, these etching methods can also be manipulated to produce very rough surfaces.

Secondary techniques, such as electro-plating and/or passive chemical treatments can also be applied to micromachined surfaces (such as a layer of the mold) to alter the finish. Certain secondary techniques (for example, lapping or superfinishing) can also be applied to non-micromachined surfaces, such as the top or bottom surfaces of a layer. In any event, using standard profile measuring techniques, described as "roughness average" ($R_a$) or "arithmetic average" (AA), the following approximate ranges for surface finish (or surface conditions) are attainable using micromachining and/or one or more secondary techniques according to certain embodiments (units in microns):

- 50 to any of: 25, 12.5, 6.3, 3.2, 1.6, 0.80, 0.40, 0.20, 0.10, 0.050, 0.025,
- 25 to any of: 12.5, 6.3, 3.2, 1.6, 0.80, 0.40, 0.20, 0.10, 0.050, 0.025,
- 12.5 to any of: 6.3, 3.2, 1.6, 0.80, 0.40, 0.20, 0.10, 0.050, 0.025,
- 6.3 to any of: 3.2, 1.6, 0.80, 0.40, 0.20, 0.10, 0.050, 0.025,
- 3.2 to any of: 1.6, 0.80, 0.40, 0.20, 0.10, 0.050, 0.025,
- 1.6 to any of: 0.80, 0.40, 0.20, 0.10, 0.050, 0.025,
- 0.80 to any of: 0.40, 0.20, 0.10, 0.050, 0.025,
- 0.40 to any of: 0.20, 0.10, 0.050, 0.025,
- 0.20 to any of: 0.10, 0.050, 0.025,
- 0.10 to any of: 0.050, 0.025,
- 0.050 to any of: 0.025, etc.

Additional Layer Features

Figure 10A:
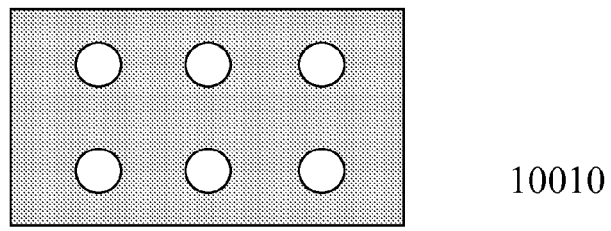
FIG. 10A is a top view an exemplary layer having a redundant array of shapes.
Figure 10B:
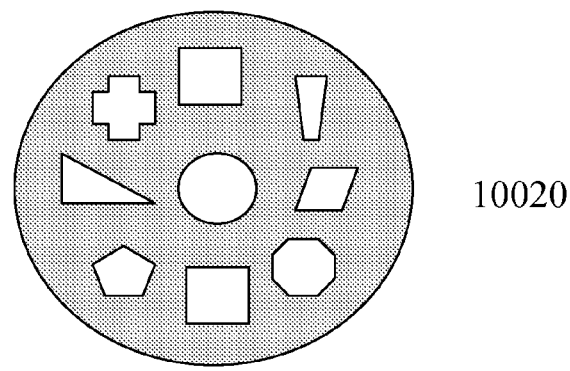
FIG. 10B is a top view of an exemplary layer having a non-redundant collection of shapes.

Certain exemplary embodiments can include layer features that can be created through the use of lithographic etching and/or deposition. These embodiments can include the size, shape, and/or positional orientation of features relative to the X- and/or Y-axes of a layer and/or their relationship to features on neighboring layers along the Z-axis of the assembled laminated mold. These parameters can define certain geometric aspects of the structure. For example, FIG. 10A is a top view of a layer 10010 having a pattern of repeating features (a redundant array of shapes), and FIG. 10B is a top view of a layer 10020 having a variety of differently shaped features (a non-redundant collection of shapes). Although not shown, a layer can have both redundant and non-redundant features. The terms "redundant" and/or "non-redundant" can refer to either positive or negative features.

Thus, these parameters also can define the shapes and/or spatial forms of features, the number of features in a given area, secondary structures and/or spaces incorporated on or around a feature, and/or the spaces between features. The control of spacing between features can provide additional functionality and, for instance, allow integration of devices with micro-electronics. For example, conductive micro features could be arrayed (redundantly or non-redundantly) to align accurately with application specific integrated circuits (ASIC) to control features. Also, features could be arrayed for applications where non-linear spacing between features could enhance device functionality. For example, filtration elements could be arrayed in such a way as to match the flow and pressure profile of a fluid passing over or through a filtration media. The spacing of the filtration elements could be arrayed to compensate for the non-linear movement of the fluid.

Cavity Definition Using Lithography

A cavity formed in accordance with certain exemplary embodiments can assume a shape and/or spatial form that includes one or more predetermined "protruding undercuts". Imaginably rotating the X-Y plane about its origin to any particular fixed orientation, a cavity is defined as having a "protruding undercut" when a first section of the cavity taken perpendicular to the Z-axis (i.e., parallel to the X-Y plane) has a predetermined dimension in the X- and/or Y-direction greater than the corresponding dimension in the X- and/or Y-direction of a second section of the cavity taken perpendicular to the Z-axis, the second section further along in the direction of eventual demolding of a cast part relative to the mold (assuming the demolding operation involves pulling the cast part free from the mold). That is, the X-dimension of the first section is intentionally greater than the X-dimension of the second section by a predetermined amount, or the Y-dimension of the first section is intentionally greater than the Y-dimension of the second section by a predetermined amount, or both. In still other words, for the purposes of this patent application, the term protruding undercut has a directional component to its definition.

Figure 11:
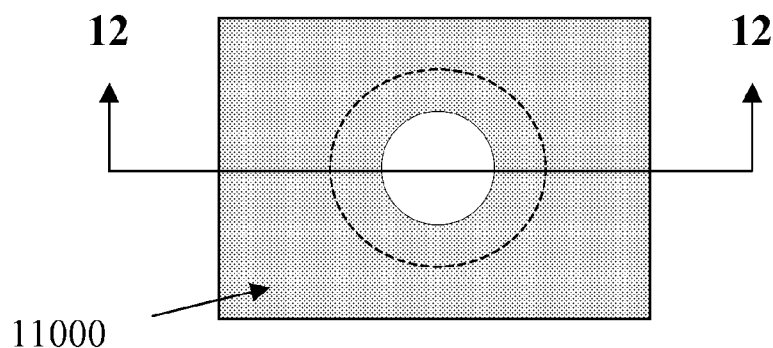
FIG. 11 is a top view of an exemplary stacked lamination mold.
Figure 12:
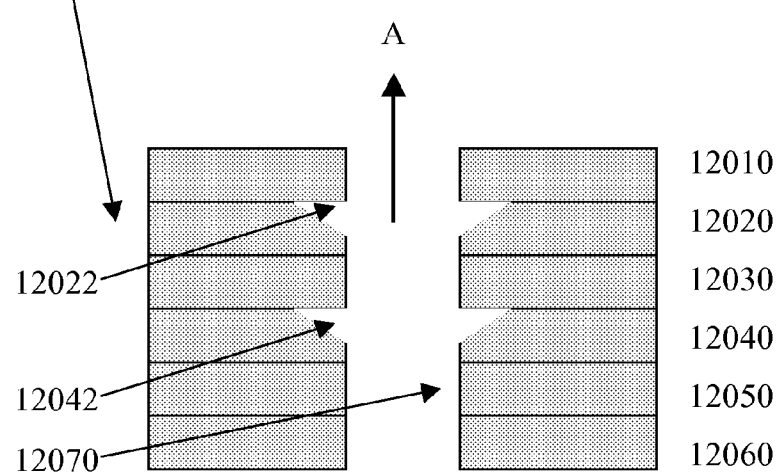
FIG. 12 is a cross-sectional view of an exemplary mold taken at section lines 12-12 of FIG. 11.
Figure 13:
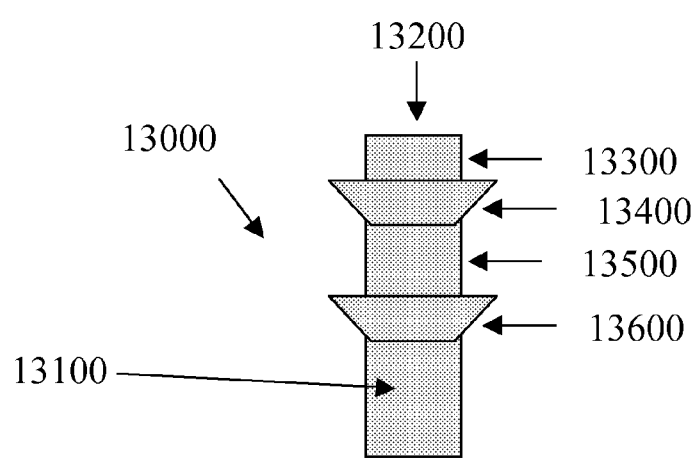
FIG. 13 is a side view of an exemplary cast part formed using the exemplary mold of FIG. 11.

FIG. 11 is a top view of an exemplary stacked laminated mold 11000. FIG. 12 is a cross-sectional view of a mold 11000 taken at section lines 12-12 of FIG. 11, and showing the layers 12010-12060 of mold 11000 that cooperatively define a cavity having protruding undercuts 12022 and 12042. Direction A is the relative direction in which a part cast using mold 11000 will be demolded, and/or pulled away, from mold 11000. FIG. 12 also shows that certain layers 12020, 12040 of mold 11000 have been formed by controlled depth etching. As shown in FIG. 12, mold 11000 defines an internal mold surface 12070, which is defined in part by protruding undercuts 12022 and 12042. FIG. 13 is a side view of a cast part 13000 formed using mold 11000. As shown in FIG. 13, cast part 13000 defines an external part periphery or surface 13100, which is defined in part by 3-dimensional micro-features 13400 and 13600 that substantially spatially invertedly replicate protruding undercuts 12022 and 12042.

To make layers for certain embodiments of a laminated mold, such as layers 2010 of FIG. 2, a photo-sensitive resist material coating (not shown) can be applied to one or more of the major surfaces (i.e., either of the relatively large planar "top" or "bottom" surfaces) of a micro-machining blank. After the blank has been provided with a photo-resist material coating on its surfaces, "mask tools" or "negatives" or "negative masks", containing a negative image of the desired pattern of openings and registration features to be etched in the blank, can be applied in alignment with each other and in intimate contact with the surfaces of the blank (photo-resist materials are also available for positive patterns). The mask tools or negatives can be made from glass, which has a relatively low thermal expansion coefficient. Materials other than glass can be used provided that such materials transmit radiation such as ultraviolet light and have a reasonably low coefficient of thermal expansion, or are utilized in a carefully thermally-controlled environment. The mask tools can be configured to provide an opening of any desired shape and further configured to provide substantially any desired pattern of openings.

The resulting sandwich of two negative masks aligned in registration and flanking both surfaces of the blank then can be exposed to radiation, typically in the form of ultraviolet light projected on both surfaces through the negative masks, to expose the photo-resist coatings to the radiation. Typically, the photo-resist that is exposed to the ultraviolet light is sensitized while the photo-resist that is not exposed is not sensitized because the light is blocked by each negative masks' features. The negative masks then can be removed and a developer solution can be applied to the surfaces of the blank to develop the exposed (sensitized) photo-resist material.

Once the photo-resist is developed, the blanks can be micro-machined using one or more of the techniques described herein. For example, when using photo-chemical-machining, an etching solution can react with and remove the layer material not covered by the photo-resist to form the precision openings in the layer. Once etching or machining is complete, the remaining unsensitized photo-resist can be removed using a chemical stripping solution.

Sub-Cavities on Layers

Figure 14:
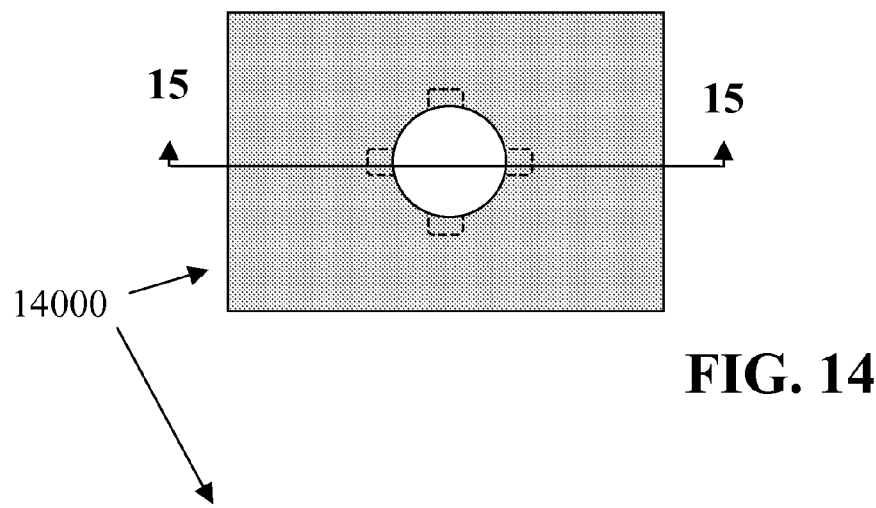
FIG. 14 is a top view of an exemplary laminated mold.
Figure 15:
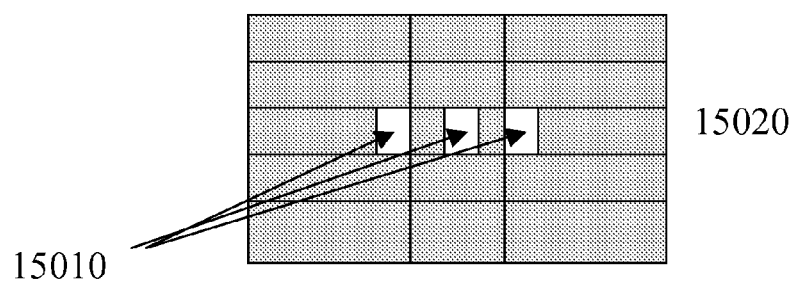
FIG. 15 is a cross-sectional view of an exemplary mold taken at section lines 15-15 of FIG. 14.
Figure 16:
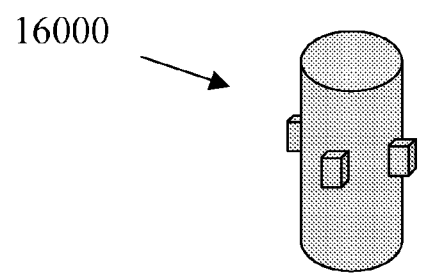
FIG. 16 is a perspective view of an exemplary cast part formed using the exemplary mold of FIG. 14.

Cavities can include sub-cavities, which can be engineered and incorporated into the molding and casting scheme using several methods. FIG. 14 is a top view of a laminated mold 14000. FIG. 15 is a cross-sectional view of mold 14000 taken at section lines 15-15 of FIG. 14, and showing the sub-cavities 15010 within layer 15030 of mold 14000. Note that because layer 15030 is sandwiched between layers 15020 and 15040, sub-cavities 15010 can be considered "sandwiched", because sub-cavities are at least partially bounded by a ceiling layer (e.g., 15020) and a floor layer (e.g., 15040). Note that, although not shown, a sub-cavity can extend to one or more outer edges of its layer, thereby forming, for example, a sandwiched channel, vent, sprew, etc. FIG. 16 is a perspective view of cast part 16000 formed using mold 14000, and having protrusions 16010 that reflectively (invertedly) replicate sandwiched sub-cavities 15010.

Because cast part can very accurately reflect the geometries of sub-cavities, such sub-cavities can be used to produce secondary features that can be incorporated with a desired structure. Examples of secondary features include fluid channels passing through or between features, protrusions such as fixation members (similar to Velcro-type hooks), reservoirs, and/or abrasive surfaces. Moreover, a secondary feature can have a wall which can have predetermined surface finish, as described herein.

There are a number of methods for producing sub-cavities in a laminated mold. For example, in the field of photo-chemical-machining, the practice of partially etching features to a specified depth is commonly referred to as "controlled depth etching" or CDE. CDE features can be incorporated around the periphery of an etched feature, such as a through-diameter. Because the CDE feature is partially etched on, for example, the top surface of the layer, it can become a closed cavity when an additional layer is placed on top.

Another method could be to fully etch the sub-cavity feature through the thickness of the layer. A cavity then can be created when the etched-through feature is sandwiched between layers without the features, such as is shown in FIG. 15.

Combinations of micro-machining techniques can be used to create sub-cavities. For example, photo-chemical-machining (PCM) can be used to create the etched-through feature in the layer, while ion etching could be applied as a secondary process to produce the sub-cavities. By combined etching techniques, the sub-cavities can be etched with much finer detail than that of PCM.

Micro-Structures, Features, and Arrays on Non-Planar Surfaces

Certain exemplary embodiments can allow the production of complex three-dimensional micro-devices on contoured surfaces through the use of a flexible cavity mold insert.

One activity of such a process can be the creation of a planar laminated mold (stack lamination), which can define the surface or 3-dimensional structures. A second mold (derived mold) can be produced from the lamination using a flexible molding material such as silicone RTV. The derived mold can be produced having a thin backing or membrane layer, which can act as a substrate for the 3-dimensional surface or features. The membrane then can be mechanically attached to the contoured surface of a mold insert, which can define the casting's final shape with the incorporated 3-dimensional features or surface.

Because a mold can be derived from a series of previous molds, any derived mold can be considered to be descended from each mold in that series. Thus, a given derived mold can have a "parent" mold, and potentially a "grandparent" mold, etc. Likewise, from a stack lamination can descend a first derived, descendant, or child mold, from which a second derived, descendent, or grandchild mold can be descended, and so forth. Thus, as used herein to describe the relationship between molds and castings, the root verbs "derive" and "descend" are considered to be synonymous.

Figure 17:
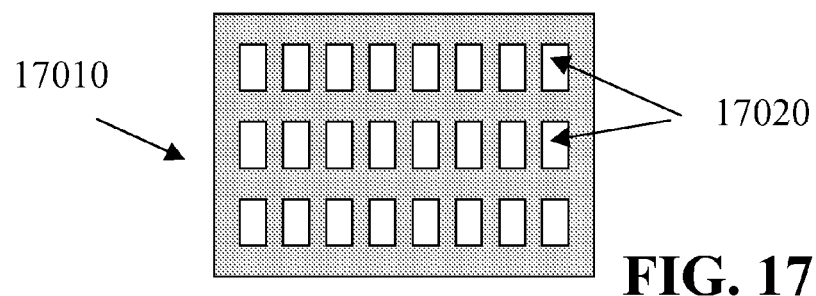
FIG. 17 is a top view of an exemplary planar laminated mold having an array of openings.
Figure 18:
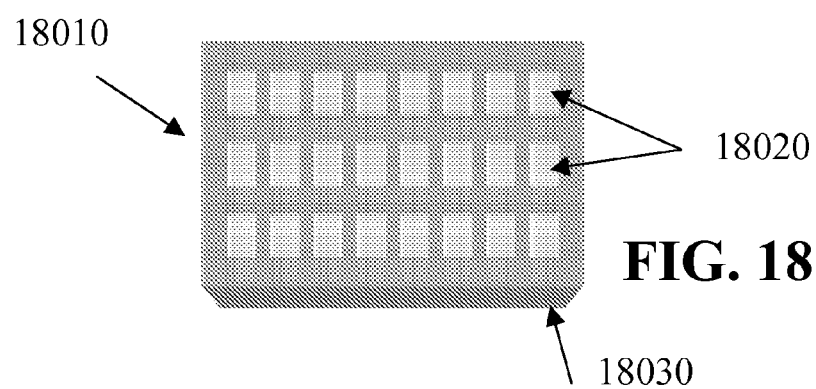
FIG. 18 is a top view of an exemplary flexible casting or mold insert molded using the laminated mold of FIG. 17.

As an example, FIG. 17 is a top view of a planar laminated mold 17010 having an array of openings 17020. FIG. 18 is a top view of a flexible casting or mold insert 18010 molded using laminated mold 17010. Flexible mold insert 18010 has an array of appendages 18020 corresponding to the array of openings 17020, and a backing layer 18030 of a controlled predetermined thickness.

Figure 19:
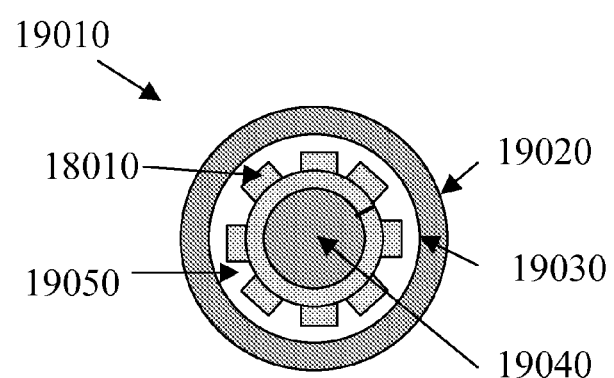
FIG. 19 is a top view of an exemplary mold fixture.

FIG. 19 is a top view of a mold fixture 19010 having an outer diameter 19020 and an inner diameter 19030. Placed around a cylinder or mandrel 19040 within mold fixture 19010 is flexible mold insert 18010, defining a pour region 19050.

Upon filling pour region 19050, a casting is formed that defines a cylindrical tube having a pattern of cavities accessible from its inner diameter and corresponding to and formed by the array of appendages 18020 of flexible mold insert 18010.

Figure 20:
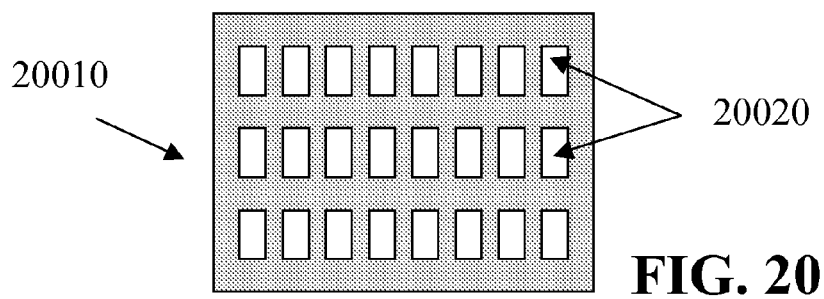
FIG. 20 is a top view of an exemplary planar laminated mold.
Figure 21:
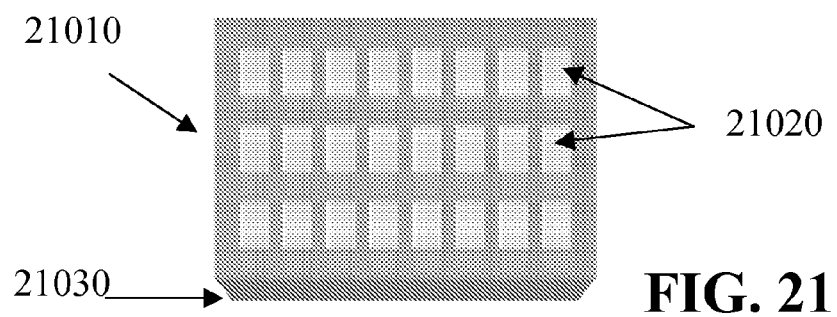
FIG. 21 is a top view of an exemplary flexible casting or mold insert molded using the laminated mold of FIG. 20.

As another example, FIG. 20 is a top view of a planar laminated mold 20010 having an array of openings 20020. FIG. 21 is a top view of a flexible casting or mold insert 21010 molded using laminated mold 20010. Flexible mold insert 21010 has an array of appendages 21020 corresponding to the array of openings 20020, and a backing layer 21030 of a controlled predetermined thickness.

Figure 22:
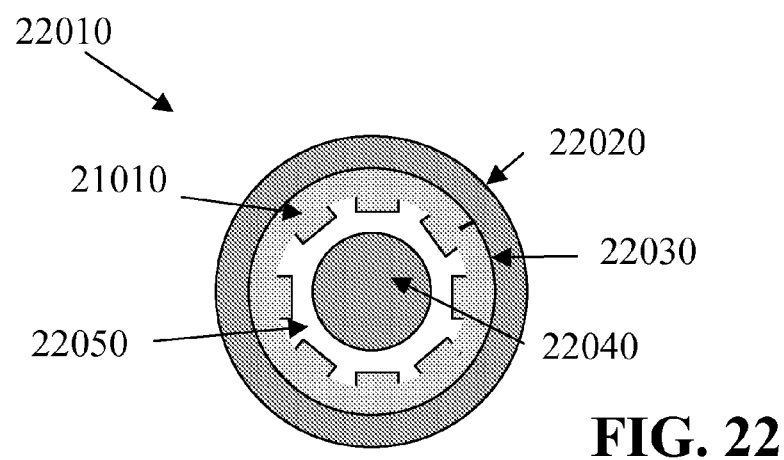
FIG. 22 is a top view of an exemplary mold fixture.

FIG. 22 is a top view of a mold fixture 22010 having an outer diameter 22020 and an inner diameter 22030. Placed around the inside diameter 22030 within mold fixture 22010 is flexible mold insert 21010, defining a pour region 22050.

Upon filling pour region 22050, a casting is formed that defines a cylindrical tube having a pattern of cavities accessible from its outer diameter and corresponding to and formed by the array of appendages 21020 of flexible mold insert 21010.

Through these and related approaches, the 3-dimensional structure or surface can be built-up at the planar stage, and can be compensated for any distortions caused by forming the membrane to the contoured surface. The fabrication of the laminated mold can use specific or combined micro-machining techniques for producing the layers that define the aspect-ratio and 3-dimensional geometry. Micro-surfaces and/or structures can be transferred to many contours and/or shapes. For example, micro-patterns can be transferred to the inside and/or outside diameter of cylinders or tubes. Specific examples demonstrating the capabilities of this method are provided later in this document.

Cavity Inserts

The term mold insert is used herein to describe a micro-machined pattern that is used for molding and/or fabrication of a cast micro-device, part, and/or item. The laminated or derived mold described in this document also can be considered a mold insert. Cavity inserts are described here as a subset of a mold insert. Cavity inserts are objects and/or assemblies that can be placed within a cavity section of a mold but that do not take up the entire cavity space, and that provide further features to a 3-dimensional mold.

Figure 23:
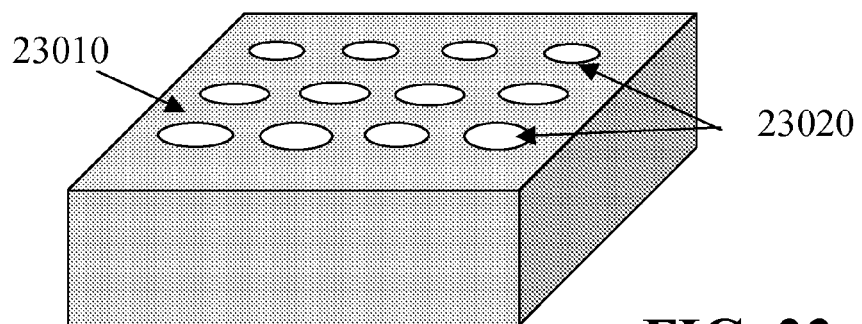
FIG. 23 is a perspective view of an exemplary laminated mold.
Figure 24:
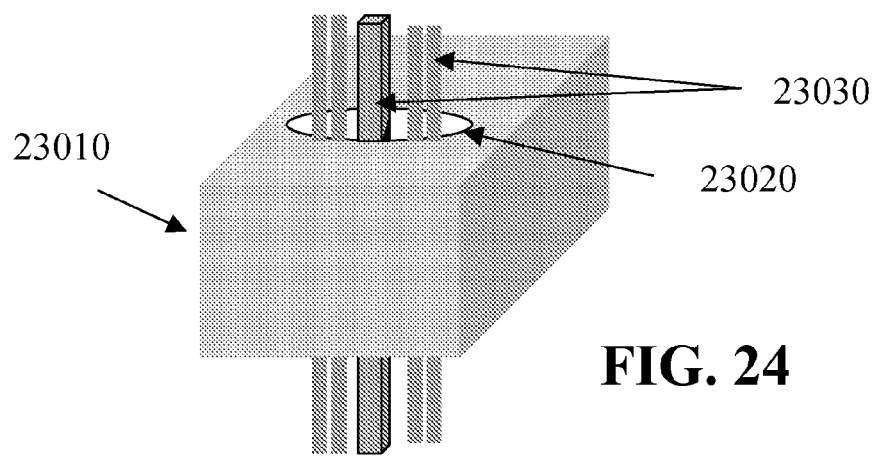
FIG. 24 is a close-up perspective view of an exemplary single cylindrical cavity of an exemplary mold.
Figure 25:
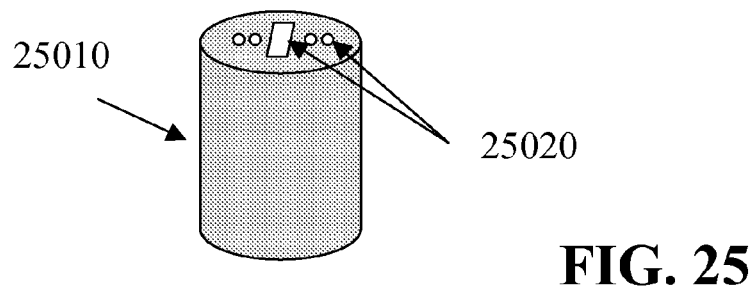
FIG. 25 is a perspective view of an exemplary cast part.

As an example, FIG. 23 is a perspective view of a laminated mold 23010 having an array of cylindrical cavities 23020, each extending from top to bottom of mold 23010. FIG. 24 is a close-up perspective view of a single cylindrical cavity 23020 of mold 23010. Suspended and extending within cavity 23020 are a number of cavity inserts 23030. FIG. 25 is a perspective view of a cast part 25010 having numerous cavities 25020 formed by cavity inserts 23030.

A cavity insert can also be produced using certain embodiments. This is further explained later in the section on non-planar molds. An insert can be a portion of a mold in the sense that the insert will be removed from the cast product to leave a space having a predetermined shape within the product. An insert alternatively can become part of a final molded product. For instance, if it is desirable to have a composite end product, then a process can be engineered to leave an insert in place in the final molded product.

As an example of a cavity insert, a 3-dimensional mold insert can be produced using one or more embodiments, the insert having an array of cavities that are through-diameters. The cast part derived from this mold can reverse the cavities of the mold as solid diameters having the shape, size and height defined by the mold. To further enhance functionality, cavity inserts can be added to the mold before the final casting is produced. In this case, the cavity insert can be a wire formed in the shape of a spring. The spring can have the physical dimensions required to fit within a cavity opening of the mold, and can be held in position with a secondary fixture scheme. The spring-shaped cavity insert can be removed from the cast part after the final casting process is completed. Thus, the cavity section of the mold can define the solid shape of the casting while the cavity insert can form a channel through the solid body in the shape and width of the insert (the spring). The cavity can serve as, for example, a reservoir and/or a fluid flow restrictor.

The examples given above demonstrate the basic principle of a cavity insert. Additional design and fabrication advances can be realized by using this method to create cavity inserts. For example, photo-chemical-machining can be used to create a mold that has larger cavity openings, while reactive-ion-etching can be used to create finer features on a cavity insert.

Fabricating the Laminated Mold

Certain exemplary embodiments can involve the fabrication of a laminated mold which is used directly and/or as an intermediate mold in one or more subsequent casting and/or molding processes.

Figure 26:
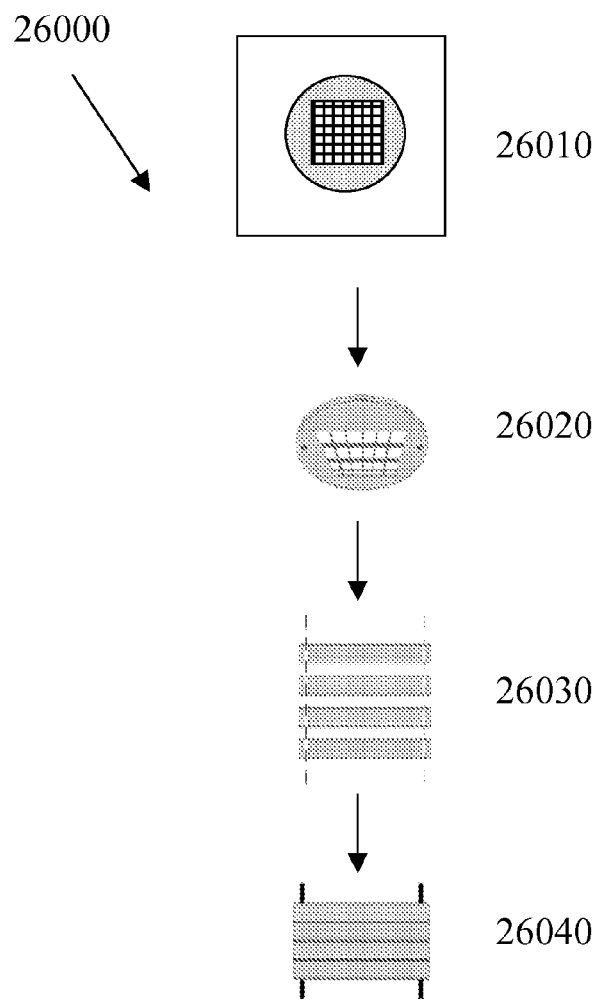
FIG. 26 is a flowchart of an exemplary method.

FIG. 26 is a block diagram illustrating various devices formed during an exemplary method 26000 for fabricating a laminated mold having micro-machined layers that can be patterned and/or etched, and stacked to create a 3-dimensional mold. The laminated mold can be produced as a negative or positive replication of the desired finished casting. For the purpose of creating a laminated mold, any of three elements can be implemented:
1) creating a lithographic mask 26010 defining the features of each unique layer,
2) using lithographic micro-machining techniques and/or micro-machining techniques to produce patterned layers 26020, and/or
3) aligning, stacking, and/or laminating the patterned layers into a stack 26030 in order to achieve the desired 3-dimensional cavity shape, aspect ratios, and/or mold parameters desired for a laminated mold 26040.

Lithographic Techniques

Using lithography as a basis for layer fabrication, parts and/or features can be designed as diameters, squares, rectangles, hexagons, and/or any other shape and/or combination of shapes. The combinations of any number of shapes can result in non-redundant design arrays (i.e. patterns in which not all shapes, sizes, and/or spacings are identical, as shown in FIG. 10). Lithographic features can represent solid or through aspects of the final part. Such feature designs can be useful for fabricating micro-structures, surfaces, and/or any other structure that can employ a redundant and/or non-redundant design for certain micro-structural aspects. Large area, dense arrays can be produced through the lithographic process, thereby enabling creation of devices with sub-features and/or the repeatable production of multiple devices in a batch format. Note that such repeatable batch production can occur without substantial degradation of the mold.

Lithography can also allow the creation of very accurate feature tolerances since those features can be derived from a potentially high-resolution photographic mask. The tolerance accuracy can include line-width resolution and/or positional accuracy of the plotted features over the desired area. In certain embodiments, such tolerance accuracy can enable micro-scale fabrication and/or accurate integration of created micro-mechanical devices with microelectronics.

Photographic masks can assist with achieving high accuracy when chemical or ion-etched, or deposition-processed layers are being used to form a laminated mold through stack lamination. Because dimensional changes can occur during the final casting process in a mold, compensation factors can be engineered at the photo-mask stage, which can be transferred into the mold design and fabrication. These compensation factors can help achieve needed accuracy and predictability throughout the molding and casting process.

Photographic masks can have a wide range of potential feature sizes and positional accuracies. For example, when using an IGI Maskwrite 800 photoplotter, an active plotting area of 22.8×31.5 inches, minimum feature size of 5 microns, and positional accuracy of +−1 micron within a 15×15 inch area is possible. Using higher resolution lithographic systems for mask generation, such as those employed for electron beam lithography, feature sizes as small as 0.25 microns are achievable, with positional tolerances similar to the Maskwrite plotter, within an area of 6×6 inches.

Layer Machining and Material Options

Another aspect to fabricating the laminated mold can be the particular technique or techniques used to machine or mill-out the features or patterns from the layer material. In certain embodiments, combining lithographic imaging and micro-machining techniques can improve the design and fabrication of high-aspect-ratio, 3-dimensional structures. Some of the micro machining techniques that can be used to fabricate layers for a laminated mold include photo-etching, laser machining, reactive ion etching, electroplating, vapor deposition, bulk micro-machining, surface micro-machining, and/or conventional machining.

In certain exemplary embodiments, a laminated mold need only embody the mechanical features (e.g., size, shape, thickness, etc.) of the final casting. That is, it does not have to embody the specific functional properties (i.e. density, conductivity) that are desired to fulfill the application of the final casting. This means that any suitable techniques or materials can be used to produce the layers of the mold.

Thus, there can be a wide variety of material and fabrication options, which can allow for a wide variety of engineered features of a layer, laminated mold, and/or derived mold. For instance, although photo-chemical machining can be limited to metallic foils, by using laser machining or reactive ion etching, the choice of materials can become greatly expanded. With regard to laser machining, Resonetics, Inc. of Nashua, N.H. commercially provides laser machining services and systems. For laser machining, a very wide range of materials can be processed using UV and infra-red laser sources. These materials include ceramics, metals, plastics, polymers, and/or inorganics. Laser micro-machining processes also can extend the limits of chemical machining with regards to feature size and/or accuracy. With little or no restriction on feature geometry, sizes on the order of 2 microns can be achievable using laser machining.

When a wide variety of materials are available for making the laminated mold, process-compatibility issues can be resolved when choosing the material from which to create the mold. An example of this would be to match the thermal properties of casting materials with those of the laminated mold, in instances where elevated temperatures are needed in the casting or molding process. Also the de-molding properties of the mold and/or casting material can be relevant to the survival of the mold. This, for example, might lead one to laser-machine the layers from a material such as Teflon, instead of a metal. The laser machining process could be compatible with the Teflon and the Teflon could have greater de-molding capabilities than a metallic stack lamination.

In certain exemplary embodiments, only a single laminated stack is needed to produce molds or castings. Also, in certain exemplary embodiments, molds and/or castings can be produced without the need for a clean-room processing environment.

For certain exemplary embodiments, the ability to create a single laminated mold and then cast the final parts can allow for using much thinner foils or advanced etching methods for producing the individual layers. Since feature size can be limited by the thickness of each foil, using thinner foils can allow finer features to be etched.

Certain exemplary embodiments can combine various micro-machining techniques to create layers that have very specific functional features that can be placed in predetermined locations along the Z-axis of the mold assembly. For example, photo-chemical-machining can be used to provide larger features and high resolution ion-etching for finer features.

Various methods, as described above, can be used to produce layers for a laminated mold. The following examples are given to demonstrate dimensional feature resolution, positional accuracy, and/or feature accuracy of the layers.

Ion Etching:

when using a Commonwealth Scientific Millitron 8000 etching system, for example, a uniform etch area of 18 inches by 18 inches is achievable. Feature widths from 0.5 microns and above are attainable, depending on the lithographic masks and imaging techniques used. A feature, for example a 5 micron wide slot, etched to a depth of 10 microns can be etched to a tolerance of +−1.25 microns in width, and +−0.1 microns in depth. The positional tolerance of features would be the same as those produced on the lithographic masks.

Photo-Chemical-Machining:

when using an Attotech XL 547 etching system, for example, a uniform etch area of 20 inches by 25 inches is achievable. Etched through-feature widths from 20 microns and above are attainable, with solid features widths of 15 microns and above also being attainable. A feature, for example a 30 micron diameter etched through 25 microns of copper, can be etched to a tolerance of +−2.5 microns or 10% of the foil thickness. The positional tolerance of such features would be the same as those produced on the lithographic masks.

Laser Micromachining:

when using a PIVOTAL laser micromachining system, for example, a uniform machining area of 3 inches by 3 inches is achievable. Machined through-feature sizes from 5 microns and above are attainable. A feature, for example a 5 micron wide slit machined through 25 microns of stainless steel, can be machined to a tolerance of +−1 micron. Positional tolerance of +−3 microns is achievable over the 3 inch by 3 inch area.

Electro-Forming:

depending on the size limitations of the photographic masks used for this process, electro-forming over areas as large as 60 inches by 60 inches is attainable. Electro-formed layers having thickness of 2 microns to 100 microns is achievable. A feature, for example a 5 micron wide slit, 15 microns deep, can be formed to a tolerance of +−1 micron. Positional tolerance of features would be the same as those produced on the lithographic masks.

Layer Assembly and Lamination

As described above, in certain exemplary embodiments, layers can be designed and produced so that feature shape and placement from layer to layer define the desired geometry along the X-, Y-, and/or Z-axes of a mold. The total number (and thickness) of layers in the assembly can define the overall height and aspect ratio of the feature. A feature can be either the solid shape or the space between given structural components.

What follows are several exemplary methods of bonding the layers together to form the laminated mold. One exemplary method used to bond layers together is a metal-to-metal brazing technique. This technique can provide a durable mold that can survive high volume production casting and/or can provide efficient release properties from the castings. Prior to assembly, the layers can have 0.00003 inches of a eutectic braze alloy deposited on the top and bottom surfaces of the layers, using standard electro-plating techniques. An example of a braze material is CuSil™, which is comprised of copper and silver, with the percentage of each being variable for specific applications. CuSil™ can be designed specifically to lower the temperatures needed to flow the alloy during the brazing process.

Figure 27:
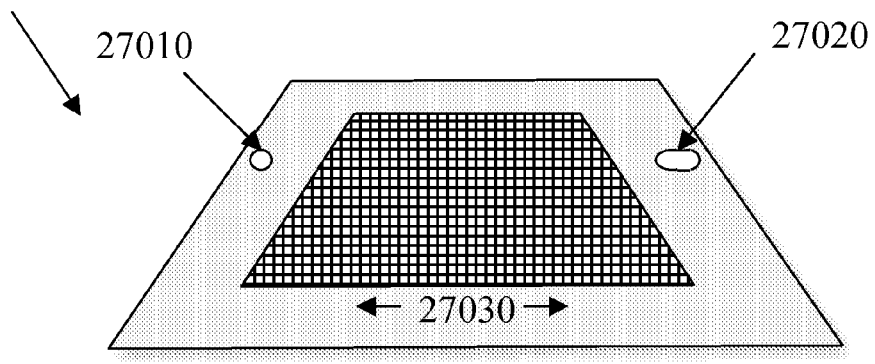
FIG. 27 is a perspective view of a plurality of exemplary layers.

One of the potential concerns during the laminating process is to maintain accurate registration of the assembly layers, and/or control the movement of the layers and the bonding fixture when brought to the elevated temperatures needed to flow the braze material. Several methods can be used to achieve this registration and/or control. The first can involve the practice of having two or more alignment features on the layers. FIG. 27 is a perspective view of a plurality of exemplary layers 27000. As illustrated in FIG. 27, one such alignment feature can be a diameter 27010, and the other alignment feature can be an elongated slot 27020. The slot and the diameter can be positioned on each layer one hundred eighty degrees opposed, for example, and can be parallel in orientation with the grain and/or perpendicular to the plane of the layer material.

Figure 28:
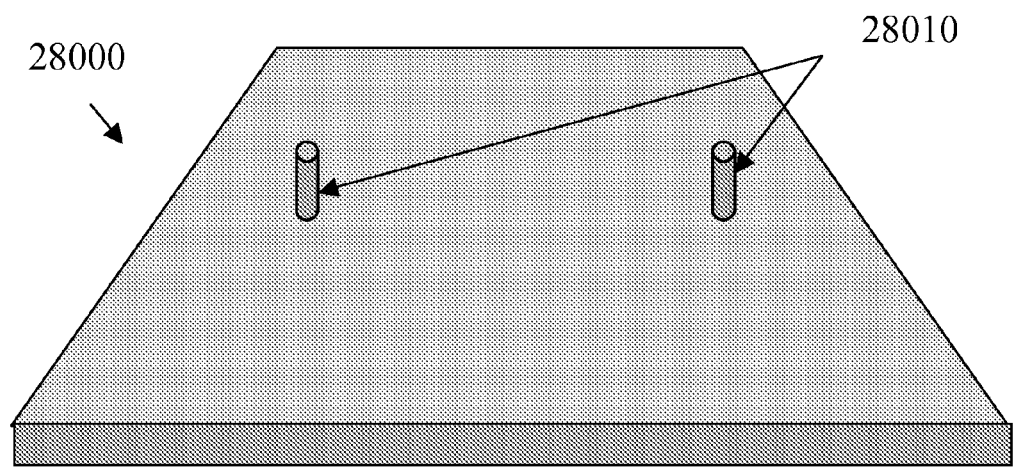
FIG. 28 is a perspective view of an exemplary laminating fixture.

FIG. 28 is a perspective view of an exemplary laminating fixture 28000, which can be fabricated from graphite, for example, and can have two graphite diameter pins 28010 that can be fixed to the lamination fixture at the same distance apart as the diameter 27010 and slot 27020 on the etched layers 27000. The layers can be placed over the pins 28010 so that each layer is orientated accurately to the layer below, using the slot and diameter to align each layer.

Alternatively, two or more diameters can be provided on the layers 27000, each of which corresponds to a pin of laminating fixture 28000.

During the brazing process, the layered assembly can be heated in a hydrogen atmosphere to a temperature of 825 degrees Celsius, which can cause the CuSil™ braze to flow. As the temperatures elevate, the layers and the fixture material can expand. The slotted alignment feature 27020 can allow the fixture 28000 material to expand or move at a dissimilar rate than the layers, by the presence of the elongated slot on the layer 27000. The slot 27020 can be greater in length than the diameter of pin 28010 in the fixture. The additional length of the slot can be determined by the different coefficient for expansion between the graphite and the assembly layers.

Other methods for maintaining the layer alignment during a heated bonding process can include fabricating the bonding fixture from the same material as the assembly layers, which can thus limit the dissimilar movement of the layers and fixture. The alignment and bonding fixture can also be made so that the alignment pins fit nearly perfectly to alignment features on the layers, but the pins in the fixture are allowed to float while being held perpendicular to the face of the alignment fixture.

In order to minimize positional errors when bonding layers (stacking errors), tolerances on certain features can be controlled. Referring to FIG. 27, the positional accuracy of features 27010 and 27020 can be controlled by the photographic masks used to produce the layers (exemplary tolerances for masks are provided in the section titled "Lithographic Techniques", above). The geometric size and tolerance of features 27010 and 27020 can be governed by the layer thickness and/or micromachining method used to produce them (exemplary tolerances for various micromachining techniques are provided in the section titled "Layer Machining and Material Options", above).

When producing a laminated mold, numerous factors can be an influence on the overall tolerances of the features of the mold and/or the casting. For example, when using a stacking fixture, any of the laminating fixture's surface flatness, the laminating fixture's perpendicularity, and the laminating fixture's parallelism can be an influence. Also, the dimensional tolerance of the alignment feature(s) of a layer and/or the positional tolerance of that feature(s) can be an influence. For example, if an alignment pin, protrusion, or other "male" feature will engage a corresponding hole, indentation, or "female" feature to assist in aligning two or more layers, the dimensional tolerance and/or vocational tolerance of male and/or female feature can be an influence on the overall tolerances.

For example, referring to FIG. 28, bonding fixture 28000 can include alignment pins 28010 fitted into the top surface of fixture 28000. In a particular experiment, through the use of a surface grinding process, followed by a planetary lapping and polishing process, the sides and top surface of bonding fixture 28000 were parallel and perpendicular to a tolerance of +−2 microns, with the top surface finish being optically flat to +− one half the wavelength of visible light (400 to 700 nanometers), or about 200 to 350 nanometers. The positional accuracy of the alignment pins and the machined diameters through fixture 28000 was +−5 microns, and the pins were perpendicular to the surface of the fixture to +−2 microns, measured at a pin height of 2 to 5 millimeters. The surface of the described fixture measured 6×6 inches, and was produced using an SIP 5000 Swiss jig boring milling center. Hardened steel alignment pins, having a diameter of 0.092 inches, were precisely ground to a tolerance of +−1.25 microns using a standard grinding operation.

The process of laminating the layers can include placing the processed layers over the alignment pins until the desired number of layers have been assembled. The assembled layers and fixture then can be placed in a brazing furnace with uniform weight applied to the top of the fixture. The furnace temperature can be raised to a temperature of 825 degrees Celsius, in a hydrogen atmosphere (a vacuum atmosphere has also been shown to work) for 45 minutes. This temperature can be sufficient to allow the braze material to uniformly flow and connect the layers together at all contact points. The fixture then can be cooled in the hydrogen atmosphere for 2 hours and removed for disassembly. The graphite pins can be removed, freeing the bonded structure from the lamination fixture.

The brazed lamination now can be ready for the final process step, which can be to coat the entire assembly with a hard nickel surface. The nickel coating can be applied to the laminated assembly using electro-plating techniques, which can deposits 0.0001 inches of nickel. The nickel-plated surface can act as an interface material that can enhance the release and durability properties of the assembled mold.

Another exemplary method that can be used to bond layers can make use of a thermo-cured epoxy rather than metal-to-metal brazing. Prior to assembly, the layers can be coated with an epoxy, MAGNA-TAC® model E645, diluted 22:1 with acetone. The thinned epoxy can be applied to the top and bottom surfaces of the layers using a standard atomizing spray gun. The layers can be spray coated in such a way that the coverage of the epoxy will bond the layers without filling the micro-machined features. A dot coverage of 50% has shown to work. The parameters for dilution and coverage can be provided by the epoxy manufacture, such as the Beacon Chemical Company.

The layers then can be assembled to a bonding fixture using, for example, the same technique described in the braze process. The assembled fixture then can be placed in a heated platen press, such as a Carver model #4122. The assembled layers and fixture can be compressed to 40 pounds per square inch and held at a temperature of 350 degrees F. for 3 hours, and allowed to cool to room temperature under constant pressure. The assembly then can be removed from the fixture using, for example, the same technique used for the brazed assembly.

In certain embodiments, the technique described in the second example can be considerably less expensive and time consuming than that used for the first. Using the epoxy process, savings can be realized due to the cost of the plating and the additional requirement imposed by the hydrogen braze process compared to epoxy stack laminating. The master derived from the first example can provide more efficient de-molding properties and also can survive a greater number of castings than the epoxy bonded mold. The epoxy-bonded mold can demonstrate a cost effective alternative to brazing and can be used for prototyping or when smaller production quantities are required.

Casting and Molding Process

Exemplary embodiments can involve the creation of a high-resolution casting mold, having high-aspect-ratio, as well as 3-dimensional features and shapes. A precision stack lamination, comprised of micro-machined layers, can be used as a laminated mold. The laminated mold can be used to produce advanced micro-devices and structures (a.k.a., "micro-electro-mechanical structures" and "MEMS") and/or can be used to create second (or greater) generation derived molds.

The following paragraphs describe the casting process in terms of the materials, fixtures, and/or methods that can be used to produce second-generation molds and final castings.

Mold Duplication and Replication

For certain exemplary embodiments, the process options for producing molds and cast parts can be numerable. For example, molds can be made as negative 4010 or positive 4020 replications of the desired cast part as shown in FIG. 4. If the mold is made as a positive, a second-generation mold can be created. If the mold is made as a negative, the final part can be cast directly from the mold.

For certain exemplary embodiments, the process used to create the layers for the laminated mold can be a determining factor. For example, some production situations can require a second- (or even third) generation derived version of the laminated mold.

In certain situations, process parameters can be greatly enhanced by combining molding and casting materials having certain predetermined values for physical properties such as durometer, elasticity, etc. For example, if the cast part is extremely rigid, with poor release properties, a second-generation consumable mold can be used to create the final casting. Further specific examples of this practice, and how they relate to 3-dimensional micro-fabrication are described later in this document.

Feature size and positional accuracy for molds and produced parts can be compensated for at the layer production stage of the process. For example, known material properties such as thermal expansion or shrinkage can be accurately accounted for due to, for example, the accuracy levels of the photographic masks and/or laser machining used to produce mold layers. Feature resolution, using various mold making and casting materials, can be accurately replicated for features having a size of 1 micron and greater. Surface finishes have also been reproduced and accurately replicated. For example, layers have been used to form a laminated mold which was used to produce a derived silicone RTV mold. The surface finish of a 0.0015 inch thick stainless steel layer (specified finish as 8-10 micro inches RA max) and a 0.002 inch thick copper layer (specified finish as 8-20 micro inches RA max) were easily identified on the molded surfaces of the derived RTV mold. The surfaces were observed at 400× magnification using a Nikon MM11 measuring scope. The same surface finishes were also easily identified when cast parts were produced from the derived mold using a casting alloy CERROBASE™. Very smooth surface finishes, such as those found on glass, have also been reproduced in molds and castings.

Materials for Molds and Castings

For certain exemplary embodiments, there can be hundreds, if not thousands of material options for mold making and casting. Described below are some potential considerations regarding the selection of mold and casting materials that can meet the requirements of, for instance, 3-dimensional MEMS.

To insure the accuracy and repeatability of certain cast micro-devices, the casting material can have the capability to resolve the fine 3-dimensional feature geometries of the laminated mold. Typical dimensions of MEMS can range from microns to millimeters. Other structures having micro features can have much larger dimensions.

For certain embodiments, the mold's cavity geometry can influence the release properties between the mold and the casting, thereby potentially implicating the flexibility (and/or measured durometer) of the materials used. Other material compatibility issues also can be considered when using a casting process.

Certain exemplary embodiments of a process have been developed in order to enable the production of 3-dimensional micro-structures from a wide range of materials, tailored to specific applications. The ability to use various materials for molds and castings can greatly expand the product possibilities using this technique.

One material that has been successfully used for creating castings from a laminated mold is an elastomeric product, referred to generally as RTV silicone rubber, although other materials could also be successful depending on process or product requirements. A wide range of silicone-based materials designed for various casting applications are commercially available through the Dow Corning Corporation of Midland, Mich. For example, the Silastic® brand products have proven successful, possibly because of their resolution capability, release characteristics, flexibility, durability, and/or the fact that they work in a wide range of process temperatures.

Although other types of silicone rubber products could be used, each of the Dow Corning Silastic® brand products that have been used consists of two components; a liquid silicone rubber and a catalyst or curing agent. Of the Dow Corning Silastic® brand products, there are two basic curing types: condensation, and addition cure. The two types can allow for a range of variations in material viscosities and cure times. The three primary products used in the earliest tests are Silastic® J RTV Silicone Rubber, Silastic® M RTV Silicone Rubber, and Silastic® S RTV Silicone Rubber. Product specifications are provided in several of the examples at the end of this document.

The Dow Corning Silastic® products used thus far have similar specifications regarding shrinkage, which increases from nil up to 0.3 percent if the silicone casting is vulcanized. Vulcanization can be accomplished by heating the silicone to a specific elevated temperature (above the casting temperature) for a period of 2 hours. Vulcanizing can be particularly useful when the casting is to be used as a regenerated mold, and will be subjected to multiple castings.

In addition to RTV silicone rubber, urethanes and other materials also have properties that can be desirable for laminated molds, derived molds, and/or castings, depending on the specific requirement. For example, when producing certain 3-dimensional micro-structures with extreme aspect ratios, very fine features, or extreme under-cuts, de-molding can be difficult. In certain situations, the rigidity of the mold also can be relevant, especially in certain cases where mold features have high-aspect ratios. For example, the practice of sacrificing or dissolving laminated second or third generation molds can be used when castings require very rigid molds, and/or where the de-molding of castings becomes impossible.

There are several families of materials that can be used for producing laminated molds, derived molds, and/or final cast devices including, for example:

Acrylics: such as, for example, PMMA acrylic powder, resins, and/or composites, as well as methacrylates such as butyl, lauryl, stearyl, isobutyl, hydroxethyl, hydroxpropyl, glycidyl and/or ethyl, etc.

Plastic polymerics: such as, for example, ABS, acetyl, acrylic, alkyd, flourothermoplastic, liquid crystal polymer, styrene acrylonitrile, polybutylene terephthalate, thermoplastic elastomer, polyketone, polypropylene, polyethylene, polystyrene, PVC, polyester, polyurethane, thermoplastic rubber, and/or polyamide, etc.

Thermo-set plastics: such as, for example, phenolic, vinyl ester, urea, and/or amelamine, etc.

Rubber: such as, for example, elastomer, natural rubber, nitrile rubber, silicone rubber, acrylic rubber, neoprene, butyl rubber, flurosilicone, TFE, SBR, and/or styrene butadiene, etc.

Ceramics: such as, for example, silicon carbide, alumina, silicon carbide, zirconium oxide, and/or fused silica, calcium sulfate, luminescent optical ceramics, bio-ceramics, and/or plaster, etc.

Alloys: such as, for example, aluminum, copper, bronze, brass, cadmium, chromium, gold, iron, lead, palladium, silver, sterling, stainless, zinc platinum, titanium, magnesium, anatomy, bismuth, nickel, and/or tin, etc.

Wax: such as, for example, injection wax, and/or plastic injection wax, etc.

There can be many material options within these groups that can be utilized when employing certain embodiments. For example, in certain embodiments, metals and metal alloys can be primarily used as structural materials of final devices, but also can add to function. Exemplary functional properties of metals and/or alloys can include conductivity, magnetism, and/or shape memory.

Polymers also can be used as structural and/or functional materials for micro-devices. Exemplary functional properties can include elasticity, optical, bio-compatibility, and/or chemical resistivity, to name a few. Materials having dual (or more) functionality, often referred to as engineered "smart" materials, could be incorporated into a final molded product or a mold. Additional functionality could utilize electro-static, mechanical, thermal, fluidic, acoustic, magnetic, dynamic, and/or piezo-electric properties. Ceramics materials also can be used for applications where specialty requirements may be needed, such as certain high-temperature environments. Depending on the material that is chosen, there can be many alternative methods to solidify the casting material. The term "solidify" includes, but is not limited to, methods such as curing, vulcanizing, heat-treating, and/or chemically treating, etc.

Mold Fixtures, Planar and Contoured

For certain exemplary embodiments, there can be a wide range of engineering options available when designing a casting mold. The casting process and geometry of the final product can determine certain details and features of the mold. Options can be available for filling and/or venting a mold, and/or for releasing the casting from the mold.

Two basic approaches have been used for demonstrating the certain exemplary methods for mold design and fabrication. These approaches can be categorized as using a single-piece open-face mold or a two-part closed mold.

In certain exemplary embodiments, each of the mold types can include inserting, aligning, and assembling the laminated mold (or duplicate copy) in a fixture. The fixture can serve several purposes, including bounding and/or defining the area in which to pour the casting material, capturing the casting material during the curing process, allowing the escape of air and/or off-gases while the casting material is degassed, and/or enabling mechanical integration with the casting apparatus.

The fixture can be configured in such a way that all sides surrounding the mold insert are equal and common, in order to, for example, equalize and limit the effects of thermal or mechanical stresses put on the mold during the casting process. The mold fixture also can accommodate the de-molding of the casting.

Certain exemplary embodiments of this method can provide the ability to mold 3-dimensional structures and surfaces on contoured surfaces. The basic technique is described earlier in this document in the design parameter section. One element of the technique can be a flexible mold insert that can be fixed to a contoured surface as shown in FIGS. 19 and 22. The mold insert can be made with a membrane or backing thickness that can allow for integration with various fixture schemes that can define the contoured shape.

For non-planar molds, the contour of the mold fixture can be produced by standard machining methods such as milling, grinding, and/or CNC machining, etc. The flexible mold insert can be attached to the surface of the mold using any of several methods. One such method is to epoxy bond the flexible insert to the fixture using an epoxy that can be applied with a uniform thickness, which can be thin enough to accommodate the mold design. Other parameters that can be considered when choosing the material to fix a membrane to a fixture include durability, material compatibility, and/or temperature compatibility, etc. A detailed description of a non-planar mold is given as an example further on.

Casting and Molding Processes

Various techniques can be used for injecting or filling cavity molds with casting materials, including injection molding, centrifugal casting, and/or vibration filling. An objective in any of these techniques can be to fill the cavity with the casting material in such a way that all of the air is forced out of the mold before the cast material has solidified. The method used for filling the cavity mold can depend on the geometry of the casting, the casting material, and/or the release properties of the mold and/or the cast part.

As has been described earlier, an open face mold, using flexible RTV rubber has been found to work effectively. In certain embodiments, an open face mold can eliminate the need for having carefully designed entrance sprue and venting ports. The open face mold can be configured to create an intermediate structure that can have a controlled backing thickness which can serve any of several purposes: 1) it can be an open cavity section in the casting mold which can serve as an entrance point in which to fill the mold; 2) it can serve as a degassing port for the air evacuation during the vacuum casting process; 3) it can create a backing to which the cast part or parts can be attached and/or which can be grasped to assist in de-molding the casting from the flexible mold.

In casting processes in which the casting material is heated, the mold temperature and the cooling of the casting can be carefully controlled. For example, when casting a lead casting alloy such as CERROBASE, the alloy can be held at a temperature of 285 degrees F., while the mold material can be preheated 25-30 degrees higher (310-315 degrees F.). The molten alloy can be poured and held at or above the melting point until it is placed in the vacuum environment. The mold then can be placed in a vacuum bell jar, and held in an atmosphere of 28 inches of mercury for 3-4 minutes. This can remove any air pockets from the molten metal before the alloy begins to solidify. As soon as the air has been evacuated, the mold can be immediately quenched or submersed in cold water to rapidly cool the molten metal. This can help minimize shrinkage of the cast metal.

In certain exemplary embodiments, no vent holes or slots are provided in the mold, and instead, air can be evacuated from the mold prior to injection. In certain exemplary embodiments, temperature variation and its effect on the micro-structure can be addressed via enhanced heating and cooling controls in or around the mold. In certain exemplary embodiments, heat can be eliminated from the curing process by replacing the molding materials with photo-curing materials.

Some of the methods that can be used for micro-molding and casting include micro-injection molding, powder injection molding, metal injection molding, photo molding, hot embossing, micro-transfer molding, jet molding, pressure casting, vacuum casting, and/or spin casting, etc. Any of these methods can make use of a laminated or derived mold produced using this method.

De-Molding and Finish Machining

A controlled backing thickness can be incorporated into the casting to create an intermediate structure. One purpose of the intermediate can be to create a rigid substrate or backing, that allows the casting to be grasped for removal from the mold without distorting the casting. The thickness of the backing can be inversely related to the geometry of the pattern or features being cast. For example, fine grid patterns can require a thicker backing while coarse patterns can have a thinner backing. The backing can be designed to have a shape and thickness that can be used to efficiently grasp and/or pull the cast part from the mold.

Following de-molding, the intermediate can be machined to remove the backing from the casting. Because the thickness of the backing can be closely controlled, the backing can be removed from the cast structure by using various precision machining processes. These processes can include wire and electrode EDM (electrode discharge machining), surface grinding, lapping, and/or fly cutting etc.

In instances where extremely fine, fragile patterns have been cast, a dissolvable filler or potting material can be poured and cured in the cast structure prior to the removal of the backing from the grid. The filler can be used to stabilize the casting features and eliminate possible damage caused by the machining process. The filler can be removed after machining-off the backing. A machinable wax has been found to be effective for filling, machining, and dissolving from the casting.

In some part designs, de-molding the casting from the mold might not be possible, due to extreme draft angles or extremely fine features. In these cases, the mold can remain intact with the cast part or can be sacrificed by dissolving the mold from casting.

EXAMPLES

A wide range of three-dimensional micro-devices can be fabricated through the use of one or more embodiments of various fabrication processes, as demonstrated in some of the following examples.

Example 1—Sub-Millimeter Feedhorn Array

This example demonstrates fabrication of an array of complex 3-dimensional cavity features having high aspect ratio. This example makes use of a second-generation derived mold for producing the final part, which is an array of sub-millimeter feedhorns. A feedhorn is a type of antenna that can be used to transmit or receive electromagnetic signals in the microwave and millimeter-wave portion of the spectrum. At higher frequencies (shorter wavelengths) the dimensions can become very small (millimeters and sub-millimeter) and fabrication can become difficult.

Using certain exemplary embodiments, a single horn, an array of hundreds or thousands of identical horns, and/or an array of hundreds or thousands of different horns can be fabricated.

Figure 29:
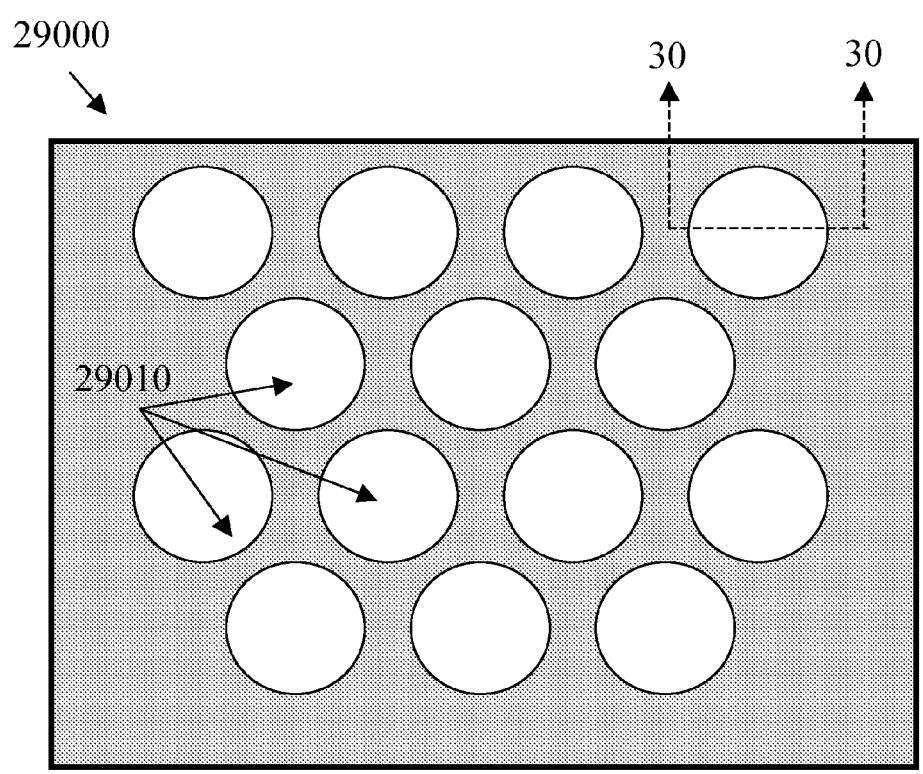
FIG. 29 is a top view of stack lamination mold that defines an array of cavities.
Figure 30:
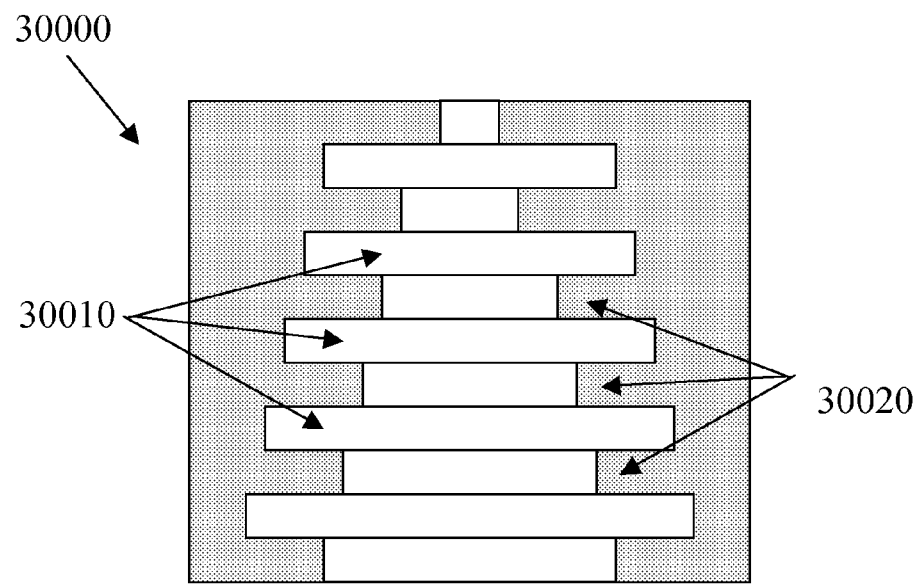
FIG. 30 is a cross-section of a cavity taken along section lines 30-30 of FIG. 29.

FIG. 29 is a top view of stack lamination mold 29000 that defines an array of cavities 29010 for fabricating feedhorns. FIG. 30 is a cross-section of a cavity 29010 taken along section lines 30-30 of FIG. 29. As shown, cavity 29010 is corrugated, having alternating cavity slots 30010 separated by mold ridges 30020 of decreasing dimensions, that can be held to close tolerances.

In an exemplary embodiment, an array of feedhorns contains one thousand twenty identical corrugated feedhorns, each designed to operate at 500 GHz, and the overall dimensions of the feed horn array are 98 millimeters wide by 91 millimeters high by 7.6 millimeters deep. The fabrication of this exemplary array can begin with the creation of a laminated mold, comprised of micro-machined layers, and assembled into a precision stack lamination.

Step 1: Creating the Laminated Mold:

The laminated mold in this example was made of 100 layers of 0.003" thick beryllium copper (BeCu) sheets that were chemically etched and then laminated together using an epoxy bonding process. Infinite Graphics, Inc. of Minneapolis, Minn. was contracted to produce the photo-masks needed for etching the layers. The masks were configured with one thousand twenty diameters having a center-to-center spacing of 2.5 millimeters. An IGI Lazerwrite photo plotter was used to create the masks, which were plotted on silver halite emulsion film. The plotter resolution accuracy was certified to 0.5 micrometers and pattern positional accuracy of plus or minus 0.40 micrometers per lineal inch. The layers were designed so that horn diameters were different from layer to layer, so that when the layers were assembled, the layers achieved the desired cross-section taper, slot, and ridge features shown in simplified form in FIG. 30. A total of 100 layers were used to create a stacked assembly 7.6 millimeters thick. The layers were processed by Tech Etch, Inc. of Plymouth, Mass., using standard photo-etching techniques and were etched in such a way that the cross-sectional shape of the etched walls for each layer are perpendicular to the top and bottom surfaces of the layer (commonly referred to as straight sidewalls).

In this example, the method chosen to bond the etched layers together used a thermo-cured epoxy (MAGNA-TAC model E645), using the process and fixturing described earlier in the section on layer assembly and lamination. The assembled fixture was then placed in a 12 inch×12 inch heated platen press, Carver model No. 4122. The fixture was compressed to 40 pounds per square inch and held at a temperature of 350 degrees F. for 3 hours, then allowed to cool to room temperature under constant pressure. The assembly was then removed from the fixture and the alignment pins removed, leaving the bonded stack lamination. The laminated mold (stack lamination) was then used to produce the final casting mold.

Step 2: Creating the Casting Mold: The second step of the process was the assembly of the final casting mold, which used the precision stack lamination made during step 1 as a laminated mold. The casting mold created was a negative version of the lamination, as shown in perspective view for a single feed horn 31000 in FIG. 31. Also shown is a feedhorn ridge 31010 that can correspond to a cavity slot 30010, and a feedhorn base 31020.

For this example, Silastic® J RTV Silicone Rubber was used to make the final casting mold. This product was chosen because it is flexible enough to allow easy release from the laminated mold without damaging the undercut slots and rings inside the feedhorns, and because of its high-resolution capability. Described below are the product specifications.

Silastic® J:
  Durometer Hardness: 56 Shore A points
  Tensile Strength, psi: 900
  Linear Coefficient of Thermal Expansion: 6.2×10-4
  Cure Time at 25 C: 24 hours The Silastic® J Silicone RTV was prepared in accordance with the manufacturer's recommendations. This included mixing the silicone and the curing agent and evacuating air (degassing) from the material prior to filling the mold-making fixture. At the time the example was prepared, the most effective way of degassing the Silicone prior to filling the mold fixture was to mix the two parts of the Silicone and place them in a bell jar and evacuate the air using a dual stage vacuum pump. The material was pumped down to an atmosphere of 28 inches of mercury and held for 5 minutes beyond the break point of the material. The Silicone was then ready to pour into the mold fixture.

Figure 32:
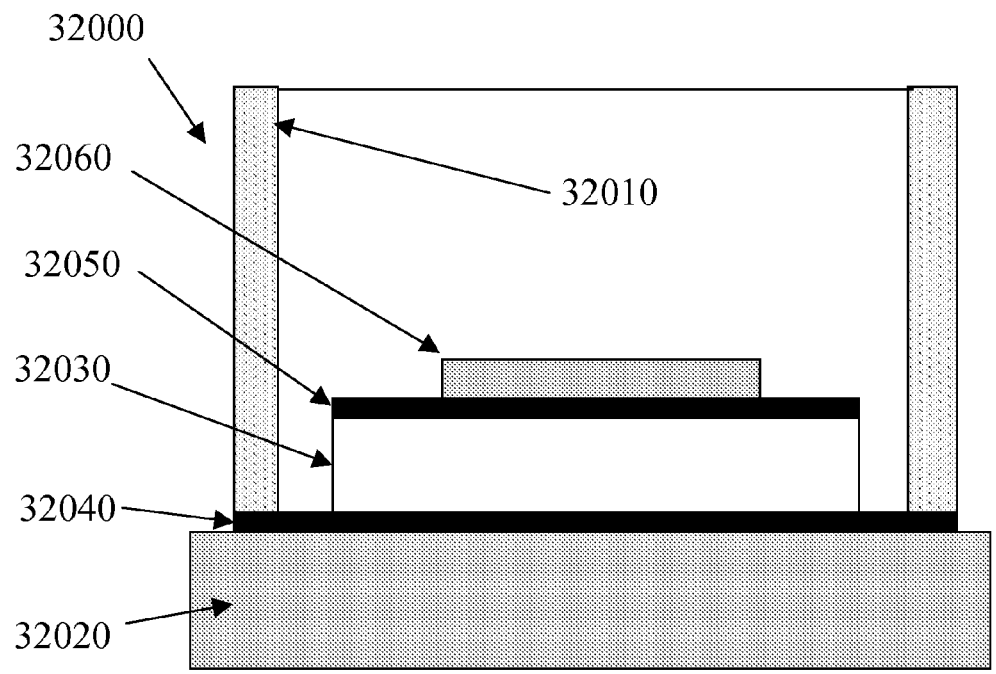
FIG. 32 is a side view of an exemplary casting fixture.

As shown in the side view of FIG. 32, an open-face fixture 32000 was prepared, the fixture having a precision-machined aluminum ring 32010, precision ground glass plate 32030, rubber gaskets 32040, 32050 and the laminated mold 32060. The base 32020 of the fixture was thick Plexiglas. On top of the Plexiglas base was a glass substrate 32030. Rubber gasket 32040 separated the glass base and the glass substrate. An additional rubber gasket 32050 was placed on the top surface of the glass substrate 32030 and the laminated mold 32060 was placed on the top gasket. The rubber gaskets were used to prevent unwanted flashing of material during casting. A precision-machined aluminum ring 32010 was placed over the laminated mold subassembly and interfaced with the lower rubber gasket 32040.

Generally, the height of the ring and dimensions of the above pieces can depend upon the dimensions of the specific structure to be cast. The ring portion 32010 of the fixture assembly served several purposes, including bounding and defining the area in which to pour mold material, capturing the material during the curing process, and providing an air escape while the mold material was degassed using vacuum. The fixture was configured in a way that all sides surrounding the laminated mold 32060 were equal and common, in order to equalize and limit the effects of thermal or mechanical stresses put on the lamination from the mold material.

An open-face mold was used for this example. The mold insert and molding fixture were assembled and filled with the silicone RTV, then the air was evacuated again using a bell jar and vacuum pump in an atmosphere of 28 inches of mercury. After allowing sufficient time for the air to be removed from the silicone, the mold was then heat-cured by placing it in a furnace heated to and held at a constant temperature of 70 degrees F. for 16 hours prior to separating the laminated mold from the derived RTV mold. The molding fixture was then prepared for disassembly, taking care to remove the laminated mold from the RTV mold without damaging the lamination, since the lamination can be used multiple times to create additional RTV molds.

Figure 31:
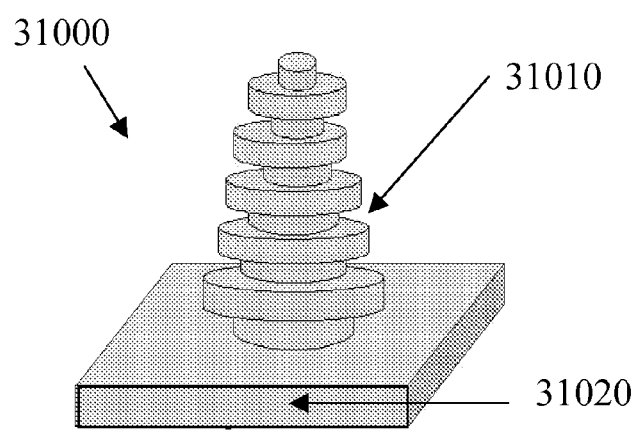
FIG. 31 is a perspective view of an exemplary single corrugated feedhorn.

The resulting RTV mold was a negative version of the entire feedhorn array consisting of an array of one thousand twenty negative feedhorns, similar to the simplified single horn 31010 shown in perspective view in FIG. 31.

Step 3: Casting the Feedhorn Array:

In this example, the cast feedhorn arrays were made of a silver loaded epoxy, which is electrically conductive. In certain exemplary embodiments, binders and/or metallic (or other) powders can be combined and/or engineered to satisfy specific application and/or process specifications. The conductive epoxy chosen for this example provided the electrical conductivity needed to integrate the feedhorn array with an electronic infrared detector array.

The conductive epoxy was purchased from the company BONDLINE™ of San Jose, Calif., which designs and manufactures engineered epoxies using powdered metals. Certain of its composite metal epoxies can be cured at room temperature, have high shear strength, low coefficient of thermal expansion, and viscosities suited for high-resolution casting.

Exemplary embodiments can utilize various techniques for injecting or filling cavity molds with casting materials. In this example, a pressure casting method was used.

The BONDLINE™ epoxy was supplied fully mixed and loaded with the silver metallic powder, in a semi-frozen state. The loaded epoxy was first normalized to room temperature and then pre-heated per the manufacturer's specification. In the pre-heated state the epoxy was uncured and ready to be cast. The uncured epoxy was then poured into the open-face mold to fill the entire mold cavity. The mold was then placed in a pressurized vessel with an applied pressure of 50 psi using dry nitrogen, and held for one hour, which provided sufficient time for the epoxy to cure. The mold was then removed from the pressure vessel and placed in an oven for 6 hours at 225 degrees F., which fully cured the conductive epoxy.

Step 4. Demolding and Finish Machining:

After the cast epoxy had been cured, it was ready for disassembly and demolding from the casting fixture and mold. The mold material (RTV silicone) was chosen to be flexible enough to allow the cast feedhorn array to be removed from the casting mold without damaging the undercuts formed by the slots and ridges. When done carefully, the mold could be reused several times to make additional feedhorn arrays.

The backing thickness 31020 of the RTV mold shown in FIG. 31 came into play during the de-molding process. The backing was cast thick enough to allow easy grasping to assist with separating the casting mold from the cast piece. In this example, the RTV casting mold was flexible and allowed easy separation without damaging the undercut slots and rings inside the cast feedhorns.

Depending on the piece being cast, machining, coating, and/or other finish work can be desirable after de-molding. In this example, a final grinding operation was used on the top surface (pour side of the mold) of the feedhorn array because an open face mold was used. This final grinding operation could have been eliminated by using a closed, two-part mold.

Example 2—Individual Feedhorns Produced in a Batch Process

This example makes use of certain exemplary embodiments to demonstrate the production of sub-millimeter feedhorns in a batch process. The example uses the same part design and fabrication process described in example 1, with several modifications detailed below.

Process Modifications:

The process detailed in example 1 was used to produce an array of one thousand twenty feedhorns. The first modification to the process was the casting material used to produce the array. The casting material for this example was a two-part casting polymer sold through the Synair Corporation of Chattanooga, Tenn. Product model "Mark 15 Por-A-Kast" was used to cast the feedhorn array and was mixed and prepared per the manufacturer's specifications. The polymer was also cast using the pressure filling method described in example 1.

The next modification was a surface treatment applied to the cast polymer array. A conductive gold surface was deposited onto the polymer array in order to integrate the feedhorns with the detector electronics. The gold surface was applied in two stages. The first stage was the application of 0.5 microns of conduction gold, which was sputter-coated using standard vacuum deposition techniques. The first gold surface was used for a conductive surface to allow a second stage electro-deposition or plating of gold to be applied. The second gold plating was applied with a thickness of 2 microns using pure conductive gold.

The final modification was to dice or cut the feedhorns from the cast and plated array into individual feedhorns, that were then suitable for detector integration. A standard dicing saw, used for wafer cutting, was used to cut the feedhorns from the cast array.

Example 3—Array of 3-Dimensional Micro-Structures

Process steps 1 and 2 described in example 1 were used to produce a large area array of micro-structures, which are described as negatives of the feedhorn cavities, shown as a single feedhorn in FIG. 31. The laminated mold and molding fixture was used to cast the micro-structures using Dow Corning's Silastic® M RTV Silicone Rubber. This product was chosen because it is flexible enough to release from the mold insert, without damaging the circular steps in the structure, but has the hardness needed to maintain the microstructures in a standing position after being released from the mold. Described below are the product specifications.

Silastic® M
  Durometer Hardness: 59 Shore A points
  Tensile Strength, psi: 650
  Linear Coefficient of Thermal Expansion: $6.2 \times 10^{-4}$
  Cure Time at 25 C: 16 hours The Silicone RTV was prepared in accordance with the manufacturer's recommendations, using the process described earlier in example 1, step 2. The laminated mold and molding fixture were assembled and filled with the silicone RTV, using the process described earlier in example 1, step 2. The molding fixture was then prepared for disassembly, taking care to separate the mold insert from the cast silicone array. The resulting casting was an array consisting of one thousand twenty 3-dimensional micro-structures. The shape and dimension of a single structure is shown in simplified form in FIG. 31.

Example #4—Cylindrical Tubing with Micro-Fluidic Channels on the Inside Diameter Certain exemplary embodiments have been used to produce a 2.5 centimeter length of clear urethane tubing, having 3-dimensional micro-fluid channels on the inside diameter of the tubing. The fluidic tubing was produced using a flexible cavity insert with a controlled backing thickness. The following example demonstrates how the cavity insert can enable the production of three-dimensional features on the inside and outside diameters of cylindrical tubing.

Figure 33:
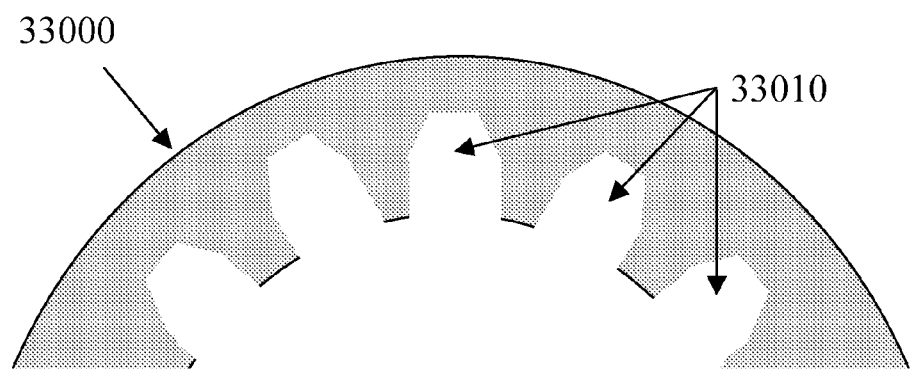
FIG. 33 is a side view of an exemplary section of cylindrical tubing that demonstrates the shape of an exemplary fluidic channel.

Step 1: Creating the Mold Insert:

The first step in the process was to fabricate the micro-machined layers used to produce the cavity insert. The cast tubing was 2.5 centimeters long, having a 3.0 millimeter outside diameter and a 2.0 millimeter inside diameter, with 50 three-dimensional micro-fluidic channels, equally spaced around the interior diameter of the tube. FIG. 33 shows a side view of the tubing 33000, the wall of which defines numerous fluidic channels 33010. Although each fluidic channel could have different dimensions, in this example each channel was 0.075 mm in diameter at the entrance of the channel from the tube, and each channel extended 0.075 mm deep. Each channel tapered to a diameter of 0.050 mm, the taper beginning 0.025 mm from the bottom of each channel.

Photo-chemical machining was used to fabricate the layers for the laminated mold. FIG. 34 is a top view of a such a laminated mold 34000, which was created using several photo masks, one of which with a similar top view. Mold 34000 includes an array of fluidic channels 34010 In this particular experiment, the length of channels 34010 was approximately 25 millimeters, and the width of each collection of channels was approximately 6.6 millimeters.

FIG. 35 is a cross-section of mold 34000 taken at section lines 35-35 of FIG. 34. To the cross-sectional shape of channel 34010, a first copper foil 35010 having a thickness of 0.025 mm, and a second copper foil 35020 having a thickness of 0.050 mm, were chemically etched and then laminated together using a metal-to-metal brazing process. Each of the layers used in the laminated mold assembly used a separate photo-mask. The masks used for layer 35020 were configured with a 9.50×0.075 mm rectangular open slot, arrayed redundantly in 50 places, a portion of which are illustrated in FIG. 34. To achieve the desired taper, two masks were used for layer 35010. The bottom mask was configured with a 9.50×0.075 mm rectangular open slot and the top mask was configured with a 9.50×0.050 rectangular open slot, each of the slots were also redundantly arrayed in 50 places. The photo-masks were produced to the same specifications, by the same vendor as those described in example 1, step 1.

The layers were designed so that the slot placement was identical from layer to layer, which when assembled, produced the cross-sectional shape for the channels as shown in FIG. 35. The final thickness of the lamination was specified at 0.083 millimeters, which required one 0.025 layer of copper foil, and one 0.050 thick layer of copper foil, leaving a total thickness amount of 0.002 millimeters for braze material on each side of each etched layer. The layers were photo-etched by the same vendor, and same sidewall condition as those described in example 1, step 1. The method chosen to bond the grid layers together was a metal-to-metal brazing technique described earlier, in detail as one of two exemplary methods of bonding layers together (eutectic braze alloy)

Figure 36:
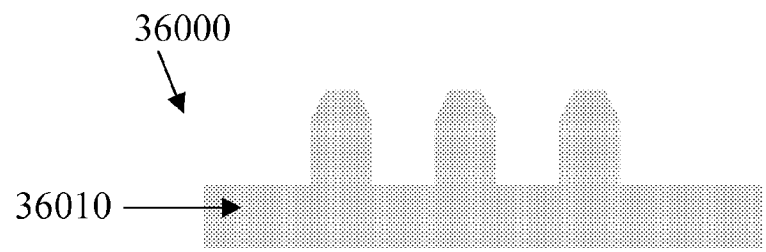
FIG. 36 is a side view of a portion of an exemplary flexible cavity insert.

Step 2: Creating the Flexible Cavity Insert:

The next step of the process was to create a flexible cavity insert from the brazed layered assembly. FIG. 36 is a side view of cavity insert 36000, which was produced from the brazed assembly with a backing 36010 having a thickness of 0.050 millimeters. The cavity insert 36000 was produced using Silastic® S RTV Silicone Rubber as the base material. The RTV Silicone Rubber was used because of its resolution capability, release properties, dimensional repeatability, and its flexibility to form the insert to a round pin that would be assembled to the final molding fixture. The material properties of Silastic® S are shown below.

Silastic® S
  Durometer Hardness: 26 Shore A points
  Tensile Strength, psi: 1000
  Linear Coefficient of Thermal Expansion: $6.2 \times 10^{-4}$
  Cure Time at 25 C: 24 hours The casting fixture used to create the RTV cavity insert was similar to that shown in FIG. 32 and is described in detail in the prior examples. A modification was made to the fixture assembly, which was a top that was placed over the pour area of the mold fixture. This top was placed and located to close the mold after air evacuation and reduce the backing thickness 36010 of the RTV insert to a thickness of 0.050 millimeters, shown in FIG. 36. The Silastic® S RTV Silicone Rubber used for the cavity insert fabrication was prepared in accordance with the manufacturers recommendations, using the process described earlier in example 1, step 2.

Figure 37:
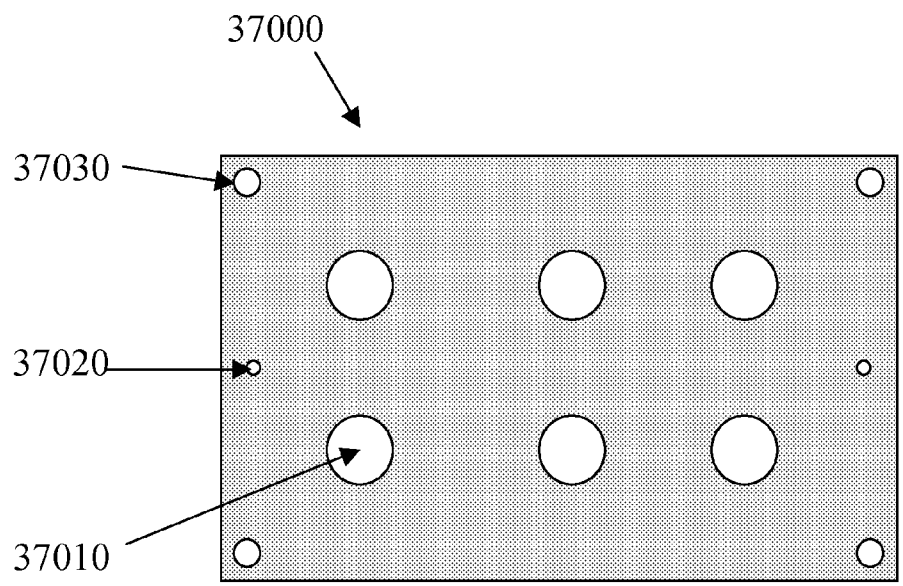
FIG. 37 is a top view of an exemplary base plate.
Figure 40:
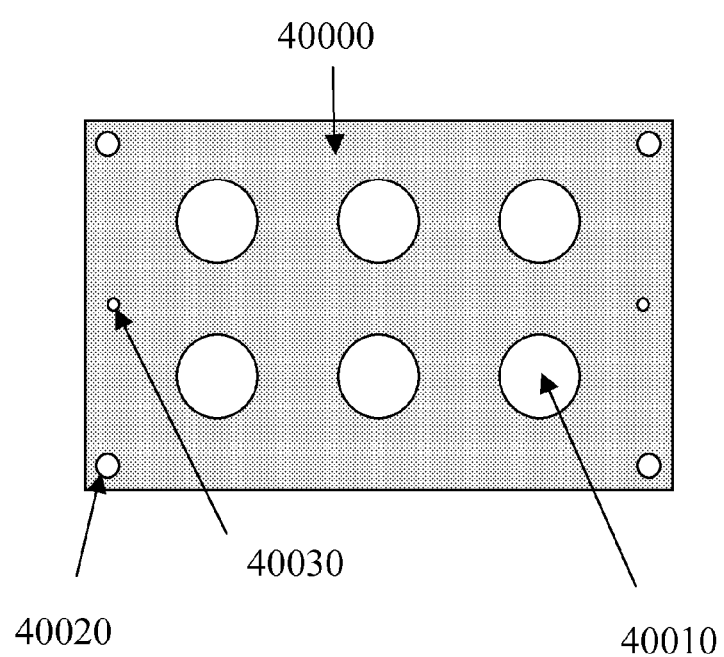
FIG. 40 is a top view of a top plate.

Step 3: Assembling the Molding Fixture:

The final molding fixture was then ready to be assembled. The molding fixture included a base plate (FIG. 37), the cavity inserts (FIG. 38), and a top plate (FIG. 40). FIG. 37 is a top view of the base plate 37000, which was made from a 0.25 inch aluminum plate that was ground flat and machined using standard CNC machining techniques. The base had six machined diameters 37010 through the plate. These six diameters would accept the cavity insert pins described later. The plate also had machined diameters through the plate, which would accept dowel pins 37020 that were used to align and assemble the top plate and the base plate, as well as 4 bolt diameters 37030 to hold the top and bottom plates together.

Figure 38:
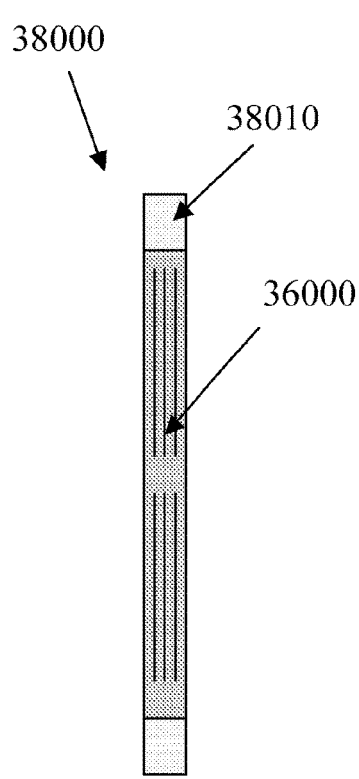
FIG. 38 is a front view of a single exemplary flexible cavity insert assembly.

FIG. 38 is a side view of an insert fixture 38000, that includes the flexible cavity insert 36000 attached to a 3 centimeter long, 1.900 millimeter diameter steel pin 38010. The pin 38010 was ground to the desired dimensions using standard machine grinding techniques. The RTV cavity insert 36000 was cut to the proper size before being attached to the pin. The RTV insert 36000 was attached to outside diameter of the pin 38010 using a controlled layer of two-part epoxy.

Figure 39:
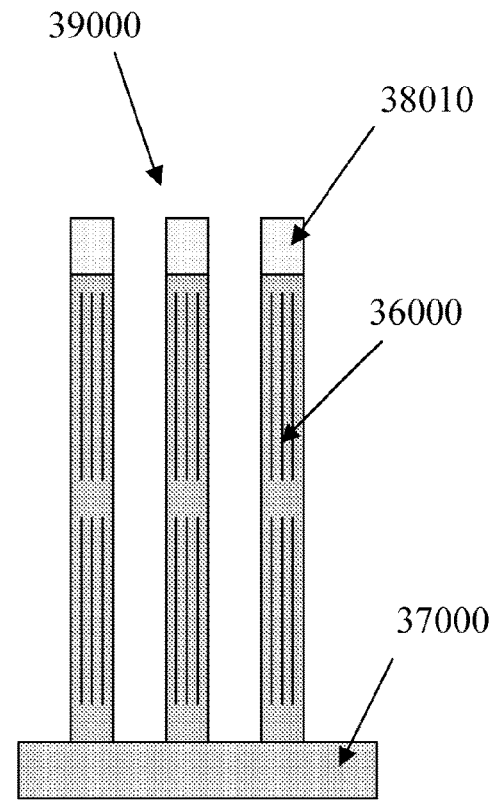
FIG. 39 is a front view of flexible cavity inserts.

FIG. 39 is a side view of several insert fixtures 39000 that have been attached to a base plate 37000. Each insert 36000 was attached its corresponding pin 38010 so that the end of pin 38010 could be assembled to a corresponding machined diameter 37010 of base plate 37000 without interference from insert 36000. Once each insert 36000 was attached around the diameter of its corresponding pin 38010 and the pin placed in the corresponding through-diameter of base plate 37010, the pin was held perpendicular to base plate 37000 and in alignment with a top plate of the fixture.

FIG. 40 is a top view of a top plate 40000 of the fixture, which was also fabricated of aluminum and machined using CNC techniques. There were six 3.0 millimeter diameters 40010 milled through the thickness of plate 40000, which was 3.0 centimeters thick. Diameters 40010 defined the cavity areas of the mold that would be filled during the final casting process, and aligned to the pins assembled to the base plate. Also incorporated into the top plate were bolt features 40020 and dowel features 40030 needed to align and assemble the top plate 40000 to the base plate 37000. The thickness of top plate 40000 was specified to slightly exceed the desired length of the final cast tubing, which was cut to its final length after casting. The casting fixture was then assembled, first by assembling the cavity insert 38000 to the base plate 37000, followed by assembling the top plate 40000 to the base using bolts and dowels. The top view of a representative cavity section for an assembled fixture is shown in FIG. 19.

Step 4: Casting the Fluidic Tubes:

Several fluidic tubes were produced using the assembled casting fixture. A clear urethane was used for the final casting because of its high-resolution, low shrink factor, and transparent properties, which allowed for final inspection of the interior diameter features through the clear wall of the tube. The casting material was purchased from the Alumilite Corporation of Kalamazoo, Mich., under the product name Water Clear urethane casting system. The manufacturer described the cured properties as follows:

Hardness, Shore D: 82
Density (gm/cc) 1.04
Shrinkage (in/in/) maximum 0.005
Cure Time (150 degrees F.) 16 hr The urethane was prepared in accordance with the manufacturer's recommendations. This included the mixing and evacuation of air (degassing) from the material prior to filling the mold. The most effective way found for degassing the urethane prior to filling the mold fixture was to mix parts A and B, place them in a bell jar, and evacuate the air using a dual stage vacuum pump. The mixture was pumped down to an atmosphere of 28 inches of mercury and held for 15 minutes beyond the break point of the material The urethane was then ready to pour into the mold fixture.

The assembled mold fixture was heated to 125 degrees F. prior to filling the cavities with the urethane. The pre-heating of the mold helped the urethane to flow and fill the cavities of the mold, and aided in the degassing process. The cavity sections of the mold were then filled with the urethane, and the air was evacuated again using a bell jar and vacuum pump in an atmosphere of 28 inches of mercury. After allowing sufficient time for the air to be removed from the urethane, the mold was then removed from the vacuum bell jar and placed in an oven. The mold was heated and held at a constant temperature of 150-180 degrees F. for 16 hours prior to separating the cast tubes from the mold. The molding fixture was then disassembled and the cast tubes were separated from the cavity inserts. The inserts were first removed from the base plate of the fixture. The tubes were easily separated from the cavity insert assembly due to the flexibility and release properties of the silicone RTV, combined with the hardness of the urethane tubes.

Example #5—Tubing with Micro-Fluidic Channels on the Outside Diameter

Example #4 described the method used for producing cast urethane tubing with micro-fluidic features on the inside diameter of the tube. The current example demonstrates how that process can be altered to produce tubing with the micro-fluidic channels on the outside diameter of the tubing. This example uses a similar part design and the fabrication process described in example 4, with several modifications detailed below.

One process modification involved step 3, assembling the molding fixture. For this step, a modification was made to the fixture design that enabled the molded features to be similar to that shown in FIGS. 20-22. The first modification was in the size of the machined diameters in the base plate and the top plate of the fixture described in example 4. The flexible RTV cavity insert that was attached to a pin in example 4 was instead attached to the inside diameters of the top fixture plate, similar to that shown in FIG. 22. In order to accommodate the existing RTV cavity insert, the cavity diameters of the top plate were milled to a size of 1.900 millimeters. The RTV cavity insert was then attached to the milled diameter of the top plate using the same epoxy technique described in example 4. The base plate of the fixture was also modified to accept a 1.0 millimeter diameter pin, and was assembled similar to the that shown in FIG. 22. The same casting process was used as described in example 4. After following the final casting process, with the altered molding fixture, the urethane tubes were produced having the same fluidic channels located on the outside diameter of the cast tube.

Additional Embodiments—X-Ray and Gamma-Ray Collimators, Grids, and Detector Arrays Certain exemplary embodiments can provide methods for fabricating grid structures having high-resolution and high-aspect ratio, which can be used for radiation collimators, scatter reduction grids, and/or detector array grids. Such devices can be used in the field of radiography to, for example, enhance image contrast and quality by filtering out and absorbing scattered radiation (sometimes referred to as "off-axis" radiation and/or "secondary" radiation).

Certain embodiments of such devices can be used in nearly every type of imaging, including astronomy, land imaging, medical imaging, magnetic resonance imaging, tomography, fluoroscopy, non-destructive inspection, non-destructive testing, optical scanning (e.g., scanning, digital copying, optical printing, optical plate-making, faxing, and so forth), photography, ultra-violet imaging, etc. Thus, certain embodiments of such devices can be comprised in telescopes, satellites, imaging machines, inspection machines, testing machines, scanners, copiers, printers, facsimile machines, cameras, etc. Moreover, these machines can process images using analog and/or digital techniques.

For the purposes of this description, the term "collimator" is used generally to describe what may also be referred to as a radiation collimator, x-ray grid, scatter reduction grid, detector array grid, or any other grid used in an imaging apparatus and/or process.

Certain collimators fabricated according to one or more exemplary embodiments can be placed between the object and the image receptor to absorb and reduce the effects of scattered x-rays. Moreover, in certain exemplary embodiments, such collimators can be used in a stationary fashion, like those used in SPECT (Single Photon Emission Computed Tomography) imaging, or can be moved in a reciprocating or oscillating motion during the exposure cycle to obscure the grid lines from the image, as is usually done in x-ray imaging systems. Grids that are moved are known as Potter-Bucky grids.

X-ray grid configurations can be specified by grid ratio, which can be defined as the ratio of the height of the grid to the distance between the septa. The density, grid ratio, cell configuration, and/or thickness of the structure can have a direct impact on the grid's ability to absorb off-axis radiation and/or on the energy level of the x-rays that the grid can block.

Certain exemplary embodiments can allow for the use of various materials, including high-density grid materials. Also, certain exemplary can make use of a production mold, which can be derived from a laminated mold.

Numerous additional aspects can be fabricated according to certain exemplary embodiments. For example, the laminated mold can be produced from a stack lamination or other method, as discussed above. Moreover, X-ray absorbent material, such as lead, lead alloys, dense metallic composites, and/or epoxies loaded with dense metallic powders can be cast into a mold to produce x-ray absorbing grids. High-temperature ceramic materials also can be cast using a production mold.

In addition, the open cells of the ceramic grid structure can be filled with detector materials that can be accurately registered to a collimator. The molds and grids can be fabricated having high-resolution grid geometries that can be made in parallel or focused configurations. The mold can remain assembled to the cast grid to provide structural integrity for grids with very fine septal walls, or can be removed using several methods, and produce an air-cell grid structure.

Figure 41:
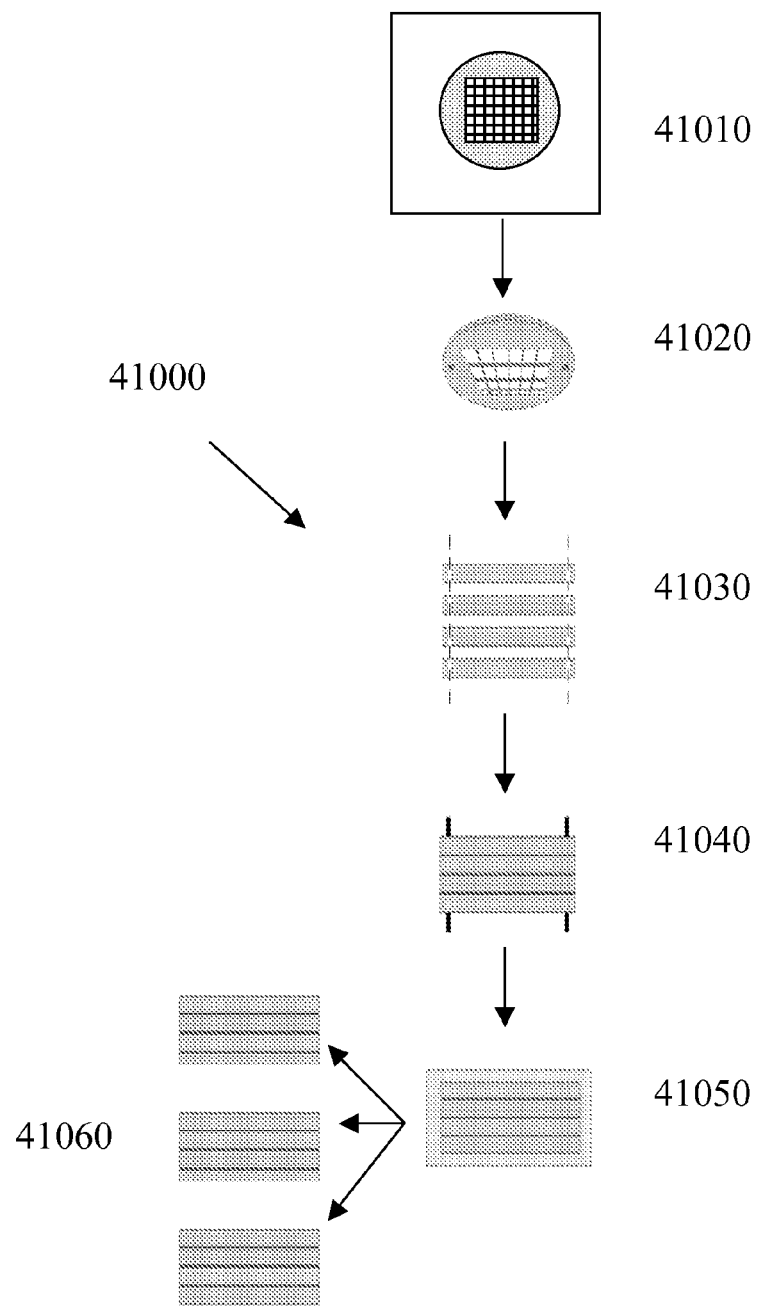
FIG. 41 is a flowchart of an exemplary embodiment of a method.

FIG. 41 is a block diagram illustrating an exemplary embodiment of a method 41000 Method 41000 can include the following activities:
1) creating a lithographic mask 41010 defining the features of each unique layer,
2) using lithographic micro-machining techniques and/or micro-machining techniques to produce patterned layers 41020, and
3) aligning, stacking, and/or laminating the patterned layers 41030 in order to achieve the desired 3-dimensional cavity shape, high-aspect ratios, and/or other device features desired for the laminated mold 41040,
4) fabricating a casting mold 41050 derived from the laminated mold, and/or
5) casting x-ray grids (or other parts) 41060 using the derived casting mold.

The following discussion describes in detail exemplary activities involved in fabricating certain exemplary embodiments of a laminated mold, fabricating a derived mold from the laminated mold, and finally casting a collimator from the derived mold. Certain variations in the overall process, its activities, and the resulting collimator are noted throughout.

In certain exemplary embodiments, the final collimator can be customized as a result of the casting process. For instance, conventional collimators have two separated flat major sides that are parallel to each other, thereby forming a flat, generally planar grid structure. Although certain exemplary embodiments includes methods for forming these collimators, exemplary embodiments of the invention also can be used to form non-planar collimators.

An exemplary embodiment of a method can begin with the acquisition, purchase, and/or fabrication of a first collimator. This first collimator can serve as the master collimator from which one or more molds can be formed. The master collimator can be made by any means, including stack lamination, but there is no limitation with respect to how the first or master collimator can be made. Also, as will be explained in more detail, because the master collimator is not necessarily going to be a collimator used in radiography, it is possible to customize this master collimator to facilitate mold formation.

The mold itself can be fabricated of many materials. When formed of a flexible material, for example, it is possible to use the mold to make a non-planar collimator. The material of the mold can be customized according to cost and performance requirements. In some embodiments, it is possible to make a mold of material that is substantially transparent to radiation transmission. The mold could be left embedded in the final cast collimator. This particular variation can be applicable when the final collimator has very narrow septal walls and the mold is needed to provide support and definition for the collimator. The mold generally also can be reused to form multiple final (or second) collimators to achieve economies of manufacturing scale.

Radiation Opaque Casting Materials for Collimators and Grids

A broad selection of base materials can be used for the fabrication of parts, such as x-ray collimators and scatter reduction grids. One potential characteristic of a grid material is sufficient absorption capacity so that it can block selective x-rays or gamma photons from reaching an image detector. In certain embodiments, this characteristic can require high density and/or high atomic number (high z) materials. Certain exemplary embodiments can utilize lead, tungsten, and/or various lead alloys for grid fabrication, but also can include the practice of loading various binders or alloys with dense powder metals, such as tungsten. The binders can be epoxies, polymers, and/or dense alloys which are described in detail below.

For certain exemplary embodiments, lead can be used for casting purposes because of its high density and low melting point, which can allow the molten lead to be poured or injected into a mold. In certain situations, however, pure lead can shrink and/or pull away from molds when it solidifies, which can inhibit the casting of fine features. This can be overcome by using lead alloys, made from high-density materials, which can allow the metal alloy to flow at lower temperatures than pure lead while reducing shrink factors.

A typical chief component in a lead alloy is bismuth, a heavy, coarse crystalline metal that can expand by 3.3% of its volume when it solidifies. The presence of bismuth can expand and/or push the alloy into the fine features of the mold, thus enabling the duplication of fine features. The chart below shows the physical properties of pure lead and two lead alloys that were used to produce collimators. The alloys were obtained from Cerro Metal Products Co. of Bellefonte, Pa. Many other alloys exist that can be used to address specific casting and application requirements.

| BASE MATERIAL | COMPOSITION | MELT POINT | DENSITY (g/cc) |
|---|---|---|---|
| Pure Lead | Pb | 621.7 degrees F. | 11.35 |
| CERROBASE ™ | 55.5% BI, 44.5% Pb | 255 degrees F. | 10.44 |
| CERROLOW-117 ™ | 44.7% BI, 22.6% Pb, 19.1% In, 8.3% Sn, 5.3% Cd, | 117 degrees F. | 9.16 |

The physical properties of lead alloys can be more process-compatible when compared to pure lead, primarily because of the much lower melting point. For example, the low melt point of CERROBASE™ can allow the use of rubber-based molds, which can be helpful when casting fine-featured pieces. This can be offset in part by a slightly lower density (about 8%). The somewhat lower density, can be compensated for, however, by designing the grid structure with an increased thickness and/or slightly wider septal walls.

Also, the alloy can be loaded with dense powder metals, such as tungsten, gold, and/or tantalum, etc., to increase density. Similarly, epoxy binders can be loaded with a metallic powder such as, for example, powdered tungsten, which has a density of 19.35 grams per cubic centimeter. In this approach, tungsten particles ranging in size from 1-150 microns, can be mixed and distributed into a binder material. The binder material can be loaded with the tungsten powder at sufficient amounts needed to achieve densities ranging between 8 and 14 grams per cubic centimeter. The tungsten powder is commercially available through the Kulite Tungsten Corporation of East Rutherford N.J., in various particle sizes, at a current cost of approximately $20-$25 dollars per pound.

The binders and metallic powders can be combined and engineered to satisfy specific application and process issues. For example, tungsten powder can be added to various epoxies and used for casting.

The company BONDLINE™ of San Jose, Calif., designs and manufactures engineered adhesives, such as epoxies, using powdered metals. Such composite metal epoxies can be cured at room temperature, can have high shear strength, low coefficient of thermal expansion, and viscosities that can be suited for high-resolution casting. Powdered materials combined with epoxy can be stronger than lead or lead alloys, but can be somewhat lower in density, having net density ranging from 7-8 grams per cubic centimeter. This density range can be acceptable for some collimator applications. In applications where material density is critical the practice of loading a lead alloy can be used. For example, tungsten powder can be combined with CERROBASE™ to raise the net density of the casting material from 10.44 up to 14.0 grams per cubic centimeter.

Certain exemplary embodiments also include the casting of grid structures from ceramic materials, such as alumina, silicon carbide, zirconium oxide, and/or fused silica. Such ceramic grid structures can be used to segment radiation imaging detector elements, such as scintillators. The Cotronics Corporation of Brooklyn, N.Y., manufactures and commercially distributes Rescor™ Cer-Cast ceramics that can be cast at room temperature, can have working times of 30-45 minutes, can have cure times of 16 hours, and can withstand temperatures ranging from 2300 to 4000 degrees F.

Additional Embodiments—Anti-Scatter Grids for Mammography and General Radiography One or more exemplary embodiments can provide cellular air cross grids for blocking scattered X-ray radiation in mammography applications. Such cross grids can be interposed between the breast and the film-screen or digital detector. In some situations, such cross grids can tend to pass only the primary, information-containing radiation to the film-screen while absorbing secondary and/or scattered radiation which typically contains no useful information about the breast being irradiated.

Certain exemplary embodiments can provide focused grids. Grids can be made to focus to a line or a point. That is, each wall defining the grid can be placed at a unique angle, so that if an imaginary plane were extended from each seemingly parallel wall, all such planes would converge on a line or a point at a specific distance above the grid center—the distance of that point from the grid known as the grid focal distance. A focused grid can allow the primary radiation from the x-ray source to pass through the grid, producing the desired image, while the off-axis scattered rays are absorbed by the walls of the grid (known as septal walls).

In certain embodiments, the septal walls can be thick enough to absorb the scattered x-rays, but also can be as thin as possible to optimize the transmission ratio (i.e., the percentage of open cell area to the total grid area including septal walls) and minimize grid artifacts (the shadow pattern of grid lines on the x-ray image) in the radiograph.

The relation of the height of the septal walls to the distance between the walls can be known as the grid ratio. Higher grid ratios can yield a higher scatter reduction capability, and thus a higher Contrast Improvement Factor (CIF), which can be defined as the ratio of the image contrast with and without a grid. A higher grid ratio can require, however, a longer exposure time to obtain the same contrast, thus potentially exposing the patient to more radiation. This dose penalty, known as the Bucky factor (BF), is given by $BF=CIF/Tp$, where $Tp$ is the fraction of primary radiation transmitted. Certain exemplary embodiments can provide a grid design that arrives at an optimal and/or near-optimal combination of these measures.

One or more exemplary embodiments can include fine-celled, focused, and/or large area molded cross-grids, which can be sturdily formed from a laminated mold formed of laminated layers of metal selectively etched by chemical milling or photo-etching techniques to provide open focused passages through the laminated stack of etched metal layers. In certain applications, such molded and/or cast cross grids can maximize contrast and accuracy of the resulting mammograms when produced with a standard radiation dosage.

In certain exemplary embodiments, the laminated mold for the molded cross grids can be fabricated using adhesive or diffusion bonding to join abutting edges of thin partition portions of the laminated abutting layers with minimum intrusion of bonding material into the open focused passages.

Exemplary embodiments can utilize any of a wide number of different materials to fabricate such molded and/or cast cross grids. A specific application can result in any of the following materials being most appropriate, depending on, for example, the net density and the cell and septa size requirements:
- Lead or lead alloy alone can offer a density of 9-11 grams per cc;
- Lead alloy can be loaded with a dense composite (e.g., tungsten, tantalum, and/or gold, etc.) powder to form a composite having a density of 12-15 grams per cc;
- Polymer can be loaded with a dense composite (e.g., lead, tungsten, tantalum, and/or gold, etc.) powder to form a composite having a density of 8-9 grams per cc;
- The cast grid made of lead alloy or any of the above combinations can be encapsulated in a low density polymer such that the transmission is minimally affected but scatter is significantly reduced.

In addition, certain embodiments can be employed to fabricate grids and/or collimators for which the mold can be pre-loaded with dense powder, followed by alloy or polymer. Alternatively, polymer or alloy can be pre-loaded with dense powder then injected into the mold. In certain embodiments, the casting can be removed from a flexible mold. In other embodiments, the mold can be dissolved or consumed to de-mold the casting. In certain embodiments, a master can be removed layer-by-layer from rigid mold. Alternatively, the lost wax approach can be used in which the model is dissolvable wax, dissolvable PMMA, dissolvable polyurethane, dissolvable high-resolution ceramic, and/or some other dissolvable material.

Additional Embodiments—Computed Tomography Collimator and Detector Array

Certain exemplary embodiments can provide a system that includes an x-ray source, a scatter collimator, and a radiation detector array having a plurality of reflective scintillators. Such a system can be used for computer-assisted tomography ("CT"). Computed tomography is often performed using a CT scanner, which can also be known as a CAT scanner. In certain embodiments, the CT scanner can look like a large doughnut, having a square outer perimeter and a round hole. The patient can be positioned in a prone position on a table that can be adjusted up and down, and can be slid into and out of the hole of the CT scanner. Within the chassis of the CT scanner is an x-ray tube on a rotating gantry which can rotate around the patient's body to produce the images. On the opposite side of the gantry from the x-ray tube can be mounted an array of x-ray detectors.

In certain exemplary embodiments, the x-ray source can project a fan-shaped beam, which can be collimated to lie within an X-Y plane of a Cartesian coordinate system, referred to as the "imaging plane". The x-ray beam can pass through the object being imaged, such as a patient. The beam, after being attenuated by the object, can impinge upon the array of radiation detectors. The intensity of the attenuated beam radiation received at the detector array can be dependent upon the attenuation of the x-ray beam by the object. Each detector element of the array can produce a separate electrical signal that can provide a measurement of the beam attenuation at the detector location. The attenuation measurements from all the detectors can be acquired separately to produce an x-ray transmission profile of the object.

For certain exemplary embodiments, the detector array can include a plurality of detector elements, and can be configured to attach to the housing. The detector elements can include scintillation elements, or scintillators, which can be coated with a light-retaining material. Moreover, in certain exemplary embodiments, the scintillators can be coated with a dielectric coating to contain within the scintillators any light events generated in the scintillators. Such coated scintillators can reduce detector element output gain loss, and thereby can extend the operational life of a detector element and/or array, without significantly increasing the costs of detector elements or detector arrays.

In certain exemplary embodiments, the x-ray source and the detector array can be rotated with a gantry within the imaging plane and around the object to be imaged so that the angle at which the x-ray beam intersects the object can constantly change. A group of x-ray attenuation measurements, i.e., projection data, from the detector array at one gantry angle can be referred to as a "view", and a "scan" of the object can comprise a set of views made at different gantry angles during one revolution of the x-ray source and detector. In an axial scan, the projection data can be processed to construct an image that corresponds to a two-dimensional slice taken through the object.

In certain exemplary embodiments, images can be reconstructed from a set of projection data according to the "filtered back projection technique". This process can convert the attenuation measurements from a scan into integers called "CT numbers" or "Hounsfield units", which can be used to control the brightness of a corresponding pixel on a cathode ray tube display.

In certain exemplary embodiments, detector elements can be configured to perform optimally when impinged by x-rays traveling a straight path from the x-ray source to the detector elements. Particularly, exemplary detector elements can include scintillation crystals that can generate light events when impinged by an x-ray beam. These light events can be output from each detector element and can be directed to photoelectrically responsive materials in order to produce an electrical signal representative of the attenuated beam radiation received at the detector element. The light events can be output to photomultipliers or photodiodes that can produce individual analog outputs. Exemplary detector elements can output a strong signal in response to impact by a straight path x-ray beam.

Without a collimator, X-rays can scatter when passing through the object being imaged. Particularly, the object can cause some, but not all, x-rays to deviate from the straight path between the x-ray source and the detector. Therefore, detector elements can be impinged by x-ray beams at varying angles. System performance can be degraded when detector elements are impinged by these scattered x-rays.

When a detector element is subjected to multiple x-rays at varying angles, the scintillation crystal can generate multiple light events. The light events corresponding to the scattered x-rays can generate noise in the scintillation crystal output, and thus can cause artifacts in the resulting image of the object.

To, for example, reduce the effects of scattered x-rays, scatter collimators can be disposed between the object of interest and the detector array. Such collimators can be constructed of x-ray absorbent material and can be positioned so that scattered x-rays are substantially absorbed before impinging upon the detector array. Such scatter collimators can be properly aligned with both the x-ray source and the detector elements so that substantially only straight path x-rays impinge on the detector elements. Also, such scatter collimators can shield from x-ray radiation damage certain detector elements that can be sensitive at certain locations, such as the detector element edges.

Certain exemplary embodiments of a scatter collimator can include a plurality of substantially parallel attenuating blades and a plurality of substantially parallel attenuating wires located within a housing. In certain exemplary embodiments, the attenuating blades, and thus the openings between adjacent attenuating blades, can be oriented substantially on a radial line emanating from the x-ray source. That is, each blade and opening can be focally aligned. The blades also can be radially aligned with the x-ray source. That is, each blade can be equidistant from the x-ray source. Scattered x-rays, that is, x-rays diverted from radial lines, can be attenuated by the blades. The attenuating wires can be oriented substantially perpendicular to the blades. The wires and blades thus can form a two-dimensional shielding grid for attenuating scattered x-rays and shielding the detector array.

At least one embodiment of the invention can include a feature that provides any of at least 5 functions: 1) separation of the collimator by a predetermined distance from an array of radiation detection elements; 2) alignment of the collimator to the array of radiation detection elements (or vice versa); 3) attachment of the collimator to the array of radiation detection elements; 4) attach the collimator to a gantry or other detector sub-assembly; and/or 5) align the collimator to a gantry or other detector sub-assembly.

As an illustrative example, one embodiment of such a feature could resemble "stilts" that can be formed independently or integrally to a collimator and that can separate the collimator by a predetermined distance from an array of radiation detection elements. In another embodiment, one or more of the stilts could serve as an alignment pin to align the collimator with the array of radiation detection elements. In another embodiment, one or more of the stilts could include and/or interface with an attachment mechanism to attach the collimator to the array of radiation detection elements. For example, an end of a stilt could slide into, via an interference fit, a socket of the array of radiation detection elements. As example, a stilt could include a hemispherical protrusion that snaps into a corresponding hemispherical indentation in a socket of the array of radiation detection elements.

As another illustrative example, one embodiment of such a feature could invert the description of the previous paragraph by providing "holes" in the collimator that interface with "stilts" attached to or integral with the radiation detection elements.

As yet another illustrative example, an embodiment of the feature could be manifested in a collimator having an array of through-holes, each having a square cross-section. At one end of all or certain through-holes could be the feature, such as a groove that extends around a perimeter of the square through-hole. A radiation detection element could have a square outer perimeter that includes a lip having corresponding dimensions to the groove that allows the radiation detection element to snap into the through-hole of the collimator via an interference fit, thereby fixing the position of the radiation detection element with respect to the collimator, aligning the radiation detection element with the collimator, and attaching the radiation detection element to the collimator.

Moreover, a modular collection of radiation detection elements, potentially cast according to an embodiment, could attach to a collimator via one or more attachment features, any of which could be formed independently of, or integrally with, either the radiation detection module and/or the collimator.

Depending on the embodiment, the scatter collimator can include blades and wires, open air cells, and/or encapsulated cells. Certain exemplary embodiments can be fabricated as a true cross grid having septa in both radial and axial directions. The cross-grid structure can be aligned in the radial and axial directions or it can be rotated. Thus, the cross grid can be aligned in two orthogonal directions.

Depending on the grid design, it might not be practical and/or possible to remove the mold from the cast grid because of its shape or size, e.g., if very thin septa or severe undercuts are involved. In such cases, a material with a low x-ray absorptivity can be used for the mold and the final grid can be left encapsulated within the mold. Materials used for encapsulation can include, but are not limited to, polyurethanes, acrylics, foam, plastics etc.

Because certain exemplary embodiments can utilize photolithography in creating the laminated mold, great flexibility can be possible in designing the shape of the open cells. Thus, round, square, hexagonal, and/or other shapes can be incorporated. Furthermore, the cells do not all need to be identical (a "redundant pattern"). Instead, they can vary in size, shape, and/or location ("non-redundant" pattern) as desired by the designer. In addition, because of the precision stack lamination of individual layers that can be employed in fabricating the master, the cell shapes can vary in the third dimension, potentially resulting in focused, tapered, and/or other shaped sidewalls going through the cell.

Because the cell shape can vary in the third dimension (i.e. going through the cell), the septa wall shape can also vary. For example, the septa can have straight, tapered, focused, bulging, and/or other possible shapes. Furthermore, the septa do not all need to be identical (a "redundant pattern"). Instead, they can vary in cross-sectional shape ("non-redundant" pattern) as desired by the designer.

Certain exemplary embodiments can provide a collimator or section of a collimator as a single cast piece, which can be inherently stronger than either a laminated structure or an assembly of precisely machined individual pieces. Such a cast collimator can be designed to withstand any mechanical damage from the significant g-forces involved in the gantry structure that can rotate as fast as 4 revolutions per second. Furthermore, such a cast structure can be substantially physically stable with respect to the alignment between collimator cells and detector elements.

Some exemplary embodiments can provide a collimator or section of a collimator as a single cast collimator in which cells and/or cell walls can be focused in the radial direction, and/or in which cells and/or cells walls can be accurately aligned in the axial direction.

Conversely, certain exemplary embodiments can provide a collimator or section of a collimator as a single cast collimator in which cells and/or cell walls can be focused (by stacking layers having slightly offset openings) in the axial direction, and/or in which cells and/or cells walls can be curved (and focused) in the radial direction.

Exemplary embodiments can utilize any of a wide number of different materials to fabricate the scatter collimator. A specific application can result in any of the following materials being most appropriate, depending on, for example, the net density and the cell and septa size requirements. Lead or lead alloy alone can offer a density of 9-11 grams per cc;

Lead alloy can be loaded with a dense composite (e.g., tungsten, tantalum, and/or gold, etc.) powder to form a composite having a density of 12-15 grams per cc;

Polymer can be loaded with a dense composite (e.g., lead, tungsten, tantalum, and/or gold, etc.) powder to form a composite having a density of 8-9 grams per cc;

The cast grid made of lead alloy or any of the above combinations can be encapsulated in a low density polymer such that the transmission is minimally affected but scatter is significantly reduced.

In addition, certain embodiments can be employed to fabricate grids and/or collimators for which the mold can be pre-loaded with dense powder, followed by alloy or polymer. Alternatively, polymer or alloy can be pre-loaded with dense powder then injected into the mold. In certain embodiments, the casting can be removed from a flexible mold. In other embodiments, the mold can be dissolved or consumed to de-mold the casting. In certain embodiments, a master can be removed layer-by-layer from rigid mold. Alternatively, the lost wax approach can be used in which the model is dissolvable wax, dissolvable PMMA, dissolvable polyurethane, dissolvable high-resolution ceramic, and/or some other dissolvable material.

The above description and examples have covered a number of aspects of certain exemplary embodiments of the invention including, for example, cell size and shape, different materials and densities, planar and non-planar orientations, and focused and unfocused collimators.

Additional Embodiments—Nuclear Medicine (SPECT) Collimator and Detector Array

In conventional X-ray or CT examinations, the radiation is emitted by a machine and then passes through the patient's body. In nuclear medicine exams, however, a radioactive material is introduced into the patient's body (by injection, inhalation or swallowing), and is then detected by a machine, such as a gamma camera or a scintillation camera.

The camera can have a detector and means to compute the detected image. The detector can have at least one a scintillator crystal, which typically is planar. The scintillator can absorb the gamma radioactive radiation, and emit a luminous scintillation in response, which can be detected by an array of photomultiplier tubes of the detector. The computation means can determine the coordinates of a locus of interaction of the gamma rays in the scintillator, which can reveal the projected image of the body.

Because the radiation source in the patient can emit radiation omnidirectionally, a collimator can be located between the body and the scintillator. This collimator can prevent the transmission of those radioactive rays that are not propagating in a chosen direction.

Certain embodiments can be used to fabricate structures useful for nuclear medicine. For example, collimators used in nuclear medicine, including pinhole, parallel-hole, diverging, and converging collimators, can be fabricated according to one or more exemplary methods.

As another example, exemplary methods can be used to fabricate high precision, high attenuation collimators with design flexibility for hole-format, which can improve the performance of pixelated gamma detectors.

Figure 47:
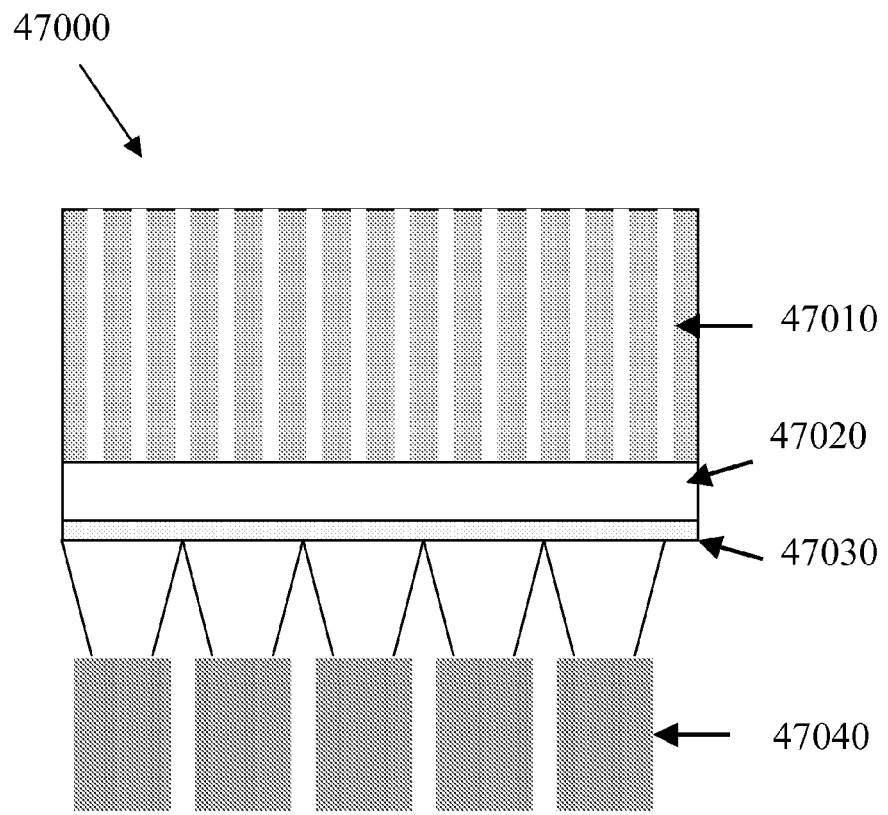
FIG. 47 is an assembly view of components of an exemplary pixilated gamma camera.

Certain exemplary embodiments of certain casting techniques can be applied to the fabrication of other components in detector systems. FIG. 47 is an assembly view of components of a typical pixelated gamma camera. Embodiments of certain casting techniques can be used to produce collimator 47010, scintillator crystals segmentation structure 47020, and optical interface 47030 between scintillator array (not visible) and photo-multiplier tubes 47040.

In an exemplary embodiment, collimator 47010 can be fabricated from lead, scintillator crystals segmentation structure 47020 can be fabricated from a ceramic, and optical interface 47030 can be fabricated from acrylic.

In certain exemplary embodiments, through the use of a common fabrication process, two or more of these components can be made to the same precision and/or positional accuracy. Moreover, two or more of these components can be designed to optimize and/or manage seams and/or dead spaces between elements, thereby potentially improving detector efficiency for a given choice of spatial resolution. For example, in a pixelated camera with non-matched detector and collimator, if the detector's open area fraction (the fraction of the detector surface that is made up of converter rather than inter-converter gap) is 0.75, and the collimator's open area fraction (the fraction of the collimator surface that is hole rather than septum) is 0.75, the overall open area fraction is approximately (0.75)=0.56. For a similar camera in which the collimator holes are directly aligned with the pixel converters, the open area fraction is 0.75, giving a 33% increase in detection efficiency without reduction in spatial resolution.

Certain embodiments can provide parallel hole collimators and/or collimators having non-parallel holes, such as fan beam, cone beam, and/or slant hole collimators. Because certain embodiments use photolithography in creating the master, flexibility is possible in designing the shape, spacing, and/or location of the open cells. For example, round, square, hexagonal, or other shapes can be incorporated. In addition, because certain embodiments use precision stack lamination of individual layers to fabricate a laminated mold, the cell shapes can vary in the third dimension, resulting in focused, tapered, and/or other shaped sidewalls going through the cell. Furthermore, the cells do not all need to be identical ("redundant"). Instead, they can vary in size, shape or location ("non-redundant") as desired by the designer, which in some circumstances can compensate for edge effects. Also, because a flexible mold can be used with certain embodiments, collimators having non-planar surfaces can be fabricated. In some cases, both surfaces are non-planar. However, certain embodiments also allow one or more surfaces to be planar and others non-planar if desired.

Certain embodiments can fabricate a collimator, or section of a collimator, as a single cast piece, which can make the collimator less susceptible to mechanical damage, more structurally stable, and/or allow more accurate alignment of the collimator with the detector.

Certain embodiments can utilize any of a number of different materials to fabricate a collimator or other component of an imaging system. A specific application could result in any of the following materials being chosen, depending, in the case of a collimator, on the net density and the cell and septa size requirements:

- Lead or lead alloy alone can offer a density of 9-11 grams per cc
- Polymer can be loaded with tungsten powder to form a composite having a density comparable to lead or lead alloys
- Polymer can also be combined with other dense powder composites such as tantalum or gold to yield a density comparable to lead or lead alloys
- Polymer can be combined with two or more dense powders to form a composite having a density comparable to lead or lead alloys
- Lead alloy can be loaded with tungsten powder to form a composite having a density of 12-15 grams per cc
- Lead alloy can be loaded with another dense composites (tantalum, gold, other) to form a composite having a density of 12-15 grams per cc
- Lead alloy can be combined with two or more dense powders to form composites having a density of 12-15 grams per cc (atomic number and attenuation)
- The cast grid made of lead alloy or any of the above combinations can be encapsulated in a low-density material such that the transmission is minimally affected but scatter is reduced.

Thus, depending on the specific application, certain embodiments can create any of a wide range of densities for the cast parts. For example, by adding tungsten (or other very dense powders) to lead alloys, net densities greater than that of lead can be achieved. In certain situations, the use of dense particles can provide high "z" properties (a measure of radiation absorption). For certain embodiments, as radiation absorption improves, finer septa walls can be made, which can increase imaging resolution and/or efficiency.

In addition, certain embodiments can be employed to fabricate grids and/or collimators for which the mold can be pre-loaded with dense powder, followed by alloy or polymer. Alternatively, polymer or alloy can be pre-loaded with dense powder then injected into the mold. In certain embodiments, the casting can be removed from a flexible mold. In other embodiments, the mold can be dissolved or consumed to de-mold the casting. In certain embodiments, a master can be removed layer-by-layer from rigid mold. Alternatively, the lost wax approach can be used in which the model is dissolvable wax, dissolvable PMMA, dissolvable polyurethane, dissolvable high-resolution ceramic, and/or some other dissolvable material.

With certain embodiments, the stack-laminated master does not need to embody the net density of the final grid. Instead, it can have approximately the same mechanical shape and size. Similarly, the final grid can be cast from relatively low cost materials such as lead alloys or polymers. Furthermore, these final grids can be loaded with tungsten or other dense powders. As discussed previously, using certain embodiments of the invention, multiple molds can be made from a single master and multiple grids can be cast at a time, if desired. Such an approach can lead to consistency of dimensions and/or geometries of the molds and/or grids.

Because of the inherent precision of the lithographic process, certain embodiments can prevent and/or minimize assembly build up error, including error buildup across the surface of the grid and/or assembly buildup error as can occur in collimators in which each grid is individually assembled from photo-etched layers. In addition, process errors can be compensated for in designing the laminated mold.

Example 6—Lead Collimator for Gamma Camera (Nuclear Medicine Application)

Step 1: Creating the Laminated Mold:

In this exemplary process, 0.05 mm thick copper foils were chemically etched and then laminated together using a metal-to-metal brazing process, for producing a laminated mold. Photo-masks were configured with a 2.0×2.0 millimeter square open cell, with a 0.170 mm septal wall separating the cells. The cells were arrayed having 10 rows and 10 columns, with a 2 mm border around the cell array. Photo-masks were produced to the same specifications, by the same vendor as those described in example 1, step 1.

Figure 42A:
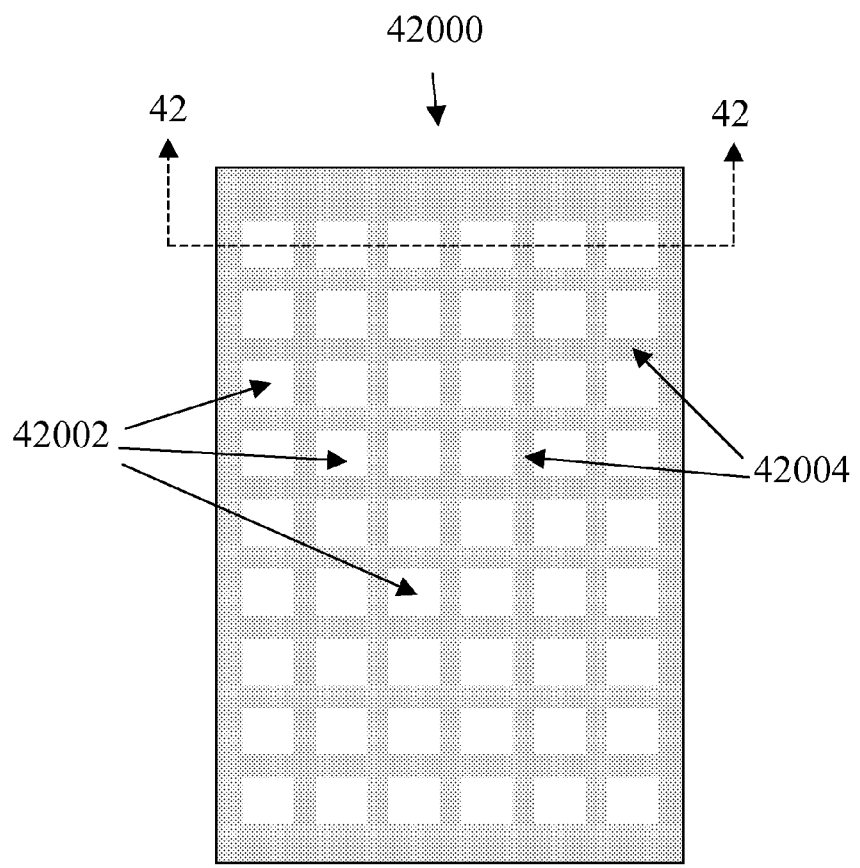
FIG. 42A is a top view of an exemplary laminated stack.
Figure 42B:
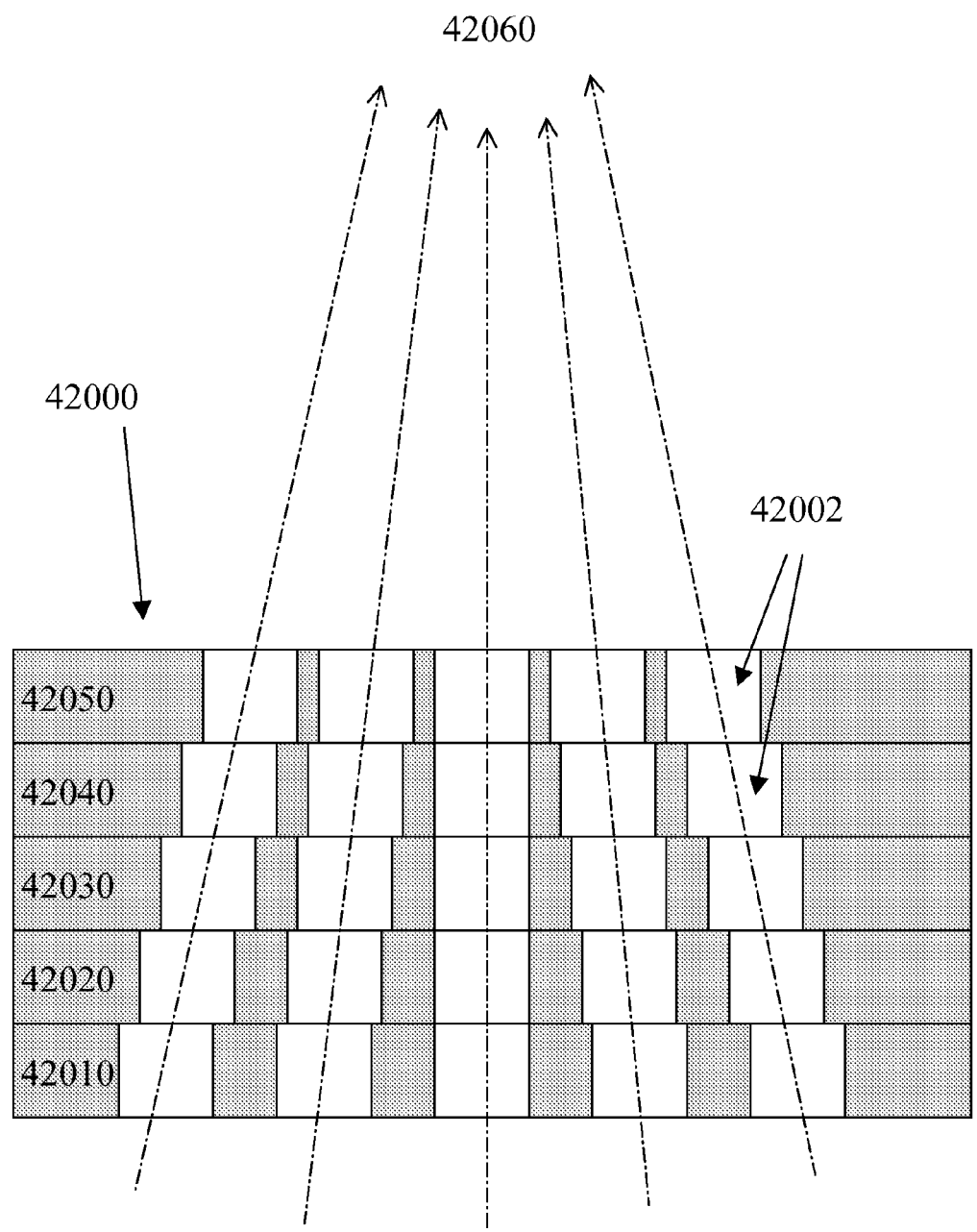
FIG. 42B is a cross-sectional view, taken at section lines 42-42 of FIG. 42A, of an exemplary laminated stack.

The layers were designed so that the cell placement was identical from layer to layer, which when assembled, produced a parallel cross-sectional shape. FIG. 42A is a top view of an x-ray grid 42000 having an array of cells 42002 separated by septal walls 42004. FIG. 42B is a cross-sectional view of x-ray grid 42000 taken along section lines 42-42 of FIG. 42B showing that the placement of cells 42002 can also be dissimilar from layer to layer 42010-42050, so that when assembled, cells 42002 are focused specifically to a point source 42060 at a known distance from x-ray grid 42000.

The total number of layers in the stack lamination defined the thickness of the casting mold and final cast grid. The final thickness of the lamination was specified at 0.118 inches, which required 57 layers of copper foil, leaving a total thickness amount of 0.00007 inches between each layer for a braze material. The layers were processed by Tech Etch of Plymouth Mass., using standard photo-etching techniques and were etched in such a way that the cross-sectional shape of the etched walls were perpendicular to the top and bottom surfaces of the foil (commonly referred to as straight sidewalls).

The method chosen to bond the grid layers together was a metal-to-metal brazing technique described earlier in detail as one of two exemplary methods of bonding layers together (eutectic braze alloy). The brazed lamination was then electro-plated with a coating of hard nickel, also described earlier.

Step 2: Creating a Derived Mold:

An RTV mold was made from the stack laminated mold from step 1. Silastic® M RTV Silicone Rubber was chosen as the base material for the derived mold. This particular material was used to demonstrate the resolution capability, release properties, multiple castings, and dimensional repeatability of the derived mold from the laminated mold. Silastic M has the hardest durometer of the Silastic® family of mold making materials. The derived mold was configured as an open face mold.

The fixture used to create the derived casting mold is shown in FIG. 32 and was comprised of a precision machined aluminum ring 32010, precision ground glass plates 32020 and 32030, rubber gaskets 32040 and 32050, and the laminated mold 32060. The base of the fixture 32020 was a 5 inch square of 1 inch thick Plexiglas. On the top surface of the Plexiglas base was a 1" thick, 3 inch diameter glass substrate 32030. The base and the glass substrate were separated by a 1/16 inch thick, 4.5 inch diameter rubber gasket 32040. An additional 3.0 inch rubber gasket 32050 was placed on the top surface of the glass substrate 32030. The rubber gaskets helped prevent unwanted flashing of molten material when casting. The laminated mold 32060 was placed on the top gasket.

The shape and thickness of the glass created the entrance area where the casting material was poured into the mold.

The material formed in this cavity was referred to as a controlled backing. It served as a release aid for the final casting, and could later be removed from the casting in a final machining process. A precision machined aluminum ring 32010 having a 4.5 inch outside diameter and a 4 inch inside diameter was placed over the master subassembly and interfaced with the lower 4.5 inch diameter rubber gasket.

As illustrated in FIG. 32, the height of the ring was configured so that the distance from the top surface of the master to the top of the ring was twice the distance from the base of the fixture to the top of the laminated mold. The additional height allowed the RTV material to rise up during the degassing process. The ring portion of the fixture assembly was used to locate the pouring of the mold material into the assembly, captivate the material during the curing process, and provide an air escape while the mold material was degassed using vacuum. The fixture was configured in such a way that all sides surrounding the laminated mold were equal and common, in order to limit the effects or stresses put on the lamination from the mold material.

The Silastic® M RTV Silicone Rubber used for the mold fabrication was prepared in accordance with the manufacturer's recommendations, using the process described earlier in example 1, step 2.

The laminated mold was characterized, before and after the mold-making process, by measuring the average pitch distance of the cells, the septal wall widths, overall distance of the open grid area, and the finished thickness of the part. These dimensions were also measured on the derived casting mold and compared with the laminated mold before and after the mold-making process. The following chart lists the dimensions of the lamination before and after the mold-making and the same dimensions of the derived RTV mold. All dimensions were taken using a Nikon MM-11 measuring scope at 200× magnification. These dimensions demonstrated the survivability of the master and the dimensional repeatability of the mold.

| Grid Feature | Master Lamination (before mold-making) | RTV Mold Silastic ® M | Master Lamination (after mold-making) |
| --- | --- | --- | --- |
| Septal Wall Width (mm) | 0.170 | 0.161 | 0.170 |
| Cell Width (mm) | 2.000 × 2.000 | 2.010 × 2.010 | 2.000 × 2.000 |
| Cell Pitch (mm) | 2.170 × 2.170 | 2.171 × 2.171 | 2.170 × 2.170 |
| Pattern area (mm) | 21.530 × 21.530 | 21.549 × 21.549 | 21.530 × 21.530 |
| Thickness (mm) | 2.862 | 2.833 | 2.862 |

Figure 43:
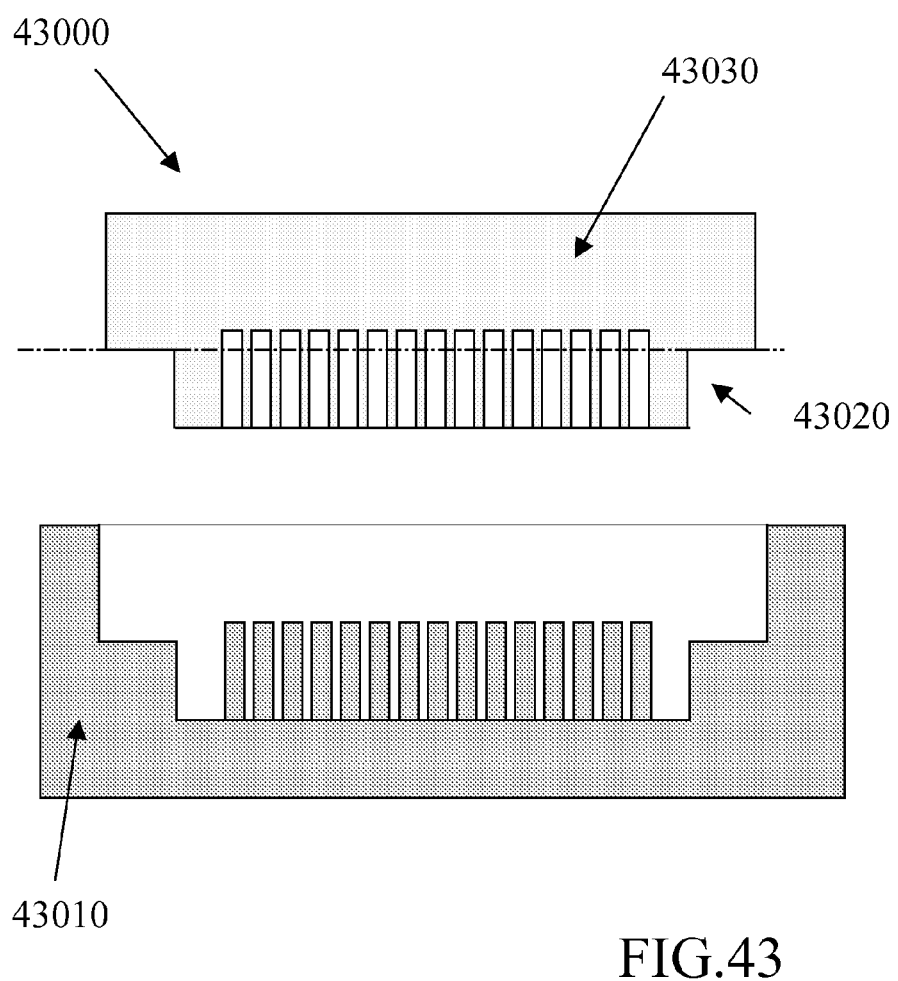
FIG. 43 is side view of an exemplary mold and casting.

Step 3: Casting the Final Collimator:

A fine-featured lead collimator was produced from the derived RTV silicone mold described in step 2. FIG. 43 is a side view of an assembly 43000 that includes an open face mold 43010 that was used to produce a casting 43020 from CERROBASE™ alloy. Casting 43020 was dimensionally measured and compared to the laminated mold 43010. The backing 43030 of casting 43020 was 6 millimeters in thickness and was removed using a machining process.

| Grid Features | Master Lamination | Cast Collimator |
| --- | --- | --- |
| Septal Wall Width (mm) | 0.170 | 0.165 |
| Cell Width (mm) | 2.000 × 2.000 | 2.005 × 2.005 |
| Cell Pitch (mm) | 2.170 × 2.170 | 2.170 × 2.170 |

The first step of the casting process was to pre-heat the derived RTV mold to a temperature of 275 degrees F., which was 20 degrees above the melting point of the CERROBASE™ alloy. The mold was placed on a heated aluminum substrate, which maintained the mold at approximately 275 degrees F. when it was placed in the vacuum bell jar.

In certain casting procedures, the material can be forced into the mold in a rapid fashion, and cooled and removed quickly. In this case, the casting process was somewhat slowed in order to fully fill and evacuate the air from the complex cavity geometry of the mold. The CERROBASE™ was then heated in an electric melting pot to a temperature of 400 degrees F., which melted the alloy sufficiently above its melt point to remain molten during the casting process.

The next step was to pour the molten alloy into the mold, in such a way as to aid in the displacement of any air in the cavity. This was accomplished by tilting the mold at a slight angle and beginning the pour at the lowest point in the cavity section of the mold. It was found that if the mold was placed in a flat orientation while pouring the molten alloy, significant amounts of air were trapped, creating problems in the degassing phase of the process. Instead, once the mold was sufficiently filled with the molten alloy, the mold was slightly vibrated or tapped in order to expel the largest pockets of air. The mold, on the heated aluminum substrate, was then placed in the vacuum bell jar, pumped down to atmosphere of 25-28 inches of mercury for 2 minutes, which was sufficient time to evacuate any remaining air pockets. The mold was then removed from the vacuum bell jar and submersed in a quenching tank filled with water cooled to a temperature of 50 degrees F. The rapid quench produced a fine crystalline grain structure when the casting material solidified. The casting was then removed from the flexible mold by grasping the backing 43030, by mechanical means or by hand, and breaking the casting free of the mold using an even rotational force, releasing the casting gradually from the mold.

The final process step was removing the backing 43030 from the attached surface of the grid casting 43020 to the line shown in FIG. 43. Prior to removing the backing, the grid structure of the final casting 43020 was filled or potted with a machinable wax, which provided the structural integrity needed to machine the backing without distorting the fine walls of the grid casting. The wax was sold under the product name MASTER™ Water Soluble Wax by the Kindt-Collins Corporation, of Cleveland, Ohio. The wax was melted at a temperature of 160-180 degrees F., and poured into the open cells of the cast grid. Using the same technique described above, the wax potted casting was placed in vacuum bell jar and air evacuated before being cooled. The wax was cooled to room temperature and was then ready for the machining of the backing.

A conventional surface grinder was used to first rough cut the backing from the lead alloy casting. The remaining casting was then placed on a lapping machine and lapped on the non-backing side of the casting using a fine abrasive compound and lapping wheel. The non-backing side of the casting was lapped first so that the surface was flat and parallel to within 0.010-0.015 millimeters to the adjacent cast grid cells. The rough-cut backing surface was then lapped using the same abrasive wheel and compound so that it was flat and parallel to within 0.100-0.015 millimeters of the non-backing side of the casting. A thickness of 2.750 millimeters was targeted as the final casting thickness. Upon completion of the lapping process, the casting was placed in an acid solution, comprised of 5% dilute HCl and water, with mild agitation until the wax was fully dissolved from the cells of the casting.

In an alternative embodiment, individual castings could also be stacked, aligned, and/or bonded to achieve thicker, higher aspect ratio collimators. Such collimators, potentially having a thicknesses measured in centimeters, can be used in nuclear medicine.

Example 7—Non-Planar Collimator

A non-planar collimator can have several applications, such as, for example, in a CT environment. To create such an example of such a collimator, the following process was followed:

Step 1: Creating a Laminated Mold:

For this example, a laminated mold was designed and fabricated using the same process and vendors described in Example 1, step 1. The laminated mold was designed to serve as the basis for a derived non-planar casting mold. The laminated mold was designed and fabricated with outside dimensions of 73.66 mm×46.66 mm, a 5 mm border around a grid area having 52×18 open cell array. The cells were 1 mm×1.980 mm separated by 0.203 septal walls.

The layers for the laminated mold were bonded using the same process described in Example 1, step 1 (thermo-cured epoxy). The dimensions of the laminated mold were specified to represent a typical collimator for CT x-ray scanning. Silastic® J RTV Silicone Rubber was chosen as a base material to create a derived non-planar casting mold because of its durometer which allowed it to more easily be formed into a non-planar configuration. The laminated mold and fixture was configured as an open face mold.

Figure 44:
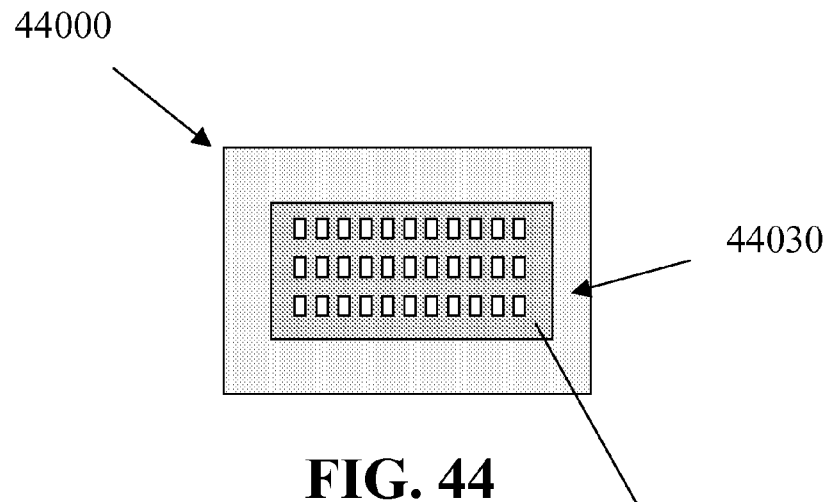
FIG. 44 is a top view of an exemplary casting fixture.
Figure 45:
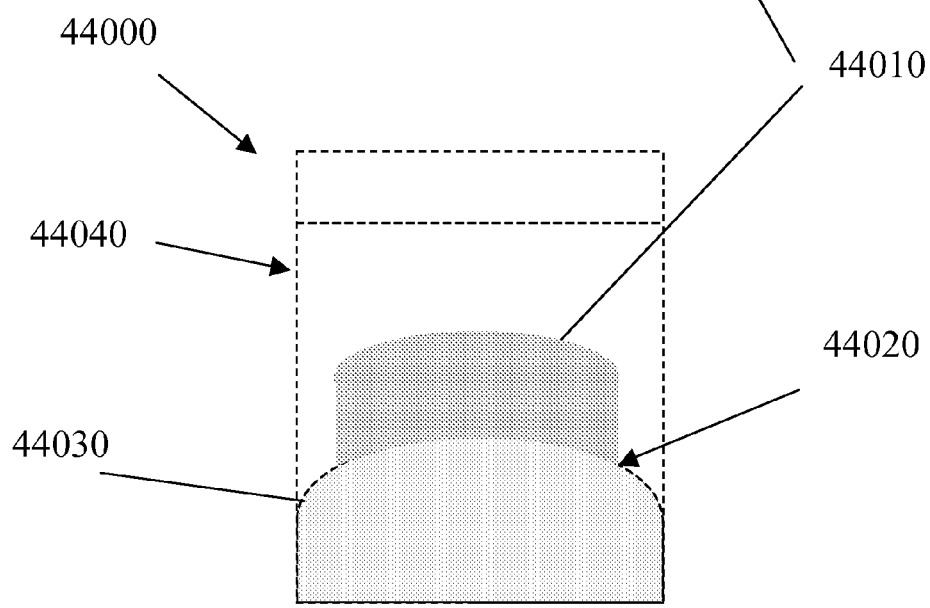
FIG. 45 is a front view of the exemplary casting fixture of FIG. 44.

Step 2: Creating a Derived Non-Planar Mold:

Silastic® J RTV Silicone Rubber was used for the derived mold fabrication and was prepared in accordance with the manufacturers recommendations, using the process described earlier in example 1, step 2. FIG. 44 is a top view of casting assembly 44000. FIG. 45 is a side view of casting assembly 44000.

The derived RTV mold 44010 was then formed into a non-planar configuration as shown in FIG. 45. The surface 44020 of casting fixture base 44030 defined a 1-meter radius arc to which mold 44010 was attached. A 1-meter radius was chosen because it is a common distance from the x-ray tube to the collimator in a CT scanner. Mold 44010 was fastened to the convex surface 44020 of casting base 44030 with a high temperature epoxy adhesive. A pour frame 44040 was placed around casting fixture base 44030. Pour frame 44040 had an open top to allow pouring the casting material to a desired fill level and to allow evacuating the air from the casting material.

The laminated mold was characterized, before and after producing the derived non-planar mold, by measuring the average pitch distance of the cells, the septal wall widths, overall distance of the open grid area, and the finished thickness of the part. These dimensions were also measured on the derived non-planar mold and compared with the master before and after the mold-making process. The following chart lists the dimensions of the master lamination before and after the mold-making and the same dimensions of the RTV mold in the planar state and curved state. All dimensions are in millimeters and were taken using a Nikon MM-11 measuring scope at 200× magnification.

| Grid Features | Master Lamination (before mold-making) | RTV Mold (planar) Silastice ® J | RTV Mold (curved) Silastice ® J |
|---|---|---|---|
| Septal Wall | 0.203 | 0.183 | 0.193* |
| Cell Width | 1.980 × 1.000 | 2.000 × 1.020 | 2.000 × 1.020 |
| Cell Pitch | 2.183 × 1.203 | 2.183 × 1.203 | 2.183 × 1.213 |
| Pattern area | 39.091 × 62.353 | 39.111 × 62.373 | 39.111 × 62.883 |
| Thickness | 7.620 | 7.544 | 7.544 |

*measured in the direction of curvature.

Step 3: Casting a Non-Planar Collimator:

The derived non-planar RTV mold described in step 2, was used to create castings. Using the derived non-planar mold, the castings were produced from CERROBASE™ alloy and were dimensionally measured and compared to the laminated mold.

| Grid Features | Master Lamination | Cast Collimator |
|---|---|---|
| Septal Wall Width (mm) | 0.203 | 0.197 * |
| Cell Width (mm) | 1.000 × 1.980 | 1.006 × 1.986 |
| Cell Pitch (mm) | 1.203 × 2.183 | 1.203 × 2.183 |

* measured in the direction of curvature.

The process used to fill the derived non-planar mold with the casting alloy and the de-molding of the casting was the same process described in Example 6.

The final process step included the removal of the backing from the grid casting. A wire EDM (electrode discharge machining) process was found to be the most effective way to remove the backing from the casting, primarily due to the curved configuration of the casting. The wire EDM process used an electrically charged wire to burn or cut through the casting material, while putting no physical forces on the parts. In this case, a fine 0.003 inch molybdenum wire was used to cut the part, at a cutting speed of 1 linear inch per minute. This EDM configuration was chosen to limit the amount of recast material left behind on the cut surface of the part, leaving the finished septal walls with a smooth surface finish. The casting was fixtured and orientated so that the radial cutting of the backing was held parallel to the curved surface of the casting, which was a 1 meter radius.

Example 8—Mammography Scatter Reduction Grid

Another exemplary application of embodiments is the fabrication of a mammography scatter reduction grid. In this example, a derived clear urethane mold for a fine-featured focused grid was made using a photo-etched stack lamination for the master model. For making this mold, the master was designed and fabricated using the lamination process detailed in Example 7. A clear urethane casting material was chosen as an example of a cast grid in which the mold was left intact with the casting as an integral part of the grid structure. This provided added strength and eliminated the need for a fragile or angled casting to be removed from the mold.

Figure 46:
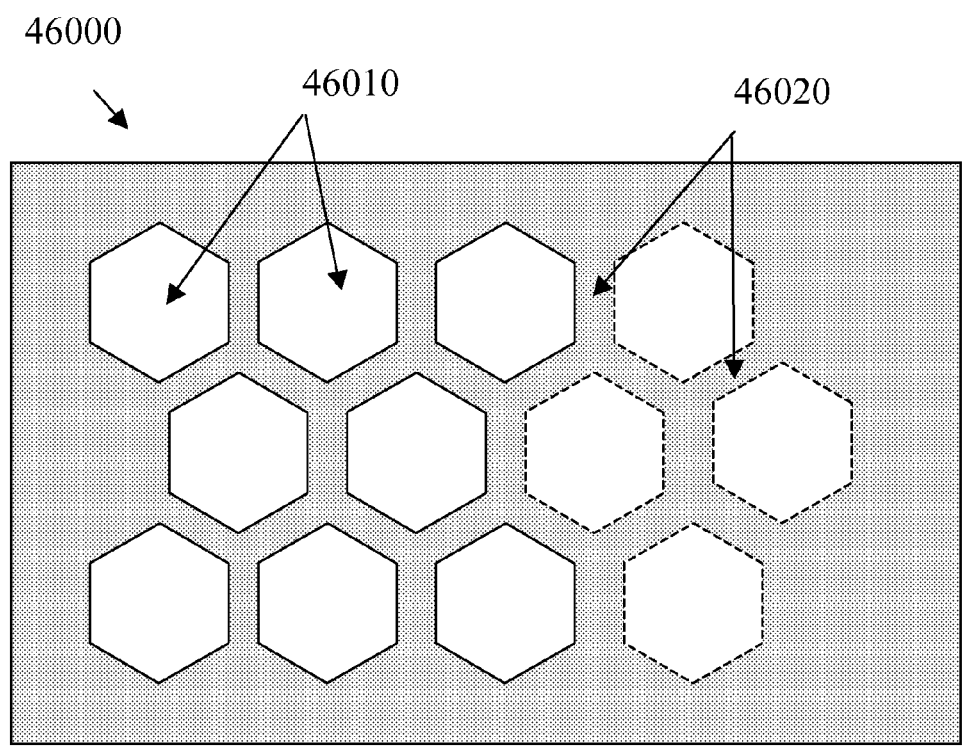
FIG. 46 is a top view of a portion of an exemplary grid pattern.

Step 1: Creating a Laminated Mold:

The laminated mold was fabricated from photo-etched layers of copper. The mold was designed to have a 63 mm outside diameter, a 5 mm border around the outside of the part, and a focused 53 mm grid area. FIG. 46 is a top view of a grid area 46000, which was comprised of hexagonal cells 46010 that were 0.445 mm wide, separated by 0.038 mm septal walls 46020. The cells were focused from the center of the grid pattern to a focal point of 60 centimeters, similar to that shown in FIG. 42B. The grid was made from 35 layers of 0.050 mm thick stainless steel, which when assembled created a 4:1 grid ratio. Each grid layer utilized a separate photo-mask in which the cells are arrayed out from the center of the grid pattern at a slightly larger distance from layer to layer. This created the focused geometry as shown in FIG. 42B. With this cell configuration, the final casting produced a hexagonal focused grid with a transmission of about 82%. The photo-masks and etched layers were produced using the same vendors and processes described in example 1, step 1.

Step 2: Creating a Derived Urethane Mold:

Urethane mold material was chosen for its high-resolution, low shrink factor, and low density. Because of its low density, the urethane is somewhat transparent to the transmission of x-rays. The mold material, properties, and process parameters were as described earlier in example 4, step 4.

The fixture used to create the derived urethane casting mold was the same as that described in Example 6, step 2.

Before assembling the mold fixture, the laminated mold was sprayed with a mold release, Stoner E236. The fixture was assembled as shown in FIG. 32 and heated to 125 degrees F. Then it was filled with the Water Clear urethane and processed using the same parameters described in example 4, step 4. The laminated mold was characterized, before and after making the derived mold, by measuring the average pitch distance of the cells, the septal wall widths, overall distance of the open grid area, and the finished thickness of the lamination. These dimensions were also measured on the derived urethane casting mold and compared with the lamination before and after the mold-making process. The following chart lists the dimensions of the lamination before and after the mold-making and the same dimensions of the urethane mold. All dimensions were in millimeters and were taken using a Nikon MM-11 measuring scope at 200× magnification.

| Grid Features | Master Lamination (before mold-making) | Urethane Casting System Water Clear | Master Lamination (after mold-making) |
| --- | --- | --- | --- |
| Septal Wall Width | 0.038 | 0.037 | 0.038 |
| Cell Width | 0.445 (hexagonal) | 0.446 (hexagonal) | 0.445 (hexagonal) |
| Cell Pitch | 0.483 | 0.483 | 0.483 |
| Pattern area (mm2) | 53.000 | 52.735 | 53.000 |
| Thickness | 1.750 | 1.729 | 1.750 |

Step 3: Casting the Anti-Scatter Grid:

A focused scatter reduction grid was produced by casting a lead alloy, CERROLOW-117™ alloy into the derived urethane mold described in step 2. The backing thickness of the casting was 2 millimeters and was removed using a surface grinding process.

The first step of the process was to pre-heat the derived urethane mold to a temperature of 137 degrees F., which was 20 degrees above the 117 degree melting point of the CERROLOW™ alloy. The mold was placed on a heated aluminum substrate, which maintained the mold to approximately 117 degrees F. when it was placed in the vacuum bell jar. The CERROLOW™ was then heated in an electric melting pot to a temperature of 120 degrees F., which melted the alloy sufficiently above the melt point of the material, keeping the material molten during the casting process. The process steps for filling the mold were the same as those described in Example 6, step 3.

The CERROLOW™ alloy was chosen for casting because of its high resolution capability, low melting point, and relatively high density. The urethane mold was left remaining to provide structural integrity for the fine lead alloy features. The urethane is also somewhat transparent to x-rays because of its low density (1 g/cm3) compared to the casting alloy.

Example 9—Collimator with Tungsten Loaded Alloy (Variation of Example 6)

Additional collimator samples have been produced using the same process described in Example 6 above, with the exception of the casting alloy and that it was loaded with tungsten powder prior to the casting process. The tungsten powder (KMP115) was purchased through the Kulite Tungsten Corporation of East Rutherford, N.J. CERROLOW™ alloy was loaded to raise the net density of the alloy from a density of 9.16 grams per cubic centimeter to 13 grams per cubic centimeter.

In certain radiological applications, elimination of secondary scattered radiation, also known as Compton scatter, and shielding can be an objective. The base density of the CERROLOW™ alloy can be sufficient on its own to absorb the scattered radiation, but the presence of the tungsten particles in the septal walls can increase the density and improve the scatter reduction performance of the part. The casting was dimensionally measured and compared to the laminated mold used to create the derived RTV mold.

| Grid Features | Master Lamination | Cast Collimator |
| --- | --- | --- |
| Material | Copper | CERROLOW-117 Plus Tungsten Powder |
| Density (g/cc) | 8.96 | 12.50 |
| Septal Wall Width | 0.038 | 0.036 |

-continued

| Grid Features | Master Lamination | Cast Collimator |
| --- | --- | --- |
| Cell Width | 0.445 (hexagonal) | 0.447 (hexagonal) |
| Cell Pitch | 0.483 | 0.483 |

*all dimensions are in millimeters.

Prior to casting, the tungsten powder was loaded or mixed into the CERROLOW™ alloy. The first step was to super-heat the alloy to 2-3 times its melting point temperature (between 234-351 degrees F.), and to maintain this temperature. The tungsten powder, having particle sizes ranging from 1-15 microns in size, was measured by weight to 50% of the base alloy weight in a furnace crucible. A resin-based, lead-compatible soldering flux was added to the tungsten powder to serve as a wetting agent when combining the powder and the alloy. The resin flux was obtained from the Indium Corporation of America of Utica N.Y., under the name Indalloy Flux #5RMA.

The flux and the powder were heated to a temperature of 200 degrees F. and mixed together after the flux became liquid. The heated CERROLOW™ alloy and the fluxed powder then were combined and mixed using a high-shear mixer at a constant temperature of 220 degrees F. The net density of the alloy loaded with the powder was measured at 12.5 grams per cubic centimeter. The loaded alloy was molded into the derived RTV mold, and finished machined using the same process described in Example 6.

Example 10—Collimator Structure Cast from a Ceramic (Variation of Example 7)

This example demonstrates a structure that could be co-aligned with a cast collimator. The structure could be filled with detector materials, such as a scintillator, for pixilation purposes. Ceramic was chosen for high temperature processing of the scintillator materials, which are normally crystals.

Additional cast samples have been produced using a castable silica ceramic material using the same mold described in Example 7 above. The ceramic material, Rescor™-750, was obtained from the Cotronics Corporation of Brooklyn, N.Y. The ceramic material was prepared prior to casting per the manufacturer's instructions. This included mixing the ceramic powder with the supplied activator. Per the manufacturer's instructions, an additional 2% of activator was used to reduce the viscosity of the mixed casting ceramic, in order to aid in filling the fine cavity features of the mold.

The mold was filled and degassed using a similar process and the same mold and non-planar fixture as Example 7 above, covered with a thin sheet of plastic, and allowed to cure for 16 hours at room temperature. The ceramic casting then was removed from the RTV mold and post cured to a temperature of 1750 degrees F., heated at a rate of 200 degrees F. per hour. Post-curing increased the strength of the cast grid structure. The ceramic casting then was ready for the final grinding and lapping process for the removal of the backing.

Additional Fields of Use

Additional exemplary fields of use, illustrative functionalities and/or technology areas, and representative cast devices are contemplated for various embodiments of the invention, as partially listed below. Note that any such device, and many others not specifically listed, can utilize any aspect of any embodiment of the invention as disclosed herein to provide any of the functionalities in any of the fields of use. For example, in the automotive industry, inertial measurement can be provided by an accelerometer, at least a component of which that has been fabricated according to a method. Likewise, in the telecommunications field, one or more components of an optical switch, and possibly an entire optical switch, can be fabricated according to a method.

Embodiments of such devices can provide any of a number of functionalities, including, for example, material, mechanical, thermal, fluidic, electrical, magnetic, optical, informational, physical, chemical, biological, and/or biochemical, etc. functionalities. Embodiments of such devices can at least in part rely on any of a number of phenomena, effects, and/or properties, including, for example, electrical, capacitance, inductance, resistance, piezoresistance, piezoelectric, electrostatic, electrokinetic, electrochemistry, electromagnetic, magnetic, hysteresis, signal propagation, chemical, hydrophilic, hydrophobic, Marangoni, phase change, heat transfer, fluidic, fluid mechanical, multiphase flow, free surface flow, surface tension, optical, optoelectronic, electro-optical, photonic, wave optic, diffusion, scattering, interference, diffraction, reflection, refraction, absorption, adsorption, mass transport, momentum transport, energy transport, species transport, mechanical, structural dynamic, dynamic, kinematic, vibration, damping, tribology, material, bimetallic, shape memory, biological, biochemical, cell transport, electrophoretic, physical, Newtonian, non-Newtonian, linear, non-linear, and/or quantum, etc. phenomena, effects, and/or properties.

Moreover, note that unless stated otherwise, any device, discrete device component, and/or integrated device component fabricated according to any method disclosed herein can have any dimension, dimensional ratio, geometric shape, configuration, feature, attribute, material of construction, functionality, and/or property disclosed herein.

Among the many contemplated industries and/or fields of use are:
Aerospace
Automotive
Avionics
Biotechnology
Chemical
Computer
Consumer Products
Defense
Electronics
Manufacturing
Medical devices
Medicine
Military
Optics
Pharmaceuticals
Process
Security
Telecommunications
Transportation
Among the many contemplated technology areas are:
Acoustics
Active structures and surfaces
Adaptive optics
Analytical instrumentation
Angiography
Arming and/or fusing
Bio-computing
Bio-filtration
Biomedical imaging
Biomedical sensors
Biomedical technologies
Cardiac and vascular technologies
Catheter based technologies
Chemical analysis
Chemical processing
Chemical testing
Communications
Computed tomography
Computer hardware
Control systems
Data storage
Display technologies
Distributed control
Distributed sensing DNA assays
Electrical hardware
Electronics
Fastener mechanisms
Fluid dynamics
Fluidics
Fluoroscopy
Genomics
Imaging
Inertial measurement
Information technologies
Instrumentation
Interventional radiography
Ion source technologies
Lab-on-a-chip
Measurements
Mechanical technologies
Medical technologies
Microbiology
Micro-fluidics
Micro-scale power generation
Non-invasive surgical devices
Optics
Orthopedics
Power generation
Pressure measurement
Printing
Propulsion
Proteomics
Radiography
RF (radio frequency) technologies
Safety systems
Satellite technologies
Security technologies
Signal analysis
Signal detection
Signal processing
Surgery
Telecommunications
Testing
Tissue engineering
Turbomachinery
Weapon safeing
Among the many contemplated cast devices and/or cast device components are at least one:
   accelerometer
   actuator
   airway
   amplifier
   antenna
   aperture
   application specific microinstrument
   atomizer
   balloon catheter
   balloon cuff
   beam
   beam splitter
   bearing
   bioelectronic component
   bio-filter
   biosensor
   bistable microfluidic amplifier
   blade passage
   blower
   bubble
   capacitive sensor
   capacitor
   cell sorting membrane
   chain
   channel
   chromatograph
   clip
   clutch
   coextrusion
   coil
   collimator
   comb
   comb drive
   combustor
   compression bar
   compressor
   conductor
   cooler
   corrosion sensor
   current regulator
   density sensor
   detector array
   diaphragm
   diffractive grating
   diffractive lens
   diffractive phase plate
   diffractor
   diffuser
   disc
   display
   disposable sensor
   distillation column
   drainage tube
   dynamic value
   ear plug
   electric generator
   electrode array
   electronic component socket
   electrosurgical hand piece
   electrosurgical tubing
   exciter
   fan
   fastener
   feeding device
   filter
   filtration membrane
   flow passage
   flow regulator
   fluid coextrusion
   fluidic amplifier
   fluidic oscillator
   fluidic rectifier
   fluidic switch
   foil
   fuel cell
   fuel processor
   fuse
   gear
   grating
   grating light valve
   gyroscope
   hearing aid
   heat exchanger
   heater
   high reflection coating
   housing
   humidity sensor
   impeller
   inducer inductor
infra-red radiation sensor
infusion sleeve
infusion test chamber
interferometer
introducer sheath
introducer tip
ion beam grid
ion deposition device
ion etching device
jet
joint
lens
lens array
lenslet
link
lock
lumen
manifold
mass exchanger
mass sensor
membrane
microbubble
microchannel plate
microcombustor
microlens
micromirror
micromirror display
microprism
microrelay
microsatellite component
microshutter
microthruster
microtiterplate
microturbine
microwell
mirror
mirror display
mixer
multiplexer
nozzle
optical attenuator
optical collimator
optical switch
ordinance control device
ordinance guidance device
orifice
phase shifter
photonic switch
pin array
plunger
polarizer
port
power regulator
pressure regulator
pressure sensor
printer head
printer head component
prism
processor
processor socket
propeller
pump
radiopaque marker
radiopaque target
rate sensor
reaction chamber
reaction well
reactor
receiver
reflector
refractor
regulator
relay
resistor
resonator
RF switch
rim
safe-arm device
satellite component
scatter grid
seal
septum
shroud
shunt
shutter
spectrometer
stent
stopper
supercharger
switch
tank
temperature regulator
temperature sensor
thruster
tissue scaffolding
titerplate
transmission component
transmitter
tunable laser
turbine
turbocharger
ultra-sound transducer
valve
vane
vessel
vibration sensor
viscosity sensor
voltage regulator
waveplate
well
wheel
wire coextrusion Additional detailed examples of some of the many possible embodiments of devices and/or device components that can be fabricated according to a method are now provided. Additional potential embodiments of these and/or other herein-described devices and/or device components are described in one or more of U.S. Patent and/or Patent Applications US2001/0031531, US2001/0034114, U.S. Pat. Nos. 408,677, 460,377, 1,164,987, 3,379,812, 3,829,536, 4,288,697, 4,356,400, 4,465,540, 4,748,328, 4,801,379, 4,812,236, 4,825,646, 4,856,043, 4,951,305, 5,002,889, 5,043,043, 5,147,761, 5,150,183, 5,190,637, 5,206,983, 5,252,881, 5,378,583, 5,447,068, 5,450,751, 5,459,320, 5,483,387, 5,551,904, 5,576,147, 5,606,589, 5,620,854, 5,638,212, 5,644,177, 5,681,661, 5,692,507, 5,702,384, 5,718,618, 5,721,687, 5,729,585, 5,763,318, 5,773,116, 5,778,468, 5,786,597, 5,795,748, 5,814,235, 5,814,807, 5,836,150, 5,849,229, 5,851,897, 5,924,277, 5,929,446, 5,932,940, 5,949,850, 5,955,801, 5,955,818, 5,962,949, 5,963,788, 5,985,204, 5,994,801, 5,994,816, 5,998,260, 6,004,500, 6,011,265, 6,014,419, 6,018,422, 6,018,680, 6,055,899, 6,068,684, 6,075,840, 6,084,626, 6,088,102, 6,124,663, 6,133,670, 6,134,294, 6,149,160, 6,152,181, 6,155,634, 6,175,615, 6,185,278, 6,188,743, 6,197,180, 6,210,644, 6,219,015, 6,226,120, 6,226,120, 6,242,163, 6,245,487, 6,245,849, 6,250,070, 6,252,938, 6,261,066, 6,276,313, 6,280,090, 6,299,300, 6,307,815, 6,310,419, 6,314,887, 6,318,069, 6,318,849, 6,324,748, 6,328,903, 6,333,584, 6,333,584, 6,336,318, 6,338,199, 6,338,249, 6,340,222, 6,344,392, 6,346,030, 6,350,983, 6,360,424, 6,363,712, 6,363,843, 6,367,911, 6,373,158, 6,375,871, 6,381,846, 6,382,588, 6,386,015, 6,387,713, 6,392,187, 6,392,313, 6,392,524, 6,393,685, 6,396,677, 6,397,677, 6,397,793, 6,398,490, 6,404,942, 6,408,884, 6,409,072, 6,410,213, 6,415,860, 6,416,168, 6,433,657, 6,440,284, 6,445,840, 6,447,727, 6,450,047, 6,453,083, 6,454,945, 6,458,263, 6,462,858, 6,467,138, 6,468,039, 6,471,471, and/ or 6,480,320, each of which are incorporated by reference herein in their entirety to its fullest enabling extent permitted by law.

Figure 48A:
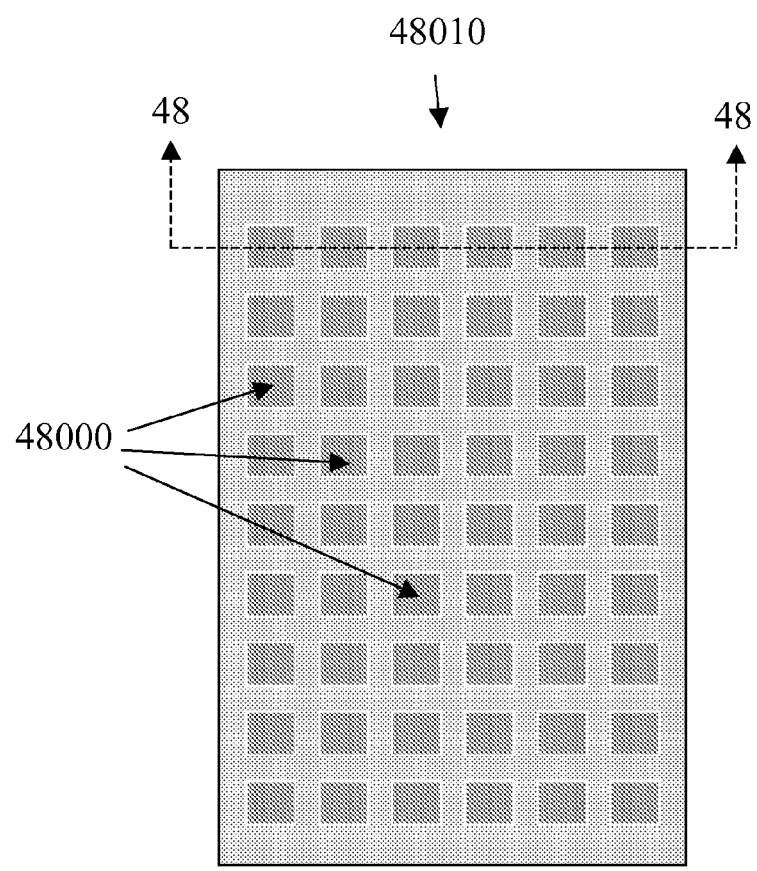
FIG. 48A is a top view of an array of generic microdevices.
Figures 48B, 49:
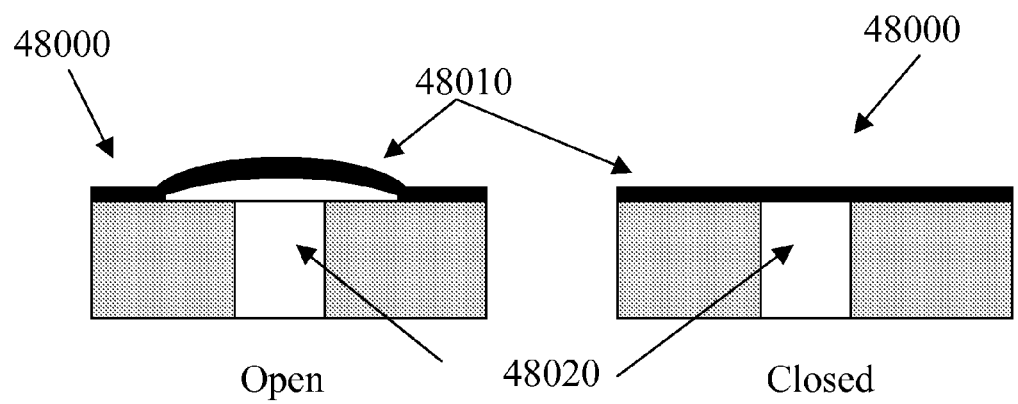
FIG. 48B is a cross-sectional view of an exemplary microdevice, taken at section lines 48-48 of FIG. 48A, in the open state.
FIG. 49 is a cross-sectional view of the exemplary microdevice of FIG. 48B, taken at section lines 48-48 of FIG. 48A, in the closed state.

Microvalves can be enabling components of many microfluidic systems that can be used in many industry segments. Microvalves are generally classified as passive or active valves, but can share similar flow characteristics through varied orifice geometries. Diaphragm microvalves can be useful in many fluidic applications. FIG. 48A is a top view of an array 48010 of generic microdevices 48000. FIG. 48B is a cross section of a particular microdevice 48000 in this instance a diaphragm microvalve, taken along section lines 48-48 of FIG. 48A, the microvalve including diaphragm 48010 and valve seat 48020, as shown in the open position. FIG. 49 is a cross section of the diaphragm microvalve 48000, again taken along section lines 48-48 of FIG. 48A, the microvalve in the closed position.

The flow rate through diaphragm microvalve 48000 can be controlled via the geometric design of the valve seat, which is often referred to as gap resistance. The physical characteristics of the valve seat, in combination with the diaphragm, can affect flow characteristics such as fluid pressure drop, inlet and outlet pressure, flow rate, and/or valve leakage. For example, the length, width, and/or height of the valve seat can be proportional to the pressure drop across the microvalve's diaphragm. Additionally, physical characteristics of the diaphragm can influence performance parameters such as fluid flow rate, which can increase significantly with a decrease in the Young's modulus of the diaphragm material. Valve leakage also can become optimized with a decrease in the Young's modulus of the diaphragm, which can enable higher deflection forces, further optimizing the valve's overall performance and/or lifetime.

Typical microvalve features and specifications can include a valve seat: The valve seat, which is sometimes referred to as the valve chamber, can be defined by its size and the material from which it is made. Using an exemplary embodiment of a method, the dimensions of the chamber can be as small as about 10 microns by about 10 microns if square, about 10 microns in diameter if round, etc., with a depth in the range of about 5 microns to millimeters or greater. Thus, aspect ratios of 50, 100, or 200:1 can be achieved. The inner walls of the chamber can have additional micro features and/or surfaces which can influence various parameters, such as flow resistance, Reynolds number, mixing capability, heat exchange fouling factor, thermal and/or electrical conductivity, etc.

The chamber material can be selected for application specific uses. As examples, a ceramic material can be used for high temperature gas flow, or a chemical resistant polymer can be used for chemical uses, and/or a biocompatible polymer can be used for biological uses, to name a few. Valve chambers can be arrayed over an area to create multi-valve configurations. Each valve chamber can have complex inlet and outlet channels and/or ports to further optimize functionality and/or provide additional functionality.

Typical microvalve features and specifications can also include a diaphragm: The diaphragm can be defined by its size, shape, thickness, durometer (Young's modulus), and/or the material from which it is made. Using an exemplary embodiment of a method, the dimensions of the diaphragm can be as small as about 25 microns by about 25 microns if square, about 25 microns in diameter if round, etc., with thickness of about 1 micron or greater. The surface of one side or both sides of the diaphragm could have micro features and/or surfaces to influence specific parameters, such as diaphragm deflection and/or flow characteristics. The diaphragm can be fabricated as a free form device that is attached to the valve in a secondary operation, and/or attached to a substrate. Diaphragms can be arrayed to accurately align to a matching array of valve chambers.

Potential performance parameters can include valve seat and diaphragm material, diaphragm deflection distance, inlet pressure, flow, and/or lifetime.

Micropumps

Figures 50, 51:
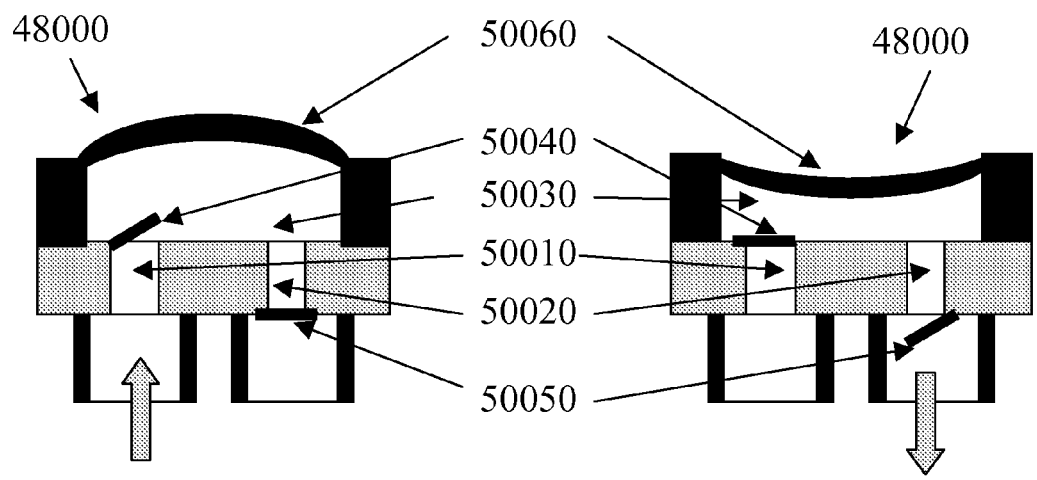
FIG. 50 is a cross-sectional view of an alternative exemplary microdevice, taken at section lines 48-48 of FIG. 48A, and shown with an inlet valve open.
FIG. 51 is a cross-sectional view of the alternative exemplary microdevice of FIG. 50, taken at section lines 48-48 of FIG. 48A, and shown with an outlet valve open.

FIGS. 50 and 51 are cross-sectional views of a particular micro-device 48000, in this case a typical simplified micropump, taken along section lines 48-48 of FIG. 48A. Micropumps can be an enabling component of many microfluidic systems that can be used in many industry segments. Reciprocating diaphragm pumps are a common pump type used in micro-fluidic systems. Micropump 50000 includes two microvalves 50010 and 50020, a pump cavity 50030, valve diaphragms 50040 and 50050, and actuator diaphragm 50060.

At the initial state of pump 50000, the actuation is off, both inlet and outlet valves 50010 and 50020 are closed, and there is no fluid flow through pump 50000. Once actuator diaphragm 50060 is moved upwards, the cavity volume will be expanded causing the inside pressure to decrease, which opens inlet valve 50010 and allows the fluid to flow into and fill pump cavity 50030, as seen in FIG. 50. Then actuator diaphragm 50060 moves downward, shrinking pump cavity 50030, which increases the pressure inside cavity 50030. This pressure opens outlet valve 50020 and the fluid flows out of the pump cavity 50030 as seen in FIG. 51. By repeating the above steps, continuous fluid flow can be achieved. The actuator diaphragm can be driven using any of various drives, including pneumatic, hydraulic, mechanical, magnetic, electrical, and/or piezoelectrical, etc. drives.

Typical microvalve features and specifications can include any of the following, each of which are similar to those features and specifications described herein under Microvalves:

Valve seats
Valve actuators (diaphragm)
Cavity chamber
Actuator diaphragm

Potential performance parameters can include valve seat, chamber material, actuator diaphragm material, valve diaphragm material, deflection distance for actuator, deflection distance for valve diaphragms, inlet pressure, outlet pressure, chamber capacity, flow rate, actuator drive characteristics (pulse width, frequency, and/or power consumption, etc.), and/or lifetime.

Microwells and Microwell Arrays

Microwells can be an enabling component in many devices used for micro-electronics, micro-mechanics, micro-optics, and/or micro-fluidic systems. Precise arrays of micro-wells, potentially having hundreds to thousands of wells, can further advance functionality and process capabilities. Microwell technology can be applied to DNA microarrays, protein micro-arrays, drug delivery chips, microwell detectors, gas proportional counters, and/or arterial stents, etc. Fields of use can include drug discovery, genetics, proteomics, medical devices, x-ray crystallography, medical imaging, and/or bio-detection, to name a few.

For example, using exemplary embodiments, microwells can be engineered in the third (Z) dimension to produce complex undercuts, pockets, and/or sub-cavities. Wells can also be arrayed over various size areas as redundant or non-redundant arrays. These features can include the dimensional accuracies and/or tolerances described earlier. Also, a range of surface treatments within the well structure are possible that can enhance the functionality of the well.

Examples of Microwell applications:

DNA Microarrays:

Scientists can rely on DNA microarrays for several purposes, including 1) to determine gene identification, presence, and/or sequence in genotype applications by comparing the DNA on a chip; 2) to assess expression and/or activity level of genes; and/or 3) to measure levels of proteins in protein based arrays, which can be similar to DNA arrays.

DNA microarrays can track tens of thousands of reactions in parallel on a single chip or array. Such tracking is possible because each probe (a gene or shorter sequence of code) can be deposited in an assigned position within the cell array. A DNA solution, representing a DNA sample that has been chopped into constituent sequences of code, can be poured over the entire array (DNA or RNA). If any sequence of the sample matches a sequence of any probe, the two will bind, and non-binding sequences can be washed away. Because each sequence in the sample or each probe can be tagged or labeled with a fluorescent, any bound sequences will remain in the cell array and can be detected by a scanner. Once an array has been scanned, a computer program can convert the raw data into a color-coded readout.

Protein Microarrays:

The design of a protein array is similar to that of a DNA chip. Hundreds to thousand of fluorescently labeled proteins can be placed in specific wells on a chip. The proteins can be deposited on the array via a pin or array of pins that are designed to draw fluidic material from a well and deposit it on the inside of the well of the array. The position and configuration of the cells on the array, the pins, and the wells are located with the accuracy needed to use high-speed pick-and-place robotics to move and align the chip over the fluidic wells. A blood sample is applied to the loaded array and scanned for bio-fluorescent reactions using a scanner.

Certain embodiments of the invention enable DNA or Protein microarrays having a potentially large number of complex 3-dimensional wells to be fabricated using any of a range of materials. For example, structures can be fabricated that combine two or more types of material in a microwell or array. Additional functionality and enhancements can be designed into a chip having an array of microwells. Wells can be produced having cavities capable of capturing accurate amounts of fluids and/or high surface-to-volume ratios. Entrance and/or exit configurations can enhance fluid deposition and/or provide visual enhancements to scanners when detecting fluorescence reactions.

Very precise well locations can enable the use of pick and place robotics when translating chips over arrays of fluidic wells. Certain embodiments of the invention can include highly engineered pins and/or pin arrays that can be accurately co-aligned to well arrays on chips and/or can have features capable of efficiently capturing and/or depositing fluids in the wells.

Arterial Stents:

Stents are small slotted cylindrical metal tubes that can be implanted by surgeons to prevent arterial walls from collapsing after surgery. Typical stents have diameters in the 2 to 4 millimeter range so as to fit inside an artery. After insertion of a stent, a large number of patients experience restenosis—a narrowing of the artery—because of the build-up of excess cells around the stent as part of the healing process. To minimize restenosis, techniques are emerging involving the use of radioactive elements or controlled-release chemicals that can be contained within the inner or outer walls of the stent.

Certain embodiments of the invention can provide complex 3-dimensional features that can be designed and fabricated into the inside, outside, and/or through surfaces of tubing or other generally cylindrical and/or contoured surfaces. Examples 4 and 5 teach such a fabrication technique for a 3 mm tube. Certain embodiments of the invention can allow the manufacture of complex 2-dimensional and/or 3-dimensional features through the wall of a stent. Micro surfaces and features can also be incorporated into the stent design. For example, microwells could be used to contain pharmaceutical materials. The wells could be arrayed in redundant configurations or otherwise. The stent features do not have to be machined into the stent surface one at a time, but can be applied essentially simultaneously. From a quality control perspective, features formed individually typically must be 100% inspected, whereas features produced in a batch typically do not. Furthermore, a variety of application specific materials (e.g., radio-opaque, biocompatible, biosorbable, biodissolvable, shape-memory) can be employed.

Microwell Detectors:

Microwells and microwell arrays can be used in gas proportional counters of various kinds, such as for example, in x-ray crystallography, in certain astrophysical applications, and/or in medical imaging. One form of microwell detector consists of a cylindrical hole formed in a dielectric material and having a cathode surrounding the top opening and anode at the bottom of the well. Other forms can employ a point or pin anode centered in the well. The microwell detector can be filled with a gas such as Xenon and a voltage can be applied between the cathode and anode to create a relatively strong electric field. Because of the electric field, each x-ray striking an atom of the gas can initiate a chain reaction resulting in an "avalanche" of hundreds or thousands of electrons, thereby producing a signal that can be detected. This is known as a gas electron multiplier. Individual microwell detectors may be used to detect the presence and energy level of x-rays, and if arrays of microwell detectors are employed, an image of the x-ray source can be formed. Such arrays can be configured as 2-dimensional and/or 3-dimensional arrays.

Figure 52:
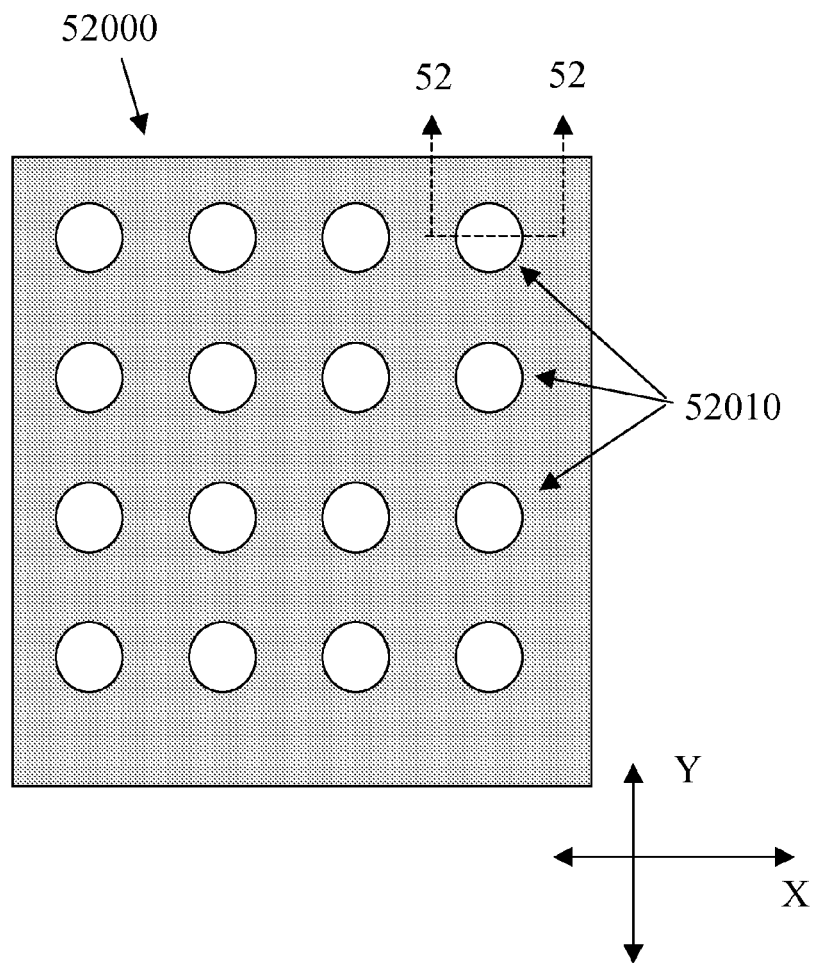
FIG. 52 is a top view of an exemplary microwell array.

Certain embodiments of the invention can enable arrays of complex 3-dimensional wells to be fabricated and bonded or coupled to other structures such as a cathode material and anode material. It is also possible to alter the surface condition of the vertical walls of the wells, which can enhance the laminar flow of electrons in the well. A number of possible materials can be used to best meet the needs of a particular application, enhancing parameters such as conductivity, die-electrical constant, and/or density. Certain embodiments of the invention can further enable the hybridizing of micro-electronics to a well array, in particular because of accurate co-alignment between the micro-electronic feature(s), and/or the structural elements of the well. Typical Microwell Features, Specifications and Potential Performance Parameters:

FIG. 52 is a top view of an exemplary microwell array 52000, showing microwells 52010, and the X- and Y-axes. Array 52000 is shown as rectangle, but could be produced as a square, circle, or any other shape. Either of the array's dimensions as measured along the X- or Y-axes can range from 20 microns to 90 centimeters. Microwells 52010 are shown having circular perimeters, but could also be squares, rectangles, or any other shape. Array 52000 is shown having a redundant array of wells 52010, but could be produced to have non-redundant wells. The positional accuracy of wells 52010 can be accurate to the specifications described herein for producing lithographic masks. Wells can range in size from 0.5 microns to millimeters, with cross-sectional configurations as described herein.

Using certain embodiments of a method, certain materials can be used to produce microwell arrays for specific uses. For example, a ceramic material can be used for high-temperature gas flow, a chemical resistant polymer can be used for chemical uses, and/or a bio-compatible polymer can be used for biological uses, to name a few. Specialty composite materials can enhance application specific functionality by being conductive, magnetic, flexible, hydrophilic, hydrophobic, piezoelectric, to name a few.

Using an embodiment of a method, microwells with certain 3-dimensional cross-sectional shapes can be produced. FIG. 52 is a top view of an exemplary array 52000 of microwells 52010.

FIG. 53 is a cross-sectional view, taken at section lines 52-52 of FIG. 52, of an exemplary microwell 53000 having an entrance 53010. Entrance 53010 is shown having a tapered angle, which could be angled from 0 degrees to nearly 180 degrees. Entrance 53010 is also shown having a different surface than well area 53020. Well area 53020 can be square, round, rectangular, or any other shape. Well area 53020 can range in size from 0.5 microns to millimeters in width and can be dimensionally controlled in the Z-axis to have aspect ratios of from about 50:1 to about 100:1. As shown in FIG. 53, microwell 53000 defines microwell surfaces 53050, 53060, 53070, 53080, 53090, 53100, 53110. As also shown in FIG. 53, a cross-sectional surface 53030 is defined that intersects microwell surfaces 53050, 53060, 53070, 53080, 53090, 53100, 53110. As further shown in FIG. 53, a central area and/or layer-less volume 53040 of cross-sectional surface 53030 comprises a majority of cross-sectional surface 53030, yet does not include any of microwell surfaces 53050, 53060, 53070, 53080, 53090, 53100, 53110, which define a periphery 53120 of central area and/or layer-less volume 53040 of microwell 53000.

FIG. 54 is a cross-sectional view, taken at section lines 52-52 of FIG. 52, of an alternative exemplary microwell 54000 that defines an entrance 54010, a well 54020, and an exit 54030. Microwell 54000 can be used in applications that require fluids that are conveyed from below or above the entrance 54010 and/or exit 54030, and deposited in well 54020. Using an embodiment of a method, microwell 54000 can be produced so that well 54020 is hydrophilic and entrance 54010 and exit 54030 are hydrophobic to, for example, enable the deposition of fluid into well 54020, and discourage the fluid deposition, retention, and/or accumulation on entrance 54010, on exit 54030, and/or on the chip's surface. For uses where microelectronic controls or chips are employed, the material surrounding and/or defining entrance 54010 and/or 54030 can be conductive or non-conductive, as required. Well 54020 can be dimensioned to accurately contain a pre-determined amount of fluid.

The shape and size of corner feature 54040 can be defined to encourage the discharge of a fluid material from a fluidic channel on a pin, when a pin is produced using any of certain embodiments of the invention. For example, pins can be produced having fluidic channels or undercuts that are positioned radially at the end of the pin. The undercuts can serve as reservoirs that increase surface area-to-volume ratios and/or hold accurate amounts of fluids. If the undercuts are designed to be relatively flexible and larger than the opening dimension at feature 54040, fluid can be squeezed from the reservoir as the fluid passes by corner feature 54040. Entrance 54010 can have an angle that promotes the visibility of a material, such as a fluid, in well 54020. The material surrounding and/or defining well 54020 can be fabricated to have micro-surface features to increase the well's surface area-to-volume ratio.

FIG. 55 is a top view of an exemplary microwell 55000 showing a well area 55010 and sub-cavities 55020. FIG. 56 is a cross-sectional view, taken at section lines 56-56 of FIG. 55, of microwell 55000 showing well 55010 and sub-cavities 55020. Well 55010 can extend through the material that defines it, as shown in FIG. 56, or can be a closed well having a solid floor. Sub-cavities 55020 can be incorporated within a well to, for example, increase an area of the surface(s) bordering the well, a volume, and/or surface area-to-volume ratio of the well. Sub-cavities 55020 can be continuous rings as shown in FIG. 55. Alternatively, sub-cavities 55020 can be discrete pockets forming sub-wells within well 55010. Sub-cavities 55020 can be positioned on a horizontal floor or subfloor of well 55010 as shown in FIG. 55, on the vertical walls of well 55010, and/or on another surface. Sub-cavities 55020 can have circular, square, rectangular, and/or any of a variety of other cross-sectional shapes. Sub-cavities 55020 can also be positioned to provide an enhanced visual perspective of a deposited material from which could be angled from 0 degrees to nearly 180 degrees, such as an approximately perpendicular angle, so as to enhance scanning performance or resolution.

Filtration

Filtration can be an important element in many industries including medical products, food and beverage, pharmaceutical and biological, dairy, waste water treatment, chemical processing, textile, and/or water treatment, to name a few. Filters are generally classified in terms of the particle size that they can separate. Micro-filtration generally refers to separation of particles in the range of approximately 0.01 microns through 20 microns. Separation of larger particles than approximately 10-20 microns is typically referred to as particle separation. There are two common forms of filtration, cross-flow and dead-end. In cross-flow separation, a fluid stream runs parallel to a membrane of a filter while in dead-end separation, the filter is perpendicular to the fluid flow. There are a very large number of different shapes, sizes, and materials used for filtration depending on the particular application.

Certain embodiments of the invention can be filters suitable for micro-filtration and/or particle filtration applications. Certain embodiments of the invention allow fabrication of complex 2-dimensional and/or 3-dimensional filters offering redundant or non-redundant pore size, shape, and/or configuration. For example, a circular filter can have an array of redundant generally circular through-features, each through-feature having a diameter slightly smaller than a target particle size. Moreover, the through-feature can have a tapered, countersunk, and/or undercut entrance, thereby better trapping any target particle that encounters the through-feature. Further, the cylindrical walls defined by the through-feature can have channels defined therein that are designed to allow a continued and/or predetermined amount of fluid flow around a particle once the particle encounters the through-feature. The fluid flow around the particle can create eddys vortices, and/or other flow patterns that better trap the particle against the filter.

Certain embodiments of the filter can have features that allow the capture of particles of various sizes at various levels of the filter. For example, an outer layer of the filter can capture larger particles, a middle layer can capture mid-sized particles, and a final layer can capture smaller particles. There are numerous techniques for accomplishing such particle segregation, including providing through-features having tapered, stepped, and/or diminishing cross-sectional areas.

In certain embodiments, the filter can include means for detecting a pressure drop across the filter, and/or across any particular area, layer, and/or level of the filter. For example, in a filter designed to filter a gas such as air, micro pitot tubes can be fabricated into each layer of the filter (or into selected layers of the filter). Such pressure measurement devices can be used to determine the pressure drop across each layer, to detect the level of "clogging" of that layer, and/or to determine what size and/or concentration of particles are entrapped in the filter.

Further, certain embodiments of the invention allow for fabrication of filters in a wide range of materials including metals, polymers, plastics, ceramics, and/or composites thereof. In biomedical applications, for instance, a biocompatible material can be used that will allow filtration of blood or other body fluids. Using certain embodiments of the invention, filtration schemes can be engineered as planar or non-planar configurations.

Sorting

Sorting can be considered a special type of filtration in which particles, solids, and/or solids are separated by size. In biomedical applications for example, it may be desirable to sort blood or other types of cells by size and deliver different sizes to different locations. Certain embodiments of the invention can enable the fabrication of complex 3-dimensional structures that allow cells to be sorted by size (potentially in a manner similar to that discussed herein for filters) and/or for cells of different sizes to be delivered through different size micro-channels or between complex 3-dimensional structures. Structures can be material specific and on planar or non-planar surfaces.

Membranes

Membranes can offer filtration via pore sizes ranging from nanometers to a few microns in size. Membrane filtration can be used for particles in the ionic and molecular range, such as for reverse osmosis processes to desalinate water. Membranes are generally fabricated of polymers, metals, or ceramics. Micro-filtration membranes can be divided into two broad types based on their pore structure. Membranes having capillary-type pores are called screen membranes, and those having so-called tortuous-type pores are called depth membranes.

Screen membranes can have nearly perfectly round pores that can be dispersed randomly over the outer surface of the membrane. Screen membranes are generally fabricated using a nuclear track and etch process. Depth membranes offer a relatively rough surface where there appear to be openings larger than the rated size pore, however, the fluid must follow a random tortuous path deeper into the membrane to achieve their pore-size rating. Depth membranes can be fabricated of silver, various cellulosic compounds, nylon, and/or polymeric compounds.

Certain embodiments of the invention enable fabrication of membranes having complex 3-dimensional shapes, sizes, and/or configurations made of polymers, plastics, metals, and/or ceramics, etc. Furthermore, such membranes can embody redundant or non-redundant pores, and can be fabricated to be flexible, rigid, and/or non-planar depending upon the material and/or application requirements.

Heaters

Certain exemplary embodiments can provide heaters and/or components thereof, potentially having high resolution and/or high aspect ratios. For example, an exemplary embodiment can provide a resistive heater having numerous wire, strip, and/or coil, etc. elements having substantially large length and/or width dimensions with respect to their thickness dimensions. Certain exemplary embodiments can provide heaters that utilize a Seebeck effect for heating.

Heat Exchangers

Certain exemplary embodiments can provide heat exchangers and/or components thereof, potentially having high resolution and/or high aspect ratios. For example, an exemplary embodiment can provide a heat exchanger having numerous "fins" or other surfaces having substantially large length and/or width dimensions with respect to their thickness dimensions, thereby providing relatively large surface area to volume ratios to facilitate heat transfer. Such heat exchangers can be used for heating and/or cooling of a target fluid and/or material. Also, exemplary embodiments can provide thin-walled tubular heat exchangers, having tubes that potentially incorporate "fins" and/or other heat transfer surfaces. Exemplary embodiments of fins and the like can have secondary features that can be useful for further increasing surface area, manipulating and/or optimizing flow, controlling fouling, etc. Certain exemplary embodiments can provide heat exchangers that utilize a Peltier, Seebeck, and/or Joule effect for cooling and/or heating.

Mass Exchangers

Certain exemplary embodiments can provide mass exchangers and/or components thereof, potentially having high resolution and/or high aspect ratios. For example, an exemplary embodiment can provide a mass exchanger having numerous "fins" or other surfaces capable of releasing an impregnated and/or bound material, and/or having receptors for receiving a target material. Each such fin can have substantially large length and/or width dimensions with respect to their thickness dimensions, thereby providing relatively large surface area to volume ratios to facilitate mass transfer. Another exemplary embodiment can provide a mass exchanger, such as pieces of packing, each having numerous surfaces and having a large surface area to volume ratio. Another exemplary embodiment can provide a mass exchanger, such as a static mixer having numerous fluid dividing/mixing surfaces. Exemplary embodiments of fins and the like can have secondary features that can be useful for further increasing surface area, manipulating and/or optimizing mass transfer, etc.

Surface Reactors

Certain exemplary embodiments can provide surface reactors and/or components thereof, potentially having high resolution and/or high aspect ratios. For example, an exemplary embodiment can provide a surface reactor having numerous "fins" or other surfaces comprising and/or bound to a material capable of reacting with a target material, and/or catalyzing such a reaction. Each such fin can have substantially large length and/or width dimensions with respect to their thickness dimensions, thereby providing relatively large surface area to volume ratios to facilitate higher reaction rates. Exemplary embodiments of fins and the like can have secondary features that can be useful for further increasing surface area, manipulating and/or optimizing reaction rates, controlling heating, cooling, mixing, and/or flow, etc.

Fuel Cells

Certain exemplary embodiments can provide a fuel cell having one or more discrete and/or integrated components such as a channel, manifold, separator, pump, valve, filter, heater, cooler, heat exchanger, mass exchanger, and/or surface reactor, etc., of any size and/or configuration. Such a fuel cell can be useful as a power cell, battery, charger, etc. For example, an embodiment of the invention can provide a fuel cell having a solid electrolyte disposed between an oxygen electrode and a fuel electrode, and one or more separators can contact the surface of one of the electrodes opposite of the electrolyte. At least one electrode of the cell can define a micro-channel pattern, wherein the micro-channel cross-section can be varied, such that reactant gas flowing through the micro channels can achieve tailored local flow, pressure, and/or velocity distributions. An exemplary embodiment of the invention can provide a proton exchange diffusion membrane fuel cell having a membrane and/or channels. An exemplary embodiment of the invention can provide a fluid fuel cell, such as a hydrogen fuel cell, proton exchange member, and/or a direct methanol fuel cell, utilizing one or more fluid mixers, mixing chambers, pumps, and/or recirculators.

Turbomachinery and Machinery

Certain exemplary embodiments can provide turbomachinery devices and/or components thereof, potentially having high resolution and/or high aspect ratios. For example, an exemplary embodiment can provide a microturbine having an impeller, rotor, blades, stages, seals, and/or nozzles, etc., any of which can high a high aspect ratio be formed from a material having a high strength, and/or be formed from a material having desired thermal performance capabilities, such as a ceramic. The microturbine can that can be coupled to a microgenerator for generating electrical power and/or can be used for generating thrust. Another exemplary embodiment can provide a microcombustion engine having free pistons magnetically coupled to electromagnets for control and power transfer.

Ion Beam Technologies

Certain exemplary embodiments can provide ion beam devices and/or components thereof, potentially having high resolution and/or high aspect ratios. For example, space propulsion, surface cleaning, ion implantation, and high energy accelerators use two or three closely spaced multiple-aperture electrodes to extractions from a source and eject them in a collimated beam. The electrodes are called "grids" because they are perforated with a large number of small holes in a regular array. A series of grids constitute an "ion optics" electrostatic ion accelerator and focusing system.

Ion Thrusters

On-board propulsion systems can be used to realize a variety of spacecraft maneuvers. In satellites, for example, these maneuvers include the processes of orbit raising (e.g., raising from a low Earth orbit to a geostationary orbit), stationkeeping (e.g., correcting the inclination, drift and eccentricity of a satellite's orbit) and attitude control (e.g., correcting attitude errors about a satellite's roll, pitch and yaw axes).

Certain exemplary embodiments can provide propulsion and/or micropropulsion devices and/or components potentially having high resolution and/or high aspect ratios. For example, an exemplary embodiment can provide an ion thruster, microthruster, Kaufman-type ion engine, and/or electric rocket engine that can be useful for maintaining the orbit and/or relative position of a geosynchronous satellite. Such a device can utilize an orifice, orifice array, and/or grid. In certain embodiments, an ion thruster grid can have a spherically-formed and/or domed screen pattern with, for example, a high resolution and/or high aspect ratio.

Ion beam sources designed for spacecraft propulsion, that is, ion thrusters, typically are preferred to have long lifetimes (10,000 hours or more), be efficient, and be lightweight. Ion thrusters have been successfully tested in space, and show promise for significant savings in propellant because of their high specific impulse (an order of magnitude higher than that of chemical rocket engines). They have yet to achieve any significant space use, however, because of lifetime limitations resulting from grid erosion and performance constraints resulting from thermal-mechanical design considerations, particularly the spacing of metallic grids, including molybdenum.

In an ion thruster, a plasma is created and confined within the body of the thruster. Ions from the plasma are electrostatically accelerated rearwardly by an ion-optics system. The reaction with the spacecraft drives it forwardly, in the opposite direction. The force produced by the ion thruster is relatively small. The ion thruster is therefore operated for a relatively long period of time to impart the required momentum to the heavy spacecraft. For some missions the ion thruster must be operable and reliable for thousands of hours of operation, and with multiple starts and stops.

The ion-optics system can include grids to which appropriate voltages are applied in order to accelerate the ions rearwardly. In a typical electron bombardment ion thruster, a cathode produces electrons that strike neutral gas atoms introduced through a propellant feed line. The electrons ionize the gas propellant and produce a diffuse plasma. In a radio frequency ion thruster, the propellant is ionized electromagnetically by an external coil, and there is no cathode. In both cases, an anode associated with the plasma raises its positive potential. To maintain the positive potential of the anode, a power supply pumps to ground potential some of the electrons that the anode collects from the plasma. These electrons are ejected into space by a neutralizer to neutralize the ion beam. Magnets act to inhibit electrons and ions from leaving the plasma. Ions drift toward the ion optics, and enter the holes in a screen grid. A voltage difference between the screen grid and an accelerator grid accelerates the ions, thereby creating thrust. The screen grid is at the plasma potential, and the accelerator grid is held at a negative potential to prevent downstream electrons from entering the thruster. Optionally, the optics can include a decelerator grid located slightly downstream of the accelerator grid and held at ground potential or at a lesser negative potential than the accelerator grid to improve beam focusing and reduce ion impingement on the negative accelerator grid.

The grids can be in a facing orientation to each other, spaced apart by relatively small clearances such as about 0.035 inches at room temperature. The grids can include aligned apertures therethrough. Some of the ions accelerated by the applied voltages can pass through the apertures, providing the propulsion. Others of the ions can impact the grids, heating them and etching away material from the grids by physical sputtering. The heating and electrostatic forces on the grids can combine to cause substantial mechanical forces at elevated temperature on the grids, which can distort the grids unevenly. The uneven distortion of the grids can cause adjacent grids to physically approach each other, rendering them less efficient and prone to shorting against each other. These effects can be taken into account in the design of the grids and the operation of the ion thruster, so that the thruster can remain functional for the required extended lifetimes. However, limitations may be placed on the operation of the ion thruster because of grid distortion, such as a relatively slow ramp-up in power during startup and operation, so that the adjacent grids do not expand so differently that they come into contact.

A factor that can affect the efficiency and/or the weight of ion thrusters is how closely and precisely the grids can be positioned while maintaining relative uniformity in the grid-to-grid spacing at high operating temperatures or in conditions where the spatial temperature is nonuniform and thermal distortion can occur because of temperature gradients.

Grids are frequently made of molybdenum formed into a domed shape. The molybdenum can resist material removal by physical sputtering. The domed shape can establish the direction of change due to thermal expansion and/or can aid in preventing a too-close approach of the adjacent grids as a result of differences in temperatures of the adjacent grids.

Exemplary embodiments of ion thruster grids, such as those formed according to an exemplary embodiment of a method, can be precisely formed into matching shapes, which can account for deformation that can occur due to thermal expansion when a thruster heats in operation. Changes in the actual spacing and the uniformity of spacing over the grid surfaces between the grids can potentially be predicted and/or controlled.

Exemplary embodiments of ion thruster grids, such as those formed according to an exemplary embodiment of a method, can be formed of any moldable material, include tungsten, molybdenum, ceramics, graphite, etc.

Exemplary embodiments of ion thruster grids, such as those formed according to an exemplary embodiment of a method, can have relatively long lifetimes, allow for precise alignment and/or spacing between grids, and/or allow for precise alignment and/or spacing of grid openings.

Ion Beam Grids

Ion beams can be used in the production of components in the micro-electronics industry and magnetic thin film devices in the storage media industry. Typically, an ion beam, such as an argon ion beam, has a large area, a high current and an energy of between 100 eV and 2 keV. The beam can be used in a number of ways to modify the surface of a substrate, for example by sputter deposition, sputter etching, milling, or implantation.

In a typical ion beam source (or ion gun) a plasma is produced by admitting a gas or vapor to a low pressure discharge chamber containing a heated cathode and an anode which serves to remove electrons from the plasma and to give a surplus of positively charged ions which pass through a screen grid or grids into a target chamber which is pumped to a lower pressure than the discharge chamber. Ions are formed in the discharge chamber by electron impact ionization and move within the body of the ion gun by random thermal motion. The plasma will thus exhibit positive plasma potential which is higher than the potential of any surface with which it comes into contact. Various arrangements of grids can be used, the potentials of which are individually controlled. In a multigrid system, the first grid encountered by the ions is usually positively biased whilst the second grid is negatively biased. A further grid may be used to decelerate the ions emerging from the ion source so as to provide a collimated beam of ions having more or less uniform energy. For ion sputtering a target is placed in the target chamber where this can be struck by the beam of ions, usually at an oblique angle, and the substrate on to which material is to be sputtered is placed in a position where sputtered material can impinge on it. When sputter etching, milling or implantation is to be practiced the substrate is placed in the path of the ion beam.

Hence, in a typical ion gun an ion arriving at a multiaperture extraction grid assembly first meets a positively biased grid. Associated with the grid is a plasma sheath. Across this sheath is dropped the potential difference between the plasma and the grid. This accelerating potential will attract ions in the sheath region to the first grid. Any ion moving through an aperture in this first grid, and entering the space between the first, positively biased grid, and the second, negatively biased, grid is strongly accelerated in an intense electrical field. As the ion passes through the aperture in the second grid and is in flight to the grounded target it is moving through a decelerating field. The ion then arrives at an grounded target with an energy equal to the potential of the first, positive, grid plus the sheath potential.

Exemplary embodiments of ion beam grids, such as those formed according to an exemplary embodiment of a method, can have relatively long lifetimes, allow for precise alignment and/or spacing between grids, and/or allow for precise alignment and/or spacing of grid openings. Such grids can be planar and/or non-planar, can have redundant and/or non-redundant grid openings, can have anisotropic and/or isotropic grid openings, and/or can be constructed of nearly any moldable material, including composite materials.

Microfluidics

Certain exemplary embodiments can provide fluidic and/or microfluidic devices and/or components thereof, potentially having high resolution and/or high aspect ratios. For example, an exemplary embodiment can provide a pressure regulator and/or controller that utilizes a valve, orifice, and/or nozzle having a high aspect ratio and formed using an embodiment.

Actuators

Certain exemplary embodiments can provide actuators and/or components thereof, potentially having high resolution and/or high aspect ratios. For example, an exemplary embodiment can provide a valve actuator having an electromagnetic, magnetic, piezoelectric, electrostatic, bimetallic, and/or shape memory component formed using an embodiment and having a high aspect ratio.

Attenuators

Certain exemplary embodiments can provide attenuators and/or components thereof, potentially having high resolution and/or high aspect ratios. For example, an exemplary embodiment can provide an acoustical attenuator having numerous microbaffles for absorbing undesired sound waves, such as sound waves of a particular frequency range. Such baffles can be textured, dimensioned, and/or shaped to enhance their performance capabilities. Likewise, attenuators can be provided for attenuating flow, electromagnetic radiation (e.g., light, electrical current, x-rays, etc.), etc.

Motion Devices

Certain exemplary embodiments can provide gyroscopes, accelerometers, tilt detectors, etc., and/or components thereof, potentially having high resolution and/or high aspect ratios. Such devices can be useful for navigation, stabilitization, airbag crash systems, vibration detection, earthquake detection, anti-theft and/or security systems, active suspensions, automated braking systems, vehicle roll-over prevention systems, headlight leveling systems, seatbelt tensioners, motor controllers, pedometers, stereo speakers, computer peripherals, flight simulators, sports training, robots, machine health monitors, etc. For example, an exemplary embodiment can provide an accelerometer having a cantilevered inertial mass coupled to at least one electrical element, such as a capacitive sensor that is adapted to generate a signal upon sufficient change in acceleration (movement) of the cantilevered inertial mass. In certain embodiments, the mass and electrical element can be substantially co-planar. In certain embodiments, the mass can have a substantial aspect ratio, and electrical elements can be provided in orthogonal and/or multiple planes, so that changes in orientation, displacement, and/or motion (e.g., linear, curvilinear, and/or rotational velocity, acceleration, jerk, pulse, etc.) in any direction can be sensed, measured, and/or analyzed.

Mirrors

Certain exemplary embodiments can provide a mirror and/or components thereof, potentially having high resolution and/or high aspect ratios. Such a mirror can be a component of an optical device and/or an opto-mechanical device, such as an opto-mechanical switching cell and/or a laser scanner, such as is used in a bar-code scanner or a holographic data storage system. Exemplary arrays of mirrors can be redundant and/or non-redundant. Exemplary mirrors can be planar and/or non-planar. Exemplary mirrors can have a reflectivity that varies in any fashion (e.g., linearly, non-linearly, polarly, radially, controllably, periodically, thermally, etc.) across a surface of the mirror.

Grating Light Valves

Grating light valves can resemble small reflectors/diffractors, each comprising several structures that resemble ribbon-like beams supported on each end, which can electrostatically actuated upwards or downwards (typically a fraction of the wavelength of visible light). The ribbon-like structures can be arranged to form an element that variably reflects or diffracts light, in either a continuous or discrete (on-off) manner. Grating light valves can have utility in optical attenuators, switches, relays, direct-to-plate printers, HDTV monitors, electronic cinema projectors, and/or commercial flight simulator displays.

Exemplary embodiments of grating light valves, such as those formed according to an exemplary embodiment of a method, can include redundant and/or non-redundant arrays of reflector and/or diffractor elements. Each such element can be planar and/or non-planar, and can include an actuator, such as those used in optical switching arrays.

Fuses

Certain exemplary embodiments can provide methods for fabricating a fuse and/or components thereof, potentially having a high-resolution and/or high-aspect ratio, which can be used for triggering and/or disconnecting the flow of fluid and/or current. For example, fluid fuse comprising a low melting (fusible) alloy can be useful for triggering and/or actuating a sprinkler head in a fire protection system. As another example, an electrical fuse comprising an electrically fusible alloy can be useful for disconnecting a current flow to an electronic and/or electrical device.

Signal Detecting Collimators and Devices

Certain exemplary embodiments can provide methods for fabricating a grid structure and/or components thereof, potentially having a high-resolution and/or high-aspect ratio, which can be used for signal detection collimators. Such devices can be used in the field of acoustics to, for example, enhance acoustical signal detection and/or analysis, by for example, reflecting, dispersing, filtering, and/or absorbing sound waves. Such devices can be used in the field of imaging to, for example, enhance image contrast and quality by refracting, diffracting, reflecting, dispersing, filtering, and/or absorbing scattered radiation (sometimes referred to as "off-axis" radiation and/or "secondary" radiation). In this context, "radiation" means electromagnetic radiation, and can include radio, television, microwave, infrared, visible light, ultraviolet, alpha-rays, beta-rays, gamma rays, and/or x-rays, etc., and can even include high energy particles, ion beams, etc. Moreover, much of the following discussion regarding radiation is analogous to acoustical energy, vibration, and/or other forms of energy that have a varying and/or frequency component (e.g., a time-varying component, a spatially-varying component, a dimensionally-varying component, etc.).

As an example, certain exemplary embodiments can provide a collimator having optical properties, such as cell walls capable of absorbing certain wavelengths, that can be used as a notch filter. Other such collimators can have certain cells filled with a material that has certain refractive properties, thereby providing a lens effect with those cells. Other such collimators can have reflective and/or curved cell walls thereby serving as a reflector and/or wave guide.

Certain exemplary embodiments can provide a collimator having at least one curved face, and possibly having both faces curved, such that each cell is "pointed" in a different direction. In various embodiments, the curve can be circular, elliptical, curvilinear, cylindrical, and/or spherical, etc., and can be concave and/or convex.

Such collimators can be useful for detecting a direction of a radiation source with respect to the collimator and/or the imaging machine comprising the collimator, particularly when the machine also comprises a pixilated detector array and an image processing capability.

Thus, in certain embodiments, such as those in which the "outer" face of the collimator is convex, such collimators can function as a form of "wide-angle lens" for whatever type of radiation the collimator is designed to pass. Moreover, by analyzing the time variance of the detected radiation, such machines can determine changes in direction or intensity of the emitted and/or incoming radiation. Further, by analyzing the frequency components of the detected radiation, such machines can determine, perhaps with a high degree of precision, the nature of the radiation source.

As an example, an imaging machine comprising such a curved collimator could be deployed at a location having a relatively wide view of a stadium parking lot. The collimator can direct light originating from any particular location in the view to a corresponding detector element. By virtue of its power, time, and/or frequency analysis capability, such an imaging machine could detect the source of a bright and rapid flash of infrared and visible light and/or other forms of radiation, such as occurs when a handgun is fired. The imaging machine could then alert authorities to the location of the fired handgun, and could trigger a video camera to turn to and zoom in on the location to capture a visible image of the scene, potentially capturing images of the faces of witnesses and/or perpetrators, license plate numbers, etc.

As another example, an imaging machine comprising such a curved collimator could be deployed at a location having a relatively wide view of a port, shipping channel, runway, rail yard, border crossing, roadway, warehouse, parking lot, etc. Once deployed, the imaging machine can detect, for example, gamma radiation, such as emitted from a radioactive source, such as a radioactive medical waste, nuclear fuel, and/or a radiation bomb. Upon detection, the imaging machine could alert authorities to the approach, movement, and/or specific location of the radioactive source.

As yet another example, an imaging machine comprising a concave collimator could be deployed at a conveyor and opposite a radiation source, such as is used for scanning passenger bags in commercial airports, train stations, bus depots, etc. In an environment with many such conveyors each having a radiation source, such a collimator can isolate radiation to that coming from its corresponding radiation source.

Additional Embodiments

Certain exemplary embodiments can provide a manufacturing process that can produce, potentially in high volume, complex, net-shape (i.e., formed to the designed configuration, no secondary finishing operations needed), and/or micro-scale (i.e., with two or more orthogonal dimensions measuring in a range of approximately sub-micron to approximately 25 microns) to meso-scale (i.e., with two or more orthogonal dimensions measuring in a range of approximately 25 microns to approximately 100 millimeters) structures, such as from advanced materials comprised of, for example, powdered metals, ceramics, and/or polymers, etc. This process, which is sometimes referred to herein as Tomo-Lithographic-Molding (TLM™), can utilize a high-resolution master tool constructed from lithographically micro-machined layers, precisely aligned and stack laminated into a monolithic solid. By combining dissimilarly patterned layers or "toma", 3D cavities of otherwise unattainable sophistication and/or precision can be created. Combining these disciplines with certain casting and/or forming methods can enable the production of cost effective, high aspect-ratio devices and/or systems with features ranging from micro-scale to meso-scale. Thousands of micro-scale and/or meso-scale features and/or structures in varied distributions and/or customized geometries can be arrayed upon large (e.g., approximately 1 square foot to approximately 10,000 square meters or larger) planar and/or non-planar, continuous and/or arrayed, surfaces. These surfaces may, in turn, be used as plies in a macro-scale (i.e., with one or more orthogonal dimensions measuring greater than 100 millimeters), laminate composite structure for potentially optimizing physical properties.

Composite Structures Manufacturing Technology

Composite materials are generally defined as a combination of two or more constituent materials; e.g., reinforcing elements, fillers, and composite matrix binders; differing in form or composition on a macro-scale. The constituents can maintain their identities, i.e., they do not dissolve or merge completely into one another although they can act in unison as a system. Super composites, that is, multi-ply composite structures wherein each ply is composed of composite materials, can be constructed by bonding together two or more distinct components, each of which can be made of metal, alloy, nonmetal, and/or composite material. Examples of composite structures include: honeycomb panels, clad plate, electrical contacts, sleeve bearings, carbide tipped drills or lathe tools, and weldments constructed of two or more different alloys. Conventional technology can be limited to materials that have uniform microstructures throughout their volume. As described herein, a Large Area Micro Mechanical System (LAMMS™) can differ from conventional technology in that each predetermined portion (e.g., cubic millimeter, cubic inch, etc.) of material volume of a LAMMS™ can be of a unique configuration designed specifically for the micro-environment in which this particular element is expected to be situated.

Overview of Certain Aspects of Synthetic Multifunctional Laminate Composites

LAMMS™ can have their micro-structure, meso-structure, and/or macro-structure designed to achieve any of a wide array of material properties and/or be tailored to achieve specific functionalities. The specific properties of this class of composites can make them attractive for high-performance, weight sensitive applications. The fabrication method for creating LAMMS™ composites can allow new embedded technologies to be incorporated into the materials, potentially further enhancing their functionality and/or utility.

Design

The LAMMS™ manufacturing process can begin by use of "Commercial Off-The-Shelf Software" (COTS) Finite Element Analysis (FEA) software to create a virtual prototype of the engineering design. The software can model one or more environmental factors, such as any potential, expected, and/or substantial stress, strain, force, moment, shear, torsion, inertia, friction, abrasion, corrosion, cavitation, creep, ablation, impact, pressure, temperature, humidity, power, voltage, current, electromagnetic radiation, magnetic flux, etc., including variations in and/or cycles of such factors, that the designed object is expected to bear throughout its entire structure and/or design lifetime. Using this information it then can be possible to calculate, with a high degree of precision, the expected environmental factors that might act upon of smaller subsections (elements) of the structure. Each of these elements then can be treated as a discreet object with its associated set of factors acting upon it—and each element might benefit from a distinct microstructure to bear those local factors. Usually the design of a macrostructure is dictated by the most extreme factor(s) it must bear. These factors might act only upon small areas of the macrostructure. Because conventional materials have essentially homogenous microstructures, their design can be driven by "the weakest link." The LAMMS™ process can make it possible to optimize the material properties of each design element, by, for example, providing higher density (and stiffness) only where expected to be needed, allowing the rest of the structure, where the higher density (and accompanying weight) is not needed, to be made lighter. The net result can be a macrostructure whose interior volume is a lattice—e.g., a unique array of microstructures—of precise design that in aggregate can be capable of withstanding the most extreme expected applied factors, but, for example, can weigh relatively little due to its parsimonious use of materials.

The LAMMS™ approach thus can provide a method to build structures that can bear some similarities to what can be observed in nature—macro-structures having locally-varying micro-structures. Examples from nature can include the potentially and/or substantially locally-varying structures of sea shells, tree trunks, and/or animal bones, etc., such as the wing bones of birds and/or the thigh bone of mammals, etc. At least some of such natural structures can comprise locally varying material compositions; densities; strengths; flexibilities; porosities; diffusabilities; surface textures; color; opacity; vibration damping; mineral concentrations; muscle, tendon, and/or ligament attachment points; blood and/or other cell production capabilities; nerve fiber and/or blood conduit capacities; and/or self-healing abilities; etc.

Fabrication

The LAMMS™ process can be suitable for large scale and/or high volume production operations that are consistent, for example, with those employed for the manufacture of aerostructures, automobiles, trucks, and maritime vessels and/or components thereof.

Description of Certain Manufacturing Processes

Tomo Lithographic Molding™

The TLM™ process can be used to create a high-resolution, laminated master tool (mold or die) by means of lithographically derived, micro-machined layers and stack laminations methods. Combining these disciplines with the following processes can enable the production of cost effective LAMMS™ with features in the micro-to-meso scale that can be arrayed over large scale planar and/or non-planar surfaces.

Continuous Flow Injection Molding

This process can comprise forming a plastic to a desired shape by forcing the heat-softened plastic into a relatively cool cavity under pressure. In the LAMMS process, the material (thick film, engineered plastic), can be fed from a spool or roll between and through a pair of rollers whereon a TLM™-derived mold, or set of molds, can be embedded. The configuration of the mold can be determined by the aforementioned Finite Element Analysis.

Hot Embossing

This process can be used to create depressions of a specific pattern in a heated plastic film or sheet, thus raising a design in relief against a surface. In the LAMMS™ process, the plastic film can be fed from a spool or roll between and through a pair of rollers whereon a TLM™-derived mold, or set of molds, is embedded. The configuration of the mold can be determined by the aforementioned Finite Element Analysis.

Blanking

This process can comprise punching, cutting, stamping, and/or shearing a piece out of stock to a predetermined shape through cutting dies. In the LAMMS process, the material (a thin metal foil or thick plastic film), can be fed from a spool or roll between and through a pair of rollers whereon a TLM™-derived cutting die, or set of dies, is embedded. The configuration of the die can be determined by the aforementioned Finite Element Analysis. The output can be a lattice of beams and/or nodes that can be used to join (e.g., in the Z or through-thickness axis) the microstructures molded or embossed upon mating plies.

Adhesive Bonding

This is a materials joining process in which an adhesive, placed between faying surfaces (adherends) can solidify to produce an adhesive bond. In the LAMMS™ process, the blanked ply (d) can be sandwiched between the molded and/or embossed material (plies b & c) and/or cemented in place by means of an adhesive and/or pressure exerted by another set of rollers in line with the aforementioned rollers.

Trimming

This process can comprise removing excess material from the part by cutting with a trimmer blade, punch, and/or shoe in a trim press and/or can be accomplished at elevated and/or ambient temperature. In the LAMMS™ process, the perimeter of the macrostructure (part) cam be trimmed from the body of the laminated composite sheet by means of TLM™-derived trimming blades embedded in a set of rollers in line with the aforementioned rollers.

Thermoforming

This process can comprise forming a thermoplastic sheet into a three-dimensional shape after heating it to the point where it is soft and flowable, and/or then applying differential pressure to make the sheet conform to the shape of the mold or die positioned below and/or above the material. Traditionally, there are three basic mold types: female (concave), male (convex), and matched (a combination of the two). In matched-mold thermoforming, the stamping force of the male mold can push the heated sheet into the female cavity. In the LAMMS™ process, the three (or more) ply, laminated structure can be thermoformed in a single operation.

Materials

The TLM™ process can provide the ability to produce parts in a number of different materials, thus allowing the best match to the end part and application. TLM™ process can be used to fabricate parts using, for example: 1) powder metals (such as tungsten, copper, and/or gold, etc.), 2) powder ceramics (such as alumina and/or zirconia, etc.), and/or 3) polymers (such as silicone rubber, urethanes, and/or epoxies, etc.). The TLM™ process can also be utilized with combinations of materials (such as ceramic and metal powder/epoxy composites, etc.).

The LAMMS™ process can be compatible with a wide variety of commercially available engineering materials such as:

engineered plastics;
metals;
ceramics;
synthetic composites; and/or
adhesives, etc.

Tooling

TLM™ master molds and master dies (master tools) can be made as negatives and/or positives of the finished part configuration. If the master is made as a negative, the finished part can be produced directly from the tool. If the master is made as a positive, it might be useful to create a second-generation (or derived) master. Some production situations might benefit from a second (or even a third) generation version of the master tool. Downstream process parameters and/or control limits might be primary design factors when contemplating the configuration (positive or negative rendition of the finished part) of the master tool. If, for example, the finished part is made of a flexible material having good release properties, a rigid master tool might be used, whereas, if the finished part was very rigid, with poor release properties, a second-generation consumable master tool might be used. Masters can be, for example: 1) rigid tools made of metal and/or ceramics, etc., 2) flexible tools made of rubber and/or various polymers, etc., and/or 3) consumable tools, made of wax and/or consumable polymers, etc. LAMMS™ master tools can be employable as inserts integral to the rollers described in Section 3. These inserts can be interchangeable. Thus, multiple product configurations can be produced on the same production line.

Application Examples

Figure 58:
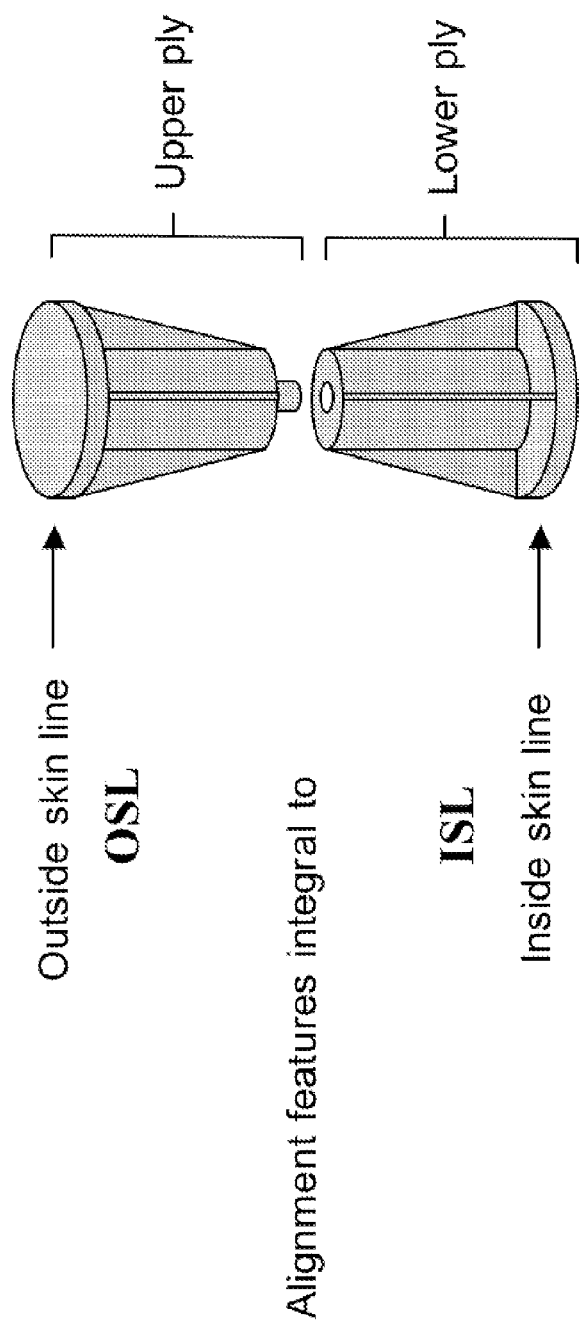
FIG. 58 is a perspective view of an exemplary embodiment of opposing interlocking microstructures formed via an exemplary method described herein.

FIG. 57 illustrates an exemplary embodiment of a microstructure derived from a finite element analysis (FEA) and formed via an exemplary method described herein. FIG. 58 is a perspective view of an exemplary embodiment of opposing interlocking microstructures formed via an exemplary method described herein. More specifically, FIGS. 57-58 show microstructures derived from a finite element analysis and extracted from a thick film plastic sheet. Note that a mold from which each microstructure is derived can be formed from a plurality of lithographically-derived, micro-machined metallic foil layers (11 such layers are shown in FIG. 57), which have been precisely aligned and stack laminated into a monolithic solid.

Figure 59:
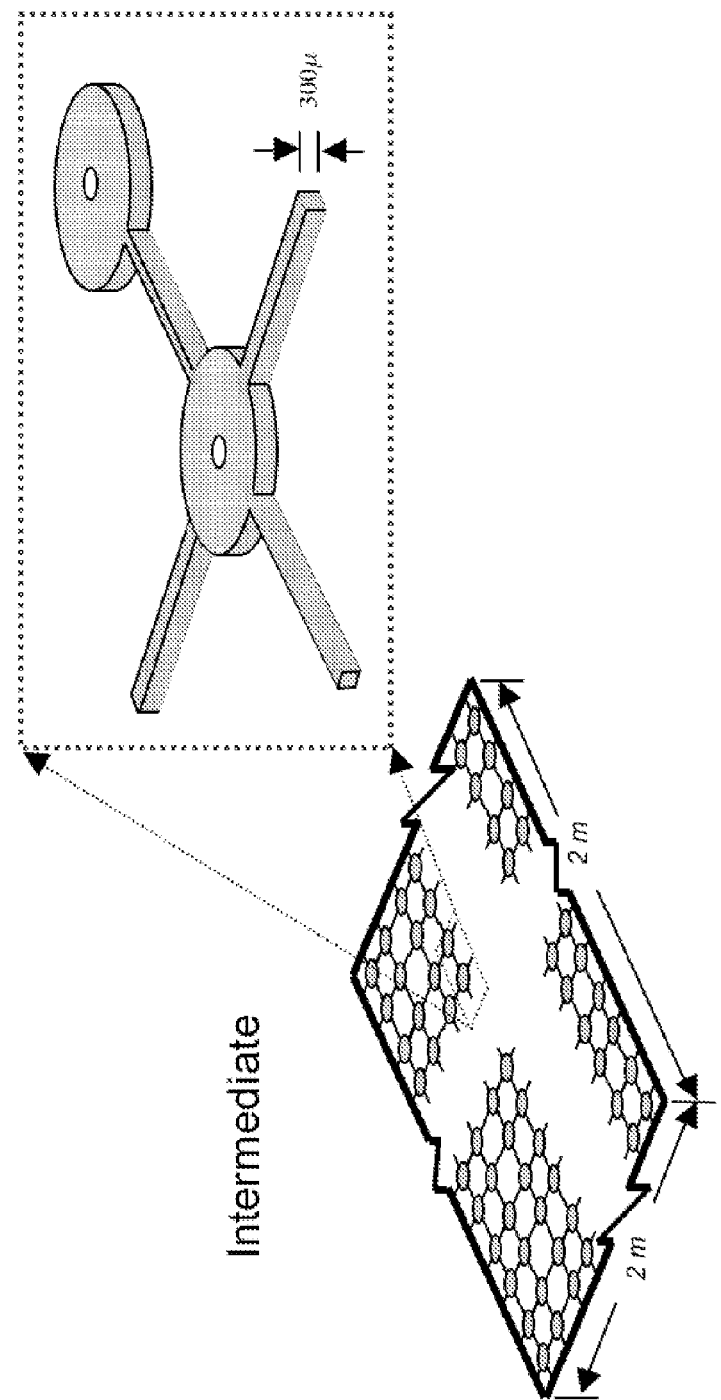
FIG. 59 is a perspective view of an exemplary embodiment of a lattice microstructure formed via an exemplary method described herein.

FIG. 59 is a perspective view of an exemplary embodiment of a lattice microstructure formed via an exemplary method described herein. More specifically, FIG. 59 shows an LAMMS array of microstructures derived from a finite element analysis and extracted from an intermediate thin metal foil.

Figure 60:
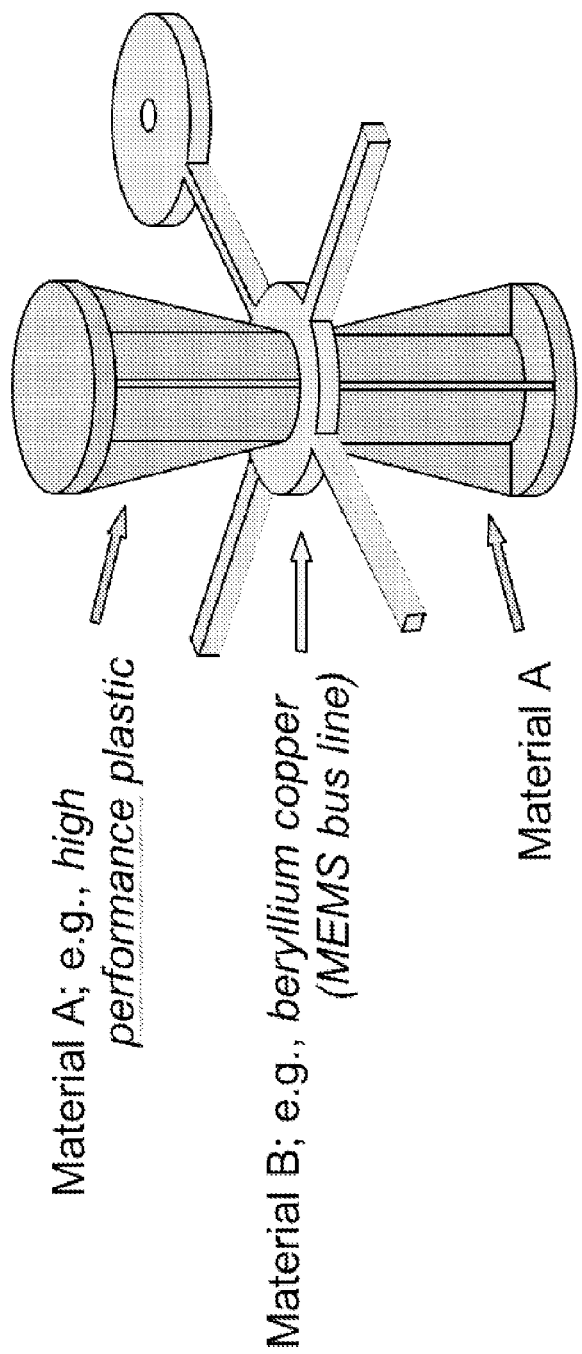
FIG. 60 is a perspective view of an exemplary embodiment of a composite microstructure formed via an exemplary method described herein.

FIG. 60 is a perspective view of an exemplary embodiment of a composite microstructure formed via an exemplary method described herein. More specifically, FIG. 60 shows a combination of the microstructures of FIG. 58 and FIG. 59.

Figure 61:
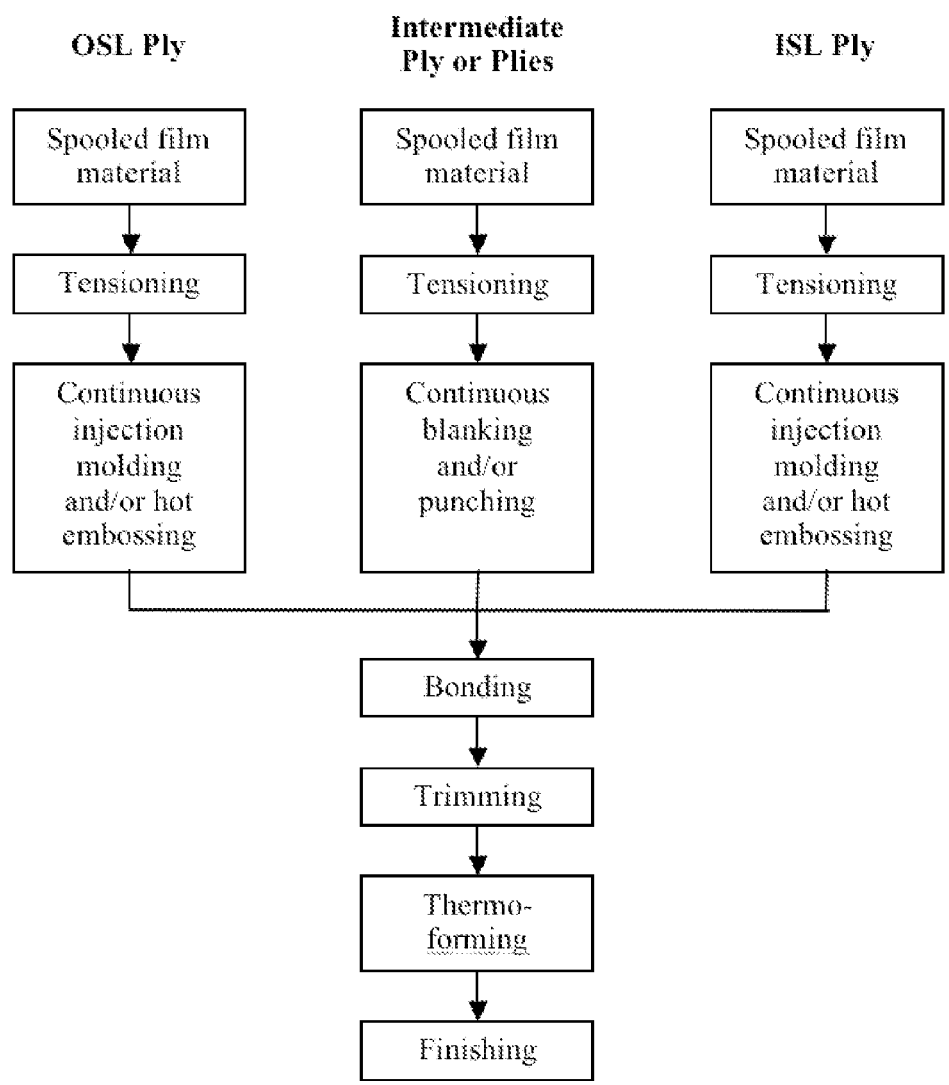
FIG. 61 is a flowchart of an exemplary embodiment of a basic sequence of an exemplary method described herein.

FIG. 61 is a flowchart of an exemplary embodiment of a basic sequence of an exemplary method described herein. More specifically, FIG. 61 is a flowchart of an exemplary manufacturing process for making certain exemplary microstructures and/or LAMMS, such as the microstructures of FIG. 60.

Figure 62:
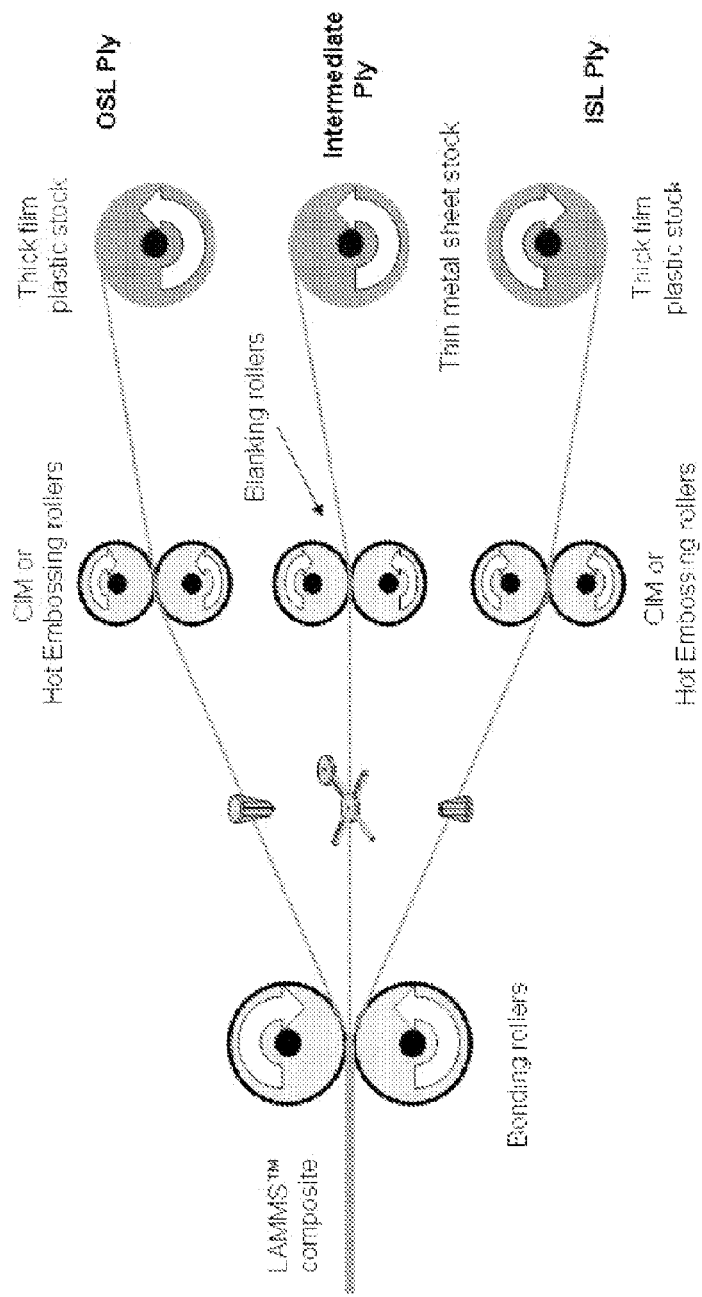
FIG. 62 is a block diagram of an exemplary embodiment of a basic sequence of an exemplary method described herein.

FIG. 62 is a block diagram of an exemplary embodiment of a basic sequence of an exemplary method described herein. More specifically, FIG. 62 is a schematic of an exemplary manufacturing process for making certain exemplary microstructures and/or LAMMS, such as the microstructures of FIG. 60.

Figure 63:
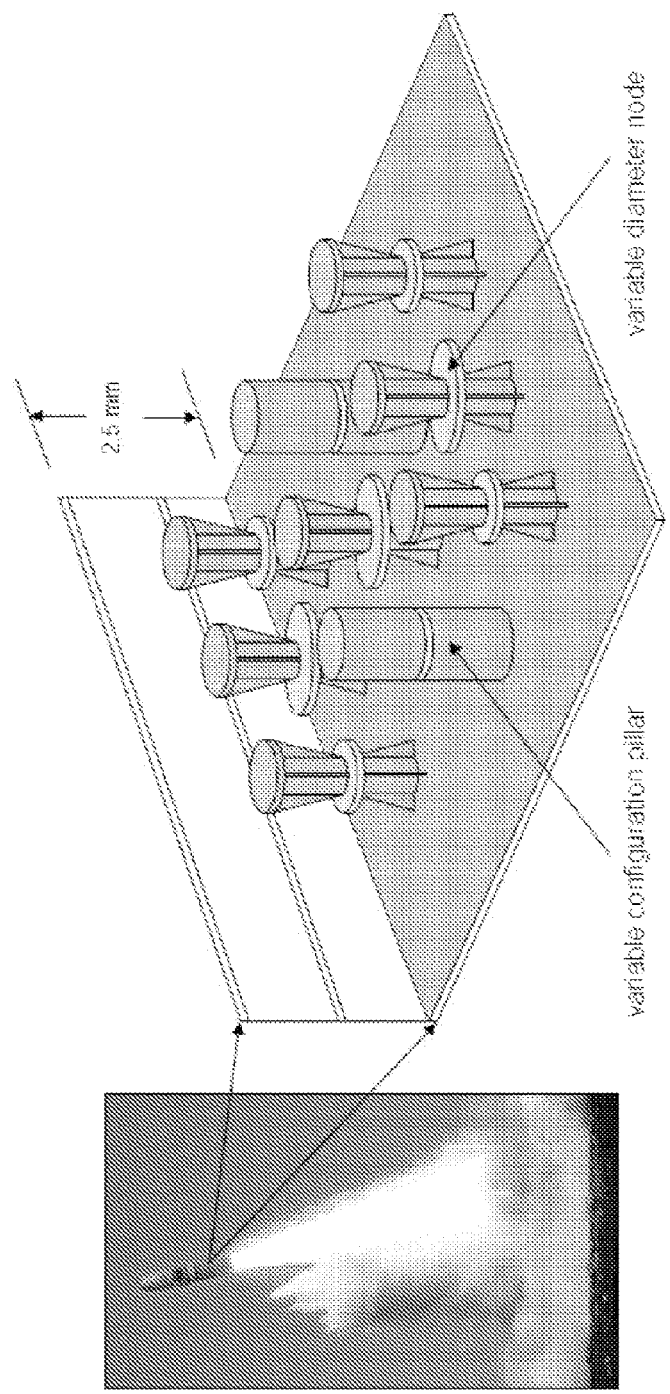
FIG. 63 is a perspective view of an exemplary embodiment of a simplified microstructure formed via an exemplary method described herein.

FIG. 63 is a perspective view of an exemplary embodiment of a simplified microstructure formed via an exemplary method described herein. More specifically, FIG. 63 illustrates an exemplary simplified LAMMS showing an array of microstructures such as those shown in FIG. 60, which can be used to form an aeroframe skin panel.

The following examples have been selected to illustrate several potential attributes of the LAMMS™ process.

Figure 64A:
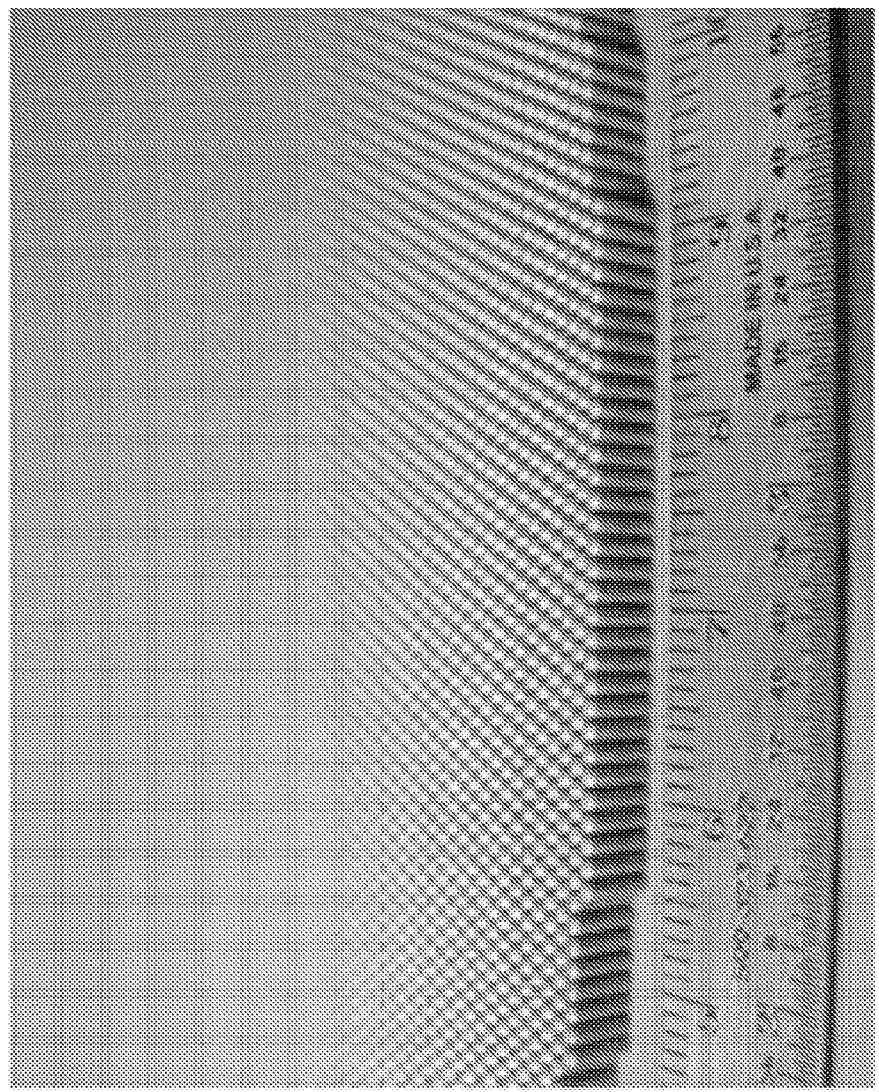
FIGS. 64A-B are perspective views of an exemplary embodiment of a macro-scale surface comprising a plurality of microstructures, the surface and microstructures formed via an exemplary method described herein.
Figure 64B:
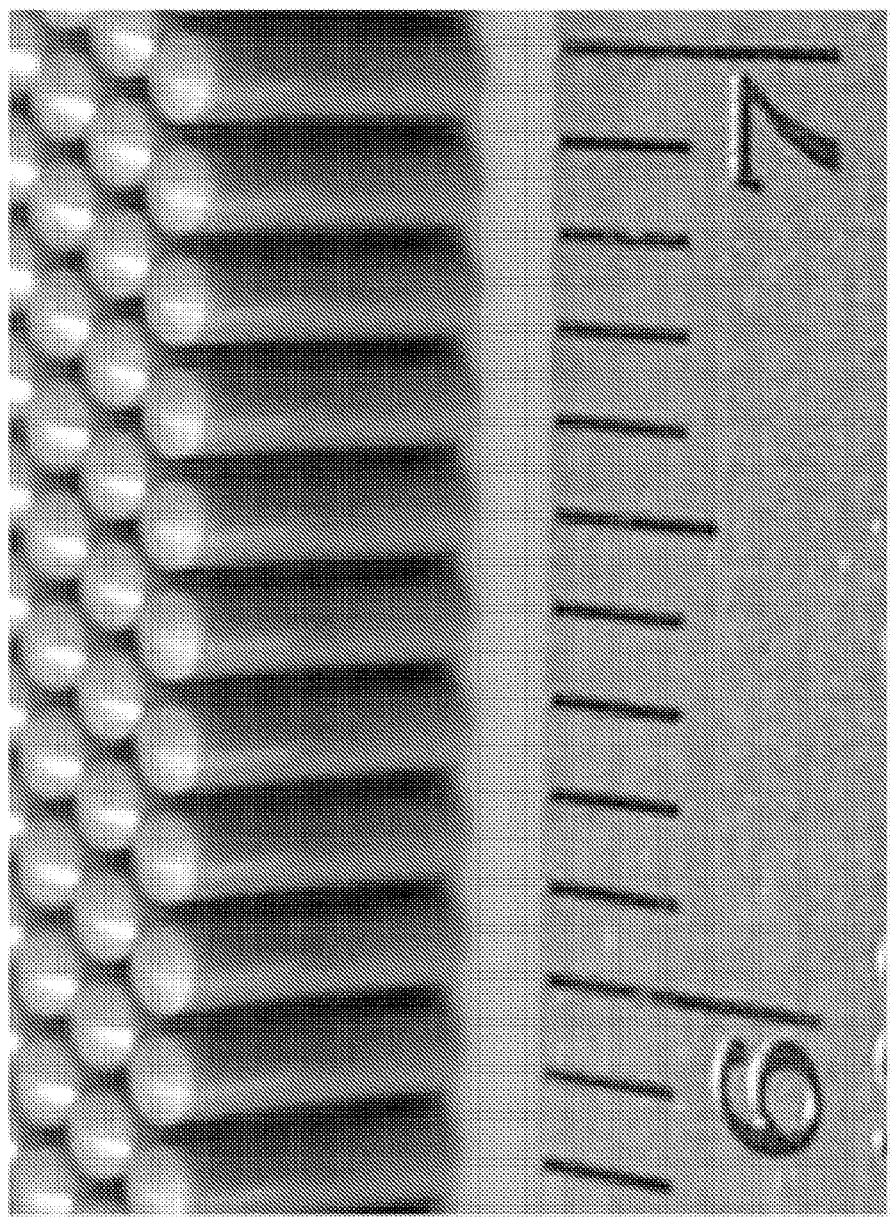

FIG. 64 is a perspective view of an exemplary embodiment of a macro-scale surface comprising a plurality of microstructures, the surface and microstructures formed via an exemplary method described herein. More specifically, FIG. 64 (example 1) demonstrates the use of LAMMS™ to array precisely angled micro-scale features across a macro-scale surface.

Figure 65A:
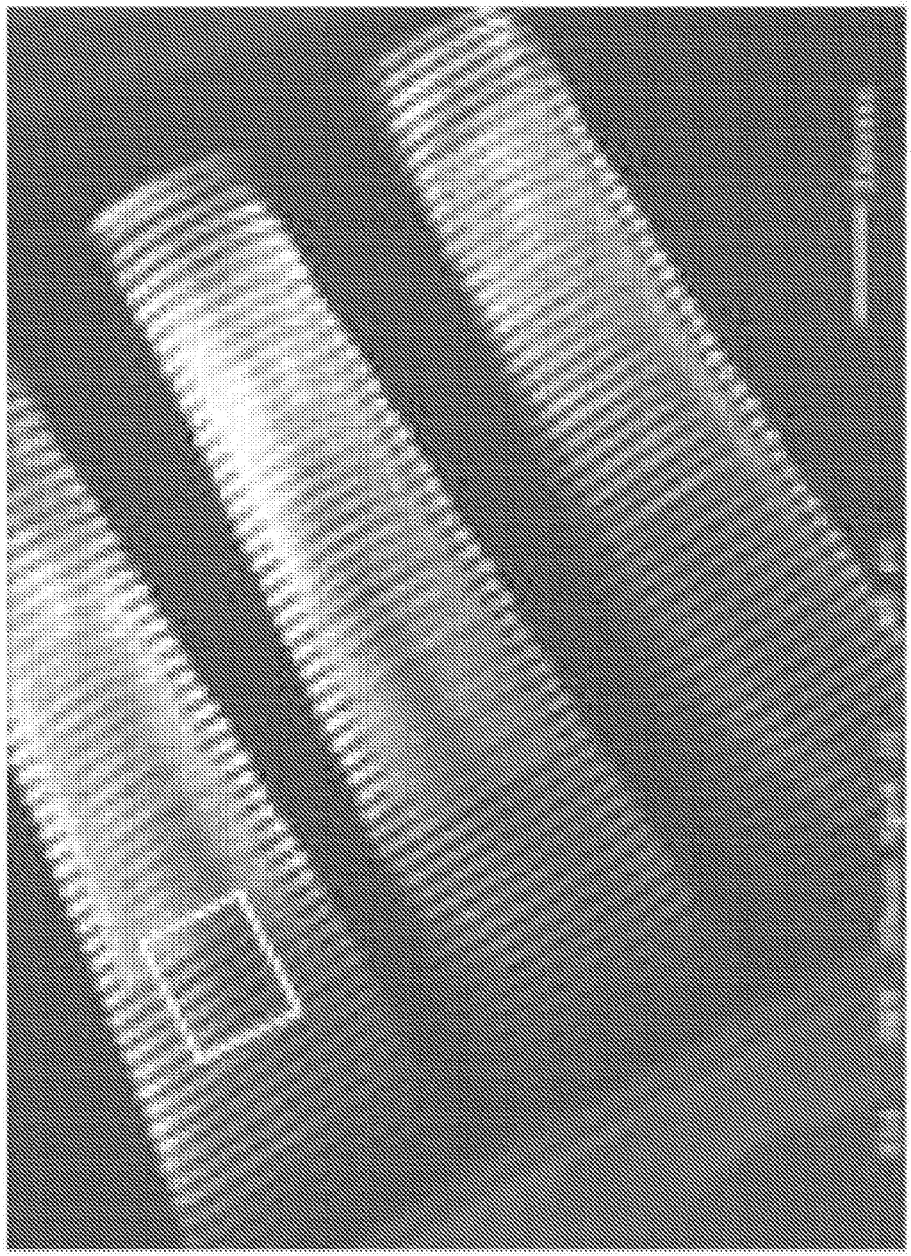
FIGS. 65A-B are photomicrographs of exemplary columnar microstructures formed via an exemplary method described herein.
Figure 65B:
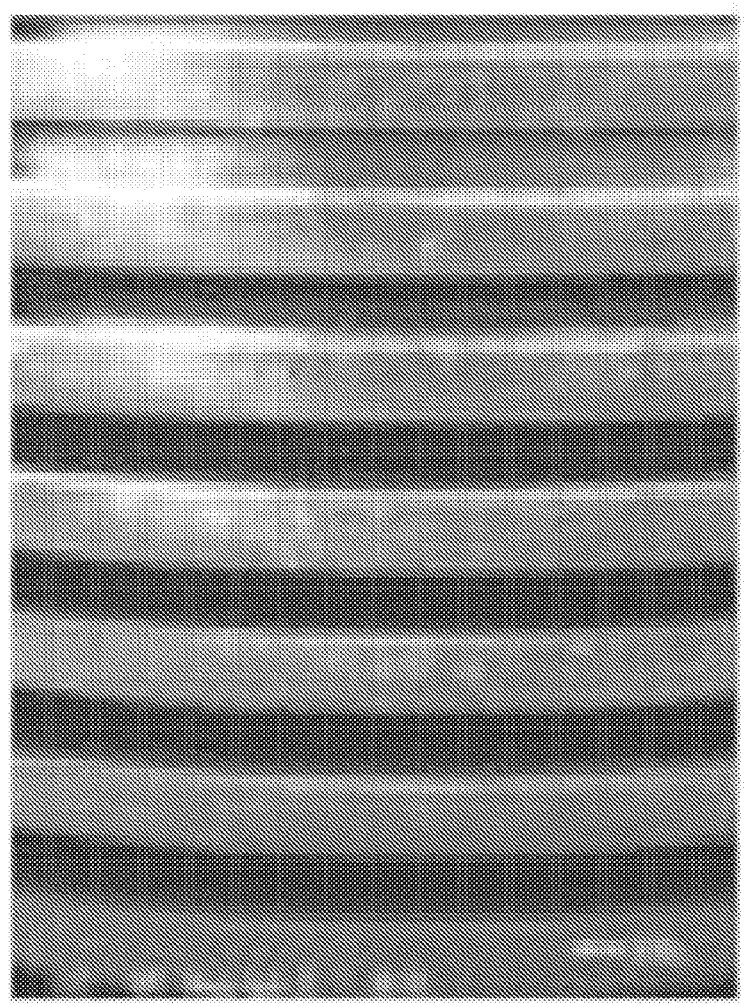
Figure 66A:
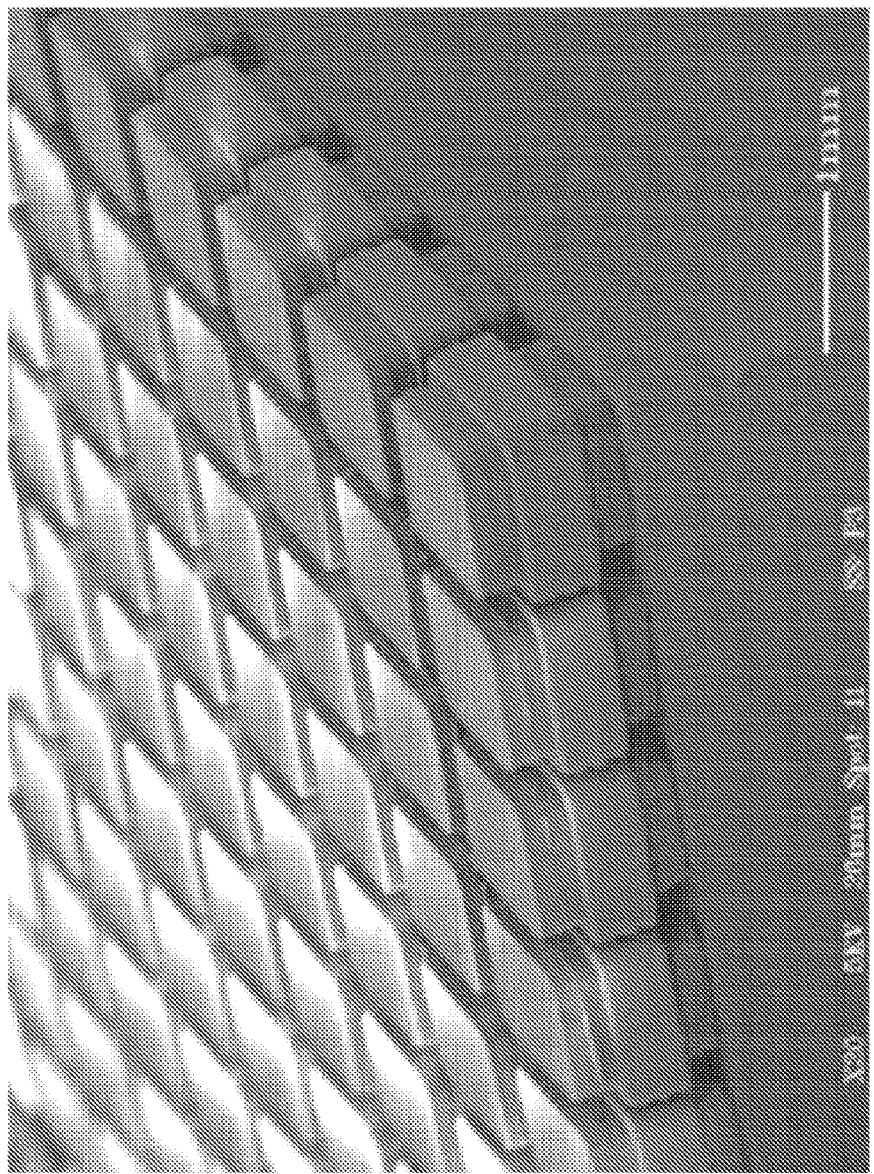
FIGS. 66A-B are photomicrographs of exemplary cast microstructures formed via an exemplary method described herein.
Figure 66B:
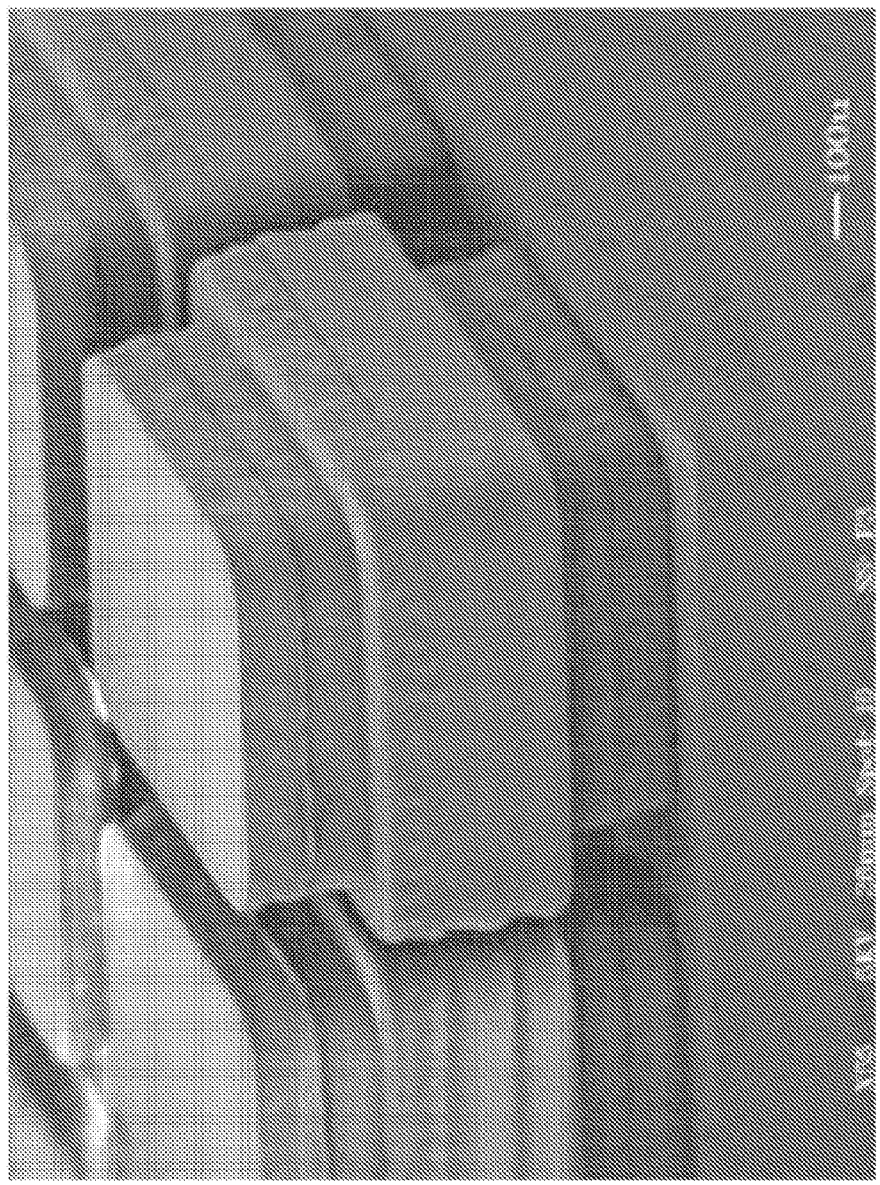

FIG. 65 is a photomicrograph of exemplary columnar microstructures formed via an exemplary method described herein. FIG. 66 is a photomicrograph of exemplary cast microstructures formed via an exemplary method described herein. More specifically, FIGS. 65 and 66 (examples 2 and 3) demonstrate production of more complex 3D features. For demonstration purposes, each example has been produced in a single-ply configuration using a casting process.

In the first example, a precision TLM™ mold was fabricated having 131,589 cylindrical shape cavities arrayed over a 45 centimeter diameter surface. The resulting cavities are 0.950 millimeters in diameter, have a depth of 3.25 millimeters, and are arrayed in staggered rows and columns to maximize the pattern density. The pitch frequency of the cavities is 1.00 millimeter.

The arrayed pattern is comprised of four identical quadrants located around a central x, y datum. The cavity located at the center of the array is perpendicular to the mold surface at an angle of 90 degrees (datum cavity). The remaining cavities in each quadrant of the mold are uniquely angled relative to the mold surface. A cumulative angle of 0.01196 degrees was applied to each cavity position within each quadrant (1.00 millimeter pitch) resulting in a focused cavity array with each cavity pointing precisely at a predetermined focal point. The focal point of the array was centered on the datum cavity at a distance of 5 meters.

Using a vacuum assisted casting process, a LAMMS™ device was derived from the TLM™ mold using a high strength poly-urethane resin. The cast resin part and the TLM™ mold were dimensionally characterized and compared for accuracy. The measurements were made using an Accugage AG24 video metrology system.

FIG. 64 shows an overall view of the micro-structure array and to the right a magnified view (the small divisions on the scale are 1 mm).

This example demonstrates the ability to produce a precision micro-structure array over a large area using a TLM™ mold. Each feature in a quadrant of the array has a unique x, y and z orientation, but the individual structures are somewhat simple and repetitive in terms of shape. Examples 2 and 3 are presented to show how more complex features within an array can be produced using the LAMMS™ process.

The second example, shown in FIG. 65, was chosen to illustrate a micro-structure array designed to increase the surface area of a single structure by a factor of four. The structures are tapered columns with corrugated ridges forming precise slots in the Z axis. The high-surface area columns were derived from a TLM™ mold using a platinum cure silicone rubber. The TLM™ mold was fabricated using photo-chemically etched, 75 micron thick copper foils which were precision stack laminated. The foils were bonded using a high-strength, thermal cure epoxy.

This high-surface area micro-structure has the following dimensional characteristics:

1020 arrayed 3D micro-columns
75×75 millimeter array area
54 circular slots on each column
75 micron width×215 micron deep slots
Column height 8.3 mm Another example involving complex 3D structures is shown in FIG. 66. This was produced using a TLM™ mold comprised of six photo-chemically machined stainless steel layers. Each layer in the mold had a thickness of 150 microns. The layers were laminated together using a eutectic CuSil™ (copper/silver) metal brazing process. The mold was designed to survive high-volume molding using a high-strength, flexible polymer casting resin to form the final part.

Figure 67:
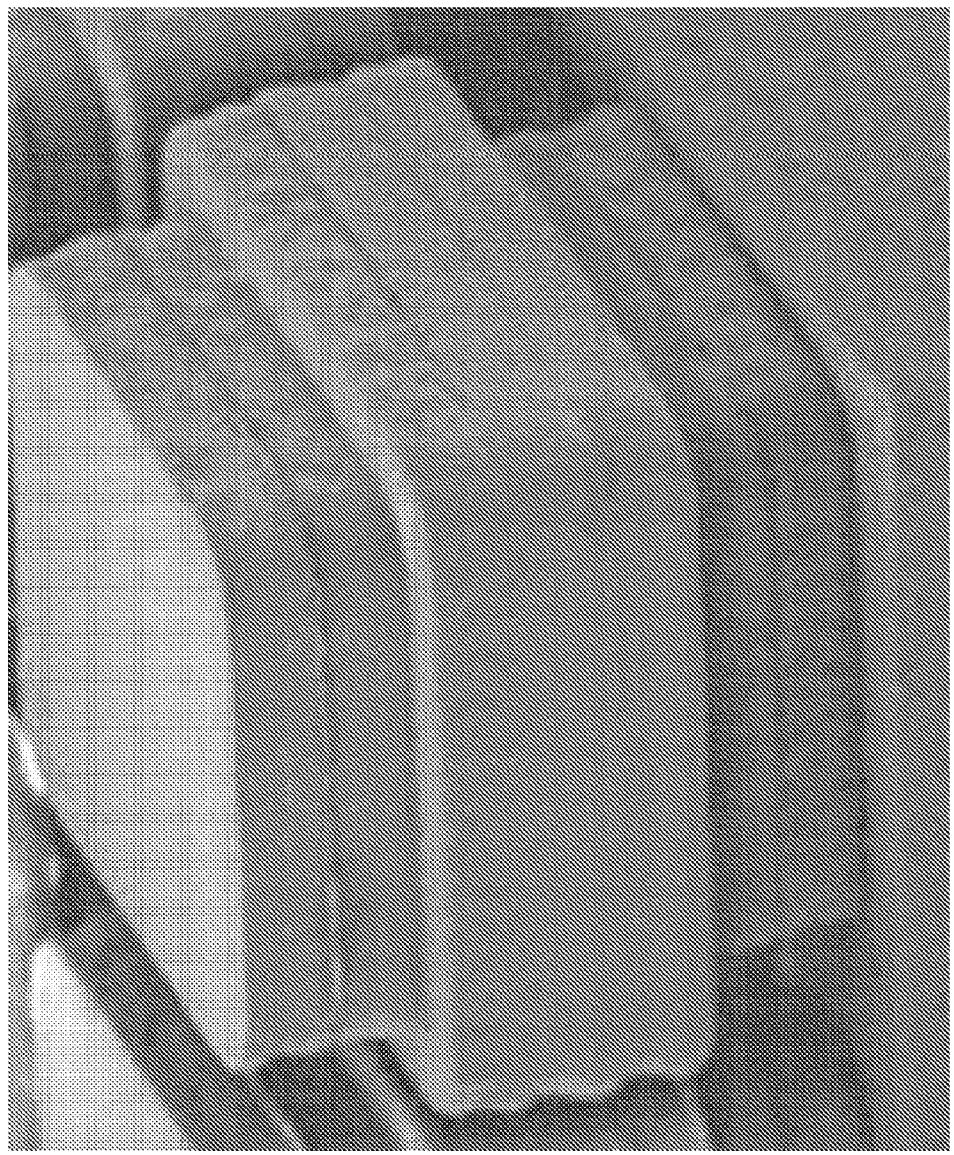
FIG. 67 is a photomicrograph of an exemplary 7-layer microstructure formed via an exemplary method described herein.
Figure 68:
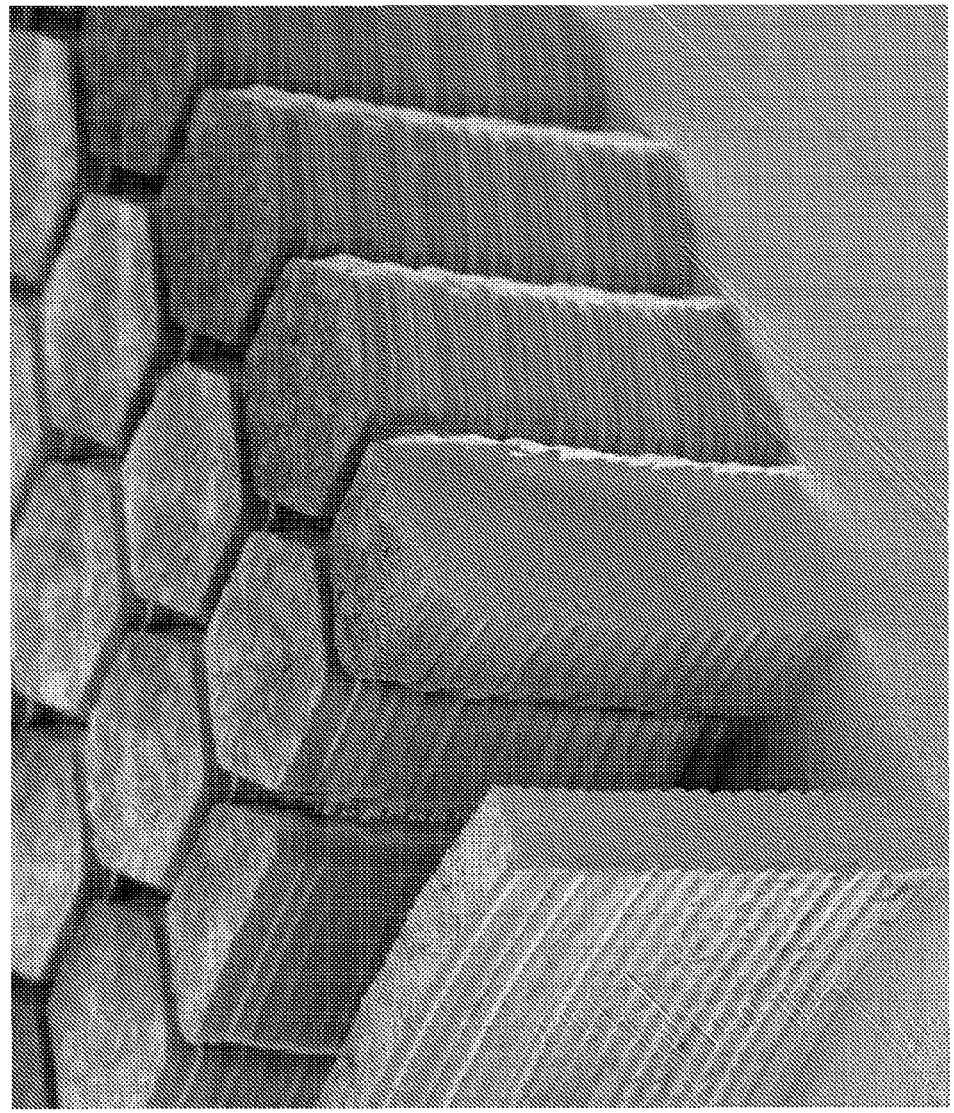
FIG. 68 is a photomicrograph of an exemplary array of microstructures formed via an exemplary method described herein.
Figure 69:
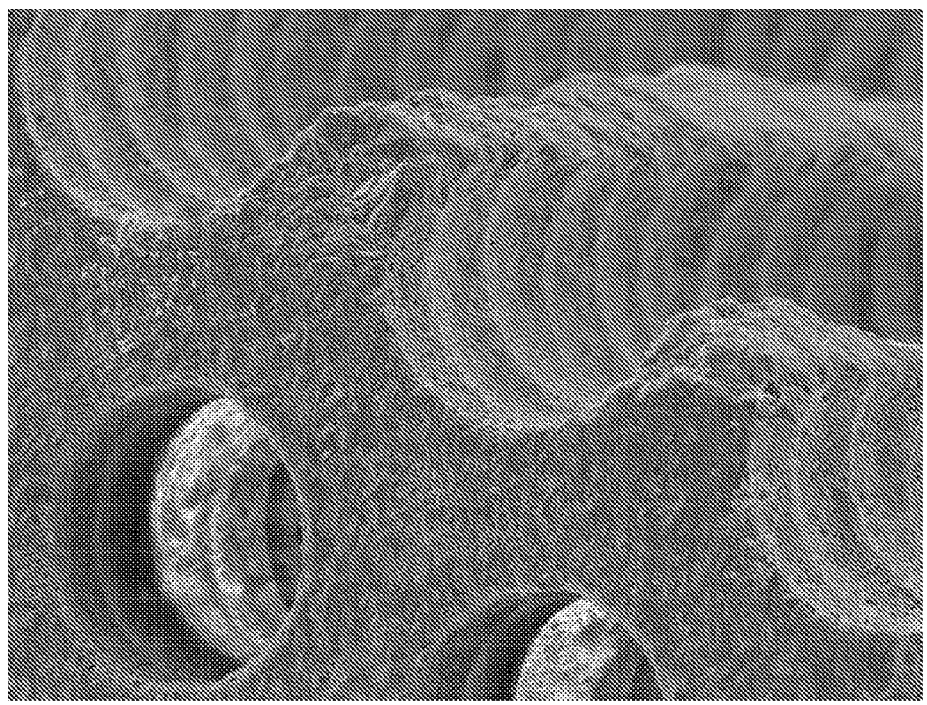
FIG. 69 is a photomicrograph of a surface of an exemplary microstructure formed via an exemplary method described herein.

FIG. 66 shows a magnified view of the cast 3D structures. A square-shaped structure was chosen for this example to further demonstrate the versatility of lithography. Features of these structures include:

Cast Polymer Micro-Structures
Micro-Structure Array=20×60
Top and Bottom Surface 870×870 microns
Center Surface 1.035×1.035 mm
Micro Structure Height 900 microns FIG. 67 is a photomicrograph of an exemplary 7-layer microstructure formed via an exemplary method described herein. FIG. 68 is a photomicrograph of an exemplary array of microstructures formed via an exemplary method described herein. FIG. 69 is a photomicrograph of a surface of an exemplary microstructure formed via an exemplary method described herein.

Note that the layers and/or features of a mold can be reflected in the microstructure and/or molded part. Although this is at least implied in FIG. 57, this is particularly apparent in FIGS. 65 and 66, each of which show a plurality of monolithic microstructures each having protruding undercuts created by one or more molds from which the microstructure is descended and/or reflecting protruding undercuts of such a mold(s). The reflection, impression, and/or artifacts of the mold layers are also shown in FIGS. 67, 68, and 69 for various microstructures. The smooth wall of the hexagonal stack and the rectangular stack at the slice mark in the foreground of FIG. 68 make apparent the fact that these microstructures are monolithic and/or unitary molded structures. That is, FIG. 68 shows that one of the microstructures sliced to reveal a solid, layer-less interior volume having periphery defined by an outer surface, at least one outer surface of each of the microstructures comprising a plurality of 3-dimensional micro-features that substantially spatially invertedly replicate a mold surface formed by a plurality of layers of a metallic foil stack lamination parent mold. That is, by reflecting and/or invertedly reproducing the surface of the parent mold, the outer surface of each hexagonal column appears to suggest that the column is a stack of layers. Yet the cut-away view shows that the column is layer-less in its interior, the column only showing artifacts, such as protruding undercuts, of the layers of the parent mold on the surface of the column.

FIG. 69 illustrates that the surface of an exemplary microstructure formed via an exemplary method described herein can comprise a plurality of 3-dimensional microfeatures that substantially spatially invertedly replicate a mold surface formed by a plurality of layers of a metallic foil stack lamination parent mold. That is, FIG. 69 makes apparent that the layers of the mold are reflected at the edges, surfaces, and/or interfaces (e.g., at the outer edges and within the holes) of these microstructures and/or molded parts.

Potential Fields of Application
a. Transportation Industry
   Technology Areas:
   Weight reduction
   Low inertia for dynamic components
   Impact resistance
   Vibration damping
   Acoustic abatement
   Electrical insulation
   Inertial measurement
   RF technology
   Communications
   Active structures and surfaces
   Hydrodynamics
   Representative Devices:
   conformable MEMS (active and passive)
   micro-satellite components
   micro combustors
   micro turbines
   micro-thrusters
   RF switches
   antennas
   phase shifters
   displays
   optical switches
   accelerometers
   gyroscopes
   rate sensors
   vibration sensors
   mass sensors
   pressure sensors
   temperature sensors
   viscosity sensors
   density sensors
   humidity sensors
   corrosion sensors
   capacitive sensors
   temperature regulators
   fuel cells
   fuel processors
   nozzle technology
   valves and regulators
   pumps
   filters
   relays
   actuators
   heaters
b. Biological and Biotechnology
   Technology Areas:
   Micro-fluidics
   Microbiology
   DNA assays
   Chemical testing
   Chemical processing
   Lab-on-a-chip
   Tissue engineering
   Analytical instrumentation
   Bio-filtration
   Test and measurement
   Bio-computing
   Biomedical imaging
   Representative Devices:
   biosensors
   bioelectronic components
   reaction wells
   microtiterplates
   pin arrays
   valves
   pumps
   bio-filters
   tissue scaffolding
   cell sorting and filtration membranes
c. Medical (Diagnostic and Therapeutic)
   Technology Areas:
   Imaging
      Computed tomography
      Angiography
      Fluoroscopy
      Radiography
      Interventional radiography
   Orthopedic
   Cardiac and vascular devices
   Catheter based tools and devices
   Non-invasive surgical devices
      Medical tubing
   Fasteners
   Surgical cutting tools
   Representative Devices:
   airways
   balloon catheters
   clips
   compression bars
   drainage tubes
   ear plugs
   hearing aids
   electrosurgical hand pieces and tubing
   feeding devices
   balloon cuffs
   wire/fluid coextrusions
   lumen assemblies
   infusion sleeves/test chambers
   introducer tips/flexible sheaths
   seals/stoppers/valves
   septums
   stents shunts
membranes
electrode arrays
ultra-sound transducers
infra-red radiation sensors
radiopaque targets or markers
collimators
scatter grids
detector arrays
d. Military
   Technology Areas:
   Weapon safeing
   Arming and fusing
   Miniature analytical instruments
   Biomedical sensors
   Inertial measurement
   Distributed sensing and control
   Information technology
   RF devices
   Representative Devices:
   MEMS fuse/safe-arm devices
   ordinance guidance and control devices
   gyroscopes
   accelerometers
   disposable sensors
   spectrometers
   active MEMS surfaces (large area)
   micro-mirror MEMS displays
   antennas
   switches
   phase shifters
   capacitors
   resistors
   conductors
   inductors
   exciters
   transmitters
   filters
   receivers
   voltage regulators
   power regulators
   current regulators In the transportation industry, such as the aerospace industry, exemplary embodiments can comprise multi-layer composite components, such as wings, ailerons, rotors, panels, doors, shrouds, and/or cowlings, etc. For such components, layers underlying the external "skin" can be constructed to optimize the component generally and/or in any specific and/or predetermined layer and/or location(s) within the component for functions, properties, and/or attributes such as material composition; density; weight; strength; impact resistance; stiffness; deflection; fatigue resistance; permeability; diffusion rate; texture; color; opacity; attachment points; cooling; vibration damping; acoustic damping; stealth properties; electromagnetic properties; conductivity; thermal insulation; heat transfer; wire, cable and/or conduit routing; fluid routing; penetration and/or leak detection; and/or environmental sensing, etc.

The external skin can be optimized generally and/or in locally for functions, properties, and/or attributes such as surface finish; impact resistance; hardness; corrosion resistance; reflectance; color; opacity; electrical conductivity; thermal conductivity; permeability; etc.

For example, the ability for helicopters to safely fly or even fly at all can be influenced by damage to the helicopter's rotor. To alert a helicopter's pilot to such damage during flight, the interior of the rotor is typically pressurized with nitrogen and the pressure of the nitrogen monitored, so that substantial penetrations of the rotor's skin result in a detectable pressure drop. By utilizing the herein described LAMMS™ technology, numerous orifices, pressure sensors, and communications networks can be built into the rotor in selected locations such that a more precise location of any substantial leaks can be determined, thereby allowing the pilot to make a more informed decision about the severity of the influence of the leak upon the helicopter's flightworthiness. That is, certain detected leaks might be tolerable and of insignificant impact on the ability of the helicopter to continue to fly safely. Other leaks, whether in critical locations or of critical size, can have a significant impact.

Similarly, exterior and/or interior components, such as panels, doors, hoods, fenders, shrouds, and/or cowlings for automobiles, trucks, and/or marine vessels can utilize the LAMMS™ technology described herein to generally and/or locally optimize the component for any of the herein described functions, properties, and/or attributes.

For example, for racing yachts and/or other marine vessels, utilizing the LAMMS™ technology described herein, hulls and/or hull surfaces can be constructed using a fish-scale type design, the fish scales varying in locations, dimensions, and/or properties as desired and/or for optimal hydrodynamic performance.

In another example, the housing of a computer and/or other electronic or electrical device can utilize the LAMMS™ technology described herein to generally and/or locally optimize the housing for any of the herein described functions, properties, and/or attributes. For example, the housing could integrate redundant and/or non-redundant acoustic damping elements; cooling channels; mechanical vibration damping features; stiffeners; electrical conductors; electromagnetic shielding; etc.

For another example, hook and loop fastener systems can be created utilizing the herein described LAMMS™ technology for creating redundant and/or non-redundant hooks and/or loops, such as hooks that vary in density and/or length across a particular dimension of hook material. A specific application for such a fastening system is a baby diaper having a hook and loop closure with a varying pattern of hooks and/or loops. The pattern can be constructed such that the closure is rather difficult, particularly for a child, to initiate opening by separating the hooks from the loops, but once opening is initiated, completing the opening requires much less pulling force than would be required if substantially uniform hooks and loops were utilized for the closure. Such a pattern can feature a predetermined variable hook and/or loop density, and/or hooks of predetermined varying lengths, orientations, stiffness, material composition, etc.

An additional application for the herein described LAMMS™ technology is to create a grinding wheel that is customized to the particular part (e.g., lens, blade, etc.) it is intended to grind. The wheel can have grinding functions, properties, and/or attributes (e.g., abrasiveness, hardness, density, surface finish, material; etc.) that vary across its face in correspondence and/or relevance to the grinding needs of the part with which the wheel will interface.

In another application, a transdermal patch can utilize the herein described LAMMS™ technology to provide multiple functional layers and/or generally and/or locally optimized functions, properties, and/or attributes. For example, a particular layer, perhaps in a particular location, can encompass a desired pharmaceutical, chemical, radioactive, and/or biological substance that can aid in treatment.

Additional applications can involve the utilization of the herein described LAMMS™ technology for large area and/ or pixelated sensors or detectors. For example, a large area neutron detector can utilize selectively conductive layers separated by a dielectric material through which an array of gas-filled wells is formed. In another example, the LAMMS™ technology can be used to form a pixelated radiography screen, the screen comprising a plurality of wells each containing a phosphor element.

Hierarchical Tessellation Structures (HTS)—a New Class of Periodic Cellular Structure Engineering Concept A: Tessellation Tessellation is the juxtaposition of shapes into a pattern of contiguous polygons. As shown in FIG. 70, hexagons, rectangles, and isosceles triangles can be arrayed in three dimensions to create honeycomb, orthogrid, and isogrid structures, respectively. One purpose and/or use of such structures is to increase and/or maximize open volume, which can reduce the overall weight of the structure.

Engineering Concept B: Fractals

Figure 71:
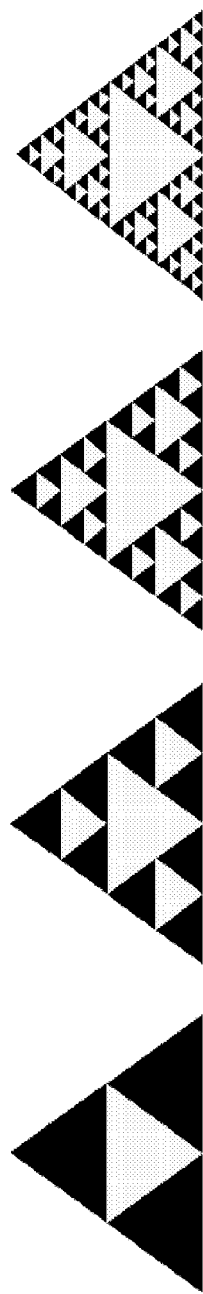
FIG. 71 illustrates some exemplary embodiments of fractal patterns.

Fractals are scalable, self-similar, geometric patterns mathematically defined by precise, iterative functions. FIG. 71 illustrates some exemplary embodiments of fractal patterns that can be created via various exemplary embodiments described herein. At least some cells within any of the aforementioned tessellation structures can subdivided into smaller, self-similar cells. One purpose of such structures is to decrease and/or minimize open area, which can increase density and/or enhance associated material and/or structural properties.

Combining these two concepts can give rise to a Hierarchical Tessellation Structure wherein the geometry, scale, and/or distribution of cells can be manipulated into continuous gradients to improve and/or optimize the strength-to-weight ratio of a structure, create substantially uniform load paths (distribution) within the structure, and/or enable more efficient transfer of loads to adjoining structures. These structures, which can be derived via a method described herein, also can exhibit low part-to-part variation in weight and/or dimensional accuracy. By varying the architecture of individual plies within a multi-ply, laminated structure, precisely engineered cavities and passageways can be created to embed remote sensing systems for structural health monitoring and/or real-time battle damage assessment.

Figure 72:
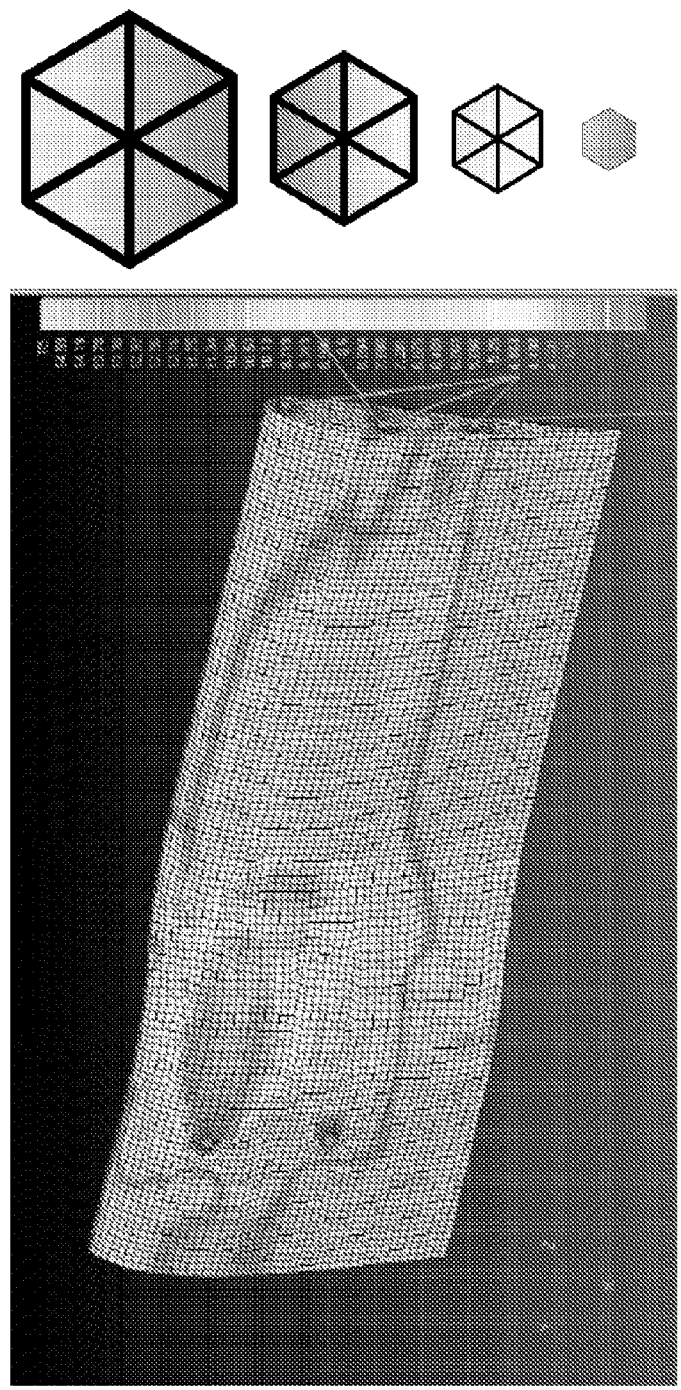
FIG. 72 illustrates an exemplary output of an exemplary finite element analysis.
Figure 73:
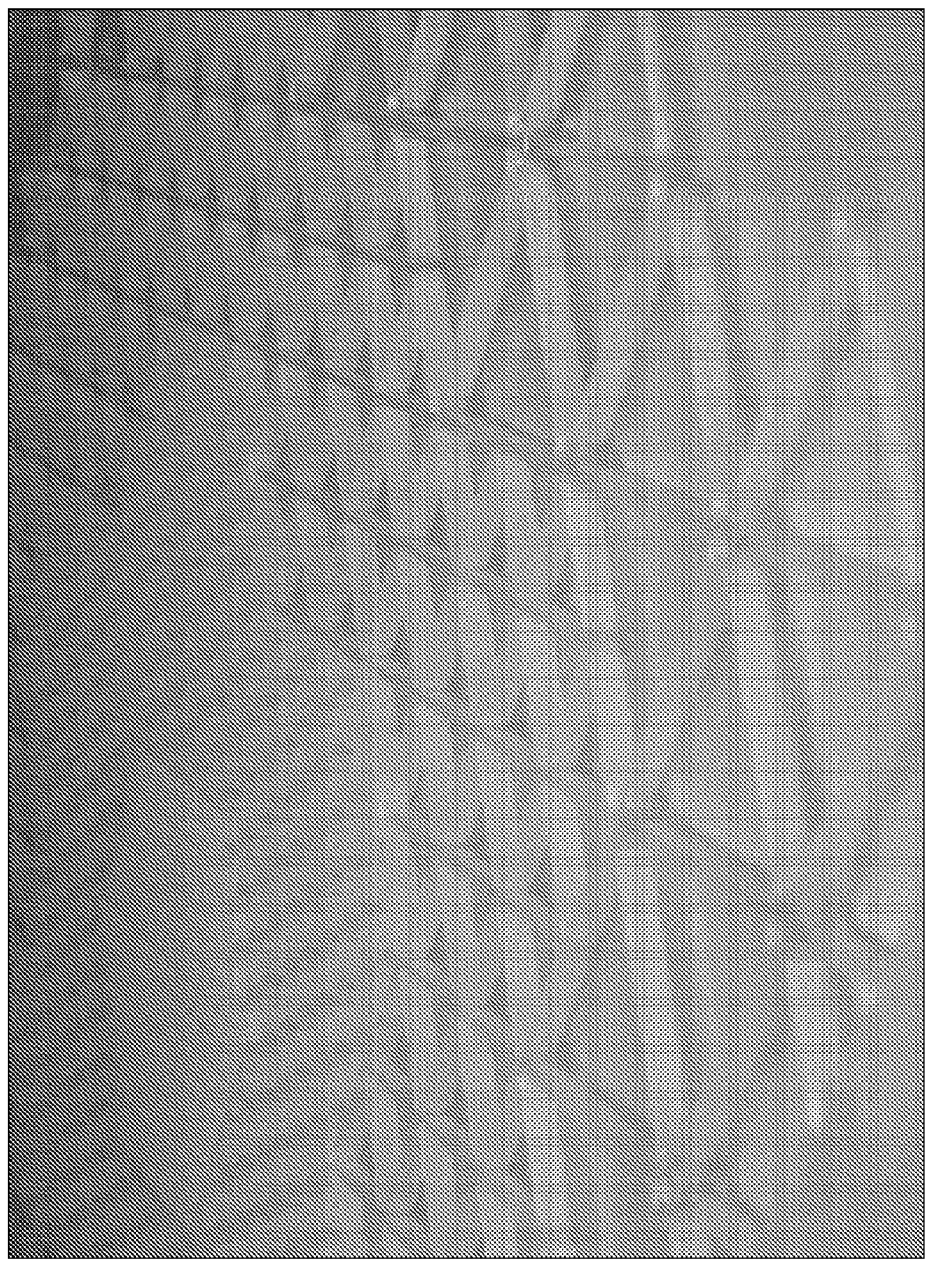
FIG. 73 shows a perspective view of an exemplary isogrid structure.

The geometry, scale, and/or distribution of cells can be determined by means of a Finite Element Analysis stress model. The design process can correlate cell architecture with the concentrations of stress generated (within the structure) by applied loads, which can enable and more and/or most parsimonious use of materials. FIG. 72 illustrates an exemplary output of an exemplary finite element analysis, showing areas of higher and lower stress values, and an approximate relative size of corresponding structures that can be used to accommodate those stress values, with larger structures corresponding to lower stress values and smaller structures used for accommodating higher stress values. FIG. 73 shows a perspective view of an exemplary isogrid structure that can be constructed based on such an output of a finite element analysis.

Application-specific materials can be combined to achieve desired and/or superior performance in such systems as low observable ('stealth") structures, ballistic impact resistant structures, and/or high-cycle fatigue resistant structures. Attributes of this technology can include, but are not limited to:

Design agility;
Facilitates carbon fiber panel lay-up by integral membranes (closed cells) on outer plies;
Large area (square meter) capability;
Reduction of septa (ligament) volume;
Reduction in core density;
Isotropic mechanical properties;
Increased resistance to rib buckling;
Increase mechanical strength of shear planes;
Variable rigidity (flexibility); and/or
Energy absorbing core structures.

Certain exemplary embodiments can provide large area micro-mechanical systems (sometimes referred to herein as "LAMMS"), which can be Finite Element Analysis ("FEA") driven;
custom mesostructure per FEA element;
variable geometry and distribution;
arrays of mm3-scale mesostructures over m2 areas;
multi-functional materials; synthetic composites;
multi-ply, laminated structures; and/or
low weight; high performance.

Certain exemplary embodiments can provide advanced core structures, which can comprise and/or be characterized by: multi-layer lamination; isogrid cell motif; loads-defined cell topography; carbon fiber face and/or back sheets; large area capability, on the scale of approximately 1 to 10 square meters; a density of approximately 19 kg/cubic meter for a cell size of 20 mm; varying cell concentrations in a continuous gradient; parsimonious use of materials; and/or uniform load distributions.

Certain exemplary embodiments can provide an isogrid cell motif, which can provide and/or be characterized by: an inherent resilience to tensile, compressive, shear, and/or bending loads; redundant load paths; resistance to impact, delamination, and/or crack propagation; optimization for a wide range of load intensities, superior strength to weight ratio.

Certain exemplary embodiments can provide an isogrid cell motif, which, from the perspective of and/or to accommodate compressive loads, can provide and/or be characterized by: a variety of rib and/or ligament thicknesses; expanded and/or condensed grid patterns; decreased aspect ratio; increased numbers of plies; grid patterns that are offset from one layer to the next; isotropic properties; and/or resistance to rib buckling.

Certain exemplary embodiments can provide an isogrid cell motif, which, from the perspective of and/or to accommodate shear loads, can provide and/or be characterized by: increased surface area; closed cells on the bond line; increased interface adhesion; textured surfaces; interlocking plies; male and female interlock components; and/or optimizable mechanical strength of shear planes.

Certain exemplary embodiments can provide an advanced multi-functional armor system, which, can provide and/or be characterized by: projectile and/or fragment defeat; blast mitigation (Behind Armor Blunt Trauma); multiple strike protection; enhanced mobility; light weight; scalable systems; low cost; high modulus outer skin; and/or an energy absorbing and/or redirecting core; a polymer matrix core; a ballistic barrier and/or ceramic back face; and/or a spall shielding (e.g., Kevlar) back face.

Certain exemplary embodiments described herein can be used to construct products, devices, assemblies, machines, and/or systems, such as those described herein and/or such as a sporting good, tennis racket, golf club shaft, fishing rod, hockey stick, backboard, goalpost, bicycle and/or motorcycle frame, fork, handlebar, seatpost, crank arm, wheel, mudflap, equestrian saddle, saddle tree, kayak, paddle, ski, ski pole, skate, skate blade, snowboard, surfboard, skateboard, helmet, guard, paintball equipment, gunstock, ballistic armor, armor, boat and/or ship hull, deck, superstructure, mast, marine equipment, satellite shell, antenna, solar panel, radome, aircraft wing, fuselage, fairing assembly, airframe, elevator, rudder, landing gear, propeller, helicopter airfoil (rotor blade), windmill airfoil (blade), turbine blade, engine component, engine exhaust shroud, exhaust baffle, driveshaft, acoustic shroud, acoustic baffle, cockpit sidewall, ceiling panel, doorliner, door panel, hood, fender, bonnet, fairing, bumper, tailgate, spoiler, bed, quarter panel, roof, pillar, floorboard, sidewall, dashboard, instrument panel, headliner, trunk deck, firewall, bulkhead, seat frame, leaf spring, wheel, rail, wall, floor support, flooring, door, window frame, railing, siding, chassis, frame, conduit, duct, pipe, pressure vessel, tank, equipment, pump, fan, damper, machine tool, robot arm, equipment housing, enclosure, fire resistant enclosure and/or panel, fireproof enclosure and/or panel, computer enclosure, keyboard, display, loud speaker, tripod, engine component, flywheel, footing, structural column, structural beam, truss, structural wall, divider, impact absorber, guardrail, signpost, light pole, power pole, structural pole, architectural signage, signage substrate, billboard substrate, tool, handle, footwear, toy, musical instrument, casket, gurney, bed frame, furniture, shelving, cabinetry, countertop, hot tub, tub, shower enclosure, pet crate, packaging, composite part, and/or composite structure, etc.

Certain exemplary embodiments described herein can be used to construct products, devices, assemblies, machines, and/or systems, such as those typically constructed using fiberglass reinforced plastic, carbon fiber reinforced plastic, fiber reinforced matrix systems, honeycombed sandwich structures, and/or sandwiched composite structures.

Certain exemplary embodiments can provide a first isogrid defining a first plurality of zones, each zone from said first plurality of zones comprising a plurality of ligaments, each zone from said first plurality of zones defining a plurality of spaces, each space bounded by a first sub-plurality of ligaments from said plurality of ligaments, each of said ligaments comprising a plurality of ligament surfaces.

Certain exemplary embodiments can provide a system comprising: a first cast isogrid defining a first plurality of zones, each zone from said first plurality of zones comprising a plurality of cast ligaments, each zone from said first plurality of zones defining a plurality of triangular spaces, each triangular space bounded by a first sub-plurality of cast ligaments from said plurality of cast ligaments, an interlock defined at an intersection of a second sub-plurality of cast ligaments from said plurality of cast ligaments, each of said cast ligaments comprising a plurality of ligament surfaces, for each of said ligaments, a ligament surface from said plurality of ligament surfaces comprising a plurality of 3-dimensional micro-features that substantially spatially invertedly replicate a mold surface formed by a plurality of layers of a metallic foil stack lamination parent mold, said plurality of 3-dimensional micro-features comprising at least one protruding undercut, said plurality of ligament surfaces for each of said ligaments defining a periphery of a layer-less volume.

ADDITIONAL EMBODIMENTS

Exemplary Embodiment #1

Engineering specimens were produced to demonstrate the ability to design and/or fabricate an advanced multi-layer structural composite using TLM™ manufacturing. The specimen embodied engineered features including: high strength ISO grid configuration, controlled corner radii at cell intersection points to eliminate or reduce fracture points, varying sized interconnected cell configurations, recessed nodes at intersections for sensor embedding or fastening points, and 45 micron bump and cavity arrays on grid ligament (and back plane surface) to promote multi-layer adhesive bonding. Figure #X shows dimensional specifications of the specimen.

Specimens were produced using methods described in U.S. patent application Ser. No. 10/479,335 and/or herein. Methods for manufacturing three-dimensional devices and devices created thereby. Specimen manufacturing methods can include CAD generation, photo-mask generation, metallic foil etching, stack lamination, mold production, and/or casting. Both open and closed molds were used to produce the specimens. Specimens were produced using a low CTE two part epoxy (Epo-tek 301-2) and a flexible polyeurathane (Resin Lab EP1218). Specimens were also produced by loading the two part epoxy with carbon powder (200 mesh obtained from Grupo Rooe, S. A. de c.v. Mexico) prior to casting. The epoxy was loaded with varying amounts of carbon powder including 20%, 30%, and 40% by weight.

Exemplary Embodiment #2

Engineering specimens were produced to demonstrate the ability to design and fabricate an advanced multi-layer structural composite using TLM™ manufacturing.

The following design specifications were embodied in the specimen: overall size 20×20 CM, 1.500 mm open hexagonal cells, cells arrayed in two regions (slant hole region and progressive angle cell region), 2.0 mm total specimen thickness. Open cells arrayed in "progressive angle cell region" decrease in angular position from 90 degrees at the focal point to 36.7 degrees at the border of the "slant hole region". Open cells remain constant in the "slant hole region" at an angle of 37.5 degrees. Cell angles and regions are shown in Figure X.

Software code written in Visual Basic was used as a means of configuring the angles of the cell openings in the specimen. Each layer of the TLM™ mold (stack lamination) had unique cell positions on each layer to produce the angled cells. The Visual Basic program was imported into AutoCad software which was then used to create a DXF file. The DXF files were used to plot the CAD data to film for photo-mask generation.

Using Visual Basic, an event driven programming language for graphical user interface applications, such as AutoCAD, we can implement the appropriate algorithms for the desired engineered design. We can manipulate patterns across a surface as well as create 3D structures within a volume with layer-to-layer pattern variations.

Example Algorithms 3D slant hole geometry can be created by programming the following algorithm into Visual Basic for specific z locations.

For integers i and j=$^1$→integer value and dR, pitch_X and pitch_Y=constants, then the insertion point could be defined:

$$X = \text{pitch\_X} * i) + (dX * Z) \quad Y = (\text{pitch\_Y} * j) + (dY * Z)$$

where Z=location in z-axis, $$dX = \frac{dR * \left(\frac{\text{pitch\_X} * i}{\text{pitch\_Y} * j}\right)}{\sqrt{\left(\frac{\text{pitch\_X} * i}{\text{pitch\_Y} * j}\right)^2 + 1}} \quad \text{and} \quad dY = \frac{dR}{\sqrt{\left(\frac{\text{pitch\_X} * i}{\text{pitch\_Y} * j}\right)^2 + 1}}$$

Specimens were produced using methods described in U.S. patent application Ser. No. 10/479,335, which is incorporated by reference herein in its entirety to its fullest enabling extent permitted by law. Methods for manufacturing three-dimensional devices and devices created thereby. Specimen manufacturing methods include CAD generation (described above), photo-mask generation, metallic foil etching, stack lamination, mold production, and casting. Both open and closed molds were used to produce the specimens. Specimens were produced using a low CTE two-part epoxy (Epo-tek 301-2) and flexible polyurethane (Resin Lab EP1218). Specimens were also produced by loading the two part epoxy with carbon powder (200 mesh obtained from Grupo Rooe, S.A. de c.v. Mexico) prior to casting. The epoxy was loaded with varying amounts of carbon powder including 20%, 30%, and 40% by weight.

Figure 74:
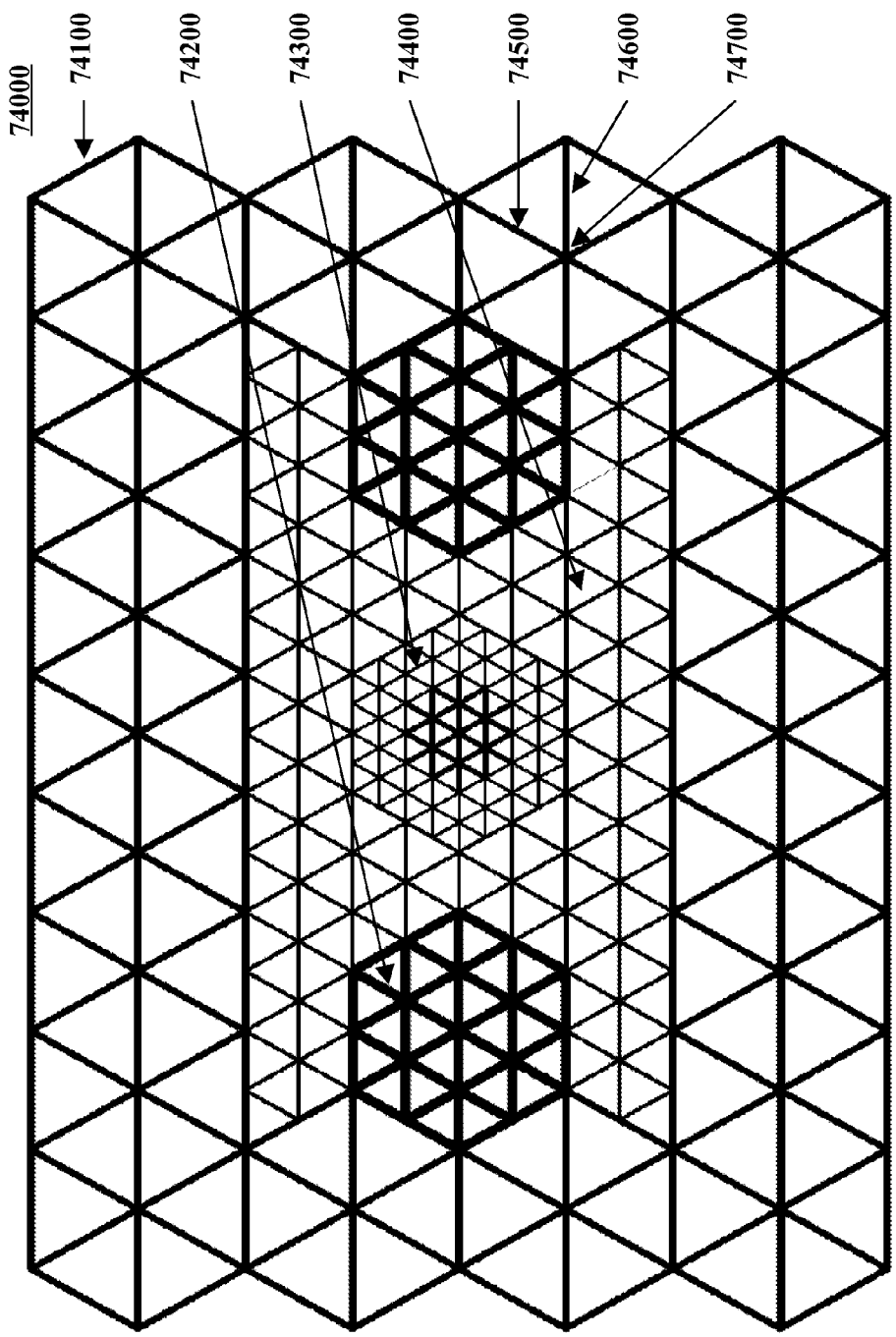
FIG. 74 is a perspective view of an exemplary embodiment of an isogrid 74000.

FIG. 74 is a perspective view of an exemplary embodiment of a cast isogrid 74000, which can comprise multiple zones 74100, 74200, 74300, 74400. Each zone can comprise multiple ligaments 74500, 74600, which can join at an intersection and/or node 74700.

Figure 75:
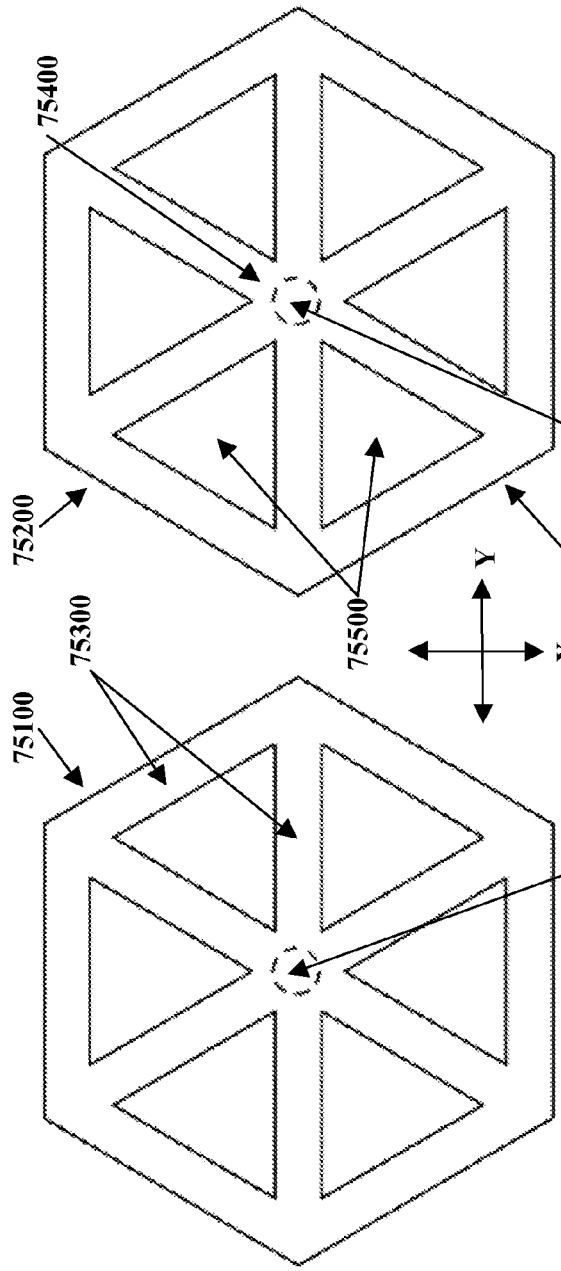
FIG. 75A and FIG. 75B are top and side views, respectively of an exemplary embodiment of a male interlocking isogrid 75100.
FIG. 75C and FIG. 75D are top and side views, respectively of an exemplary embodiment of a female interlocking isogrid 75200.

FIG. 75A and FIG. 75B are a top and side views, respectively of an exemplary embodiment of a male interlocking isogrid 75100, and FIG. 75C and FIG. 75D are a top and side views, respectively, of an exemplary embodiment of a female interlocking isogrid 75200. Any isogrid 75100, 75200 can comprise multiple ligaments 75300, which can join at an intersection and/or node 75400, and which can define spaces, such as triangular space 75500. A maximum dimension measured between a pair of ligaments defining a triangular space 75500 can be, for example, from approximately 0.0625 inches to approximately 0.375 inches, including all values and subranges therebetween, such as from approximately 0.1875 inches to approximately 0.375 inches. Each ligament can have a variable and/or substantially uniform thickness, such as a thickness of from approximately 0.0007 inches to approximately 0.005 inches, including all values and subranges therebetween. A ligament 75300 can comprise a ligament surface 75600, which can comprise a plurality of 3-dimensional micro-features that substantially spatially invertedly replicate a mold surface formed by a plurality of layers of a metallic foil stack lamination parent mold, said plurality of 3-dimensional micro-features comprising at least one protruding undercut, said plurality of ligament surfaces for each of said ligaments defining a periphery of a layer-less volume, such as shown in FIG. 68.

Figure 76:
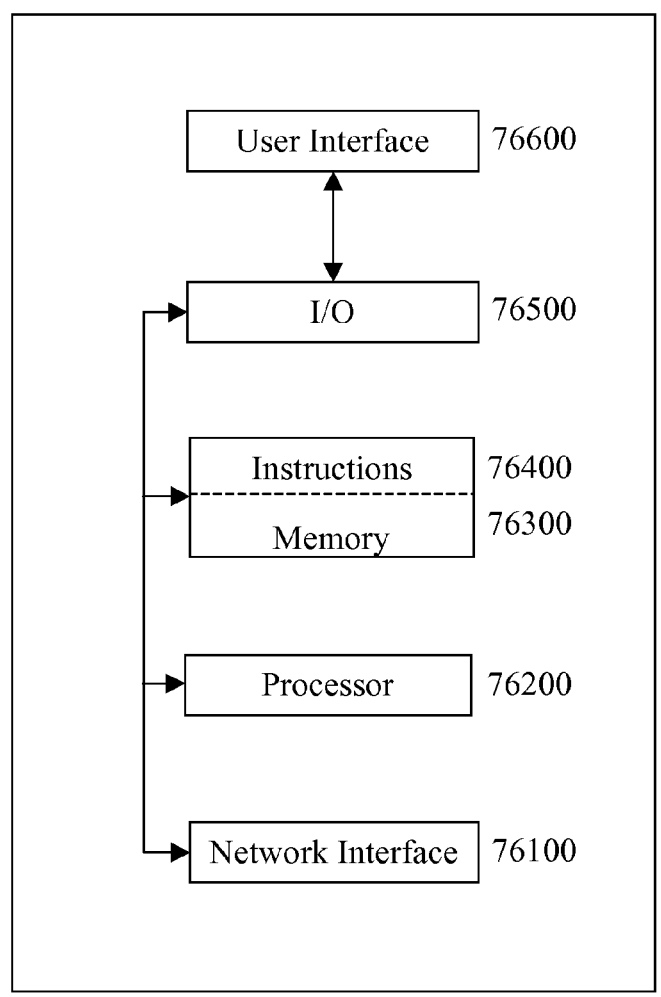
FIG. 76 is a block diagram of an exemplary embodiment of an information device 76000.

FIG. 76 is a block diagram of an exemplary embodiment of an information device 76000, which in certain operative embodiments can comprise, for example, a computer, such as a computer used to perform a finite element analysis. Information device 76000 can comprise any of numerous components, such as for example, one or more network interfaces 76100, one or more processors 76200, one or more memories 76300 containing instructions 76400, one or more input/output (I/O) devices 76500, and/or one or more user interfaces 76600 coupled to I/O device 76500, etc.

In certain exemplary embodiments, via one or more user interfaces 76600, such as a graphical user interface, a user can view a rendering of information related to researching, designing, modeling, creating, developing, building, manufacturing, operating, maintaining, storing, marketing, selling, delivering, selecting, specifying, requesting, ordering, receiving, returning, rating, and/or recommending any of the products, services, methods, and/or information described herein.

Figure 77A:
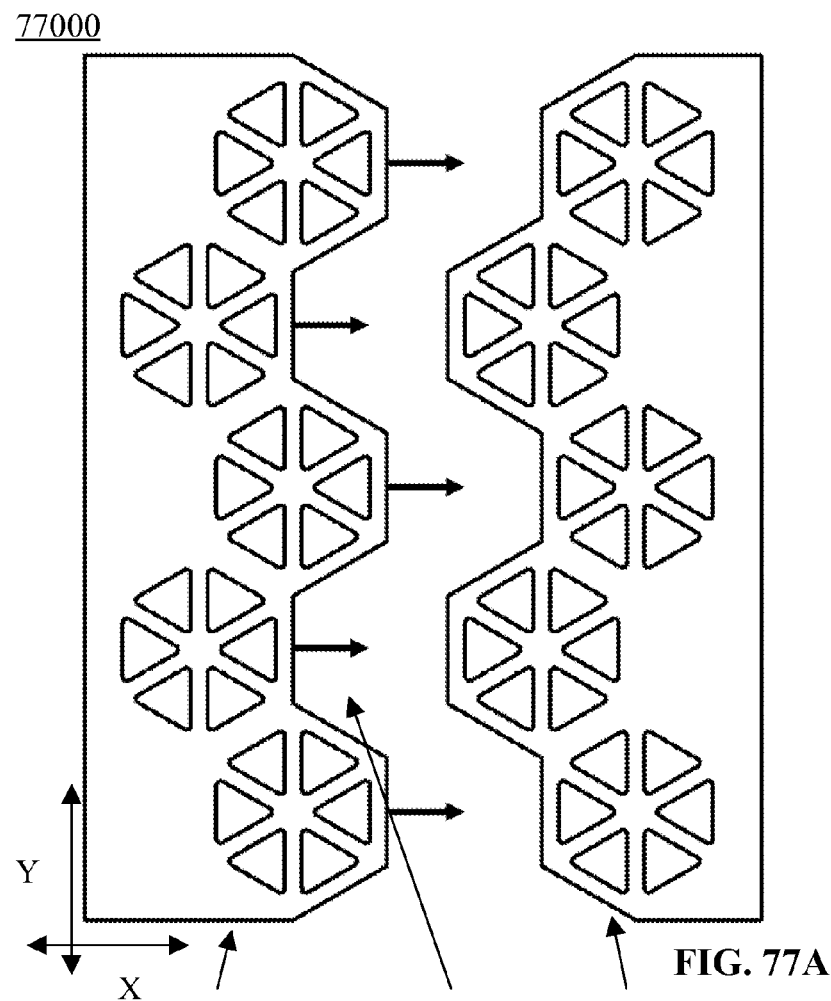
FIG. 77A is a top view of an exemplary embodiment of a system 77000 comprising an isogrid tiling positioner.
Figure 77B:
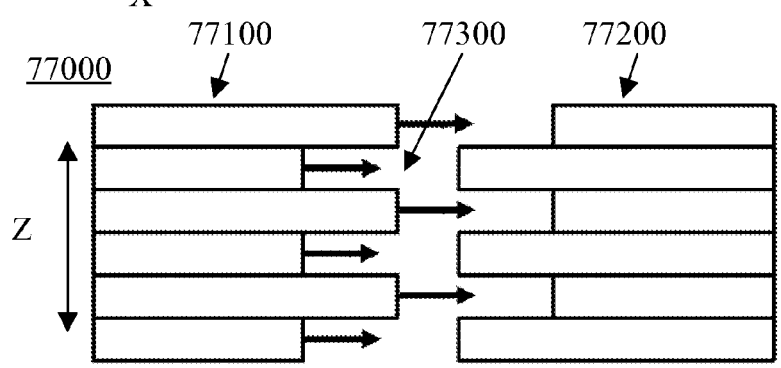
FIG. 77B is a front view of an exemplary embodiment of the system 77000 of FIG. 77A.

FIG. 77A is a top view of an exemplary embodiment of a system 77000, and FIG. 77B is a front view of an exemplary embodiment of the system 77000 of FIG. 77A. System 77000 comprises isogrid 77100 and isogrid 77200, as well as an isogrid tiling positioner 77300 formed by features of isogrid 77100 and isogrid 77200 at multiple layers of each isogrid. Thus, in this exemplary embodiment, isogrid tiling positioner 77300 serves as an interlocking isogrid stacking positioner, because it constrains and/or prevents movement of isogrid 77100 with respect to isogrid 77200 in the Z direction, and serves as an isogrid tiling positioner because it constrains and/or prevents movement of isogrid 77100 with respect to isogrid 77200 in the X direction and/or Y direction.

FIG. 78A is a top view, and FIG. 78B is a front view, of an exemplary embodiment of a system 78000 comprising a channeled isogrid 78100 comprising channels 78200, 78300 within a plurality of its ligaments. Such channels can provide a variety of uses, such as conveying fluids, positioning electrical conductors, and/or positioning optical waveguides.

Figure 79A:
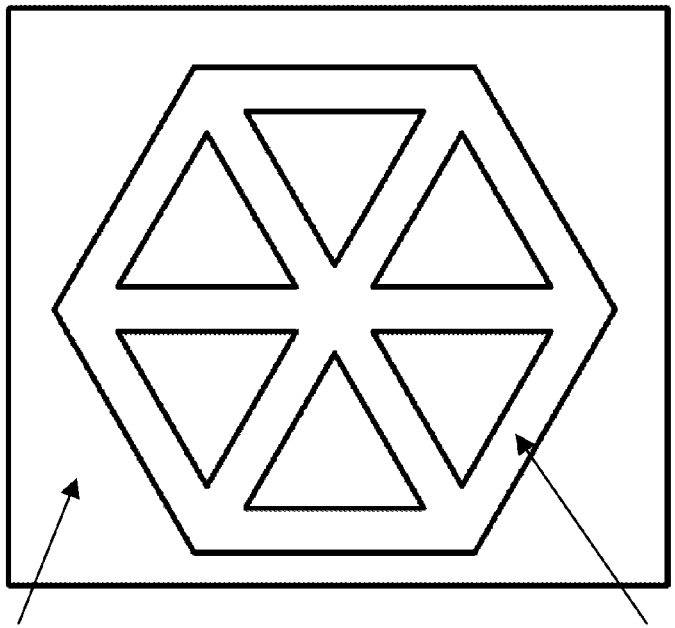
FIG. 79A is a top view of an exemplary embodiment of a system 79000 comprising an isogrid attached to a face plate.

FIG. 79A is a top view of an exemplary embodiment of a system 79000 comprising an isogrid 79200 attached to a face plate 79100.

Figure 79B:
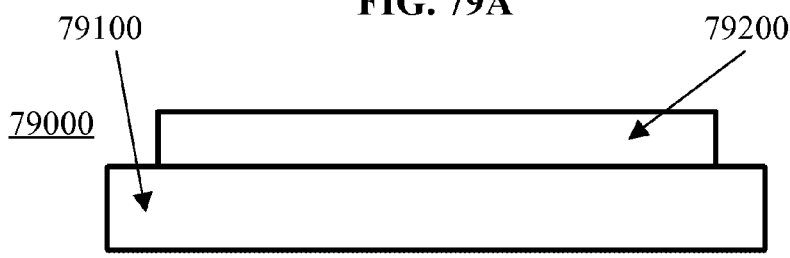
FIG. 79B is a front view of an exemplary embodiment of system 79000 of FIG. 79A.

FIG. 79B is a front view of an exemplary embodiment of system 79000 of FIG. 79A, in which isogrid 79200 and face plate 79100 are positioned adjacent and in parallel flat planes.

Figure 79C:
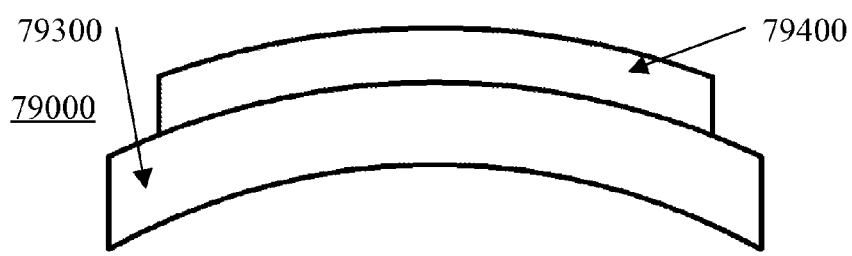
FIG. 79C is a front view of an exemplary embodiment of system 79000 of FIG. 79A.

FIG. 79C is a front view of an exemplary embodiment of system 79000 of FIG. 79A, in which isogrid 79200 and face plate 79100 are positioned adjacent and in parallel curved planes.

Figure 80A:
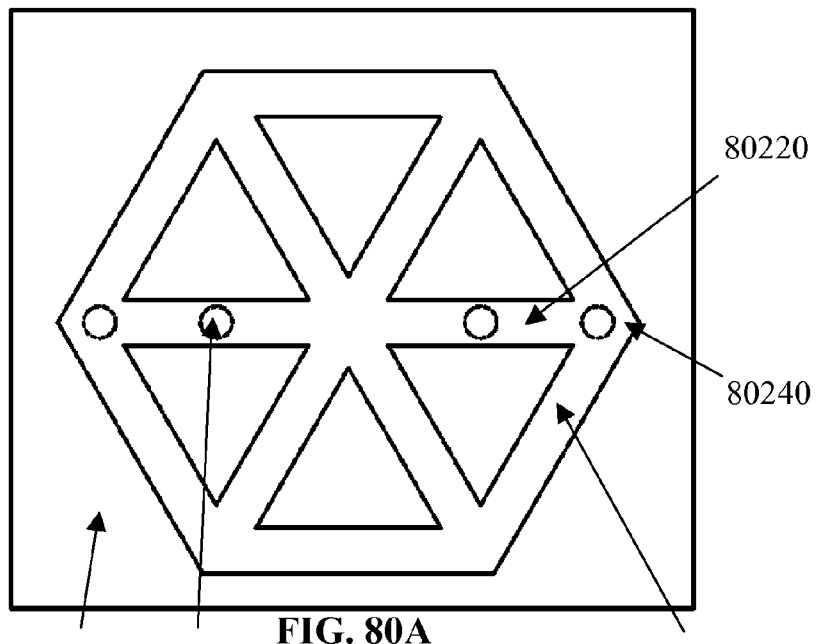
FIG. 80A is a top view of an exemplary embodiment of a system 80000 comprising an isogrid stacking positioner.

FIG. 80A is a top view of an exemplary embodiment of a system 80000 comprising an isogrid 80200 attachable to a face plate 80100 via one or more male isogrid stacking positioners 80300, which can be located along a ligament 80220 and/or at a node 80240 where ligaments intersect.

Figure 80B:
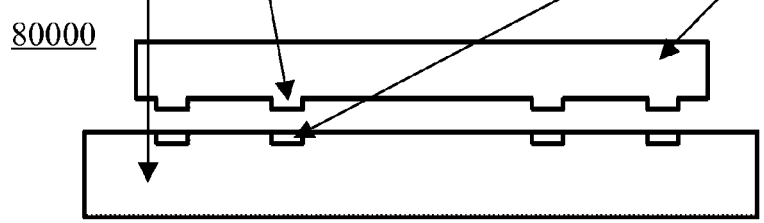
FIG. 80B is a front view of an exemplary embodiment of system 80000 of FIG. 80A.

FIG. 80B is a front view of an exemplary embodiment of system 80000 of FIG. 80A, showing a plurality of female isogrid stacking positioners 80400, and that isogrid 80200 and face plate 80100 can be positioned in adjacent parallel flat planes.

Figure 80C:
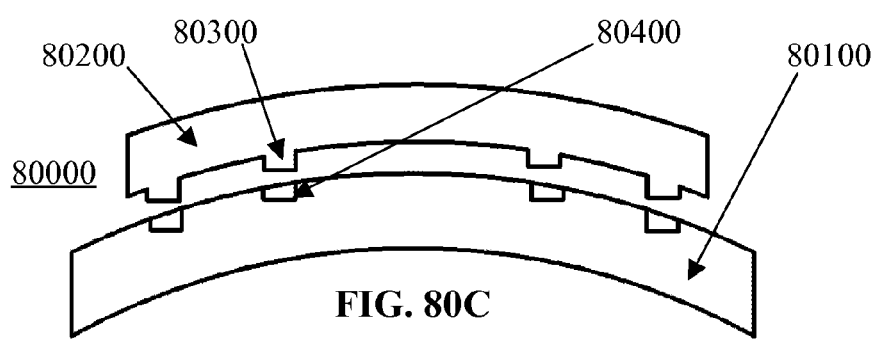
FIG. 80C is a front view of an exemplary embodiment of system 80000 of FIG. 80A.

FIG. 80C is a front view of an exemplary embodiment of system 80000 of FIG. 80A, showing a plurality of female isogrid stacking positioners 80400, and that isogrid 80200 and face plate 80100 can be positioned in adjacent parallel curved planes.

FIG. 81A is a top view of an exemplary embodiment of a system 81000 comprising a isogrid stacking positioner 81300 located at a node 81200 of an isogrid 81100.

FIG. 81B is a front view of an exemplary embodiment of system 81000 of FIG. 81A, and showing that isogrid stacking positioner 81300 can be male, thereby serving as a mechanical positioner.

FIG. 82A is a top view of an exemplary embodiment of a system 82000 comprising an isogrid stacking positioner 82300 located at a node 82200 of an isogrid 82100.

FIG. 82B is a front view of an exemplary embodiment of system 82000 of FIG. 82A, and showing that isogrid stacking positioner 82300 can be female, thereby serving as a mechanical positioner.

FIG. 82C is a front view of an exemplary embodiment of system 82000 of FIG. 82A, and showing that isogrid stacking positioner 81300 can be a through hole, thereby serving as a visual and/or optical positioner.

FIG. 83A is a top view, and FIG. 83B is a front view, of an exemplary embodiment of a system 83000 comprising a fillet 83300 joining two ligaments 83400, 83500 at a node 83200 of an isogrid 83100, the fillet 83300 having a radius R.

Figure 84:
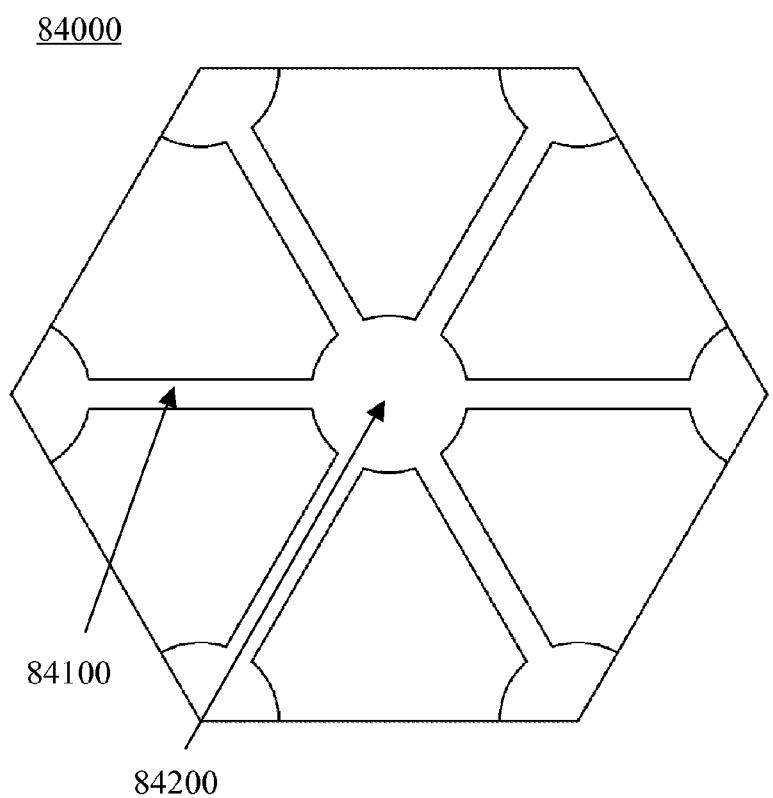
FIG. 84 is a top view of an exemplary embodiment of a system 84000 comprising a substantially circular node.

FIG. 84 is a top view of an exemplary embodiment of a system 84000 comprising a substantially circular node 84200 joining a plurality of ligaments of an isogrid 84100.

Figure 85:
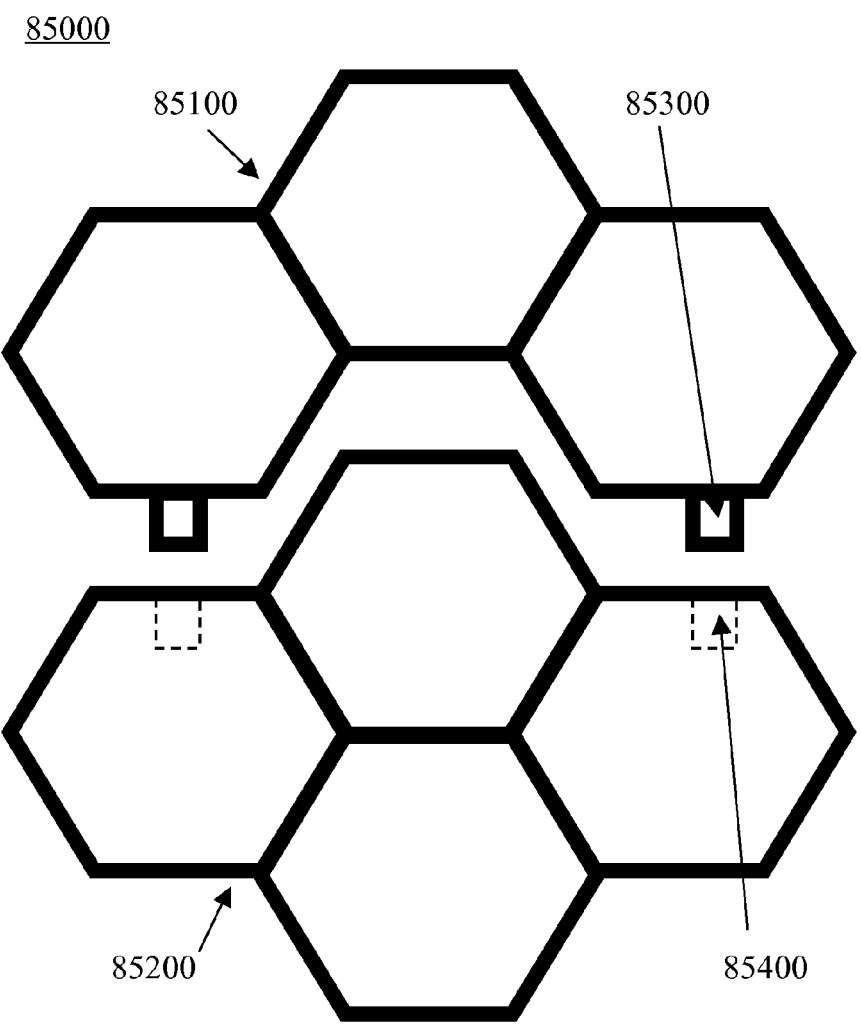
FIG. 85 is a top view of an exemplary embodiment of a system 85000 comprising an isogrid tiling positioner.

FIG. 85 is a top view of an exemplary embodiment of a system 85000 comprising a first isogrid 85100 comprising a male isogrid tiling positioner 85300 located at a predetermined position along a ligament of first isogrid 85100 and adapted constrain and/or interlock first isogrid 85100 relative to a second isogrid 85200 via mating with a female isogrid tiling positioner 85400 located at a corresponding predetermined position along a ligament of second isogrid 85200.

Figure 86:
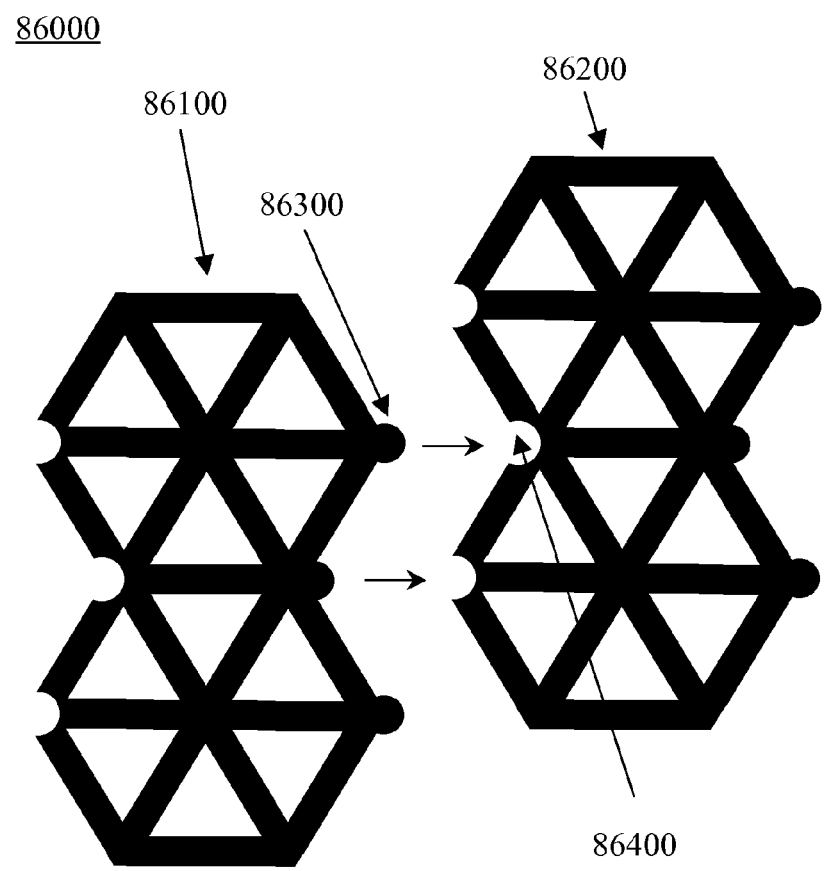
FIG. 86 is a top view of an exemplary embodiment of a system 86000 comprising an interlocking isogrid tiling positioner.

FIG. 86 is a top view of an exemplary embodiment of a system 86000 comprising a first isogrid 86100 comprising a male isogrid tiling positioner 86300 located at a node of first isogrid 86100 and adapted constrain, connect, and/or interlock first isogrid 86100 relative to a second isogrid 86200 via mating with a female isogrid tiling positioner 86400 located at a corresponding node of second isogrid 86200. Depending on the precise configuration, dimensions, and/or material properties of male isogrid tiling positioner 86300 and/or female isogrid tiling positioner 86400, the interlock formed thereby can be either non-destructively releasable, thereby allowing first isogrid 86100 to be easily released and reunited with second isogrid 86200, such as to facilitate testing, repair, and/or maintenance, or destructively releasable, thereby preventing first isogrid 86100 from being easily released and/or reunited with second isogrid 86200.

Additional Exemplary Embodiments

Jet engine manufacturers often seek to produce engines capable of operating at ever higher temperatures. The advantages derived thereby can include:
higher combustion efficiency,
higher thrust,
improved fuel efficiency, and/or
lower emissions.

A potential impediment to increasing the engine operating temperature (specifically, the turbine inlet temperature) can be the diminution of structural integrity that can occur in turbine airfoils at high temperature. "Hot section" airfoils often must maintain structural integrity in an environment of extreme temperatures and corrosive gases. The manufacture of such airfoils typically requires the use of special superalloys that are resistant to high temperature, corrosion, and stress. In short, turbine blade and vane survivability at higher operating temperatures can be a key to improving engine performance.

Modern gas turbine airfoils are typically hollow, monolithic structures that embody highly-engineered passages and orifices. During typical operation, cold (relatively) compressed air courses through these passages to extract heat from the structure, exits through arrays of orifices on the airfoil surfaces, and flows off the airfoil in lamellar fashion. Thus, the external surfaces of the airfoil are usually insulated from higher temperature gas in the mainstream. Airfoil design engineers have devised ways to increase the efficacy and efficiency of this "film cooling" process. Typically, the complex internal shapes of advanced, film-cooled airfoils can be achieved only with advanced investment casting technology and, more specifically, with the placement of a sophisticated casting core within the casting mold. Implementation of the most advanced film cooling designs tends to require investment casting cores of configurations that exceed the capability of conventional manufacturing technology.

Certain exemplary embodiments can address the need to rapidly and/or economically produce tools and/or prototype hardware whereby an advanced design can be empirically tested and optimized and/or the need to increase core manufacturing process capability (quality and/or reliability) in a recurring production environment.

Certain exemplary embodiments can enable faster and/or less-costly prototyping of complex investment casting cores and/or enhance the manufacturability of these optimized designs in a recurring production environment. Today's core manufacturing methods often impose significant constraints on engine designers as the need for more complex airfoils becomes greater. The high cost and long lead-time required to produce new prototypes often further impedes the design evolution process.

Certain exemplary embodiments can provide the ability to manufacture advanced investment casting cores embodying state-of-the-art designs for film cooling turbine airfoils. Via certain exemplary embodiments, this can be achieved with unprecedented design flexibility, accuracy, and/or cost efficiency. For certain exemplary embodiments, an enabling technology can be that found herein and/or in U.S. Pat. No. 7,141,812, dated 28 Nov. 2006, which is incorporated by reference herein in its entirety to its fullest enabling extent permitted by law, a portion of which we sometimes refer to herein as the Tomo-Lithographic-Molding™ (TLM™) process.

TLM master molds can be composed of a series of chemically-machined metal foils precisely aligned and/or bonded into a laminated, monolithic solid object. Each foil can be as thin as 0.0005" and/or can embody the cross-sectional features corresponding to a single "clipping plane" of a virtual solid (CAD model). The nearly unlimited flexibility to array features on the X-Y plane of each foil, and/or the Z axis among foils, can be inherent to the process.

TLM can be considered a distant derivative of the photolithographic methods commonly employed in the production of integrated circuits. Optical scaling techniques can be used to produce ultra-precise photo masks. This approach can enable one to chemically machine metal foils to dimensional tolerances of ±0.00002" positional accuracy and/or ±0.0001" feature accuracy.

The TLM process can inexpensively replicate the master mold without affecting dimensional accuracy. These high-fidelity replicas can be produced using standard shop practices—neither clean-rooms nor stringent environmental controls are necessarily required. Master mold fabrication can be a nonrecurring task and/or can be accomplished for a fraction of the cost required for conventionally-machined molds and/or dies. The derived molds can be used for production operations.

Film cooling—Film cooling is a process whereby compressor exit flow can bypass the combustor, course through the hollow interior of individual turbine airfoils, and/or exit through an array of holes in the surfaces of each airfoil. Film cooling can effectively form an insulating boundary layer over the pressure and/or suction sides of each airfoil, thus maintaining surface temperatures below the mainstream total temperature. Engine performance can decrease in proportion to the volume of compressed air that bypasses the combustor and is consumed in the film cooling process. Therefore, film cooling designs typically must maximize insulating capacity (efficacy) while minimizing compressed air consumption (efficiency).

Modeling—Advanced Computational Fluid Dynamics (CFD) models indicate that insulating capacity can be further optimized by manipulation of film cooling process parameters such as blowing ratio, injection angle, discharge coefficient, and/or discharge trajectory. Flow in a gas turbine engine can be extremely complicated. The equations governing the problem are typically considered to be the continuity (conservation of mass), the Navier-Stokes (conservation of momentum), and the energy equations. Together, these equations can form a system of coupled non-linear partial differential equations (PDEs). Because of the non-linear terms in these PDEs, analytical methods typically yield few solutions. Computational Fluid Dynamics is often considered to be as much art as science in the substitution of the differential equation governing the fluid (gas) flow with a set of algebraic equations (a process referred to as discretization). These equations, with the aid of a digital computer, can be used to calculate approximate solutions. There is no film cooling design handbook for arbitrary airfoil shapes and conditions. Designs are typically evolutionary; the convention is to adapt what worked in the last engine to fulfill the requirements for a future engine. This iterative process is frequently costly in terms of both time and money. Schedule and budget constraints generally lead to conservative designs. Unfortunately, many CFD-optimized designs have not been implemented because the enabling manufacturing technology does not exist within the investment casting industry.

Manufacturability—Film cooling passages and exit features within an airfoil can be created by means of a ceramic core situated within an investment casting mold cavity. The core can be a solid structure; its geometry can be reciprocal to the desired film cooling passages and exit features; i.e., it can be a solid rendition of the desired voids within the finished casting. A fine balance often must be achieved between the strength and density of investment casting cores for turbine airfoils. The cores often must be durable enough to withstand transportation and handling, strong enough to retain their shape during wax injection molding and metal casting, sufficiently weak to crush under loads associated with metal solidification, chemically inert to casting alloys, and/or be porous enough and of such material composition as to be chemically dissolved during subsequent leaching operations.

The service environment is usually most demanding of first and second stage turbine airfoils. These components are typically produced by means of the single crystal (SX) casting process. The extended solidification time associated with this process (generally several hours) tends to accentuate the need for chemically inert core material compositions and mechanical stability.

Certain exemplary embodiments can allow variation in certain design parameters, such as:
  cooling channel turbulator ribs (which can promote site-specific vortices and/or increase blowing ratio),
  plenum lattice structures (which can optimize flow dynamics, heat transfer, and/or airfoil strength),
  integral film holes of varied geometry and inclination (which can allow manipulation of discharge coefficient),
  film hole-turbulator alignment (to manipulate discharge coefficient), and/or
  film hole distribution (which can allow improvements in cascade flow and/or heat transfer coefficient).

Certain exemplary embodiments can enhance the strength, geometric stability, dimensional accuracy, and/or overall survivability of such intricate features during exposure to DS and/or SX casting temperature regimes and/or casting alloys (notably, nickel-based super alloys containing hafnium and/or yttrium).

Because TLM™ can be a fault-tolerant, highly-repeatable, manufacturing process, TLM™-derived structures can exhibit low part-to-part variation. Complex shapes can be produced as monolithic solids thus potentially obviating the need for assembly operations. The opportunity for error and cumulative, negative effects of tolerance build-up thereby can be minimized. This can greatly reduce the need to segregate, categorize, and/or match sets of airfoils according to blowing ratio.

Certain exemplary embodiments can provide a composition, system, machine, device, manufacture, circuit, and/or user interface adapted for, and/or a method and/or machine-readable medium comprising machine-implementable instructions for, activities that can comprise, after removing a cast device from a stack-lamination-derived mold, said cast device formed from a molding composition, applying a desired shape to said cast device to form a shaped cast device, said molding composition comprising: a ceramic composition comprising silica; an cycloaliphatic epoxy binder composition, said cycloaliphatic epoxy binder composition present in said molding composition in an amount up to 30% by weight of said molding composition; a silicone composition comprising a siloxane resin, said silicone composition present in said molding composition in an amount up to 30% by weight of said molding composition; and a solvent composition adapted to dissolve said cycloaliphatic epoxy binder composition and said silicone composition.

Certain exemplary embodiments can provide novel systems, devices, and/or methods for manufacturing castings, such as cast parts. Such a cast part can serve, for example, as an internal form, sometimes called a "core", for an investment cast product that will at least partially surround the core. Such investment cast products can include, for example, foils, blades, vanes, nozzles, seals, disks, ducts, sensors, stators, and/or rotors of any fan section, compressor section, combustor section, and/or turbine section, of any turbomachine, such as those used for steam turbines, industrial gas turbines, ship propulsion, and/or aeronautical power plants. Such investment cast parts can include automobile parts, such as: intake manifolds; exhaust manifolds; turbochargers; superchargers; pistons; connecting rods; crank shafts; cam shafts; gears; engine blocks; transmission housings; fuel pumps; fuel injectors; brake master cylinders, rotors and/or drums; alternators; starters; motor frames; vehicle frames; seat frames and/or supports; suspension members; etc. Such investment cast parts can include and/or be incorporated in sensors, actuators, valves, control valves, rotary valves, controls, armatures, spools, pulleys, gears, couplings, linkages, propellers, impellers, pumps, housings, casings, enclosures, structural members, frames, tubes, hinges, triggers, firearm hammers, jewelry, art, sporting goods, bicycle parts, equestrian gear, golf club heads, cryogenic parts, heat sinks, injectors, igniter tubes, hydraulic devices, pneumatic devices, electric motors, air motors, machinery, machine parts, compressors, fasteners, lugs, drill bits, blades, chain links, hardware, instruments, power tools, hand tools, medical tools, surgical tools, medical devices, general prothesis, dental prothesis, etc. Certain exemplary embodiments can enable faster and/or less-costly prototyping of complex investment casting cores, optimization of their designs, and/or enhancement of their manufacturability in a recurring production environment.

Certain exemplary embodiments of such cast parts and/or their molds can utilize the Tomo Lithographic Molding (TLM™) process, which is described herein.

Certain exemplary embodiments can prepare cast parts and/or cores, such as cast parts that are removable, leachable, dissolvable, friable, and/or fracturable, etc., for any type of investment casting, such as single crystal (SX) investment casting, directional solidification (DS) investment casting, and/or equiax investment casting, etc.

Generally, a process for manufacturing cast parts, such as investment casting cores, can include:
  develop 3D CAD model of cast part;
  adjust model as needed:
    scale model to account for shrinkage of cast material;
    split model to create part line/pull plane for cast part mold;
    "flatten" model to make faces planar;
    incorporate cast part mold half co-alignment features in model as desired; and/or
    incorporate other features in model as desired for alignment, inter-connecting cast parts, mold venting, part handling, etc.;
  prepare laminated stack foil mold, such as per the TLM™ process, to correspond to adjusted model of cast part:
    output adjusted model;
    create photo masks from outputted model;
    create foils using photo masks;
    create alignment fixtures as needed; and/or
    stack, align, and bond foils to form mold for cast part;
  form initial cat part using mold:
    fill mold with casting components;
    mix components in situ;
    heat filled mold to form cured cast part; and/or
    de-mold cured cast part;
  adjust cured cast part to desired shape, hardness, crystal structure, etc.:
    form cast part to desired curvature using forming fixture;
    heat cast part to initially solidify;
    cool cast part to form desired crystal structure in cast part; and/or
    fire cast part to sinter its particles; and/or
  cast investment material around cast part.

To prepare the model, solid modeling software, such as SolidWorks, Pro/Engineering (Pro/E), etc., can be utilized. The model can be scaled to account for shrinkage of cast material using standard scale commands that are part of the solid modeling software. The entire model, or features of the model can selected and scaled to reduce or enlarge the model or features to compensate for shrinkage during ceramic sintering.

The model can be split to create a part line/pull plane for the cast part mold by dividing and/or part the model into two sections, typically from the root portion of the part to the tip (through the overall thickness). The part line can be placed in the middle of the part's thickness or any other plane from the top most surface to the bottom most surface of the part.

The model can be "flattened" to make its faces planar using one or more commands in the solid modeling software. For example, in SolidWorks, the "Flex" command initially can be used to roughly flatten out the 3D model in one direction at a time using a straight line extending along the model or the feature being flattened. The Flex command can be repeated by rotating the line across the model at various angles, each time further flattening the model. A series of Flex commands can be performed until the model is in a near planar or flattened condition. Next, a surface plane (zero thickness) can be created that extends slightly beyond the outer edges of the model and can be located in the Z-axis at the part line location (part line described above) of the model. In SolidWorks, the "Deform" command can be used to fully planarize the model using the surface plane at the part line as the planar base. The Deform command basically can form the nearly flattened model surfaces onto the surface plane at the part line.

The model halves can be sliced to the desired thickness corresponding to the thickness of the metal foil layers that will be used to produce the stack lamination. In SolidWorks, the command "Intersection Curve" can be used to slice the model. Once sliced, the layer slices can be exported in a DXF file format, which then can be used to produce the output data for plotting the photographic masks.

To initially form the cast part, a mold can be formed in one or more pieces and/or portions, potentially using non-lithographic methods to produce coarse featured portions of the part and/or combining other portions produced using TLM™ for creating part areas (such a leading edge and/or a trailing edge) having finer features. For example, a portion of a mold for creating a part body could be produced using CNC machining while the trailing edge and/or leading edge portions of the mold can be produced using TLM™. Alignment features between the mold portions and/or parts created thereby can be incorporated to align the mold portions together on a fixture before deriving a complete mold.

The mold can be formed of a flexible material such as described herein. The material of the mold can be used to transfer vibrational energy to the molding composition that fills the mold to allow for appropriate particle packing and/or breaking and/or separating of particle agglomerates. For example, the mold fixture can be attached to a vibration table and vibrated for a period of time sufficient to allow the ceramic powder particles to settle to the bottom of the mold cavity. The amount of time required can depend upon many factors including the table type, the vibration action (linear or rotary), table manufacturer, the particular ceramic powder and polymer materials used, and/or the density required in the final ceramic part, etc. For the example, an FMC J-50 linear action Jogger table can be used at a power setting of 10-90% at a frequency of 250-3600 or 3600-5000 pulses per minute for approximately 2 minutes to approximately 120 minutes. The mold can be used repeatedly, without substantial wear and/or abrasion, to create multiple cast parts. Vacuum assistance can be used with to aid in filling the mold features and/or evacuating air from the mold.

To prepare and/or provide a molding composition for at least partially filling the mold, a powder material can be combined with a binder system to form a molding composition, such as a slurry. The powder can comprise any of ceramic, silica, alumina, zirconia, silicon carbide, boron nitride, and/or yttria, etc. The powder, molding composition, and/or casting method can be any of those described herein, including any of those described in the following set of US patent documents, each of which is incorporated by reference herein in its entirety to its fullest enabling extent permitted by law:
  U.S. Pat. No. 2,961,751, titled "Ceramic Metal Casting Process";
  U.S. Pat. No. 3,957,715, titled "Casting of High Melting Point Metals and Cores Therefore";
  U.S. Pat. No. 4,190,450, titled "Ceramic Cores for Manufacturing Hollow Metal Castings";
  U.S. Pat. No. 4,284,121, titled "Process and Materials for Making Refractory Cores";

U.S. Pat. No. 4,837,187, titled "Alumina-Based Core Containing Yttria";

U.S. Pat. No. 5,394,932, titled "Multiple Part Cores for Investment Casting";

U.S. Pat. No. 6,588,484, titled "Ceramic Casting Cores with Controlled Surface Textures";

U.S. Pat. No. 7,413,001, titled "Synthetic Model Casting"; and

US Patent Application Publication 2008/0169081, titled "Method and Apparatus for Production of a Cast Component".

What follows are several examples of potential molding composition for parts, whose approximate composition can range as follows:

Silica 10%-99%; alumina 1%-90%; cristobalite 1%-20%; zircon 1% 20%; magnesium oxide 0.01%-1.0%; silicone resin 1%-30%; organic binder 1%-30%.

Ceramic materials, such as those of the type described in U.S. Pat. No. 4,837,187, which is incorporated by reference herein in its entirety to its fullest enabling extent permitted by law, can be used for the molding composition and/or in forming core parts of gas turbine engine blade cores by low pressure injection molding. Specifically, a molding composition with a composition of: approximately 1 wt % to approximately 90 wt % alumina, such as 84.5 wt % alumina; approximately 1 wt % yttria to approximately 20 wt % yttria, such as approximately 7.0 wt % yttria; approximately 0.05 wt % magnesia to approximately 10 wt % magnesia, such as 1.9 wt % magnesia; and/or approximately 1 wt % graphite (flour) to approximately 15 wt % graphite (flour), such as approximately 6.6 wt % graphite (flour) was found to perform acceptably in a two piece core construction. For example, an illustrative molding composition can comprise approximately 94 wt % of 200 mesh fused silica, approximately 6 wt % of 400 mesh Cristobalite, approximately 6 wt % of 325 mesh tabular alumina, and/or approximately 0.2% superfine MgO.

The alumina component of a produced exemplary embodiment of this molding composition included approximately 70.2% of approximately 37 micrometer sized grains, approximately 11.3% of approximately 5 micrometer grains, and approximately 3% of approximately 0.7 micrometer grains. The grain sizes of the other components were: graphite—approximately 17.5 micrometer; yttria—approximately 4 micrometer; and magnesia—approximately 4 micrometer. The thermoplastic binder used included the following components (wt % of mixture): Okerin 1865Q (Astor Chemical); paraffin based wax approximately 14.41 wt %; DuPont Elvax 310 FINNECAN, approximately 0.49 wt %; oleic acid—approximately 0.59 wt %. Other ceramic material components and thermoplastic binders could be used, including those set forth in U.S. Pat. No. 4,837,187.

In certain exemplary embodiments of the molding composition, any of a wide variety of silicone resins can be used. For example, siloxanes of the type described in U.S. Pat. Nos. 3,090,691 and 3,108,985, each of which is incorporated by reference herein in its entirety to its fullest enabling extent permitted by law, can be utilized, including any organic siloxane in which the substituent groups are hydrogen atoms or organic radicals attached directly to the silicone atoms. In general, siloxanes containing 1 to 3 hydrogen and/or organic substituents per silicon atom, and the organic group contains 1-12 carbon atoms, optionally substituted by a group containing an oxygen atom and/or a nitrogen atom can be utilized. As used herein, the term "siloxane" is intended to refer to and include a material which contains at least one linkage per molecule. In an exemplary embodiment, approximately 11 g to 19 g (including all values and subranges therebetween) of Momentive 355 silicone resin can be used with each 100 g of ceramic powder.

Certain exemplary embodiments of the molding composition can employ siloxane resins such as dimethyl siloxane, monomethyl siloxane, phenylmethyl siloxane, monophenyl siloxane, diphenyl siloxane, monethyl siloxane, ethylmethyl siloxane, diethyl siloxane, phenylethyl siloxane, monopropyl siloxane, ethylpropyl siloxane, divinyl siloxane, monovinyl siloxane, ethyl vinyl siloxane, phenyl vinyl siloxane, diallyl siloxane, monoallyl siloxane, allylethyl siloxane, allylvinyl siloxane, monocyclohexyl siloxane, gamma-hydroxypropylmethyl siloxane, beta-methoxyethylmethyl siloxane, gamma-carboxypropyl siloxane, gamma-aminopropyl siloxane, and/or gamma-cyanopropylmethyl siloxane, etc.

Certain exemplary embodiments of the molding composition can utilize any of a variety of filler materials of the type typically used in the preparation of molds and cast parts, such as the Group IVB metals, including refractory and/or ceramic materials, such as silica, alumina, and/or zircon, etc. As indicated above, the filler particles can be bonded together by a siliceous bond on firing of the pre-formed part as a result of partial decomposition of the siloxane resin. The bulk density, apparent density, apparent porosity, and/or other properties of the baked or fired part can be controlled by varying the relative proportions of the filler and/or siloxane resin, by varying the size distribution of the ceramic particles employed in the molding composition, and/or by adding to the molding composition graphite and/or wood flour which can burn-out on firing to increase the porosity of the part.

When silica is the primary filler, the baked and/or fired part can have a bulk density within the range of approximately 1 to approximately 3 g/ml, such as, for example, from approximately 1.4 to approximately 2.0 g/ml. This range can correspond to an apparent solid density of approximately 1.80 to approximately 2.50 g/ml and an apparent porosity of approximately 15 to approximately 35 percent. For this purpose, use can be made of filler material having particle sizes within the range of approximately 100 to approximately 400 mesh.

Graphite can be used as the filler material in combination with a silicone resin as described above for molding a pre-formed part configuration. On baking and firing, a carbon and/or graphite bond can be formed in addition to the siliceous bond to form the desired part having a minimum bulk density of approximately 1.2 g/ml, and a maximum of approximately 5 g/ml. Such graphite parts can be particularly useful in the production of intricately cored, precision cast titanium components.

In addition to the filler, silicone resin, and/or catalyst components, the molding composition can be formulated to include, if desired, a plasticizer for the silicone resin to improve its working characteristics during molding of the composition in the preparation of a pre-formed part. As the plasticizer component, use can be made of any of a variety of plasticizers for silicone resins as represented by paraffin waxes, styrene, phenol or low molecular weight phenolic resins, and/or fatty amines such as N,N'-distearyl ethylenediamine, etc. The amount of plasticizer in the molding composition can be varied from approximately 0 to approximately 7% by weight of the resin content of the molding composition.

Any of a number of additives, such as parting agents or lubricants can be added to the molding composition to improve the processing characteristics of the molding composition during molding in the preparation of the pre-formed core configuration. Representative materials include, for example, calcium stearate as well as other metal salts of fatty acids.

The molding composition can be formulated in accordance with well known mixing techniques, including dry blending, wet mixing, hot mixing, etc., and then molded in a conventional manner using conventional molding techniques, such as transfer molding, injection molding, and/or compression molding, etc. Molding parameters including pressures, die temperatures, compound temperatures, and/or cure times can vary depending somewhat on the configuration of the part being molded and/or the particular composition of the molding composition. Typical pressure ranges normally used for transfer or injection molding can be from approximately 100 psig to approximately 10,000 psig, and approximately 100 psig to approximately 5,000 psig for compression molding. Compound and/or die temperatures usually can range from approximately room temperature up to approximately 400 F and/or can be timed from approximately 1 to approximately 10 minutes.

The distribution of the particles of the powder comprised by the molding composition can be controlled over the entire cast part and/or any portion thereof, such as, in the case of a core, the core body, trailing edge of the core, and/or leading edge of the core, etc.

The binder system can comprise one or more urethane and/or epoxy resins, one or more solvents and/or wetting agents, and/or one or more plasticizers (plasticizers described above), etc. Binder systems can be produced using acrylics such as, for example, PMMA acrylic powder, resins, 2 part epoxy systems and/or composites, and/or methacrylates such as butyl, lauryl, stearyl, isobutyl, hydroxethyl, hydroxpropyl, glycidyl and/or ethyl, etc.; thermoplastics, such as, for example, ABS, acetyl, acrylic, alkyd, flouro-thermoplastic, liquid crystal polymer, styrene acrylonitrile, polybutylene terephthalate, thermoplastic elastomer, polyketone, polypropylene, polyethylene, polystyrene, PVC, polyester, polyurethane, thermoplastic rubber, and/or polyamide, etc., thermo-sets, such as, for example, phenolic, vinyl ester, urea, and/or amelamine, etc.; and/or rubbers: such as, for example, elastomer, natural rubber, nitrile rubber, silicone rubber, acrylic rubber, neoprene, butyl rubber, flurosilicone, TFE, SBR, and/or styrene butadiene, etc. Certain exemplary embodiments can employ a cycloaliphatic thermal cure epoxy. For example, approximately 10 g to 20 g of W032701-8 epoxy from Resinlab of Germantown, Wis. can be used per 100 g of total ceramic powder weight, blended according to the manufacturer's directions of A:B approximately equals 0.94:1.

Binder materials and/or components can be liquids that can be fully soluable in, and/or diluted using, various solvents such as MEK, acetone, heptane, and/or isopropyl alcohol, etc. In the case of MEK, solvent additions can range between 10-22 grams per 100 grams of total ceramic powder weight. In the case of acetone, solvent additions can range between 14 grams and 27 grams per 100 grams of total ceramic powder weight. In the case of isopropyl alcohol, solvent additions can range between 11-21 grams per 100 grams of total ceramic powder weight. The binder system can comprise any of those appropriate materials described herein, including any of those described in any of the patents incorporated herein.

It has been found that ceramic cores having the desired thermal stability at temperatures as high as approximately 2700 F and above can be produced when the molding composition is formulated to replace all or at least part of the silica component with a crystalline phase of silica which can be identified as Cristobalite. When Cristobalite is present as a constituent of the molding composition in an amount greater than approximately 2.5%, but not greater than approximately 10% by weight, the high temperature stability of the ceramic core can be superior to that of a core in which the silica component is formed of amorphous fused silica or fused silica combinations with zircon and/or alumina as the ceramic component of the core.

The amount of Cristobalite in the core body, at the time that the molten metal is cast into the mold cavity, can be important. The quantity can be sufficient to achieve the desired improvement in high temperature stability without adversely affecting the strength of the core or the thermal shock properties. While beneficial use can be obtained when all of the silica is replaced with Cristobalite, it can be desirable to limit the maximum concentration in the fired core to approximately 35% by weight and/or approximately 5 to approximately 20% by weight Cristobalite in the fired core. The remainder of the core can be formulated with fused silica and/or fused silica and zircon, and/or fused silica, zircon and/or alumina, with binders such as organo silicone resins, such as described in the aforementioned U.S. Pat. No. 3,957,715. The presence of Cristobalite can be achieved by the direct addition of Cristobalite to the components making up the molding composition. For this purpose, Cristobalite can be used in finely divided form such as in the range of approximately 70 to approximately −325 mesh. The core can be formed by transfer molding technique using silicone resins as the binder.

The following example identifies the approximate ingredient ranges for the molding composition by weight: silica 10%-99%; alumina 1%-90%; cristobalite 1%-20%; zircon 1%-20%; magnesium oxide 0.01%-1.0%; silicone resin 1%-30%; organic binder 1%-30%. For example, a composition of fused silica (60%) and alumina (40%) can be used.

The above compositions can include additional ingredients such as calcium stearate as a lubricant, and/or a catalyst that can be in the form of finely divided magnesium oxide and/or benzoic acid in equal parts by weight, with the lubricant being present in an amount within the range of approximately 0.2 to approximately 2% by weight and the catalyst being present in an amount within the range of approximately 0.2 to approximately 2% by weight.

The binder can be partially and/or fully mixed using standard mixing techniques. For example, a kitchen mixer such as a food blender and/or a ceramic slurry mixer such as an approximately 1 horsepower Ross Dispersion Mixer, model 100 LC, can be used. Mixing times to disperse the binder and/or mix it into the powder can range from approximately 1 minute to approximately 24 hours. The binder can be partially and/or fully mixed with the powder prior to filling mold with the molding composition or directly in the mold. The mixing can occur via any known technique, including shear, vibration, centrifugal force, resonant mixing, static mixing, and/or rotational ball-milling, etc.

The slurry composition can comprise any desired wetting agent and/or alternate binder system, which can comprise poly-vinyl alcohol and poly-ethylene glycol.

Generally, the viscosities ranging from approximately 500 to approximately 10,000 cps of the powder, binder, and/or molding composition can be appropriate to allow them to flow into and/or fill the mold. The binder concentration (ranging from approximately 10 percent to approximately 20 percent binder to ceramic powder by weight) of the molding composition can be sufficiently low to facilitate burnout of the binder and/or allow for the sintering of the powder.

Adequate time can be allowed to vent and/or de-gas the filled mold and/or to cure and/or set the cast part in the mold. For example, the time for venting, de-gassing, and/or mold filling can range from approximately 1 minute to approximately 60 minutes. The cast part can be released from the mold after the binder has at least partially cross-linked and/or cured. The cure temperature of the binder can be compatible with the mold material. The cure temperature can range from approximately 90 F to approximately 350 F. The cure time can range from approximately 15 minutes to approximately 24 hours. The binder can have compatible reversion properties that can allow the cured "green" state ceramic part to be heated and thermo-formed prior to binder burn-out and sintering. The thermo-forming temperature is dependant on the initial cure temperature used to produce the green state ceramic core and the specific glass transition temperature (Tg) of the polymer binder. Manufacturers of resins, epoxies, urethanes and other organic polymers (binders) specify the Tg of their products on the materials properties data sheet. During sintering, the binder can burn-out clean, leaving substantially no carbon to react with the investment casting material.

The mold can be configured to be closed before, during, and/or after filling. In certain exemplary embodiments, the mold can be configured as two or more mold portions that remain open during and/or after filling, which can potentially more easily vent air from the mold, de-gas solvent in the molding composition, de-mold the cast part, etc.

The mold can be filled via any known technique, such as gravity pouring, injection pressure, vacuum, and/or dispersion, etc. The mold can be overfilled to insure a proper fill. A vacuum can be used to assist with air venting and/or de-gassing.

During and/or after filling of the mold with the molding composition, its particles can be compacted, densified, and/or packed in a maximum density configuration to substantially eliminate gaps between ceramic particles, thereby helping the particles to sinter to each other during ceramic firing That is, the location, size distribution, count, and/or packing density of the particles can be adjusted (such as per the particle sizes described in the Minco silica product literature) and/or controlled via applying energy, such as vibrational energy, to the mold during and/or after filling. As desired, adjustments can be made to the pre-vibration settling time (approximately 2 minutes to approximately 2 hours), vibration time (approximately 2 minutes to approximately 2 hours), the vibration frequency range and/or amplitude, post-vibration settling time (approximately 2 minutes to approximately 2 hours), and/or solvent separation time (approximately 2 minutes to approximately 2 hours), etc. A linear action Jogger table can be used at a power setting range of approximately 10% to approximately 90% to adjust the amplitude and at a frequency of approximately 250-5000, approximately 250-3600, and/or approximately 3600-5000 pulses per minute. While the mold is being vibrated, the mold can stay open to allow the solvent to more easily evaporate out of the molding composition. While the mold is being vibrated and/or while open, the mold can be heated (temperature range from approximately 100 F to approximately 350 F for approximately 15 minutes to approximately 24 hours) and/or cooled (temperature range from approximately 60 F to approximately 80 F for approximately 1 minute to approximately 3 hours) to affect molding composition flow, densification, and/or curing, etc.

By using open molds, one or more inserts can be inserted into the mold and/or molding composition prior to, during, and/or after filling of the mold and/or initial setting of the molding composition. An insert can serve as a reinforcement member to the cast part, such as to add compressive, tensile, shear, and/or torsional strength to the cast part. An insert can provide physical, electrical, magnetic, optical, chemical, biological, mechanical, thermal, and/or fluidic properties to the cast part, such as described under "Cavity Inserts" in U.S. Pat. No. 7,410,606, which is incorporated by reference herein in its entirety to its fullest enabling extent permitted by law.

An insert can be formed by any known technique, such as via casting, extruding, stamping, forging, machining, thermoforming, photo-etching, and/or TLM, etc. An insert can be formed of any known material, such as metal, polymer, and/or ceramic, etc. For example, an insert can be formed of tungsten, molybdenum, etc. Once installed in a cast part, an insert can be removable, leachable, dissolvable, friable, and/or fracturable, etc. The structure of an insert can be solid, hollow, and/or web-like, etc. A surface of an insert can be treated via any known technique, such as via dipping, coating, brushing, spraying, plating, vapor deposition, abrading, blasting, etching, cavitating, and/or chemical reaction, etc. The surface treatment can be compatible with the material of the insert, the molding composition, the cast part, and/or the investment casting material. The insert can be incorporated into the part and/or ceramic core to act as a reinforcement or strengthening system, such as steel rebar in a concrete structure. Using techniques such as photo-etching to produce the insert, the reinforcement pattern of the insert can be configured to selectively strengthen the ceramic material in predetermined areas of a part and/or ceramic core. For example, a trailing edge portion of a core having fine features or very thin cross sectional thickness can use the reinforcement insert to aid in core survivability during DS, SX or other investment casting methods, and/or steps prior to the actual casting stage of investment casting, such as wax injection and/or shell firing. The insert can be produced from a material, such as tungsten and/or molybdenum, which has a low coefficient of thermal expansion (CTE) value and/or is CTE matched with the ceramic material. The insert can be process compatible with the process used to leach and/or dissolve the molded part and/or core from the investment cast part. If the insert is produced using photo-lithographic techniques, the alignment of the insert can very accurately match the TLM™ mold, therefore simplifying the integration of the insert with the mold. An insert can be produced using TLM™. For example, an insert having a reinforcement pattern can be produced using TLM™ from a ceramic (such as any of those described) that is mixed with a metal powder, such as tungsten and/or molybdenum. The TLM™ insert can be used in the green state and/or after the ceramic material has been sintered. An entire TLM™ core, and/or a portion of a core can be produced from a metal powder combined with any of the ceramic materials and/or combinations of materials and/or methods described in this document. The metal powder can be a refractory metal such as molybdenum, tungsten, and/or any other metal powder. The metal powder ratio to ceramic can be approximately 1% to approximately 90% by weight.

If and/or when desired, the mold portions and/or halves can be brought together and/or closed. Alignment between the mold portions can be achieved using mold features and/or fixture features, either of which can be substantially incompressible. The mold can be closed when:
  all halves and/or portions of the cast part are uncured;
  one half and/or portion is cured; and/or
  all halves and/or portions are cured.

The closed mold can be further filled, de-gassed, vibrated, and/or spun (centrifuge), etc.

The cast part and/or the binder in the molding composition can be cured to a partial and/or fully cross-linked and/or polymerized state by subjecting the cast part and/or mixture to an appropriate temperature for an appropriate time, to arrive at a cast part in a "green" (unfired) state. This process can occur while the molding composition is in the mold.

Once in the green state, the cast part can be separated from the mold and/or demolded, such as by opening the mold and pulling the cast part along the pull-plane. After removing the green cast part from the mold, the cast part can be shaped to a final desired shape and/or curvature such as those of a turbine airfoil blade or vane and/or a golf club head using traditional machining and/or a shaping tool, such as a mandrel and/or form, etc. Prior to such shaping, the cast part can be aligned with a machine tool and/or a shaping tool using features in the cast part and/or of the cast part, such as alignment features spatially invertedly reflecting those formed in the part mold using the TLM™ process.

After shaping, the cast part can be fired and/or sintered, such as via the methods described in any patent incorporated herein. Sinter temperatures can range from approximately 1000 C to approximately 1700 C. Sinter times can range from approximately 1 hour to approximately 24 hours. The sintering atmosphere can be air and/or any inert gas atmosphere such as nitrogen, helium, and/or argon, etc.

At any appropriate time, such as after initial casting, while in the green state, and/or after sintering, etc., a cast part can be coupled and/or attached to one or more additional parts, such as via an interlock. Any of the additional parts can be created using any process, such as any process described herein.

Prior to sintering, a part can be oriented as desired to determine and/or control feature distortion, dimensional changes, and/or shrinkage due to sintering. For example, a part can be oriented horizontally, vertically, and/or on edge. As another example, an overall size of core tooling can be increased, such as by 10%, to compensate for part shrinkage during sintering.

Additional adjustments can be made to improve the final part, such as:
- elimination of sharp (90°) corners from core features and/or addition of controlled radii to mitigate stress concentration ("raisers") during sintering;
- removal of controlled amounts of material from high mass areas of the core body to improve mass balancing and/or control warpage during sintering;
- addition of controlled radii at termination points between trailing edge tapers for increased strength during sintering, wax injection, and/or casting;
- incorporation of various controlled frame areas around the finest features of the core specimen to reduce and/or eliminate warpage during sintering; and/or
- arraying of core specimens to increase manufacturing throughput.

One or more exemplary parts can be formed via:
- mold lay-up—a core specimen can be aligned and/or fixtured into a machined mold for wax forming;
- wax injection—molten wax can be injected into the mold and around the core;
- demolding—the wax casting (with the core inside) can be removed from the mold;
- shelling—a thin silica ceramic coating can be applied to the wax casting. The coating can be applied by successively dipping the wax part into a silica slurry, removing it and allowing it to dry. The process can be repeated 4-6 times depending on the desired shell thickness;
- shell firing—the shelled part can be placed in an autoclave furnace and the wax is melted out leaving the core in the shell. Into the resulting cavity molten metal alloy can be poured to produce the metal casting; and/or
- investment casting—parts, such as equiaxed aluminum parts can be cast using the gravity pour casting process.

Parts can be inspected visually using a 35 KeV x-ray source and/or a high resolution digital detector.

Figure 87:
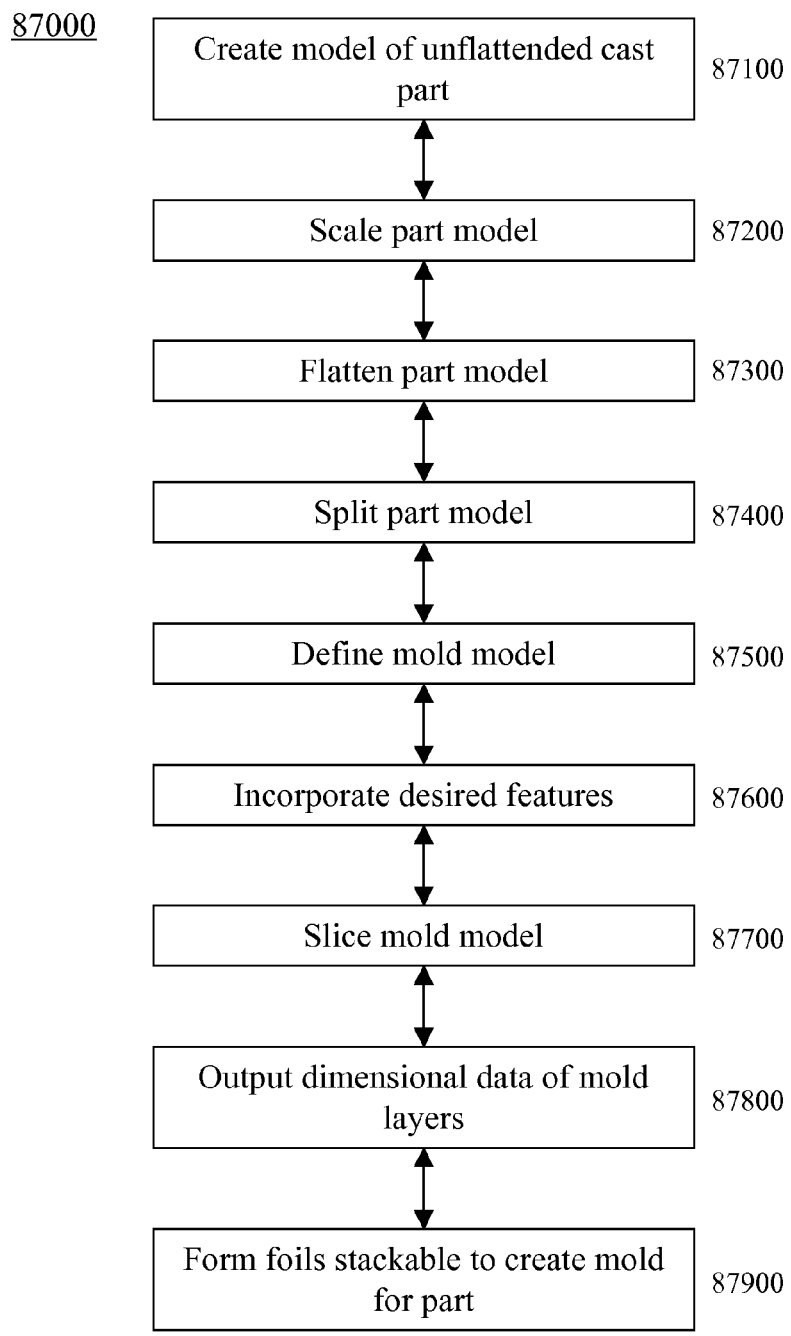
FIG. 87 is a flowchart of an exemplary embodiment of a method.

FIG. 87 is a flowchart of an exemplary embodiment of a method 87000. At activity 87100, a computer-based, 3-dimensional, graphical virtual model can be created of a desired or predetermined unflattened cast part. At activity 87200, via computer software, such as the computer software used to create the initial model of the cast part, the model can be scaled. At activity 87300, the model can be flattened, so that one or more of its major surfaces become planar and/or substantially flat. At activity 87400, the part model can be split, such as into 2 or more portions. At activity 87500, a mold model can be defined, that mold model invertedly reflecting the geometry of the flattened and/or split part model, such that at least virtually, the part model can be formed from the mold model. At activity 87600, desired features can be incorporated into the mold model, such as alignment features, injection molding features, de-molding features, etc. At activity 87700, the mold model can be virtually sliced, such as into sheets that are substantially co-planar with one another and/or one or more flattened major surfaces of the flattened model, those sheets having thicknesses corresponding to the thicknesses of metallic foils that can be stacked to physically re-create the model of the mold and/or part. At activity 87800, dimensional data of the mold model and/or its constituent sheets can be output so that the stackable foils can be specified. At activity 87900, foils that are stackable to create the mold for the part can be formed.

Figure 88:
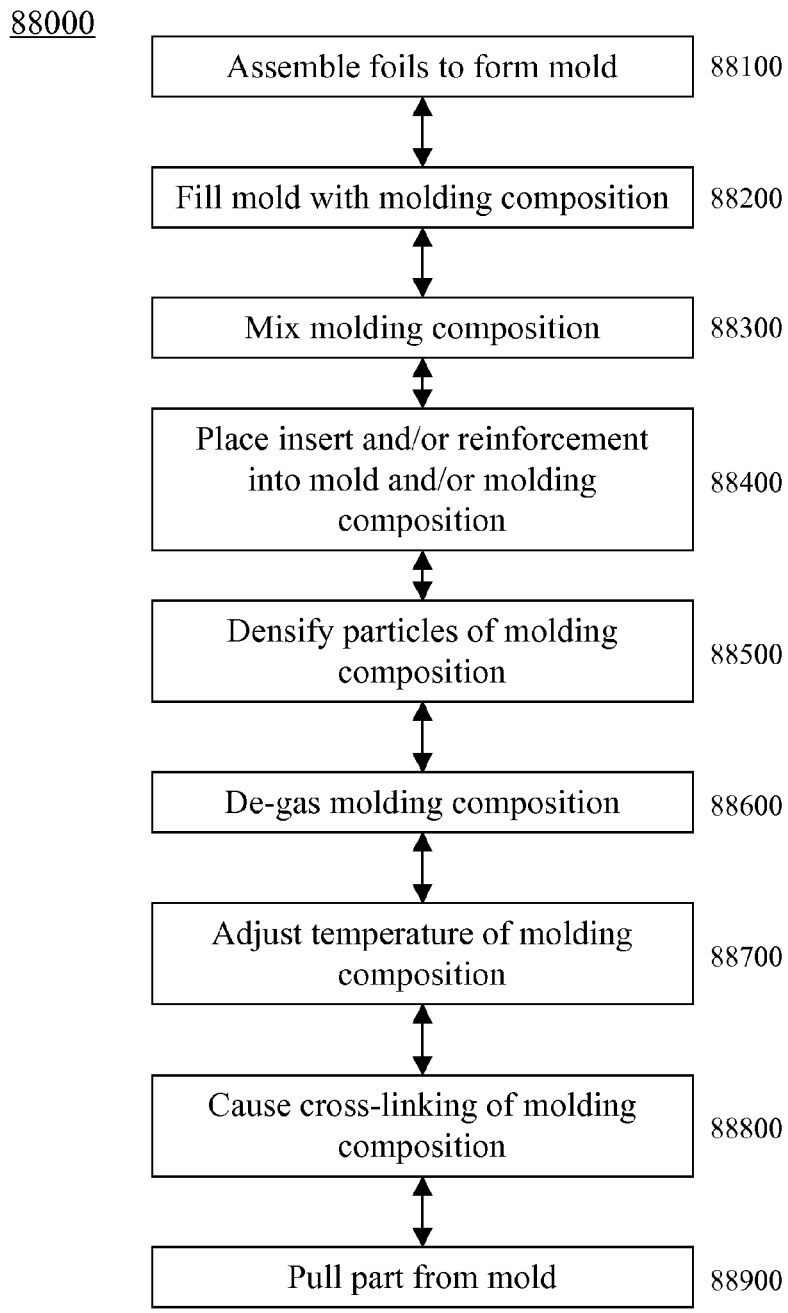
FIG. 88 is a flowchart of an exemplary embodiment of a method.

FIG. 88 is a flowchart of an exemplary embodiment of a method. At activity 88100, the foils can be aligned, stacked, bonded, compressed, connected, and/or assembled to form a physical mold for the unflattened, flattened, un-split, and/or split part. At activity 88200, the mold can be at least partially, and potentially completely, filled with a predetermined molding composition and/or one or more of its constituents. At activity 88300, the molding composition and/or one or more of its constituents can be mixed, such as in the mold. At activity 88400, one or more predetermined inserts can be placed into the mold, the molding composition, and/or one or more of the constituents of that molding composition. At activity 88500, constituent particles of the molding composition can be densified, that is, caused to move within the mold such that the molding composition can have substantially different densities at different locations within the mold. At activity 88600, the molding composition can be de-gassed, potentially while outside of and/or within the mold. At activity 88700, the temperature of the molding composition can be adjusted, potentially while outside of and/or within the mold. At activity 88800, the composition and/or one or more of its constituents can be allowed to cross-link, potentially while outside of and/or within the mold. At activity 88900, a molded part, which can be formed from and/or comprise the cross-linked composition and/or one or more of its constituents, can be pulled from the mold.

Figure 89:
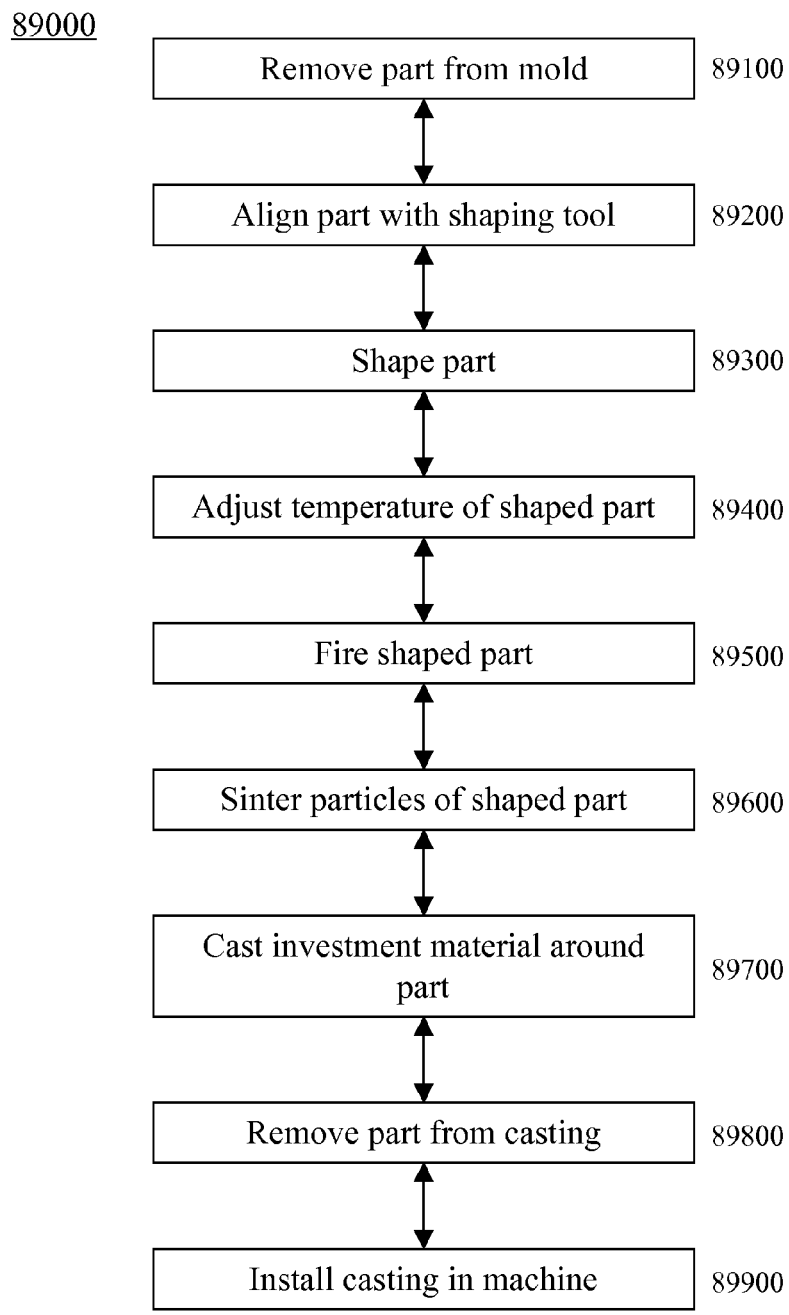
FIG. 89 is a flowchart of an exemplary embodiment of a method.

FIG. 89 is a flowchart of an exemplary embodiment of a method. At activity 89100, which can be formed from and/or comprise the cross-linked composition (described above) and/or one or more of its constituents, a molded part can be pulled and/or removed from the mold. At activity 89200, the part can be aligned with a shaping tool. At activity 89300, the part can be shaped. At activity 89400, the temperature of the part can be adjusted (raised and/or lowered) as desired. At activity 89500, the shaped part can be fired. At activity 89600, particles forming the shaped part can be sintered. At activity 89700, investment material can be cast around and/or in the fired part. At activity 89800, the part can be removed from the casting. At activity 89900, the casting can be installed in a machine, so that it can serve as a component of the machine. For example, as described herein, the casting can serve, for example, as an internal form, sometimes called a "core", for an investment cast product that will at least partially surround the core.

Figure 90:
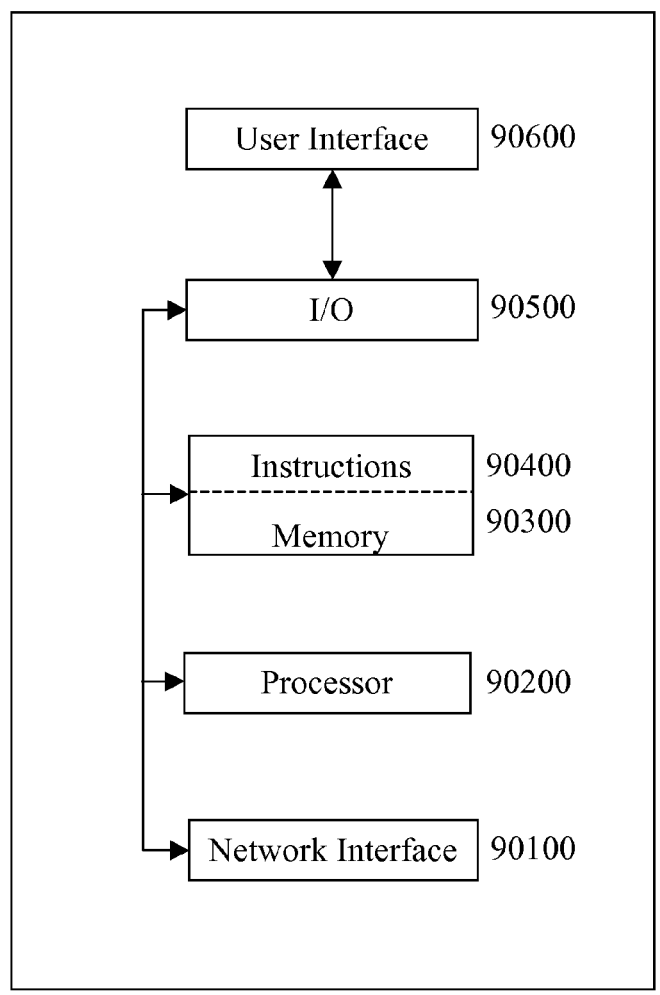
FIG. 90 is a block diagram of an exemplary embodiment of an information device.

FIG. 90 is a block diagram of an exemplary embodiment of an information device 90000, which in certain operative embodiments can comprise, for example . . . . Information device 90000 can comprise any of numerous transform circuits, which can be formed via any of numerous communicatively-, electrically-, magnetically-, optically-, fluidically-, and/or mechanically-coupled physical components, such as for example, one or more network interfaces 90100, one or more processors 90200, one or more memories 90300 containing instructions 90400, one or more input/output (I/O) devices 90500, and/or one or more user interfaces 90600 coupled to I/O device 90500, etc.

In certain exemplary embodiments, via one or more user interfaces 90600, such as a graphical user interface, a user can view a rendering of information related to researching, designing, modeling, creating, developing, building, manufacturing, operating, maintaining, storing, marketing, selling, delivering, selecting, specifying, requesting, ordering, receiving, returning, rating, and/or recommending any of the products, services, methods, user interfaces, and/or information described herein.

Figure 91:
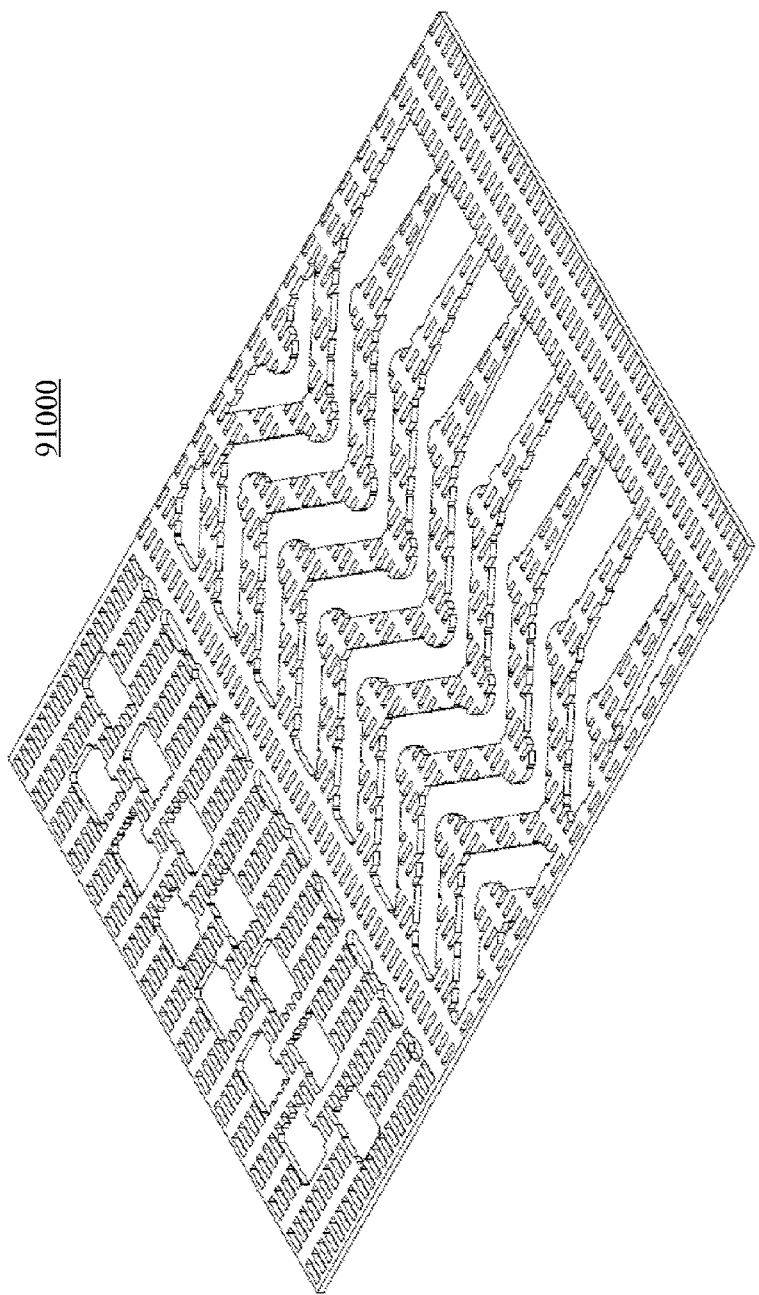
FIG. 91 is a perspective view of an exemplary embodiment of a foil structure.

FIG. 91 is a perspective view of an exemplary embodiment of a metallic and/or ceramic foil structure 91000.

Figure 92:
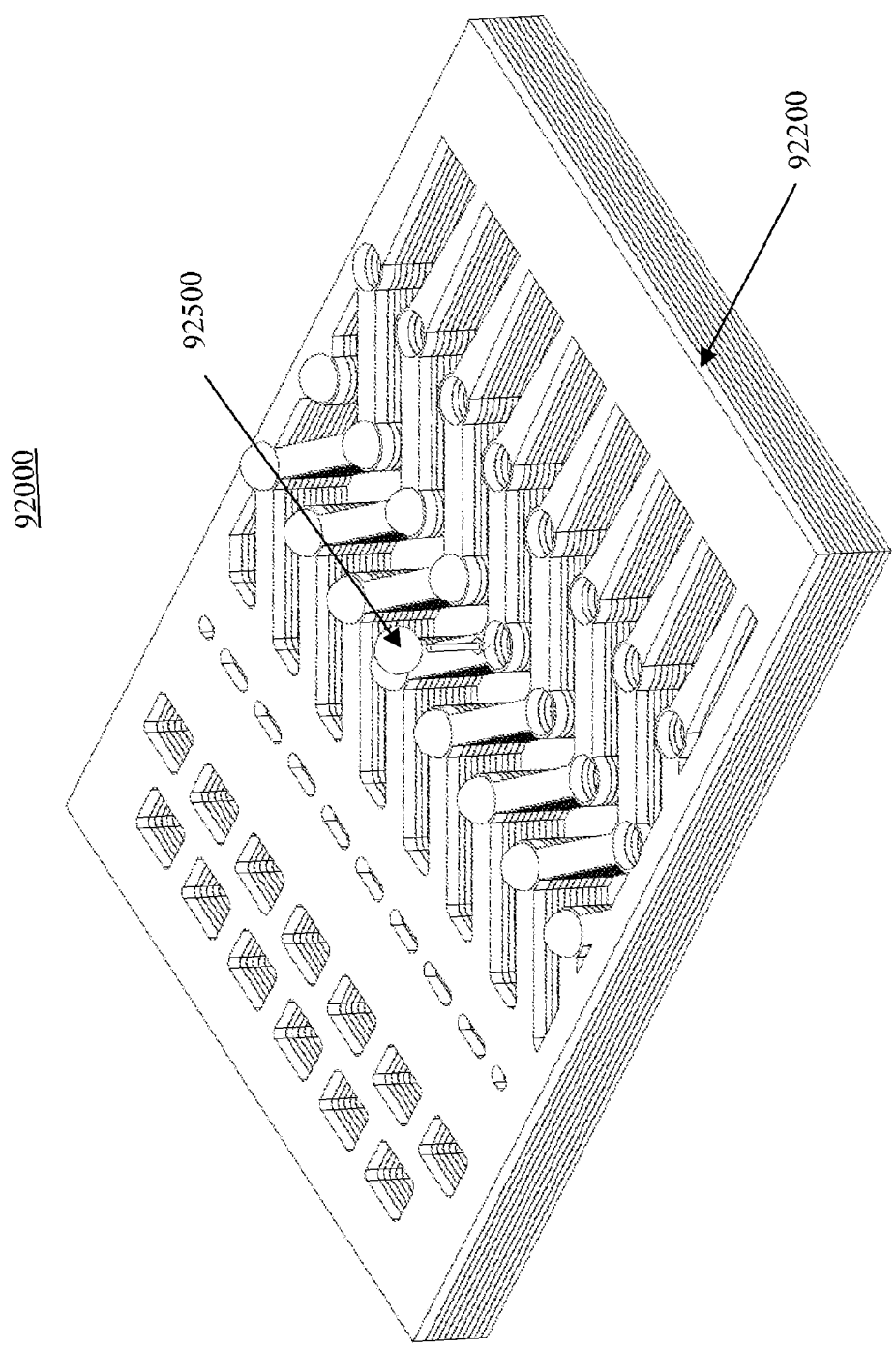
FIG. 92 is a perspective view of an exemplary embodiment of a metallic foil stack that includes a plurality of inserted spherical mold inserts.

FIG. 92 is a perspective view of an exemplary embodiment of a stack 92000 that includes a stacked plurality of foils 92200 and a plurality of spherical mold inserts 92500 into one or more foils 92200.

Figure 93:
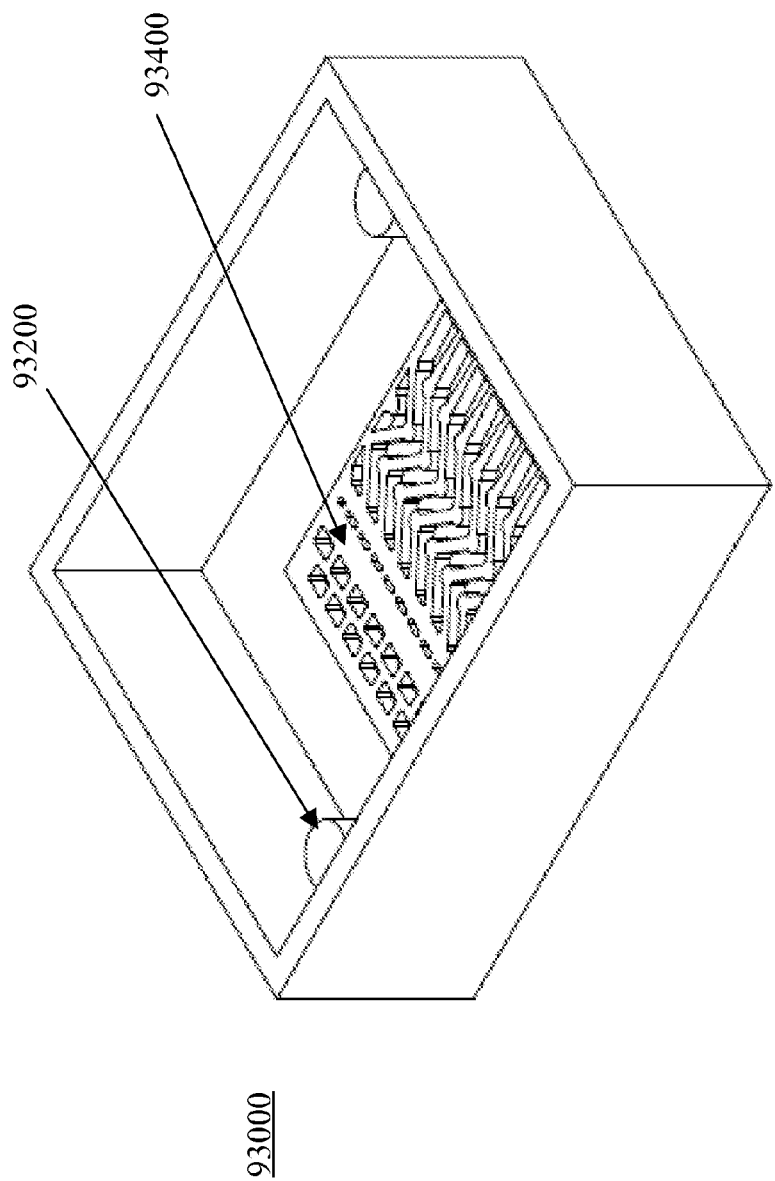
FIG. 93 is a perspective view of an exemplary embodiment of a metallic foil stack fixture.

FIG. 93 is a perspective view of an exemplary embodiment of a stack fixture 93000 having an alignment feature 93200 that aligns a foil 93400 in stack fixture 93000.

Figure 94:
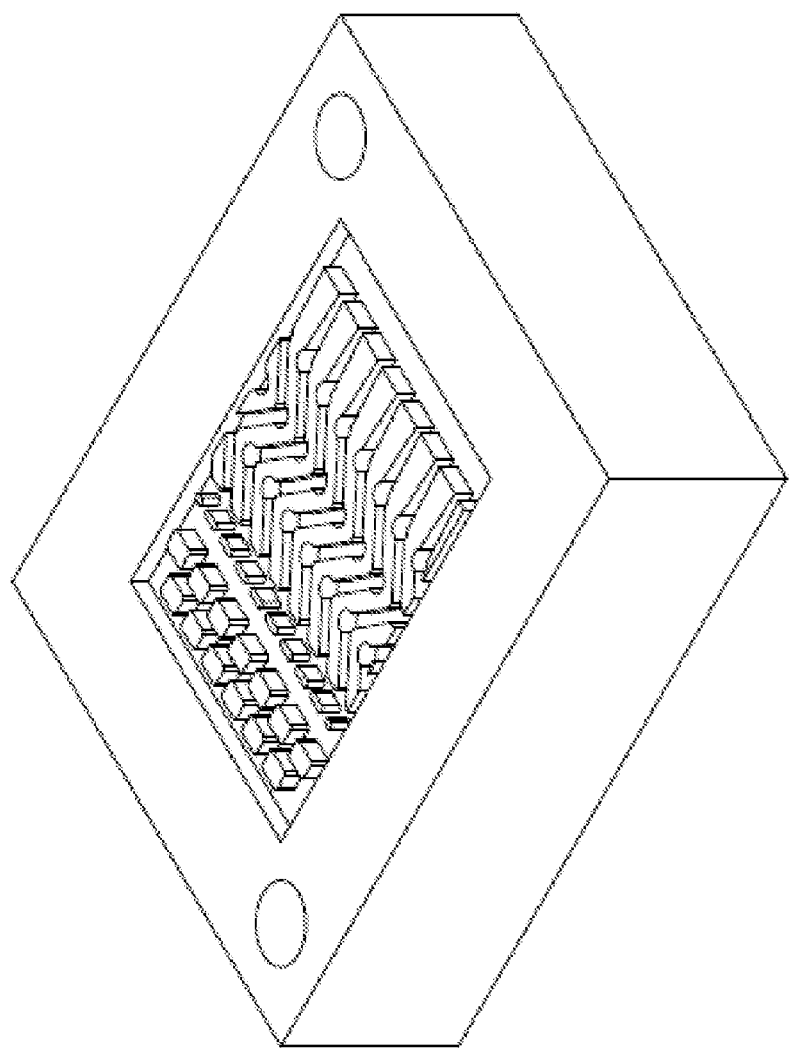
FIG. 94 is a perspective view of an exemplary embodiment of a mold of a metallic foil stack fixture containing a laminated stack of metallic foils.

FIG. 94 is a perspective view of an exemplary embodiment of a mold 94000 of a metallic foil stack fixture containing a laminated stack of metallic foils, such as shown in FIG. 93.

Figure 95:
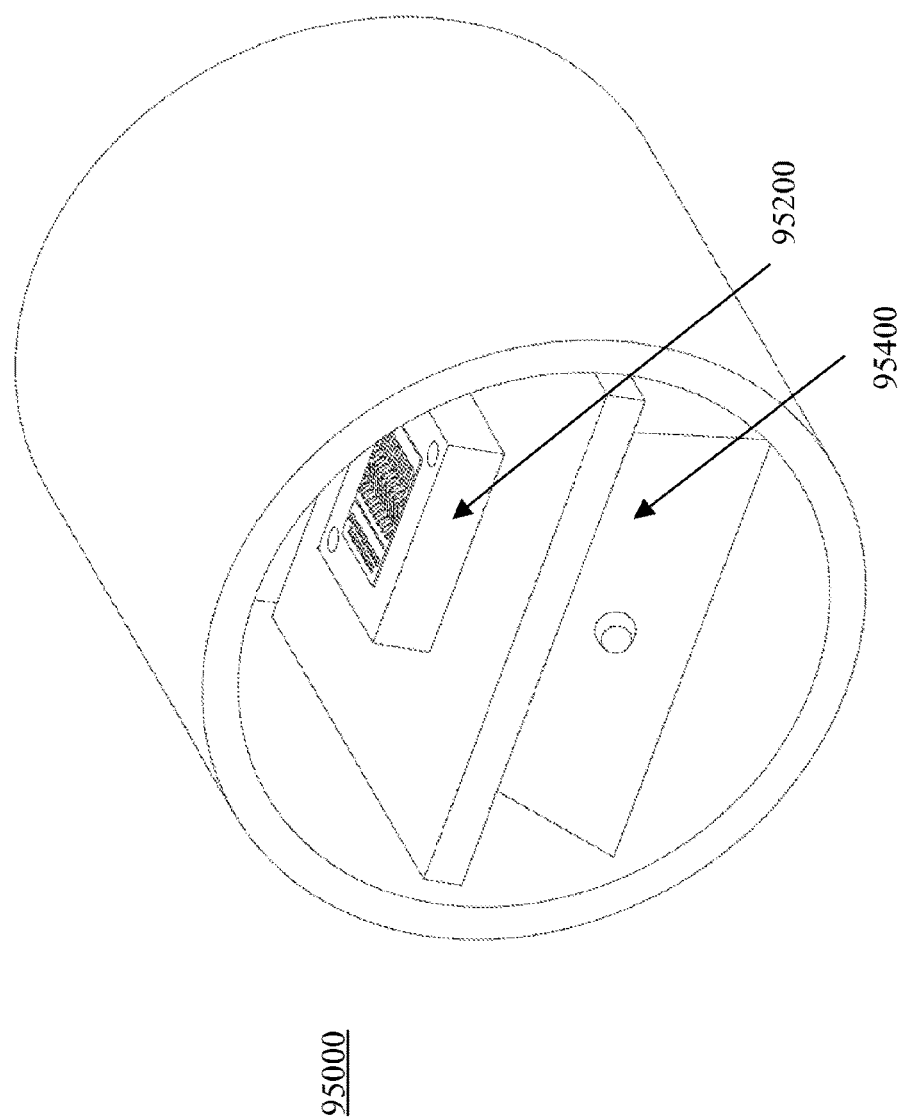
FIG. 95 is a perspective view of an exemplary embodiment of a metallic foil stack fixture on an exemplary vibration table.

FIG. 95 is a perspective view of an exemplary embodiment of a filled mold 95200 on an exemplary vibration table 95400 within a vacuum chamber 95600.

Figure 96:
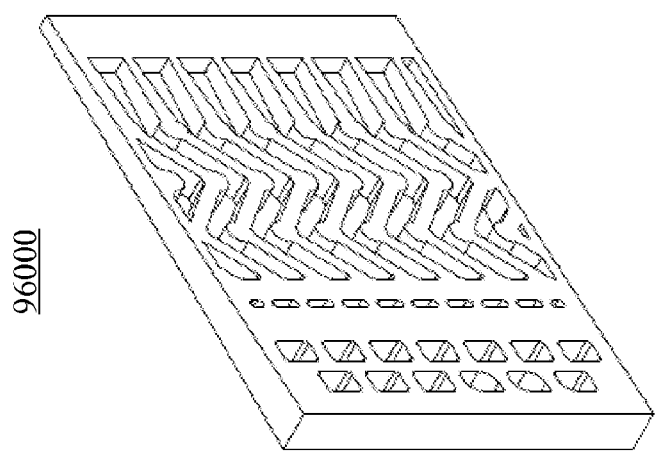
FIG. 96 is a perspective view of an exemplary embodiment of a green cast part.

FIG. 96 is a perspective view of an exemplary embodiment of a green cast part 96000 having a tapered thickness.

Figure 97:
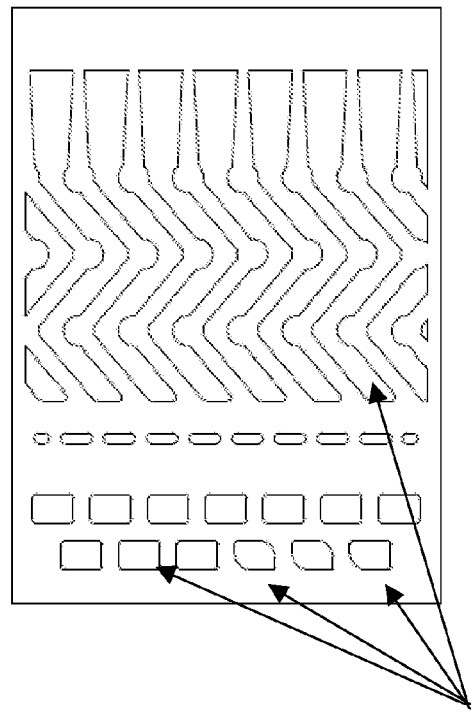
FIG. 97 is a front view of an exemplary embodiment of a green cast part.

FIG. 97 is a front view of an exemplary embodiment of a green cast part 9700 showing a plurality of apertures 97200 having various radii and curvatures.

Figure 98:
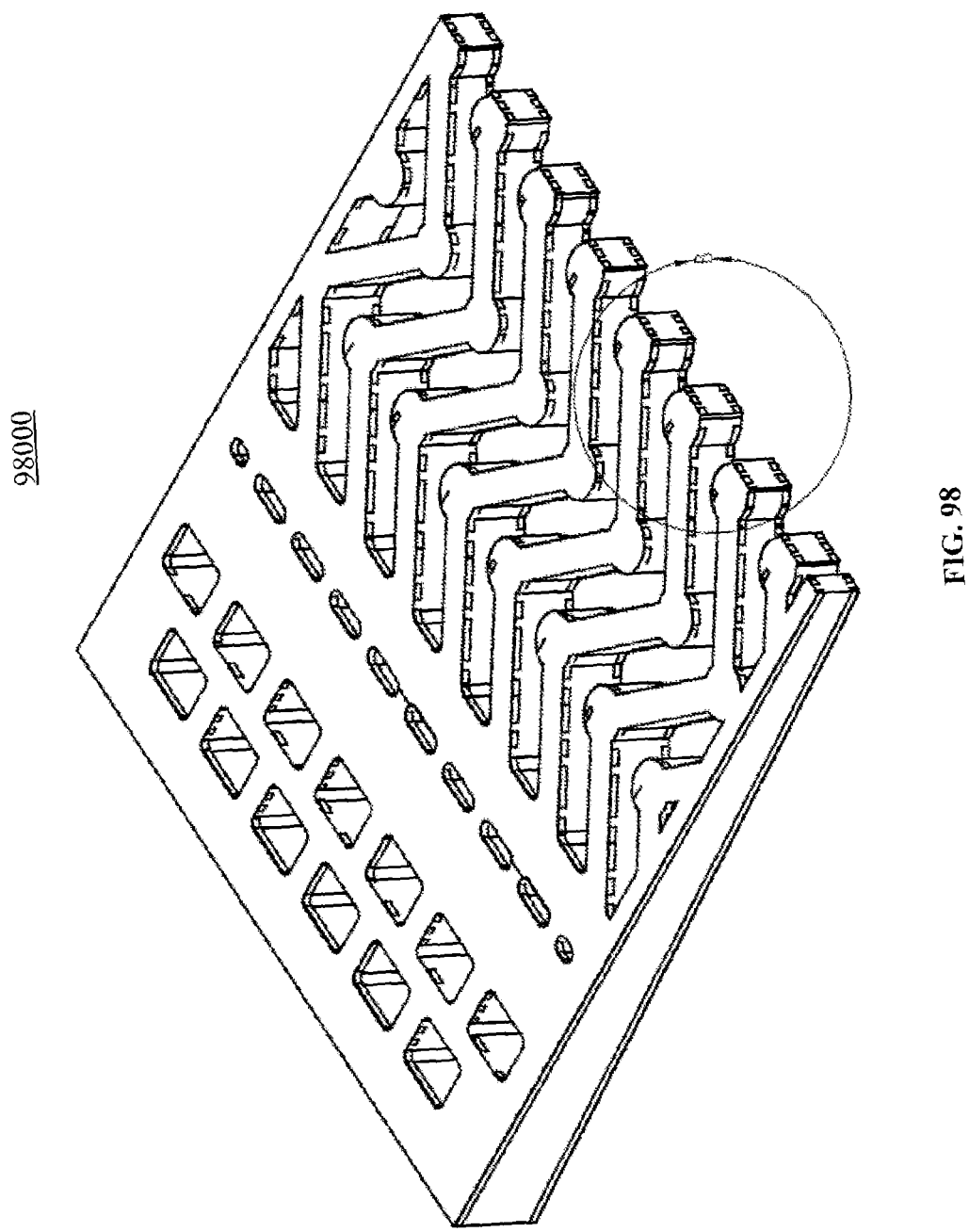
FIG. 98 is a perspective view of an exemplary embodiment of a green cast part.

FIG. 98 is a perspective view of an exemplary embodiment of a green cast part 98000.

Figure 99:
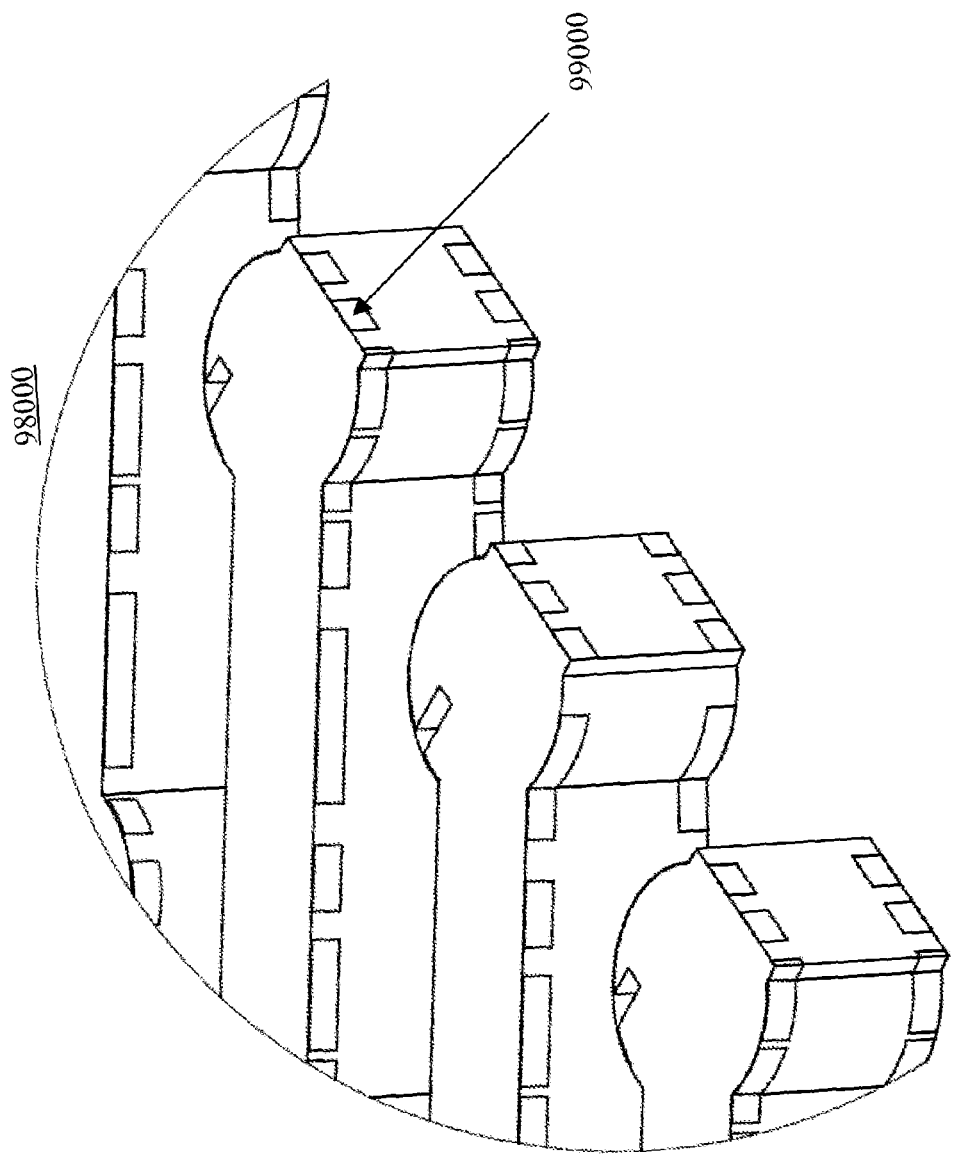
FIG. 99 is a close-up perspective view of an exemplary embodiment of a green cast part that includes an inserted metallic foil mold insert, taken at section B of FIG. 98.

FIG. 99 is a close-up perspective view of an exemplary embodiment of a green cast part 98000 that includes an inserted metallic foil mold insert 99000, taken at section B of FIG. 98.

Figures 100, 101:
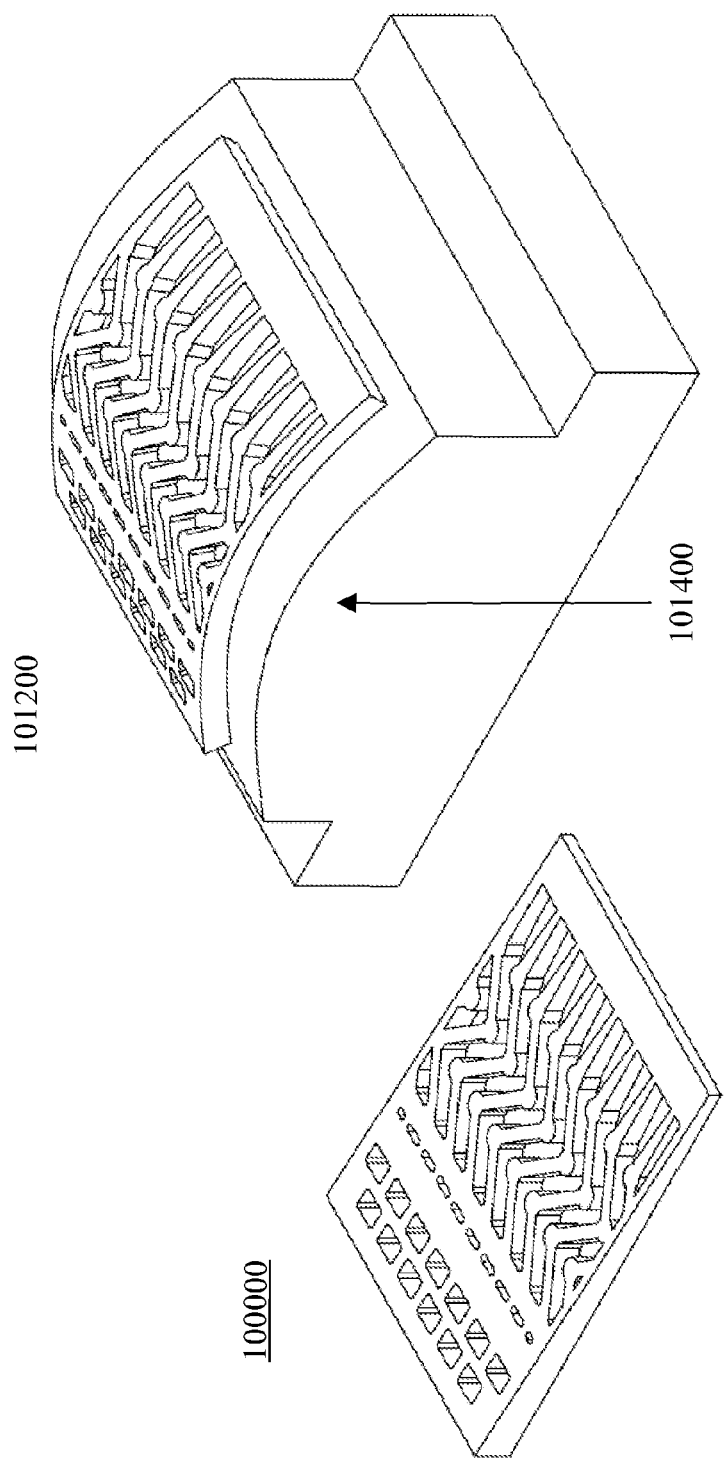
FIG. 100 is a perspective view of an exemplary embodiment of a green cast part.
FIG. 101 is a perspective view of an exemplary embodiment of a green cast part being shaped.

FIG. 100 is a perspective view of an exemplary embodiment of a green cast part 100000 prior to being shaped.

FIG. 101 is a perspective view of an exemplary embodiment of a green cast part 101200 being shaped on a shaping mandrel 101400.

Figure 102:
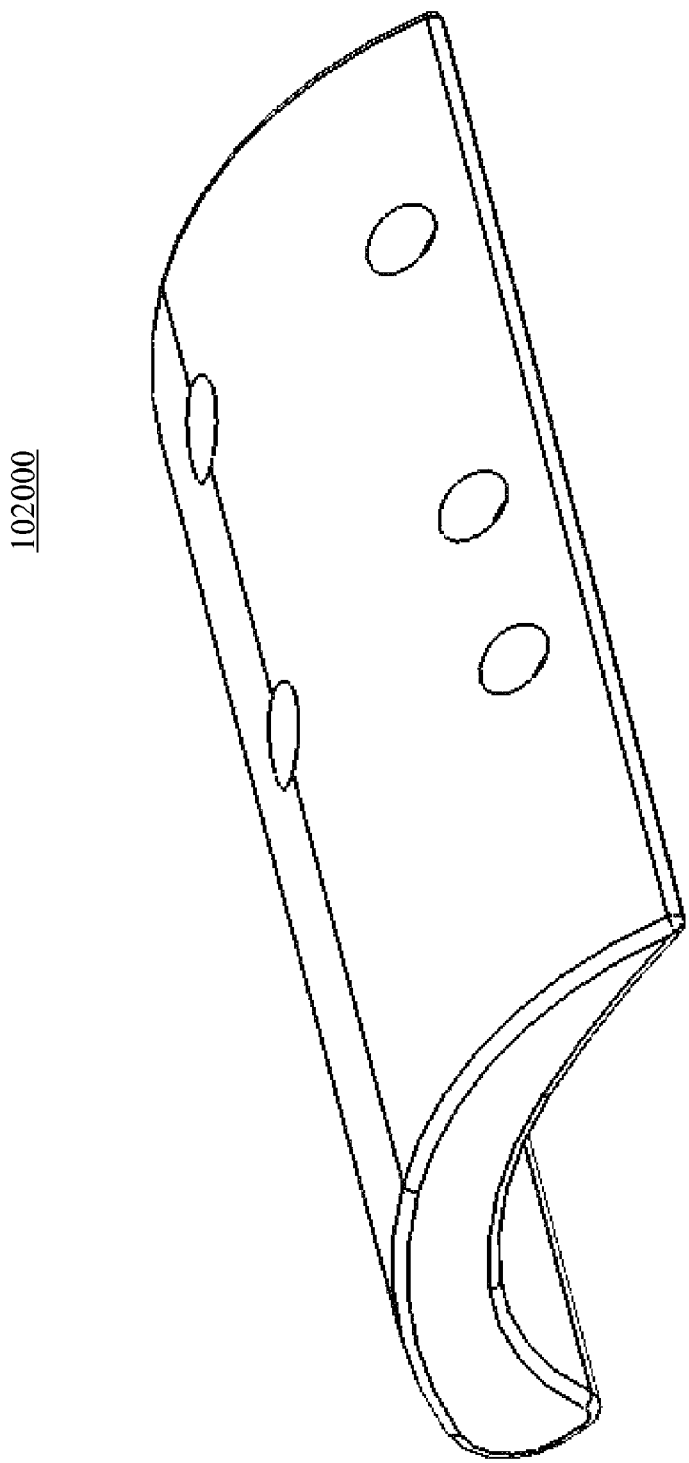
FIG. 102 is a perspective view of an exemplary embodiment of a shaped cast part.

FIG. 102 is a perspective view of an exemplary embodiment of a shaped cast part 102000, which can function as a core for a turbo-machine part, such as an airfoil, blade, vane, nozzle, etc.

Figure 103:
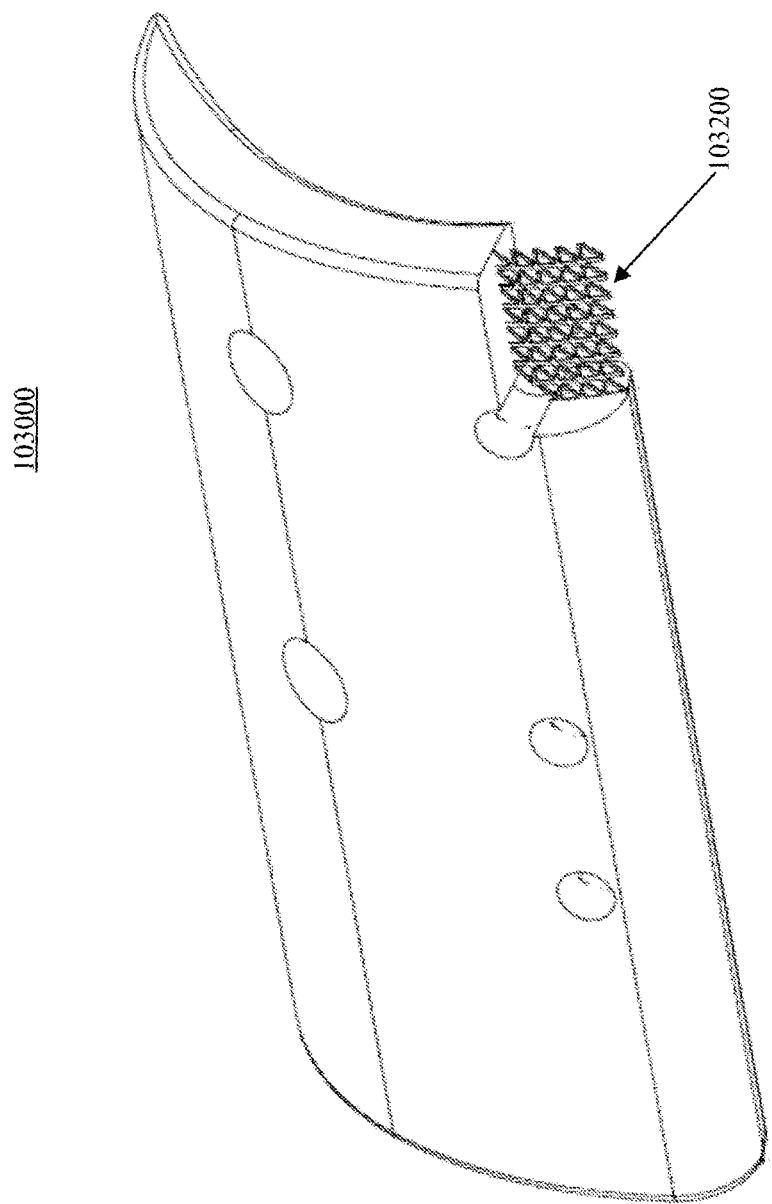
FIG. 103 is a perspective view of an exemplary embodiment of a shaped cast part and showing a reinforcing metallic foil mold insert.

FIG. 103 is a perspective view of an exemplary embodiment of a shaped cast part 103000 and showing a reinforcing metallic foil mold insert 103200.

Figure 104:
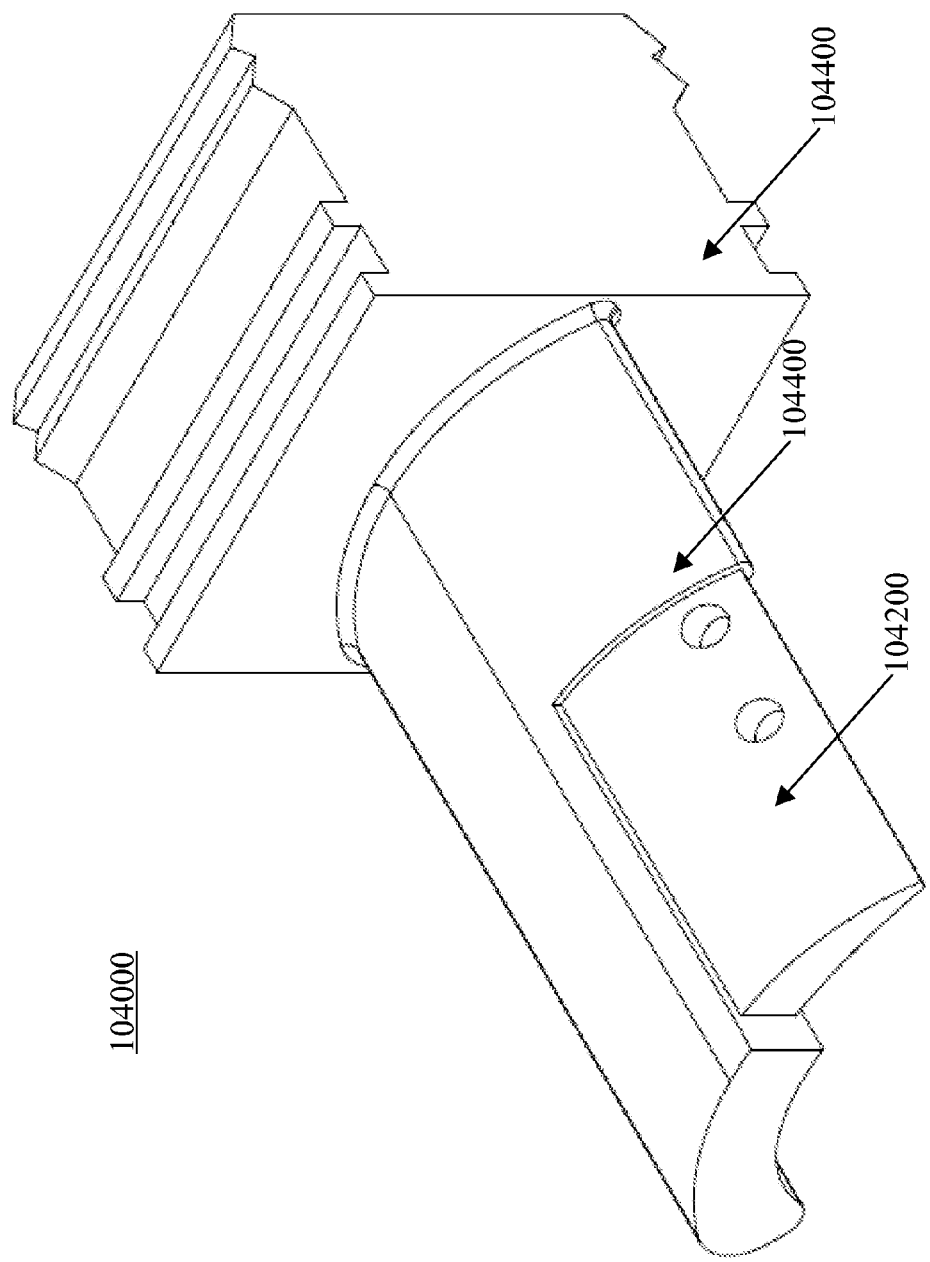

FIG. 104 is a perspective view of an exemplary embodiment of a device 104000 comprising a shaped cast part 104200, which can serve as a potentially removable, leachable, and/or dissolvable core of a cast device 104400, such as a turbo-machine airfoil, blade, nozzle, vane, etc., which can be attached to an attachment device 104600 not formed via a stack lamination mold, such as a root of an airfoil, blade, nozzle, and/or vane, etc., which can allow the device to be removably attached to a rotor and/or stator of a turbo-machine. Note that the removal of core 104200 can create passages through which air can flow to cool cast device 104400.

Figure 105:
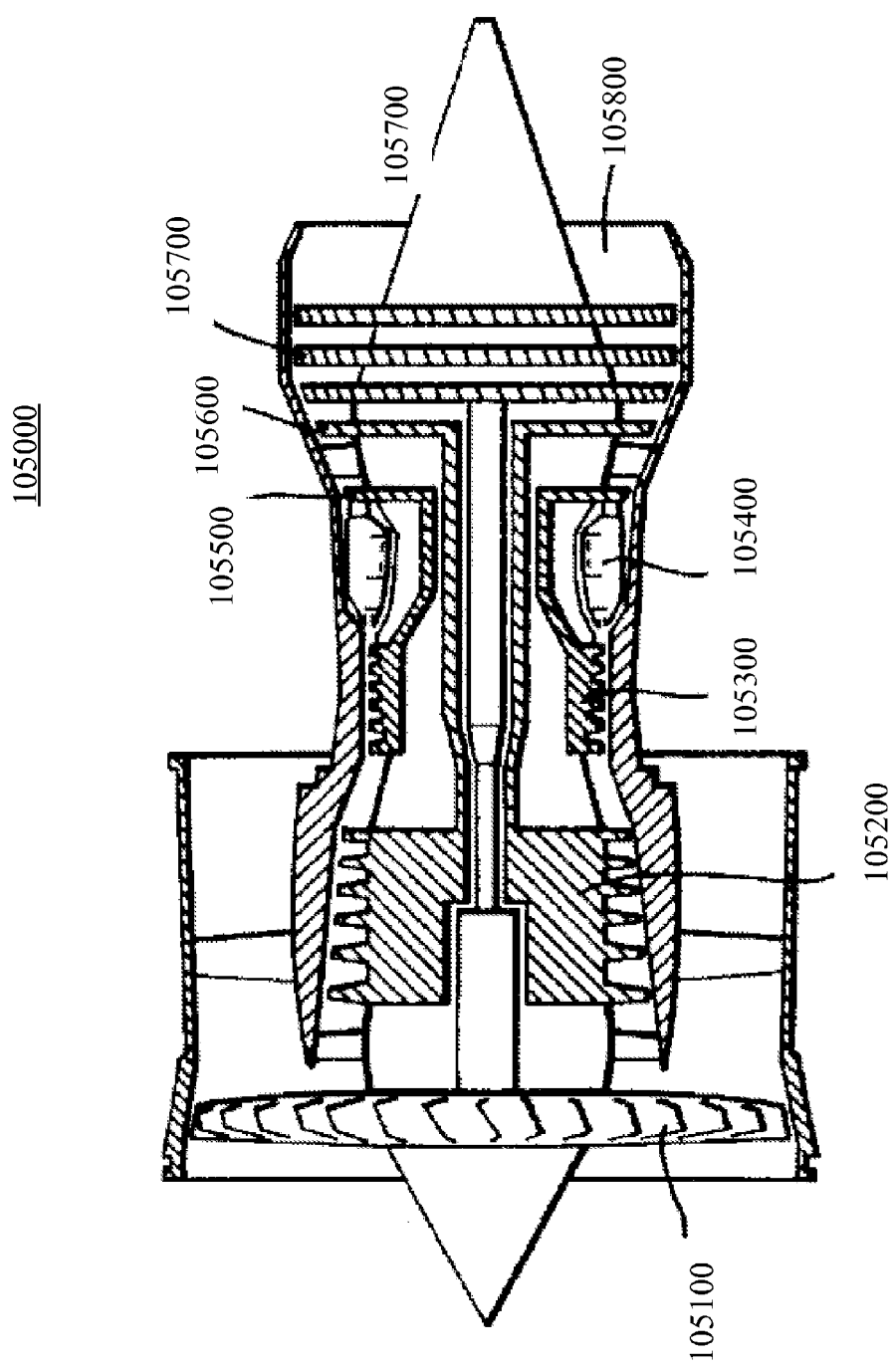

FIG. 105 is a perspective view of an exemplary embodiment of a turbo-machine 105000, such as a ducted fan gas turbine engine, which can comprise, in axial flow series, a fan 105100, intermediate pressure compressor 105200, high pressure compressor 105300, combustion equipment 105400, high, intermediate and low pressure turbines 105500, 105600 and 105700 respectively and an exhaust nozzle 105800. Air can be accelerated by fan 105100 to produce two flows of air, the larger of which can be exhausted from the engine 105000 to provide propulsive thrust. The smaller flow of air can be directed into the intermediate pressure compressor 105200 where it can be compressed and then into the high pressure compressor 105300 where further compression can take place. The compressed air then can be mixed with fuel in the combustion equipment 105400 and the mixture combusted. The resultant combustion products then can expand through the high, intermediate, and low pressure turbines 105500, 105600, and 105700 respectively before being exhausted to atmosphere through the exhaust nozzle 105800 to provide additional propulsive thrust.

Figure 106:
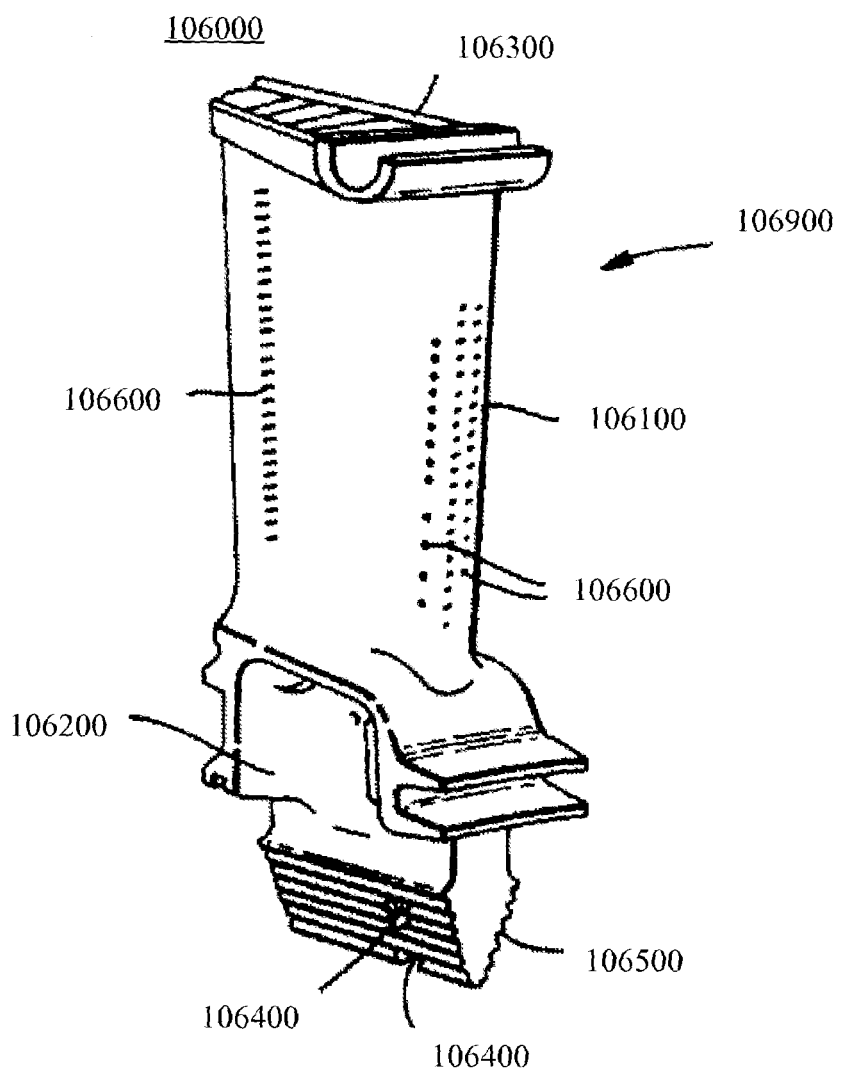

Referring to FIG. 105, and to FIG. 106, which is a perspective view of an exemplary embodiment of a turbo-machine assembly 106000, the high pressure turbine (or other turbo-machine) 105000 can include a rotor disc (not shown), which can carry an annular array of similar radially extending air cooled aerofoil blades, one of which 106900 can be seen in FIG. 106. The aerofoil blade 106900 can be made up of a root 106500, an aerofoil portion 106100, a shank 106200 that can interconnect the root 106500 and aerofoil portion 106100, and a shroud 106300 attached to the opposite end of the aerofoil portion 106100 to the shank 106200. The root 106200 can be of the well known "fir tree" cross-sectional configuration to facilitate its attachment to its rotor disc. Thus the rotor disc can be provided with a plurality of similar fir-tree cross-section slots in its periphery; each one receiving a turbine blade root 106200.

The root 106200 can be provided with apertures 106400 which can be positioned so as to receive flows of cooling air supplied by conventional means to the rotor disc. The apertures 106400 can direct the cooling air into cooling air passages, such as can be formed by a formed cast part as described herein, which can extend through any portion of the turbine blade 106900. Some of the air that passes through the air passages can be exhausted through small film cooling holes 106600 provided in the external surface of the aerofoil portion 106100, thereby providing cooling of that surface.

The remainder of the air can pass through any portion of the aerofoil portion 106100, thereby cooling it. When the remaining air finally reaches the shroud 106300, some of that air can be exhausted radially outwards through apertures extending through the shroud 106300. However, the remainder can be directed into a circumferentially extending passage provided within the shroud 106300. The passage can be open at each of its extents so that the passages of adjacent the turbine blade shrouds 106300 can be in air flow communication with each other.

Figure 107:
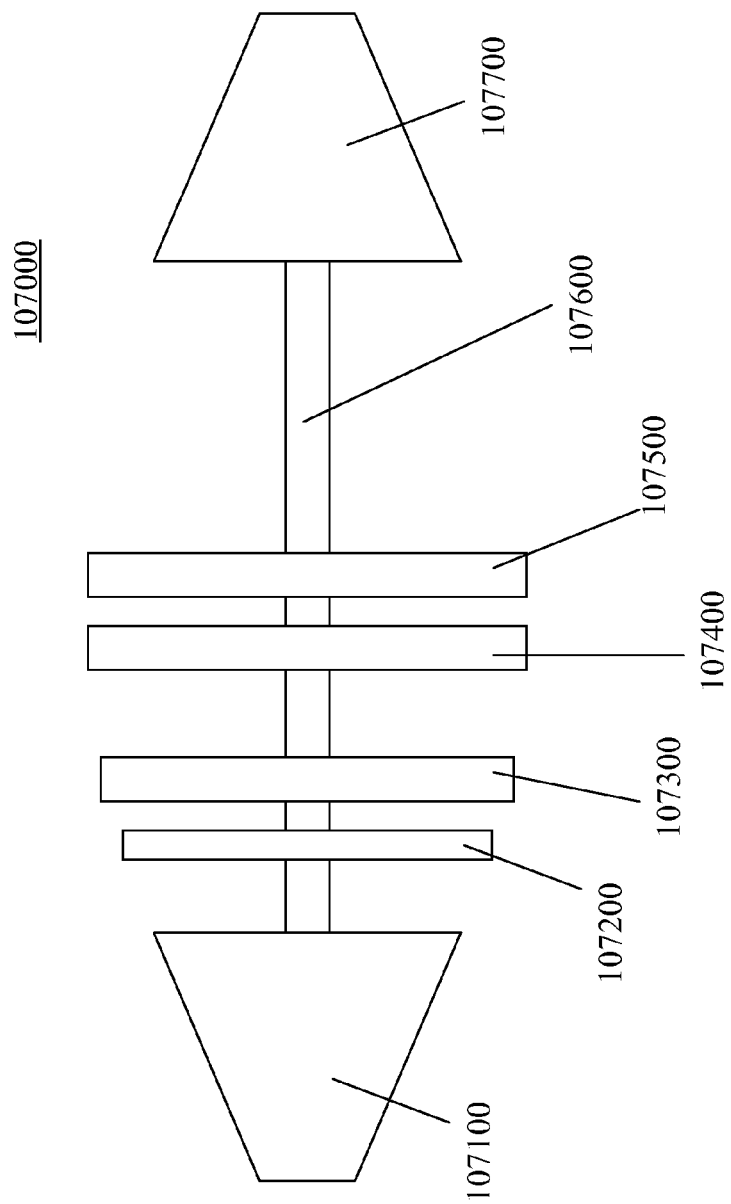

FIG. 107 is a schematic diagram of an exemplary embodiment of a turbo-machine 107000, which can comprise an inlet 107100, airfoils 107200, vanes 107300, blades 107400, nozzles 107500, rotor 107600, and/or outlet or exhaust 107700. In certain exemplary embodiments, airfoils 107200 and/or blades 107400 can be attached to rotor 107600. In certain exemplary embodiments, vanes 107300 and/or nozzles 107500 can be attached to a stator (not shown).

Certain exemplary embodiments can provide a composition, system, machine, device, manufacture, circuit, and/or user interface adapted for, and/or a method and/or machine-readable medium comprising machine-implementable instructions for, activities that can comprise:
via a predetermined and/or special purpose computer:
flattening a three-dimensional simulated model of a physical unflattened cast part to define a three-dimensional simulated model of a physical flattened cast part and to make substantially planar a first major face of said unflattened cast part model and a second major face of said unflattened cast part model, wherein after said flattening, a first plane substantially defining said first major face is substantially parallel to a second plane substantially defining said second major face;
after said flattening, defining a three-dimensional simulated model of a physical mold adapted to form said flattened cast part;
slicing said mold model into a plurality of mold model layers;
outputting dimensional data associated with said plurality of mold model layers, said dimensional data sufficient to physically form a plurality of metallic foils stackable to physically create said mold for said physical flattened cast part;
creating said model of said unflattened cast part;
scaling said unflattened cast part model, said flattened cast part model, and/or said mold model to account for expected shrinkage of a molding composition used to physically form said physical flattened cast part;
scaling said unflattened cast part model, said flattened cast part model, and/or said mold model to account for predetermined dimensional changes of said physical unflattened cast part, said physical flattened cast part, and/or said physical mold;
splitting said mold model to define a first mold portion model and a second mold portion model, said first mold portion model adapted to substantially mate with said second mold portion model along a pull-plane adapted to facilitate physical demolding of said flattened cast part from said mold;
incorporating corresponding alignment features into said first mold portion model and said second mold portion model;
incorporating inter-connecting part features into said mold model;
incorporating mold venting features into said mold model;
incorporating flattened cast part handling features into said mold model.

Certain exemplary embodiments can provide a composition, system, machine, device, manufacture, circuit, and/or user interface adapted for, and/or a method and/or machine-readable medium comprising machine-implementable instructions for, activities that can comprise:
outputting dimensional data associated with a plurality of layers of a flat cast part mold model, said dimensional data sufficient to physically form a plurality of metallic foils stackable to physically create a physical flat cast part mold for a physical flat cast part, said plurality of layers formed by slicing said flat cast part mold model, said mold model a three-dimensional simulated model of said flat cast part mold model, said physical flat cast part mold adapted to form said flat cast part, said flat cast part mold model a three-dimensional simulated model of a physical flat cast part, said flat cast part mold model formed from flattening a three-dimensional simulated unflattened cast part model of a physical unflattened cast part, said flattening making substantially planar a first major face of said unflattened cast part model and a second major face of said unflattened cast part model, wherein after said flattening, a first plane substantially defining said first major face is substantially parallel to a second plane substantially defining said second major face;
flattening said three-dimensional simulated unflattened cast part model of said physical unflattened cast part;
defining said flat cast part mold model; and/or
slicing said flat cast part mold model into said plurality of layers.

Certain exemplary embodiments can provide a molding composition comprising:
a ceramic composition comprising silica;
an cycloaliphatic epoxy binder composition, said cycloaliphatic epoxy binder composition present in said molding composition in an amount up to 30% by weight of said molding composition;
a silicone composition comprising a siloxane resin, said silicone composition present in said molding composition in an amount up to 30% by weight of said molding composition; and/or
a solvent composition adapted to dissolve said cycloaliphatic epoxy binder composition and said silicone composition; wherein:
said ceramic composition comprises approximately 1 percent to approximately 20 percent cristobalite by weight of said ceramic composition;
said ceramic composition comprises zircon;
said ceramic composition comprises alumina; and/or
said epoxy binder composition and said silicone composition are dissolvable via a predetermined solvent.

Certain exemplary embodiments can provide a composition, system, machine, device, manufacture, circuit, and/or user interface adapted for, and/or a method and/or machine-readable medium comprising machine-implementable instructions for, activities that can comprise:
causing crosslinking of at least a portion of a plurality of cross-linkable molecules comprised by a predetermined molding composition while said molding composition is located within a stack-lamination-derived mold, said molding composition comprising:

a ceramic composition comprising silica;
an cycloaliphatic epoxy binder composition, said cycloaliphatic epoxy binder composition present in said molding composition in an amount up to 30% by weight of said molding composition;
a silicone composition comprising a siloxane resin, said silicone composition present in said molding composition in an amount up to 30% by weight of said molding composition; and/or
a solvent composition adapted to dissolve said cycloaliphatic epoxy binder composition and said silicone composition;
causing cross-linking of at least a portion of a plurality of cross-linkable molecules comprised by a molding composition while said molding composition is within a stack-lamination-derived mold;
mixing ingredients of said molding composition in said stack-lamination-derived mold;
creating said molding composition in said stack-lamination-derived mold;
filling said stack-lamination-derived mold with said molding composition;
placing a photolithographically-derived foil structure into said stack-lamination-derived mold such that a first alignment feature of said foil structure interacts with a corresponding second alignment feature formed in said stack-lamination-derived mold, said foil structure comprising a plurality of apertures;
while said molding composition is present within said stack-lamination-derived mold, placing an insert into said molding composition;
while said molding composition is present within said stack-lamination-derived mold, placing an insert into said molding composition, said insert comprising an insert alignment feature that aligns with a mold alignment feature comprised by said stack-lamination-derived mold;
while said molding composition is present within said stack-lamination-derived mold, placing a photolithographically-derived insert into said molding composition;
while said molding composition is present within said stack-lamination-derived mold, vibrating said molding composition;
while said molding composition is present within said stack-lamination-derived mold, densifying particles of said ceramic composition in said molding composition;
while said molding composition is present within said stack-lamination-derived mold, applying a vacuum to said molding composition;
while said molding composition is present within said stack-lamination-derived mold, degassing said molding composition;
while said molding composition is present within said stack-lamination-derived mold, reducing a concentration of said solvent composition in said molding composition;
while said molding composition is present within said stack-lamination-derived mold, closing said stack-lamination-derived mold;
while said molding composition is present within said stack-lamination-derived mold, heating said molding composition;
while said molding composition is present within said stack-lamination-derived mold, cooling said molding composition;
while said molding composition is present within said stack-lamination-derived mold, opening said stack-lamination-derived mold;
after said causing cross-linking, separating said molding composition from said stack-lamination-derived mold;
after said causing cross-linking, separating a cast device from said stack-lamination-derived mold;
after said causing cross-linking, pulling a cast device from said stack-lamination-derived mold perpendicular to a pull-plane of said stack-lamination-derived mold; and/or after said causing cross-linking, applying a desired shape to a cast device formed from said molding composition;
wherein said stack-lamination-derived mold is derived from a photolithographically-generated stack-foil lamination mold; and/or
wherein said stack-lamination-derived mold defines a plurality of wall surfaces, a wall surface from said plurality of wall surfaces comprising a plurality of 3-dimensional micro-features that substantially spatially invertedly replicate an ancestor mold surface defined by a plurality of layers of a metallic foil stack lamination ancestor mold, said plurality of 3-dimensional micro-features comprising at least one protruding undercut, said plurality of wall surfaces defining a periphery of a layer-less volume.

Certain exemplary embodiments can provide a composition, system, machine, device, manufacture, circuit, and/or user interface adapted for, and/or a method and/or machine-readable medium comprising machine-implementable instructions for, activities that can comprise:
filling a stack-lamination-derived mold with a molding composition comprising a plurality of cross-linkable molecules, such that said molding composition surrounds at least a portion of a photolithographically-derived foil structure located within said stack-lamination-derived mold, a first alignment feature of said foil structure interfaced with a corresponding second alignment feature formed in said mold, said foil structure comprising a plurality of apertures, said molding composition substantially filling said plurality of apertures.

Certain exemplary embodiments can provide a composition, system, machine, device, manufacture, circuit, and/or user interface adapted for, and/or a method and/or machine-readable medium comprising machine-implementable instructions for, activities that can comprise:
placing a photolithographically-derived foil structure into a stack-lamination-derived mold such that a first alignment feature of said foil structure interacts with a corresponding second alignment feature formed in said mold, said foil structure comprising a plurality of apertures;
filling said mold with a molding composition comprising a plurality of cross-linkable molecules, such that said molding composition fills said plurality of apertures and surrounds at least a portion of said foil structure; and causing cross-linking of at least a portion of said plurality of cross-linkable molecules; wherein:
said foil structure comprises a single monolithic metallic foil; and/or
said foil structure comprises a plurality of monolithic metallic foils.

Certain exemplary embodiments can provide a composition, system, machine, device, manufacture, and/or circuit that can comprise:

a first planar surface, and
a thermoformable composition comprising:
  a ceramic composition comprising silica;
  an cycloaliphatic epoxy binder composition, said cycloaliphatic epoxy binder composition present in said thermoformable composition in an amount up to 30 percent by weight of said thermoformable composition; and
  a silicone composition comprising a siloxane resin, said silicone composition present in said thermoformable composition in an amount up to 30 percent by weight of said device;
  wherein said first planar surface is adapted to be transformed into a non-planar surface via thermoforming said thermoformable composition; wherein:
  said ceramic composition comprises approximately 1 percent to approximately 20 percent cristobalite by weight of said ceramic composition;
  said ceramic composition comprises zircon;
  said ceramic composition comprises alumina; and/or
  said epoxy binder composition and said silicone composition are dissolvable via a predetermined solvent.

Certain exemplary embodiments can provide a system, machine, device, manufacture, circuit, and/or user interface that can comprise:
  a device composition comprising:
    a ceramic composition comprising silica;
    an cycloaliphatic epoxy binder composition, said cycloaliphatic epoxy binder composition present in said molding composition in an amount up to 30% by weight of said device composition; and/or
    a silicone composition comprising a siloxane resin, said silicone composition present in said molding composition in an amount up to 30% by weight of said device composition; wherein:
      said system, machine, device, manufacture, circuit, and/or user interface can be formed via a predetermined stack-lamination-derived mold, said device defining a plurality of wall surfaces, a wall surface from said plurality of wall surfaces comprising a plurality of 3-dimensional micro-features that substantially spatially invertedly replicate an ancestor mold surface defined by a plurality of layers of a metallic foil stack lamination ancestor mold, said plurality of 3-dimensional micro-features comprising at least one protruding undercut, said plurality of wall surfaces defining a periphery of a layer-less volume.

Certain exemplary embodiments can provide a composition, system, machine, device, manufacture, circuit, and/or user interface adapted for, and/or a method and/or machine-readable medium comprising machine-implementable instructions for, activities that can comprise:
  after removing a cast device from a stack-lamination-derived mold, said cast device formed from a molding composition, applying a desired shape to said cast device to form a shaped cast device, said molding composition comprising:
    a ceramic composition comprising silica;
    an cycloaliphatic epoxy binder composition, said cycloaliphatic epoxy binder composition present in said molding composition in an amount up to 30% by weight of said molding composition;
    a silicone composition comprising a siloxane resin, said silicone composition present in said molding composition in an amount up to 30% by weight of said molding composition; and/or
    a solvent composition adapted to dissolve said cycloaliphatic epoxy binder composition and said silicone composition.

Certain exemplary embodiments can provide a composition, system, machine, device, manufacture, circuit, and/or user interface adapted for, and/or a method and/or machine-readable medium comprising machine-implementable instructions for, activities that can comprise:
  after removing a cast device from a stack-lamination-derived mold, said cast device comprising a reduced solvent version of a herein described molding composition, applying a desired shape to said cast device to form a shaped cast device;
  removing said cast device from said stack-lamination-derived mold;
  prior to said applying a desired shape, aligning said cast device with a shaping tool;
  heating said shaped cast device;
  cooling said shaped cast device;
  firing said shaped cast device;
  sintering particles of said ceramic composition in said shaped cast device; coupling said cast device to a part;
  coupling said shaped cast device to a part;
  casting investment material around said shaped cast device;
  casting investment material around said shaped cast device to form an investment cast part;
  after casting investment material around said shaped cast device to form an investment cast part, removing said shaped cast device from said investment cast part; and/or
  casting investment material around said shaped cast device to form an investment cast part, said investment cast part defining a plurality of wall surfaces, a wall surface from said plurality of wall surfaces comprising a plurality of 3-dimensional micro-features that substantially spatially invertedly replicate an ancestor mold surface defined by a plurality of layers of a metallic foil stack lamination ancestor mold, said plurality of 3-dimensional micro-features comprising at least one protruding undercut, said plurality of wall surfaces defining a periphery of a layer-less volume; wherein:
    said cast device defines a plurality of wall surfaces, a wall surface from said plurality of wall surfaces comprising a plurality of 3-dimensional micro-features that substantially spatially invertedly replicate an ancestor mold surface defined by a plurality of layers of a metallic foil stack lamination ancestor mold, said plurality of 3-dimensional micro-features comprising at least one protruding undercut, said plurality of wall surfaces defining a periphery of a layer-less volume.
    said shaped cast device defines a plurality of wall surfaces, a wall surface from said plurality of wall surfaces comprising a plurality of 3-dimensional micro-features that substantially spatially invertedly replicate an ancestor mold surface defined by a plurality of layers of a metallic foil stack lamination ancestor mold, said plurality of 3-dimensional micro-features comprising at least one protruding undercut, said plurality of wall surfaces defining a periphery of a layer-less volume.

Certain exemplary embodiments can provide a system, machine, device, manufacture, circuit, and/or user interface that can comprise:

a ceramic composition comprising silica;
said system, machine, device, manufacture, circuit, and/or user interface formed via a predetermined stack-lamination-derived mold, said device defining a plurality of wall surfaces, a wall surface from said plurality of wall surfaces comprising a plurality of 3-dimensional micro-features that substantially spatially invertedly replicate an ancestor mold surface defined by a plurality of layers of a metallic foil stack lamination ancestor mold, said plurality of 3-dimensional micro-features comprising at least one protruding undercut, said plurality of wall surfaces defining a periphery of a layer-less volume; and/or
a photolithographically-derived foil structure substantially surrounded by said ceramic composition; wherein:
said ceramic composition comprises approximately 1 percent to approximately 20 percent cristobalite by weight of said ceramic composition;
said ceramic composition comprises zircon;
said ceramic composition comprises alumina;
said device is an investment casting core;
said device is a core for an investment cast product;
said device is a core for an investment cast turbomachine component;
said device is a core for an investment cast air foil;
said device is a core for an investment cast blade;
said device is a core for an investment cast vane;
said device is a core for an investment cast nozzle; and/or
said device defines a plurality of cooling passages for an investment cast product.

Certain exemplary embodiments can provide a system, machine, device, manufacture, circuit, and/or user interface that can comprise:
a ceramic composition comprising silica; and
a photolithographically-derived foil structure substantially surrounded by said ceramic composition; wherein:
said system, machine, device, manufacture, circuit, and/or user interface can be formed via a predetermined stack-lamination-derived mold, said device defining a plurality of wall surfaces, a wall surface from said plurality of wall surfaces comprising a plurality of 3-dimensional micro-features that substantially spatially invertedly replicate an ancestor mold surface defined by a plurality of layers of a metallic foil stack lamination ancestor mold, said plurality of 3-dimensional micro-features comprising at least one protruding undercut, said plurality of wall surfaces defining a periphery of a layer-less volume;
said device is a core for an investment cast product;
said device is a core for an investment cast turbomachine component; and/or
said device is a core for an investment cast air foil.

Certain exemplary embodiments can provide a composition, system, machine, device, manufacture, circuit, and/or user interface adapted for, and/or a method and/or machine-readable medium comprising machine-implementable instructions for, activities that can comprise:
casting investment material around a shaped cast device to form an investment cast part, said investment cast part defining a plurality of wall surfaces, a wall surface from said plurality of wall surfaces comprising a plurality of 3-dimensional micro-features that substantially spatially invertedly replicate an ancestor mold surface defined by a plurality of layers of a metallic foil stack lamination ancestor mold, said plurality of 3-dimensional micro-features comprising at least one protruding undercut, said plurality of wall surfaces defining a periphery of a layer-less volume, said shaped cast device formed from a flat cast device, said flat cast device formed from a molding composition, said molding composition comprising:
a ceramic composition comprising silica;
an cycloaliphatic epoxy binder composition, said cycloaliphatic epoxy binder composition present in said molding composition in an amount up to 30% by weight of said molding composition;
a silicone composition comprising a siloxane resin, said silicone composition present in said molding composition in an amount up to 30% by weight of said molding composition; and/or
a solvent composition adapted to dissolve said cycloaliphatic epoxy binder composition and said silicone composition.

Certain exemplary embodiments can provide a composition, system, machine, device, manufacture, circuit, and/or user interface adapted for, and/or a method and/or machine-readable medium comprising machine-implementable instructions for, activities that can comprise:
casting investment material around a shaped cast device to form an investment cast part, said investment cast part defining a plurality of wall surfaces, a wall surface from said plurality of wall surfaces comprising a plurality of 3-dimensional micro-features that substantially spatially invertedly replicate an ancestor mold surface defined by a plurality of layers of a metallic foil stack lamination ancestor mold, said plurality of 3-dimensional micro-features comprising at least one protruding undercut, said plurality of wall surfaces defining a periphery of a layer-less volume, said shaped cast device formed from a flat cast device.

Certain exemplary embodiments can provide a composition, system, machine, device, manufacture, circuit, and/or user interface adapted for, and/or a method and/or machine-readable medium comprising machine-implementable instructions for, activities that can comprise:
casting investment material around a shaped cast device to form an investment cast part, said investment cast part defining a plurality of wall surfaces, a wall surface from said plurality of wall surfaces comprising a plurality of 3-dimensional micro-features that substantially spatially invertedly replicate an ancestor mold surface defined by a plurality of layers of a metallic foil stack lamination ancestor mold, said plurality of 3-dimensional micro-features comprising at least one protruding undercut, said plurality of wall surfaces defining a periphery of a layer-less volume, said shaped cast device comprising:
a ceramic composition comprising silica; and/or
a silicone composition comprising a siloxane resin, said silicone composition present in said molding composition in an amount up to 30% by weight of said shaped cast device.

Certain exemplary embodiments can provide a system, machine, device, manufacture, circuit, and/or user interface that can comprise:
a first device formed via a predetermined stack-lamination-derived mold, said first device defining a plurality of wall surfaces, a wall surface from said plurality of wall surfaces comprising a plurality of 3-dimensional micro-features that substantially spatially invertedly replicate an ancestor mold surface defined by a plurality of layers of a metallic foil stack lamination ancestor mold, said plurality of 3-dimensional micro-features comprising at least one protruding undercut, said plurality of wall surfaces defining a periphery of a layerless volume; and/or a second device not formed via any stack-lamination-derived mold, said second device operatively fastened to said first device.

Definitions

When the following terms are used substantively herein, the accompanying definitions apply. These terms and definitions are presented without prejudice, and, consistent with the application, the right to redefine these terms via amendment during the prosecution of this application or any application claiming priority hereto is reserved. For the purpose of interpreting a claim of any patent that claims priority hereto, each definition in that patent functions as a clear and unambiguous disavowal of the subject matter outside of that definition.

3-dimensional/three-dimensional—involving or relating to three mutually orthogonal dimensions and/or definable via coordinates relative to three mutually perpendicular axes.

a—at least one.

account—to accommodate, adjust for, and/or take into consideration.

activity—an action, act, step, and/or process or portion thereof.

adapted to—suitable, fit, and/or capable of performing a specified function.

adjacent—in close proximity to, near, next to, and/or adjoining.

after—subsequent to.

air foil—a body, cross-section of a body, and/or surface designed to develop a desired force by reaction with a fluid that is flowing across the surface. The cross sections of wings, propeller blades, windmill blades, compressor and turbine blades in a jet engine, and hydrofoils on a high-speed ship are examples of airfoils.

align—to place objects such that at least some of their faces are in line with each other and/or so that their centerlines are on the same axis.

all—an entirety of a set.

along—through, on, beside, over, in line with, and/or parallel to the length and/or direction of; and/or from one end to the other of.

alumina—aluminum oxide and/or $Al_2O_3$.

amount—a quantity.

ancestor—an entity from which another entity is descended; a forebear, forerunner, predecessor, and/or progenitor.

and/or—either in conjunction with or in alternative to.

any—one, some, every, and/or all without specification.

aperture—an opening, hole, gap, passage, and/or slit.

apparatus—an appliance and/or device for a particular purpose.

applying—to put to use for a purpose.

approximately—about and/or nearly the same as.

around—about, surrounding, and/or on substantially all sides of.

associate—to join, connect together, accompany, and/or relate.

associated with—related to.

at least—not less than, and possibly more than.

attach—to fasten, secure, couple, and/or join.

automatically—acting or operating in a manner essentially independent of external influence or control. For example, an automatic light switch can turn on upon "seeing" a person in its view, without the person manually operating the light switch.

between—in a separating interval and/or intermediate to.

bind—to combine chemically or form a chemical bond.

binder—a substance and/or something used to bind separate particles together and/or facilitate adhesion.

blade—an arm of a rotating mechanism.

Boolean logic—a complete system for logical operations.

bound—to limit an extent.

can—is capable of, in at least some embodiments.

cast—(n) the process and/or act of casting; (adjective) formed in a mold; (v) to form (e.g., wax, liquid polymer, and/or liquid metal, etc.) into a particular shape by pouring into a mold and allowing to solidify within the mold prior to removal from the mold.

cause—to bring about, provoke, precipitate, produce, elicit, be the reason for, result in, and/or effect.

ceramic—any of various hard, brittle, heat-resistant, and corrosion-resistant materials made by shaping and then firing a nonmetallic mineral, such as clay, at a high temperature, and/or the nonmetallic mineral from which such materials can be formed, such as, for example, silica, silicon carbide, alumina, zirconium oxide, and/or fused silica, calcium sulfate, luminescent optical ceramics, bio-ceramics, and/or plaster, etc.

change—(v.) to cause to be different; (n.) the act, process, and/or result of altering or modifying.

channel—a defined passage, conduit, and/or groove for conveying one or more fluids.

characterize—to define, describe, classify, and/or constrain the qualities, characteristics, and/or peculiarities of.

circuit—a physical system comprising: an electrically conductive pathway and/or a communications connection established across a switching device (such as logic gates); and/or an electrically conductive pathway and/or a communications connection established across two or more switching devices comprised by a network and between corresponding end systems connected to, but not comprised by the network.

circular—round and/or having the shape of a circle.

close—to move (a door, for example) so that an opening or passage is covered and/or obstructed; to shut; and/or to draw and/or bind together.

component—a constituent element and/or part.

composition—a composition of matter and/or an aggregate, mixture, reaction product, and/or result of combining two or more substances.

compressive—pertaining to forces on a body or part of a body that tend to crush and/or compress the body.

comprised—included in; a part of.

comprises—includes, but is not limited to, what follows.

comprising—including but not limited to.

concentration—a measure of the amount of dissolved substance contained per unit of volume and/or the amount of a specified substance in a unit amount of another substance.

configure—to make suitable or fit for a specific use or situation.

connect—to join and/or fasten together.

containing—including but not limited to.

convert—to transform, adapt, and/or change.

cooling—reducing a temperature of a substance.

core—a substantially innermost and/or central, and potentially removable, object around which another material will be cast.

corresponding—related, associated, accompanying, similar in purpose and/or position, conforming in every respect, and/or equivalent and/or agreeing in amount, quantity, magnitude, quality, and/or degree.

coupling—(n) a device adapted to join, connect, and/or link. (v) joining, connecting, and/or linking.

create—to make, form, produce, generate, bring into being, and/or cause to exist.

cristobalite—a crystalline form of silica that tends to be stable at high temperatures and/or a polymorph of quartz.

cross-link—to join (adjacent chains of a polymer or protein) by creating covalent bonds.

cycloaliphatic—of, relating to, and/or being an organic compound that contains a ring but is not aromatic.

data—distinct pieces of information, usually formatted in a special or predetermined way and/or organized to express concepts, and/or represented in a form suitable for processing by an information device.

data structure—an organization of a collection of data that allows the data to be manipulated effectively and/or a logical relationship among data elements that is designed to support specific data manipulation functions. A data structure can comprise meta data to describe the properties of the data structure. Examples of data structures can include: array, dictionary, graph, hash, heap, linked list, matrix, object, queue, ring, stack, tree, and/or vector.

define—to establish the meaning, relationship, outline, form, and/or structure of and/or to precisely and/or distinctly describe and/or specify.

demold—to remove from a mold.

densify—to increase the density of.

derive—to obtain from a source.

desired—indicated, expressed, and/or requested.

determine—to obtain, calculate, decide, deduce, and/or ascertain.

device—a machine, manufacture, and/or collection thereof.

differ—to be unlike, dissimilar, and/or distinct in nature and/or quality.

digital—non-analog and/or discrete.

dimension—an extension in a given direction and/or a measurement in length, width, or thickness.

direction—a spatial relation between something and a course along which it points and/or moves; a distance independent relationship between two points in space that specifies the position of either with respect to the other; and/or a relationship by which the alignment and/or orientation of any position with respect to any other position is established.

dissolve—to cause to pass into solution.

each—every one of a group considered individually.

embodiment—an implementation and/or a concrete representation of a concept.

epoxy—having the structure of an epoxide; of and/or containing an oxygen atom joined to two different groups that are themselves joined to other groups; any of a class of resins derived by polymerization from epoxides: used chiefly in adhesives, coatings, electrical insulation, solder mix, and/or castings; and/or any of various usually thermosetting resins capable of forming tight cross-linked polymer structures characterized by toughness, strong adhesion, and low shrinkage, used especially in surface coatings and adhesives.

exemplary—serving as a model.

expected—predicted.

extending—existing, located, placed, and/or stretched lengthwise.

face—the most significant or prominent surface of an object.

facilitate—to encourage and/or allow.

fasten—to attach to something else and/or to hold something in place.

feature—a prominent and/or distinctive aspect, structure, component, quality, and/or characteristic.

fill—to supply, introduce into, and/or put into a container, potentially to the fullest extent of the container.

fillet—concave easing of an interior corner of a part design.

fire—to bake in a kiln and/or dry by heating.

first—an initial entity in an ordering of entities; immediately preceding the second in an ordering.

flat—having a substantially planar major face and/or having a relatively broad surface in relation to thickness or depth.

flatten—to make flat.

foil—a very thin, often flexible sheet and/of leaf, typically formed of metal.

form—to make, create, generate, construct, and/or shape.

formations—concave and/or convex elements on a surface; dimples; and/or protrusions.

from—used to indicate a source.

further—in addition.

generate—to create, produce, render, give rise to, and/or bring into existence.

handling—of and/or relating to manual (and/or mechanical) carrying, moving, delivering, and/or working with something.

haptic—involving the human sense of kinesthetic movement and/or the human sense of touch. Among the many potential haptic experiences are numerous sensations, body-positional differences in sensations, and time-based changes in sensations that are perceived at least partially in non-visual, non-audible, and non-olfactory manners, including the experiences of tactile touch (being touched), active touch, grasping, pressure, friction, traction, slip, stretch, force, torque, impact, puncture, vibration, motion, acceleration, jerk, pulse, orientation, limb position, gravity, texture, gap, recess, viscosity, pain, itch, moisture, temperature, thermal conductivity, and thermal capacity.

having—possessing, characterized by, and/or comprising.

heating—transferring energy from one substance to another resulting in an increase in temperature of one substance.

human-machine interface—hardware and/or software adapted to render information to a user and/or receive information from the user; and/or a user interface.

including—having, but not limited to, what follows.

incorporating—causing to comprise.

information device—any device capable of processing data and/or information, such as any general purpose and/or special purpose computer, such as a personal computer, workstation, server, minicomputer, mainframe, supercomputer, computer terminal, laptop, wearable computer, and/or Personal Digital Assistant (PDA), mobile terminal, Bluetooth device, communicator, "smart" phone (such as an iPhone and/or Treo-like device), messaging service (e.g., Blackberry)

receiver, pager, facsimile, cellular telephone, a traditional telephone, telephonic device, a programmed microprocessor or microcontroller and/or peripheral integrated circuit elements, an ASIC or other integrated circuit, a hardware electronic logic circuit such as a discrete element circuit, and/or a programmable logic device such as a PLD, PLA, FPGA, or PAL, or the like, etc. In general any device on which resides a finite state machine capable of implementing at least a portion of a method, structure, and/or or graphical user interface described herein may be used as an information device. An information device can comprise components such as one or more network interfaces, one or more processors, one or more memories containing instructions, and/or one or more input/output (I/O) devices, one or more user interfaces coupled to an I/O device, etc.

ingredient—an element and/or component in a mixture, compound, and/or composition.

input/output (I/O) device—any sensory-oriented input and/or output device, such as an audio, visual, haptic, olfactory, and/or taste-oriented device, including, for example, a monitor, display, projector, overhead display, keyboard, keypad, mouse, trackball, joystick, gamepad, wheel, touchpad, touch panel, pointing device, microphone, speaker, video camera, camera, scanner, printer, haptic device, vibrator, tactile simulator, and/or tactile pad, potentially including a port to which an I/O device can be attached or connected.

insert—to put or introduce into.

install—to connect or set in position and prepare for use.

instructions—directions, which can be implemented as firmware and/or software, the directions adapted to perform a particular operation or function.

integral—formed or united into another entity.

interact—to act on each other.

inter-connecting—joined and/or fastened together reciprocally and/or with each other.

interface—(n) a boundary across which two independent systems meet and act on and/or communicate with each other. (v) to connect with and/or interact with by way of an interface.

interlock—(v) to fit, connect, unite, lock, and/or join together and/or closely in a non-destructively and/or destructively releasable manner; (n) a device for non-destructively and/or destructively releasably preventing substantial relative motion between two elements of a structure.

intersection—a point and/or line segment defined by the meeting of two or more items.

into—to a condition, state, or form of invert—to reverse the position, order, condition, nature, and/or effect of.

invertedly—in an reversed and/or opposing position, order, condition, nature, and/or effect.

investment casting—a forming technique and/or process that offers repeatable production of net shape components, typically with minutely precise details, from a variety of initially molten metals and/or high-performance alloys.

investment material—a material from which investment castings are formed.

isogrid—a structural arrangement formed of a lattice of intersecting ligaments that define one or more arrays of triangular spaces.

isogrid positioner—a mechanical, optical, and/or magnetic feature adapted to constrain, locate, and/or align the position of one isogrid relative to an adjacent isogrid.

isogrid stacking positioner—a mechanical, optical, and/or magnetic feature adapted to constrain, locate, and/or align the position of a first isogrid relative to an adjacent second isogrid whose lattice spans in a substantially parallel, but non-coplanar, flat and/or curved plane as the first isogrid.

isogrid tiling positioner—a mechanical, optical, and/or magnetic feature adapted to constrain, locate, and/or align the position of a first isogrid relative to an adjacent second isogrid whose lattice spans in substantially the same flat and/or curved plane as the first isogrid.

laminate—to construct from layers of material bonded together.

lamination—a bonded, adhered, and/or attached structure and/or arrangement, typically formed of thin sheets; and/or a laminated structure and/or arrangement.

layer—a single thickness of a material covering a surface or forming an overlying part or segment; a ply, strata, and/or sheet.

layer-less—not formed of, and/or lacking a collection and/or stack of, plies, strata, and/or sheets.

less than—having a measurably smaller magnitude and/or degree as compared to something else.

ligament—a connecting member such as a wall, beam, and/or rib.

link—(n) a chemical bond, such as a covalent bond; (v) to bond chemically, such as via covalent bond.

located—situated in a particular spot and/or position.

logic gate—a physical device adapted to perform a logical operation on one or more logic inputs and to produce a single logic output, which is manifested physically. Because the output is also a logic-level value, an output of one logic gate can connect to the input of one or more other logic gates, and via such combinations, complex operations can be performed. The logic normally performed is Boolean logic and is most commonly found in digital circuits. The most common implementations of logic gates are based on electronics using resistors, transistors, and/or diodes, and such implementations often appear in large arrays in the form of integrated circuits (a.k.a., IC's, microcircuits, microchips, silicon chips, and/or chips). It is possible, however, to create logic gates that operate based on vacuum tubes, electromagnetics (e.g., relays), mechanics (e.g., gears), fluidics, optics, chemical reactions, and/or DNA, including on a molecular scale. Each electronically-implemented logic gate typically has two inputs and one output, each having a logic level or state typically physically represented by a voltage. At any given moment, every terminal is in one of the two binary logic states ("false" (a.k.a., "low" or "0") or "true" (a.k.a., "high" or "1"), represented by different voltage levels, yet the logic state of a terminal can, and generally does, change often, as the circuit processes data. Thus, each electronic logic gate typically requires power so that it can source and/or sink currents to achieve the correct output voltage. Typically, machine-implementable instructions are ultimately encoded into binary values of "0" s and/or "1" s and, are typically written into and/or onto a memory device, such as a "register", which records the binary value as a change in a physical property of the memory device, such as a change in voltage, current, charge, phase, pressure, weight, height, tension, level, gap, position, velocity, momentum, force, temperature, polarity, magnetic field, magnetic force, magnetic orientation, reflectivity, molecular linkage, molecular weight, etc. An exemplary register might store a value of "01101100", which encodes a total of 8 "bits" (one byte), where each value of either "0" or "1" is called a "bit" (and 8 bits are collectively called a "byte"). Note that because a binary bit can only have one of two different values (either "0" or "1"), any physical medium capable of switching between two saturated states can be used to represent a bit. Therefore, any physical system capable of representing binary bits is able to represent numerical quantities, and potentially can manipulate those numbers via particular encoded machine-implementable instructions. This is one of the basic concepts underlying digital computing. At the register and/or gate level, a computer does not treat these "0" s and "1" s as numbers per se, but typically as voltage levels (in the case of an electronically-implemented computer), for example, a high voltage of approximately +3 volts might represent a "1" or "logical true" and a low voltage of approximately 0 volts might represent a "0" or "logical false" (or vice versa, depending on how the circuitry is designed). These high and low voltages (or other physical properties, depending on the nature of the implementation) are typically fed into a series of logic gates, which in turn, through the correct logic design, produce the physical and logical results specified by the particular encoded machine-implementable instructions. For example, if the encoding request a calculation, the logic gates might add the first two bits of the encoding together, produce a result "1" ("0"+"1"="1"), and then write this result into another register for subsequent retrieval and reading. Or, if the encoding is a request for some kind of service, the logic gates might in turn access or write into some other registers which would in turn trigger other logic gates to initiate the requested service.

logical—a conceptual representation.

machine-implementable instructions—directions adapted to cause a machine, such as an information device, to perform one or more particular activities, operations, and/or functions. The directions, which can sometimes form an entity called a "processor", "kernel", "operating system", "program", "application", "utility", "subroutine", "script", "macro", "file", "project", "module", "library", "class", and/or "object", etc., can be embodied and/or encoded as machine code, source code, object code, compiled code, assembled code, interpretable code, and/or executable code, etc., in hardware, firmware, and/or software.

machine-readable medium—a physical structure from which a machine, such as an information device, computer, microprocessor, and/or controller, etc., can store and/or obtain machine-implementable instructions, data, and/or information. Examples include a memory device, punch cards, etc.

major—relatively great in size or extent.

make—to create, generate, build, and/or construct.

mate—to join closely and/or pair.

material—a substance and/or composition.

may—is allowed and/or permitted to, in at least some embodiments.

measured—determined, as a dimension, quantification, and/or capacity, etc. by observation.

memory device—an apparatus capable of storing, sometimes permanently, machine-implementable instructions, data, and/or information, in analog and/or digital format. Examples include at least one non-volatile memory, volatile memory, register, relay, switch, Random Access Memory, RAM, Read Only Memory, ROM, flash memory, magnetic media, hard disk, floppy disk, magnetic tape, optical media, optical disk, compact disk, CD, digital versatile disk, DVD, and/or raid array, etc. The memory device can be coupled to a processor and/or can store and provide instructions adapted to be executed by processor, such as according to an embodiment disclosed herein.

metallic—comprising a metal.

method—one or more acts that are performed upon subject matter to be transformed to a different state or thing and/or are tied to a particular apparatus, said one or more acts not a fundamental principal and not pre-emptying all uses of a fundamental principal.

micro-features—irregularities, such as ridges and/or valleys, forming a roughness average on a surface of between approximately 1 microns and approximately 500 microns.

misaligned—to place out of alignment and/or to offset.

mix—to create and/or form by combining and/or blending ingredients.

model—a mathematical and/or schematic description of an entity and/or system.

mold—(n) a substantially hollow form, cavity, and/or matrix into and/or on which a molten, liquid, and/or plastic composition is placed and from which that composition takes form in a reverse image from that of the mold; (v) to shape and/or form in and/or on a mold.

molecule—the smallest particle of a substance that retains the chemical and physical properties of the substance and is composed of two or more atoms; and/or a group of like or different atoms held together by chemical forces.

monolithic—constituting and/or acting as a single, substantially uniform and/or unbroken, whole.

network—a communicatively coupled plurality of nodes, communication devices, and/or information devices. Via a network, such nodes and/or devices can be linked, such as via various wireline and/or wireless media, such as cables, telephone lines, power lines, optical fibers, radio waves, and/or light beams, etc., to share resources (such as printers and/or memory devices), exchange files, and/or allow electronic communications therebetween. A network can be and/or can utilize any of a wide variety of sub-networks and/or protocols, such as a circuit switched, public-switched, packet switched, connection-less, wireless, virtual, radio, data, telephone, twisted pair, POTS, non-POTS, DSL, cellular, telecommunications, video distribution, cable, terrestrial, microwave, broadcast, satellite, broadband, corporate, global, national, regional, wide area, backbone, packet-switched TCP/IP, IEEE 802.03, Ethernet, Fast Ethernet, Token Ring, local area, wide area, IP, public Internet, intranet, private, ATM, Ultra Wide Band (UWB), Wi-Fi, BlueTooth, Airport, IEEE 802.11, IEEE 802.11a, IEEE 802.11b, IEEE 802.11g, X-10, electrical power, multi-domain, and/or multi-zone sub-network and/or protocol, one or more Internet service providers, one or more network interfaces, and/or one or more information devices, such as a switch, router, and/or gateway not directly connected to a local area network, etc., and/or any equivalents thereof.

network interface—any physical and/or logical device, system, and/or process capable of coupling an information device to a network. Exemplary network interfaces comprise a telephone, cellular phone, cellular modem, telephone data modem, fax modem, wireless transceiver, communications port, ethernet card, cable modem, digital subscriber line interface, bridge, hub, router, or other similar device, software to manage such a device, and/or software to provide a function of such a device.

node—a junctions and/or intersection of a plurality of non-co-linear ligaments.

non—not.

not—a negation of something.

nozzle—a burner structured and/or utilized such that combustible gas issues therefrom to form a steady flame; a short tube, usually tapering, forming the vent of a pipe-like structure; and/or a component that produces thrust by converting the thermal energy of hot chamber gases into kinetic energy and directing that energy along the nozzle's longitudinal axis.

offsetably—characterized by a misalignment, jog, and/or short displacement in an otherwise parallel and/or straight orientation and/or arrangement.

open—to release from a closed and/or fastened position, to remove obstructions from, and/or to clear.

orthogonal—perpendicular.

output—(n) something produced and/or generated; data produced by an information device executing machine-readable instructions; and/or the energy, power, work, signal, and/or information produced by a system. (v) to provide, produce, manufacture, and/or generate.

overlappingly—characterized by extending over and covering a part of something else.

packet—a generic term for a bundle of data organized in a specific way for transmission, such as within and/or across a network, such as a digital packet-switching network, and comprising the data to be transmitted and certain control information, such as a destination address.

parallel—of, relating to, or designating lines, curves, planes, and/or or surfaces everywhere equidistant and/or an arrangement of components in an electrical circuit that splits an electrical current into two or more paths.

parent—an entity from which another is descended; and/or a source, origin, and/or cause.

part—component.

particle—a small piece or part. A particle can be and/or be comprised by a powder, bead, crumb, crystal, dust, grain, grit, meal, pounce, pulverulence, and/or seed, etc.

passage—a path, channel, and/or duct through, over, and/or along which something may pass.

percent—one part in one hundred.

perceptible—capable of being perceived by the human senses.

periphery—the outer limits, surface, and/or boundary of a surface, area, and/or object.

perpendicular—intersecting at and/or forming substantially right angles.

photolithography—a process whereby metallic foils, fluidic circuits, and/or printed circuits can be created by exposing a photosensitive substrate to a pattern, such as a predesigned structural pattern and/or a circuit pattern, and chemically etching away either the exposed or unexposed portion of the substrate.

physical—tangible, real, and/or actual.

physically—existing, happening, occurring, acting, and/or operating in a manner that is tangible, real, and/or actual.

place—to put in a particular place and/or position.

planar—shaped as a substantially flat two-dimensional surface.

plane—a substantially flat surface and/or a surface containing all the straight lines that connect any two points on it.

plurality—the state of being plural and/or more than one.

portion—a part, component, section, percentage, ratio, and/or quantity that is less than a larger whole. Can be visually, physically, and/or virtually distinguishable and/or non-distinguishable.

predetermined—established in advance.

present—to introduce, provide, show, display and/or offer for consideration.

prior—before processor—a hardware, firmware, and/or software machine and/or virtual machine physically adaptable to perform, via boolean logic operating on a plurality of logic gates, a specific task defined by a set of machine-implementable instructions. A processor can utilize mechanical, pneumatic, hydraulic, electrical, magnetic, optical, informational, chemical, and/or biological principles, mechanisms, adaptations, signals, inputs, and/or outputs to perform the task(s). In certain embodiments, a processor can act upon information by manipulating, analyzing, modifying, and/or converting it, transmitting the information for use by machine-implementable instructions and/or an information device, and/or routing the information to an output device. A processor can function as a central processing unit, local controller, remote controller, parallel controller, and/or distributed controller, etc. Unless stated otherwise, the processor can be a general-purpose device, such as a microcontroller and/or a microprocessor, such the Pentium family of microprocessor manufactured by the Intel Corporation of Santa Clara, Calif. In certain embodiments, the processor can be dedicated purpose device, such as an Application Specific Integrated Circuit (ASIC) or a Field Programmable Gate Array (FPGA) that has been designed to implement in its hardware and/or firmware at least a part of an embodiment disclosed herein. A processor can reside on and use the capabilities of a controller.

product—something produced by human or mechanical effort or by a natural process.

protrude—to bulge, jut, project, and/or extend out and/or into space.

protrusion—that which protrudes.

provide—to furnish, supply, give, convey, send, and/or make available.

pull—to remove from a fixed position, to extract, and/or to apply force to so as to cause and/or tend to cause motion toward the source of the force.

pull-plane—a plane along and/or perpendicular to which a cast device is adapted to be urged to withdraw the cast device from a mold without substantial damage to the cast device and/or mold.

radius—the length of a line segment between the center and circumference of a circle or sphere.

reduce—to make and/or become lesser and/or smaller.

remove—to eliminate, remove, and/or delete, and/or to move from a place or position occupied.

render—to, e.g., physically, chemically, biologically, electronically, electrically, magnetically, optically, acoustically, fluidically, and/or mechanically, etc., transform information into a form perceptible to a human as, for example, data, commands, text, graphics, audio, video, animation, and/or hyperlinks, etc., such as via a visual, audio, and/or haptic, etc., means and/or depiction, such as via a display, monitor, electric paper, ocular implant, cochlear implant, speaker, vibrator, shaker, force-feedback device, stylus, joystick, steering wheel, glove, blower, heater, cooler, pin array, tactile touchscreen, etc.

repeatedly—again and again; repetitively.

replicate—to make a substantially identical copy, duplicate, reproduction, and/or repetition of something.

resin—any of numerous physically similar polymerized synthetics and/or chemically modified natural resins including thermoplastic materials such as polyvinyl, polystyrene, and polyethylene, and thermosetting materials such as polyesters, epoxies, and silicones that are used with fillers, stabilizers, pigments, and/or other components to form plastics.

said—when used in a system or device claim, an article indicating a subsequent claim term that has been previously introduced.

scale—(n) a progressive classification, such as of size, amount, importance, and/or rank; (v) to increase or reduce proportionately in size.

second—immediately following the first in an ordering.

select—to make a choice or selection from alternatives.

separate—(n) distinct; (v) to disunite, space, set, or keep apart and/or to be positioned intermediate to.

server—an information device and/or a process running thereon, that is adapted to be communicatively coupled to a network and that is adapted to provide at least one service for at least one client, i.e., for at least one other information device communicatively coupled to the network and/or for at least one process running on another information device communicatively coupled to the network. One example is a file server, which has a local drive and services requests from remote clients to read, write, and/or manage files on that drive. Another example is an e-mail server, which provides at least one program that accepts, temporarily stores, relays, and/or delivers e-mail messages. Still another example is a database server, which processes database queries. Yet another example is a device server, which provides networked and/or programmable: access to, and/or monitoring, management, and/or control of, shared physical resources and/or devices, such as information devices, printers, modems, scanners, projectors, displays, lights, cameras, security equipment, proximity readers, card readers, kiosks, POS/retail equipment, phone systems, residential equipment, HVAC equipment, medical equipment, laboratory equipment, industrial equipment, machine tools, pumps, fans, motor drives, scales, programmable logic controllers, sensors, data collectors, actuators, alarms, annunciators, and/or input/output devices, etc.

set—a related plurality of predetermined elements; and/or one or more distinct items and/or entities having a specific common property or properties.

shape—(v) to apply a characteristic surface, outline, and/or contour to an entity.

shape—a characteristic surface, outline, and/or contour of an entity.

shear—a deformation resulting from stresses that cause contiguous parts of a body to slide relatively to each other in a direction parallel to their plane of contact; a deformation of an object in which parallel planes remain parallel but are shifted in a direction parallel to themselves; "the shear changed the quadrilateral into a parallelogram".

sheet—a broad, relatively thin, surface, layer, and/or covering shrinkage—the process of shrinking and/or the amount or proportion by which something shrinks.

signal—automatically detectable variations in a physical variable, such as a pneumatic, hydraulic, acoustic, fluidic, mechanical, electrical, magnetic, optical, chemical, and/or biological variable, such as power, energy, pressure, flowrate, viscosity, density, torque, impact, force, frequency, phase, voltage, current, resistance, magnetomotive force, magnetic field intensity, magnetic field flux, magnetic flux density, reluctance, permeability, index of refraction, optical wavelength, polarization, reflectance, transmittance, phase shift, concentration, and/or temperature, etc., that encode information, such as machine-implementable instructions for activities and/or one or more letters, words, characters, symbols, signal flags, visual displays, and/or special sounds, etc., having prearranged meaning. Depending on the context, a signal and/or the information encoded therein can be synchronous, asynchronous, hard real-time, soft real-time, non-real time, continuously generated, continuously varying, analog, discretely generated, discretely varying, quantized, digital, broadcast, multicast, unicast, transmitted, conveyed, received, continuously measured, discretely measured, processed, encoded, encrypted, multiplexed, modulated, spread, de-spread, demodulated, detected, de-multiplexed, decrypted, and/or decoded, etc.

silica—silicon dioxide ($SiO_2$), which is a hard, glossy, white, and/or colorless crystalline compound and/or mineral, which occurs naturally and/or abundantly as quartz, quartz, sand, flint, agate, and many other minerals, and used to manufacture a wide variety of materials, especially glass and concrete.

silicone—any of a class and/or group of chemical compounds and/or semi-inorganic polymers based on the structural unit $R_2SiO$, where R is an organic group and/or radical, such as a methyl ($CH_3$) group and/or a phenyl ($C_6H_5$) group, typically characterized by wide-range thermal stability, high lubricity, extreme water repellence, and/or physiological inertness, often used in adhesives, lubricants, protective coatings, paints, electrical insulation, synthetic rubber, and/or prosthetic replacements for body parts.

siloxane—any of a class of organic and/or inorganic chemical compounds of silicon, oxygen, and usually carbon and hydrogen, based on the structural unit $R_2SiO$, where R is an alkyl group, usually methyl.

simulated—created as a representation or model of another thing.

single—existing alone or consisting of one entity.

sinter—to cause (e.g., a ceramic and/or metallic powder) to form a coherent mass by heating without melting.

slice—(n) a thin broad piece cut from a larger three dimensional object; (v) to cut and/or divide a three dimensional object into slices.

solvent—a substance in which another substance is dissolved, forming a solution; and/or a substance, usually a liquid, capable of dissolving another substance.

space—an area and/or volume.

spatial—relating to an area or volume.

spatially—existing or occurring in space.

special purpose computer—a computer and/or information device comprising a processor device having a plurality of logic gates, whereby at least a portion of those logic gates, via implementation of specific machine-implementable instructions by the processor, experience a change in at least one physical and measurable property, such as a voltage, current, charge, phase, pressure, weight, height, tension, level, gap, position, velocity, momentum, force, temperature, polarity, magnetic field, magnetic force, magnetic orientation, reflectivity, molecular linkage, molecular weight, etc., thereby directly tying the specific machine-implementable instructions to the logic gate's specific configuration and property(ies). In the context of an electronic computer, each such change in the logic gates creates a specific electrical circuit, thereby directly tying the specific machine-implementable instructions to that specific electrical circuit.

special purpose processor—a processor device, having a plurality of logic gates, whereby at least a portion of those logic gates, via implementation of specific machine-implementable instructions by the processor, experience a change in at least one physical and measurable property, such as a voltage, current, charge, phase, pressure, weight, height, tension, level, gap, position, velocity, momentum, force, temperature, polarity, magnetic field, magnetic force, magnetic orientation, reflectivity, molecular linkage, molecular weight, etc., thereby directly tying the specific machine-implementable instructions to the logic gate's specific configuration and property(ies). In the context of an electronic computer, each such change in the logic gates creates a specific electrical circuit, thereby directly tying the specific machine-implementable instructions to that specific electrical circuit.

split—to break, divide, and/or separate into separate pieces.

stack—(n) a substantially orderly pile and/or group, especially one arranged in and/or defined by layers; (v) to place and/or arrange in a stack.

store—to place, hold, and/or retain data, typically in a memory.

strength—a measure of the ability of a material to support a load; the maximum nominal stress a material can sustain; and/or a level of stress at which there is a significant change in the state of the material, e.g., yielding and/or rupture.

structure—that which is complexly constructed and/or a manner in which components are organized and/or form a whole.

sub-plurality—a subset.

substantially—to a considerable, large, and/or great, but not necessarily whole and/or entire, extent and/or degree.

sufficiently—to a degree necessary to achieve a predetermined result.

support—to bear the weight of, especially from below.

surface—any face and/or outer boundary of a body, object, and/or thing surround—to encircle, enclose, and/or confine on several and/or all sides.

system—a collection of mechanisms, devices, machines, articles of manufacture, processes, data, and/or instructions, the collection designed to perform one or more specific functions.

tensile—pertaining to forces on a body that tend to stretch, or elongate, the body. A rope or wire under load is subject to tensile forces.

terminate—to end.

thermoform—to shape (especially plastic) by the use of heat and pressure.

thickness—the measure of the smallest dimension of a solid figure.

through—in one side and out the opposite or another side of, across, among, and/or between.

tool—something used to accomplish a task.

transform—to change in measurable: form, appearance, nature, and/or character.

transmit—to send as a signal, provide, furnish, and/or supply.

triangular—pertaining to or having the form of a triangle; three-cornered.

turbomachine—a device in which energy is transferred to and/or from a continuously flowing fluid by dynamic interaction of the fluid with one or more moving and/or rotating blade rows, such as a turbine (e.g., windmill, water wheel, hydroelectric turbine, automotive engine turbocharger, and/or gas turbine, etc.) and/or an impeller (e.g., liquid pump, fan, blower, and/or compressor, etc.).

undercut—a notch, groove, and/or cut beneath.

user interface—any device for rendering information to a user and/or requesting information from the user. A user interface includes at least one of textual, graphical, audio, video, animation, and/or haptic elements. A textual element can be provided, for example, by a printer, monitor, display, projector, etc. A graphical element can be provided, for example, via a monitor, display, projector, and/or visual indication device, such as a light, flag, beacon, etc. An audio element can be provided, for example, via a speaker, microphone, and/or other sound generating and/or receiving device. A video element or animation element can be provided, for example, via a monitor, display, projector, and/or other visual device. A haptic element can be provided, for example, via a very low frequency speaker, vibrator, tactile stimulator, tactile pad, simulator, keyboard, keypad, mouse, trackball, joystick, gamepad, wheel, touchpad, touch panel, pointing device, and/or other haptic device, etc. A user interface can include one or more textual elements such as, for example, one or more letters, number, symbols, etc. A user interface can include one or more graphical elements such as, for example, an image, photograph, drawing, icon, window, title bar, panel, sheet, tab, drawer, matrix, table, form, calendar, outline view, frame, dialog box, static text, text box, list, pick list, pop-up list, pull-down list, menu, tool bar, dock, check box, radio button, hyperlink, browser, button, control, palette, preview panel, color wheel, dial, slider, scroll bar, cursor, status bar, stepper, and/or progress indicator, etc. A textual and/or graphical element can be used for selecting, programming, adjusting, changing, specifying, etc. an appearance, background color, background style, border style, border thickness, foreground color, font, font style, font size, alignment, line spacing, indent, maximum data length, validation, query, cursor type, pointer type, autosizing, position, and/or dimension, etc. A user interface can include one or more audio elements such as, for example, a volume control, pitch control, speed control, voice selector, and/or one or more elements for controlling audio play, speed, pause, fast forward, reverse, etc. A user interface can include one or more video elements such as, for example, elements controlling video play, speed, pause, fast forward, reverse, zoom-in, zoom-out, rotate, and/or tilt, etc. A user interface can include one or more animation elements such as, for example, elements controlling animation play, pause, fast forward, reverse, zoom-in, zoom-out, rotate, tilt, color, intensity, speed, frequency, appearance, etc. A user interface can include one or more haptic elements such as, for example, elements utilizing tactile stimulus, force, pressure, vibration, motion, displacement, temperature, etc.

vacuum—a pressure that is significantly lower than atmospheric pressure and/or approaching 0 psia.

vane—any of several usually relatively thin, rigid, flat, and/or sometimes curved surfaces radially mounted along an axis, as a blade in a turbine or a sail on a windmill, that is turned by and/or used to turn a fluid.

variance—a measure of variation of a set of observations defined by a sum of the squares of deviations from a mean, divided by a number of degrees of freedom in the set of observations.

vent—to release from confinement.

version—a particular form or variation of an earlier and/or original type.

via—by way of and/or utilizing.

vibrate—to move back and forth or to and fro, especially rhythmically and/or rapidly.

volume—a mass and/or a three-dimensional region that an object and/or substance occupies.

wall—a partition, structure, and/or mass that serves to enclose, divide, separate, segregate, define, and/or protect a volume and/or to support a floor, ceiling, and/or another wall.

weight—a force with which a body is attracted to Earth or another celestial body, equal to the product of the object's mass and the acceleration of gravity; and/or a factor assigned to a number in a computation, such as in determining an average, to make the number's effect on the computation reflect its importance.

wherein—in regard to which; and; and/or in addition to.

while—for as long as, during the time that, and/or at the same time that.

within—inside.

zircon—a hard, brown to colorless mineral consisting of zirconium silicate (ZrSiO4).

zone—a portion of an isogrid containing an array of substantially identically-dimensioned triangular spaces. Within such an array, certain physical properties of the isogrid and/or its ligaments (such as compressive strength, shear strength, elasticity, density, opacity, and/or thermal conductivity, etc.) can be substantially isotropic, that is, substantially equal in all directions.

Note

Various substantially and specifically practical and useful exemplary embodiments of the claimed subject matter, are described herein, textually and/or graphically, including the best mode, if any, known to the inventors for carrying out the claimed subject matter. Variations (e.g., modifications and/or enhancements) of one or more embodiments described herein might become apparent to those of ordinary skill in the art upon reading this application. The inventors expect skilled artisans to employ such variations as appropriate, and the inventors intend for the claimed subject matter to be practiced other than as specifically described herein. Accordingly, as permitted by law, the claimed subject matter includes and covers all equivalents of the claimed subject matter and all improvements to the claimed subject matter. Moreover, every combination of the above described elements, activities, and all possible variations thereof are encompassed by the claimed subject matter unless otherwise clearly indicated herein, clearly and specifically disclaimed, or otherwise clearly contradicted by context.

The use of any and all examples, or exemplary language (e.g., "such as") provided herein, is intended merely to better illuminate one or more embodiments and does not pose a limitation on the scope of any claimed subject matter unless otherwise stated. No language in the specification should be construed as indicating any non-claimed subject matter as essential to the practice of the claimed subject matter.

Thus, regardless of the content of any portion (e.g., title, field, background, summary, description, abstract, drawing figure, etc.) of this application, unless clearly specified to the contrary, such as via explicit definition, assertion, or argument, or clearly contradicted by context, with respect to any claim, whether of this application and/or any claim of any application claiming priority hereto, and whether originally presented or otherwise:

there is no requirement for the inclusion of any particular described or illustrated characteristic, function, activity, or element, any particular sequence of activities, or any particular interrelationship of elements;

no characteristic, function, activity, or element is "essential";

any elements can be integrated, segregated, and/or duplicated;

any activity can be repeated, any activity can be performed by multiple entities, and/or any activity can be performed in multiple jurisdictions; and any activity or element can be specifically excluded, the sequence of activities can vary, and/or the interrelationship of elements can vary.

The use of the terms "a", "an", "said", "the", and/or similar referents in the context of describing various embodiments (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted.

Moreover, when any number or range is described herein, unless clearly stated otherwise, that number or range is approximate. Recitation of ranges of values herein are merely intended to serve as a shorthand method of referring individually to each separate value falling within the range, unless otherwise indicated herein, and each separate value and each separate subrange defined by such separate values is incorporated into the specification as if it were individually recited herein. For example, if a range of 1 to 10 is described, that range includes all values therebetween, such as for example, 1.1, 2.5, 3.335, 5, 6.179, 8.9999, etc., and includes all subranges therebetween, such as for example, 1 to 3.65, 2.8 to 8.14, 1.93 to 9, etc.

When any claim element is followed by a drawing element number, that drawing element number is exemplary and non-limiting on claim scope. No claim of this application is intended to invoke paragraph six of 35 USC 112 unless the precise phrase "means for" is followed by a gerund.

Any information in any material (e.g., a United States patent, United States patent application, book, article, etc.) that has been incorporated by reference herein, is incorporated by reference herein in its entirety to its fullest enabling extent permitted by law yet only to the extent that no conflict exists between such information and the other statements and drawings set forth herein. In the event of such conflict, including a conflict that would render invalid any claim herein or seeking priority hereto, then any such conflicting information in such material is specifically not incorporated by reference herein.

Accordingly, every portion (e.g., title, field, background, summary, description, abstract, drawing figure, etc.) of this application, other than the claims themselves, is to be regarded as illustrative in nature, and not as restrictive, and the scope of subject matter protected by any patent that issues based on this application is defined only by the claims of that patent.

What is claimed is:

1. A device comprising:
    a device composition comprising:
        a ceramic composition comprising a plurality of crystalline forms of silica, a first crystalline form of silica from the plurality of crystalline forms of silica being cristobalite in an amount greater than 2.5% and less than 10% by weight of the device composition;
        an cycloaliphatic epoxy binder composition, the cycloaliphatic epoxy binder composition present in the device composition in an amount up to 30% by weight of the device composition; and
        a silicone composition comprising a siloxane resin, the silicone composition present in the device composition in an amount up to 30% by weight of the device composition;
    the device defining a plurality of wall surfaces, a wall surface from the plurality of wall surfaces comprising a plurality of 3-dimensional micro-features, the plurality of 3-dimensional micro-features comprising at least one protruding undercut, the plurality of wall surfaces defining a periphery of a layer-less volume;
    the device configured to be substantially carbon-free after sintering;
    the device having a post-sintering measured apparent porosity of 15 to 35 percent and a predetermined surface characteristic.

2. The device of claim 1, wherein:
    the ceramic composition comprises approximately 6 percent to approximately 10 percent cristobalite by weight of the device composition.

3. The device of claim 1, wherein:
    the device composition comprises zircon.

4. The device of claim 1, wherein:
    the device composition comprises alumina.

5. The device of claim 1, further comprising:
    a photolithographically-derived foil structure substantially surrounded by the ceramic composition.

6. The device of claim 1, wherein:
    the device is configured to serve as an investment casting core.

7. The device of claim 1, wherein:
    the device is configured to serve as a core for an investment cast product.

8. The device of claim 1, wherein:
    the device is configured to serve as a core for an investment cast turbomachine component.

9. The device of claim 1, wherein:
    the device is configured to serve as a core for an investment cast air foil.

10. The device of claim 1, wherein:
    the device is configured to serve as a core for an investment cast blade.

11. The device of claim 1, wherein:
    the device is configured to serve as a core for an investment cast vane.

12. The device of claim 1, wherein:
    the device is configured to serve as a core for an investment cast nozzle.

13. The device of claim 1, wherein:
    the device defines a plurality of cooling passages for an investment cast product.

14. The device of claim 1, wherein:
    the device comprises a first planar surface configured to be transformed into a non-planar surface via thermoforming the ceramic composition.

15. The device of claim 1, wherein:
    the device is removable, from an ancestor mold having a surface that comprises a plurality of substantially spatially inverted replicas of the plurality of 3-dimensional microfeatures, the mold having an opening defined by an opening cross-sectional area that is smaller than a largest cross-sectional area of the device, without damage to the device and without damage to the ancestor mold.

* * * * *